United States Patent
Voigt et al.

(10) Patent No.: US 12,281,299 B2
(45) Date of Patent: Apr. 22, 2025

(54) CONTROL OF NITROGEN FIXATION IN RHIZOBIA THAT ASSOCIATE WITH CEREALS

(71) Applicant: Massachusetts Institute of Technology, Cambridge, MA (US)

(72) Inventors: Christopher A. Voigt, Belmont, MA (US); Min-Hyung Ryu, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1027 days.

(21) Appl. No.: 16/746,215

(22) Filed: Jan. 17, 2020

(65) Prior Publication Data

US 2020/0299637 A1 Sep. 24, 2020

Related U.S. Application Data

(60) Provisional application No. 62/820,765, filed on Mar. 19, 2019.

(51) Int. Cl.
*C12N 1/20* (2006.01)
*C05F 11/08* (2006.01)
*C12N 15/87* (2006.01)

(52) U.S. Cl.
CPC .......... *C12N 1/20* (2013.01); *C05F 11/08* (2013.01); *C12N 15/87* (2013.01); *C12N 2510/00* (2013.01)

(58) Field of Classification Search
None
See application file for complete search history.

(56) References Cited

U.S. PATENT DOCUMENTS

| | | |
|---|---|---|
| 1,520,545 A | 12/1924 | Murphy |
| 4,782,022 A | 11/1988 | Puhler et al. |
| 4,832,728 A | 5/1989 | Allan et al. |
| 5,071,743 A | 12/1991 | Slilaty et al. |
| 5,116,506 A | 5/1992 | Williamson et al. |
| 5,188,960 A | 2/1993 | Payne et al. |
| 5,229,291 A | 7/1993 | Nielsen et al. |
| 5,354,670 A | 10/1994 | Nickoloff et al. |
| 5,427,785 A | 6/1995 | Ronson et al. |
| 5,610,044 A | 3/1997 | Lam et al. |
| 5,780,270 A | 7/1998 | Lesley |
| 5,789,166 A | 8/1998 | Bauer et al. |
| 5,877,012 A | 3/1999 | Estruch et al. |
| 5,880,275 A | 3/1999 | Fischhoff et al. |
| 5,916,029 A | 6/1999 | Smith et al. |
| 6,033,861 A | 3/2000 | Schaffer et al. |
| 6,033,874 A | 3/2000 | Baum et al. |
| 6,083,499 A | 7/2000 | Narva et al. |
| 6,107,279 A | 8/2000 | Estruch et al. |
| 6,114,148 A | 9/2000 | Seed et al. |
| 6,127,180 A | 10/2000 | Narva et al. |
| 6,137,033 A | 10/2000 | Estruch et al. |
| 6,218,188 B1 | 4/2001 | Cardineau et al. |
| 6,248,535 B1 | 6/2001 | Danenberg et al. |
| 6,326,351 B1 | 12/2001 | Donovan et al. |
| 6,340,593 B1 | 1/2002 | Cardineau et al. |
| 6,391,548 B1 | 5/2002 | Bauer et al. |
| 6,399,330 B1 | 6/2002 | Donovan et al. |
| 6,548,289 B1 | 4/2003 | Beynon et al. |
| 6,548,291 B1 | 4/2003 | Narva et al. |
| 6,596,509 B1 | 7/2003 | Bauer et al. |
| 6,624,145 B1 | 9/2003 | Narva et al. |
| 6,673,610 B2 | 1/2004 | Miyawaki et al. |
| 6,713,063 B1 | 3/2004 | Malvar et al. |
| 6,713,285 B2 | 3/2004 | Bauer et al. |
| 6,773,900 B2 | 8/2004 | Short et al. |
| 6,841,358 B1 | 1/2005 | Locht et al. |
| 6,949,626 B2 | 9/2005 | Donovan et al. |
| 6,962,705 B2 | 11/2005 | Malvar et al. |
| 7,064,249 B2 | 6/2006 | Corbin et al. |
| 7,070,982 B2 | 7/2006 | Malvar et al. |
| 7,084,331 B2 | 8/2006 | Isawa et al. |
| 7,105,332 B2 | 9/2006 | Abad et al. |
| 7,132,265 B2 | 11/2006 | Bauer et al. |
| 7,244,820 B2 | 7/2007 | Miles et al. |
| 7,329,736 B2 | 2/2008 | Abad et al. |
| 7,378,499 B2 | 5/2008 | Abad et al. |
| 7,385,107 B2 | 6/2008 | Donovan et al. |
| 7,449,552 B2 | 11/2008 | Abad et al. |
| 7,462,760 B2 | 12/2008 | Abad et al. |

(Continued)

FOREIGN PATENT DOCUMENTS

| | | |
|---|---|---|
| AU | 636565 B2 | 5/1993 |
| CA | 2051071 A1 | 3/1993 |

(Continued)

OTHER PUBLICATIONS

Bashor, "Understanding biological regulation through synthetic biology." (2018). (Year: 2018).*
Venkateshwaran, Muthusubramanian. "Exploring the feasibility of transferring nitrogen fixation to cereal crops." Principles of plant-microbe interactions. Springer, Cham, 2015. 403-410. (Year: 2015).*
Wang, et al. (PLoS One 8.7 (2013): e68677). (Year: 2013).*
Dessaux et al. (Trends in plant science 21.3 (2016): 266-278). (Year: 2016).*
Berrada, et al. (British Microbiology Research Journal 4.6 (2014): 616). (Year: 2014).*

(Continued)

*Primary Examiner* — Charles Logsdon

(74) *Attorney, Agent, or Firm* — Wolf, Greenfield & Sacks, P.C.

(57) ABSTRACT

Disclosed herein are engineered rhizobia having nif clusters that enable the fixation of nitrogen under free-living conditions, as well as ammonium and oxygen tolerant nitrogen fixation under free-living conditions. Also provided are methods for producing nitrogen for consumption by a cereal crop using these engineered rhizobia.

19 Claims, 47 Drawing Sheets

Specification includes a Sequence Listing.

(56) References Cited

U.S. PATENT DOCUMENTS

| | | |
|---|---|---|
| 7,470,427 B2 | 12/2008 | Cocking |
| 7,476,781 B2 | 1/2009 | Abad et al. |
| 7,485,451 B2 | 2/2009 | Vandergheynst et al. |
| 7,491,698 B2 | 2/2009 | Hey et al. |
| 7,491,869 B2 | 2/2009 | Abad et al. |
| 7,504,229 B2 | 3/2009 | Donovan et al. |
| 7,615,686 B2 | 11/2009 | Miles et al. |
| 7,803,943 B2 | 9/2010 | Mao et al. |
| 7,858,849 B2 | 12/2010 | Cerf et al. |
| 7,888,552 B2 | 2/2011 | Ye et al. |
| 7,923,602 B2 | 4/2011 | Carozzi et al. |
| 8,076,142 B2 | 12/2011 | Huang et al. |
| 8,084,416 B2 | 12/2011 | Sampson et al. |
| 8,084,418 B2 | 12/2011 | Hey et al. |
| 8,137,665 B2 | 3/2012 | Cocking |
| 8,236,757 B2 | 8/2012 | Carozzi et al. |
| 8,237,020 B2 | 8/2012 | Miles et al. |
| 8,268,584 B1 | 9/2012 | Hardwood et al. |
| 8,304,604 B2 | 11/2012 | Lira et al. |
| 8,304,605 B2 | 11/2012 | Lira et al. |
| 8,319,019 B2 | 11/2012 | Abad et al. |
| 8,334,366 B1 | 12/2012 | Hughes et al. |
| 8,334,431 B2 | 12/2012 | Sampson et al. |
| 8,377,671 B2 | 2/2013 | Cournac et al. |
| 8,481,026 B1 | 7/2013 | Woodruff et al. |
| 8,513,494 B2 | 8/2013 | Wu et al. |
| 8,530,411 B2 | 9/2013 | Cerf et al. |
| 8,575,433 B2 | 11/2013 | Cerf et al. |
| 8,686,233 B2 | 4/2014 | Cerf et al. |
| 8,759,619 B2 | 6/2014 | Sampson et al. |
| 8,795,965 B2 | 8/2014 | Zjang |
| 8,802,933 B2 | 8/2014 | Abad et al. |
| 8,802,934 B2 | 8/2014 | Abad et al. |
| 9,150,851 B2 | 10/2015 | Wigley et al. |
| 9,321,697 B2 | 4/2016 | Das et al. |
| 9,487,451 B2 | 11/2016 | Doty et al. |
| 9,512,431 B2 | 12/2016 | Mirsky et al. |
| 9,657,298 B2 | 5/2017 | Soto, Sr. et al. |
| 9,796,957 B2 | 10/2017 | Barney et al. |
| 9,957,509 B2 | 5/2018 | Mirsky et al. |
| 9,975,817 B2 | 5/2018 | Temme et al. |
| 9,994,557 B2 | 6/2018 | Davidson et al. |
| 10,384,983 B2 | 8/2019 | Temme et al. |
| 10,525,318 B2 | 1/2020 | Dougherty |
| 10,556,839 B2 | 2/2020 | Temme et al. |
| 10,662,432 B2 | 5/2020 | Mirsky et al. |
| 10,919,814 B2 | 2/2021 | Temme et al. |
| 10,934,226 B2 | 3/2021 | Temme et al. |
| 10,968,446 B2 | 4/2021 | Zhao et al. |
| 11,479,516 B2 | 10/2022 | Voigt et al. |
| 11,946,162 B2 | 4/2024 | Zhao et al. |
| 2002/0061579 A1* | 5/2002 | Farrand .................. C12N 15/65 800/294 |
| 2004/0197916 A1 | 10/2004 | Carozzi et al. |
| 2004/0197917 A1 | 10/2004 | Carozzi et al. |
| 2004/0210964 A1 | 10/2004 | Carozzi et al. |
| 2004/0210965 A1 | 10/2004 | Carozzi et al. |
| 2004/0216186 A1 | 10/2004 | Carozzi et al. |
| 2004/0235663 A1 | 11/2004 | Cocking |
| 2004/0241847 A1 | 12/2004 | Okuyama et al. |
| 2004/0250311 A1 | 12/2004 | Carozzi et al. |
| 2005/0081262 A1 | 4/2005 | Cook et al. |
| 2005/0266541 A1 | 12/2005 | Dillon |
| 2006/0033867 A1 | 2/2006 | Krisko et al. |
| 2006/0096918 A1 | 5/2006 | Semmens |
| 2006/0112447 A1 | 5/2006 | Bogdanova et al. |
| 2006/0127988 A1 | 6/2006 | Wood et al. |
| 2006/0191034 A1 | 8/2006 | Baum |
| 2006/0243011 A1 | 11/2006 | Someus |
| 2008/0295207 A1 | 11/2008 | Baum et al. |
| 2008/0311632 A1 | 12/2008 | Figge et al. |
| 2009/0105076 A1 | 4/2009 | Stewart et al. |
| 2009/0137390 A1 | 5/2009 | Triplett |
| 2009/0144852 A1 | 6/2009 | Tomso et al. |
| 2009/0152195 A1 | 6/2009 | Rodgers et al. |
| 2009/0162477 A1 | 6/2009 | Nadel |
| 2009/0258404 A1 | 10/2009 | Mikkelsen et al. |
| 2009/0308121 A1 | 12/2009 | Reddy et al. |
| 2010/0005543 A1 | 1/2010 | Sampson et al. |
| 2010/0017914 A1 | 1/2010 | Hart et al. |
| 2010/0028870 A1 | 2/2010 | Welch et al. |
| 2010/0184038 A1 | 7/2010 | Boddy et al. |
| 2010/0197592 A1 | 8/2010 | Heinrichs |
| 2010/0267147 A1 | 10/2010 | Qiao |
| 2010/0298211 A1 | 11/2010 | Carozzi et al. |
| 2011/0023184 A1 | 1/2011 | Desai et al. |
| 2011/0064710 A1 | 3/2011 | Benson et al. |
| 2011/0104690 A1 | 5/2011 | Yu et al. |
| 2011/0263488 A1 | 10/2011 | Carozzi et al. |
| 2012/0015806 A1 | 1/2012 | Paikray et al. |
| 2012/0107889 A1 | 5/2012 | Doty et al. |
| 2012/0192605 A1 | 8/2012 | McSpadden Gardener et al. |
| 2012/0266332 A1 | 10/2012 | Kuykendall |
| 2012/0278954 A1 | 11/2012 | Bowen et al. |
| 2012/0284813 A1 | 11/2012 | Oliver et al. |
| 2012/0311745 A1 | 12/2012 | Meade et al. |
| 2012/0311746 A1 | 12/2012 | Meade et al. |
| 2012/0317681 A1 | 12/2012 | Meade et al. |
| 2012/0317682 A1 | 12/2012 | Meade et al. |
| 2012/0324605 A1 | 12/2012 | Meade et al. |
| 2012/0324606 A1 | 12/2012 | Meade et al. |
| 2012/0331589 A1 | 12/2012 | Meade et al. |
| 2012/0331590 A1 | 12/2012 | Meade et al. |
| 2013/0116170 A1 | 5/2013 | Graser et al. |
| 2013/0126428 A1 | 5/2013 | Jones et al. |
| 2013/0167268 A1 | 6/2013 | Narva et al. |
| 2013/0167269 A1 | 6/2013 | Narva et al. |
| 2014/0011261 A1 | 1/2014 | Wang et al. |
| 2014/0155283 A1 | 6/2014 | Venkateswaran et al. |
| 2014/0182018 A1 | 6/2014 | Lang et al. |
| 2014/0223598 A1 | 8/2014 | Sampson et al. |
| 2014/0223599 A1 | 8/2014 | Sampson et al. |
| 2014/0230504 A1 | 8/2014 | Finlayson et al. |
| 2014/0273226 A1 | 9/2014 | Wu |
| 2014/0301990 A1 | 10/2014 | Gregory et al. |
| 2014/0329326 A1 | 11/2014 | Mirsky |
| 2014/0336050 A1* | 11/2014 | Soto, Sr. .................. A01N 63/60 504/117 |
| 2015/0080261 A1 | 3/2015 | Wigley et al. |
| 2015/0101373 A1 | 4/2015 | Munusamy et al. |
| 2015/0128670 A1 | 5/2015 | Das |
| 2015/0237807 A1 | 8/2015 | Valiquette |
| 2015/0239789 A1 | 8/2015 | Kang et al. |
| 2015/0315570 A1 | 11/2015 | Zhao et al. |
| 2016/0174570 A1 | 6/2016 | Vujanovic et al. |
| 2016/0264929 A1 | 9/2016 | Barney et al. |
| 2016/0292355 A1 | 10/2016 | Lou et al. |
| 2016/0295868 A1 | 10/2016 | Jones et al. |
| 2017/0086402 A1 | 3/2017 | Meadows-Smith et al. |
| 2017/0119690 A1 | 5/2017 | Hansen et al. |
| 2017/0152519 A1 | 6/2017 | Mirsky et al. |
| 2017/0267997 A1 | 9/2017 | Nicol et al. |
| 2017/0367349 A1 | 12/2017 | Gruver et al. |
| 2018/0002243 A1 | 1/2018 | Temme et al. |
| 2018/0020671 A1 | 1/2018 | Wigley et al. |
| 2018/0065896 A1 | 3/2018 | Ibema et al. |
| 2018/0073028 A1 | 3/2018 | Mirsky et al. |
| 2018/0273437 A1 | 9/2018 | Temme et al. |
| 2018/0290942 A1 | 10/2018 | Voigt et al. |
| 2018/0297905 A1 | 10/2018 | Temme et al. |
| 2018/0297906 A1 | 10/2018 | Temme et al. |
| 2019/0039964 A1 | 2/2019 | Temme et al. |
| 2019/0144352 A1 | 5/2019 | Temme et al. |
| 2020/0087221 A1 | 3/2020 | Temme et al. |
| 2020/0115715 A1 | 4/2020 | Mirsky et al. |
| 2020/0308594 A1 | 10/2020 | Tamsir et al. |
| 2020/0331820 A1* | 10/2020 | Tamsir ............ C12Y 603/01002 |
| 2021/0009483 A1 | 1/2021 | Temme et al. |
| 2021/0163374 A1 | 6/2021 | Bioch et al. |
| 2021/0214282 A1 | 7/2021 | Temme et al. |
| 2021/0284995 A1 | 9/2021 | Zhao et al. |
| 2021/0315212 A1 | 10/2021 | Rezaei et al. |

(56) References Cited

U.S. PATENT DOCUMENTS

| | | |
|---|---|---|
| 2022/0017911 A1 | 1/2022 | Temme et al. |
| 2022/0079163 A1 | 3/2022 | Reisinger et al. |
| 2022/0411344 A1 | 12/2022 | Voigt et al. |

FOREIGN PATENT DOCUMENTS

| | | |
|---|---|---|
| CN | 1289852 | 4/2001 |
| CN | 1500801 | 6/2004 |
| CN | 103451130 A | 12/2004 |
| CN | 1746304 A | 3/2006 |
| CN | 101880676 | 11/2010 |
| CN | 102041241 | 5/2011 |
| CN | 102417882 | 4/2012 |
| CN | 102690808 A | 9/2012 |
| CN | 1552846 A | 12/2013 |
| CN | 104136599 A | 11/2014 |
| CN | 104204211 | 12/2014 |
| EP | 0256889 B1 | 2/1988 |
| EP | 292984 | 11/1988 |
| EP | 339830 B1 | 11/1989 |
| EP | 1535913 B1 | 6/2005 |
| EP | 2186890 A1 | 5/2010 |
| EP | 3322679 A1 | 5/2018 |
| FR | 2910230 A1 | 6/2008 |
| JP | S63-501924 A | 8/1988 |
| JP | H01-225483 A | 9/1989 |
| JP | H02-131581 A | 5/1990 |
| JP | 2009-232721 | 10/2009 |
| JP | 2014096996 A | 5/2014 |
| JP | 2015-037385 A | 2/2015 |
| JP | 2015042633 | 3/2015 |
| JP | 2015-113274 A | 6/2015 |
| JP | 2015-518023 A | 6/2015 |
| JP | 2015-519352 A | 7/2015 |
| WO | WO 1987/004182 A1 | 7/1987 |
| WO | WO 1993/005154 A1 | 3/1993 |
| WO | WO 1998/010088 A1 | 3/1998 |
| WO | WO 1999/009834 A2 | 3/1999 |
| WO | WO 2000/057183 A1 | 9/2000 |
| WO | WO 2001/007567 A1 | 2/2001 |
| WO | WO 2004/074462 A2 | 9/2004 |
| WO | WO 2005/021585 A2 | 3/2005 |
| WO | WO 2005/038032 A1 | 4/2005 |
| WO | WO 2006/005100 A1 | 1/2006 |
| WO | WO 2006/083891 A2 | 8/2006 |
| WO | WO 2006/098225 | 9/2006 |
| WO | WO 2006/119457 A2 | 11/2006 |
| WO | WO 2007/027776 A1 | 3/2007 |
| WO | WO 2009/060012 A2 | 5/2009 |
| WO | WO 2009/091557 A1 | 7/2009 |
| WO | WO 2010/080184 | 7/2010 |
| WO | WO 2011/099019 A1 | 8/2011 |
| WO | WO 2011/099024 A1 | 8/2011 |
| WO | WO 2011/103247 A2 | 8/2011 |
| WO | WO 2011/103248 A2 | 8/2011 |
| WO | WO 2011/154960 A1 | 12/2011 |
| WO | WO 2012/139004 A1 | 10/2012 |
| WO | WO 2012/154651 | 11/2012 |
| WO | WO 2012/174271 A2 | 12/2012 |
| WO | WO 2013/076687 A2 | 5/2013 |
| WO | WO 2013/132518 | 9/2013 |
| WO | WO 2014/042517 A2 | 3/2014 |
| WO | WO 2014/071182 A1 | 5/2014 |
| WO | WO 2014/201044 A2 | 12/2014 |
| WO | WO 2016/016629 A1 | 2/2016 |
| WO | WO 2016/016630 A1 | 2/2016 |
| WO | WO 2016/100727 A1 | 6/2016 |
| WO | WO 2016/146955 A1 | 9/2016 |
| WO | WO 2016/178580 A2 | 11/2016 |
| WO | WO 2016/179046 A1 | 11/2016 |
| WO | WO 2016/181228 A2 | 11/2016 |
| WO | WO 2016/191828 A1 | 12/2016 |
| WO | WO 2017/011602 A1 | 1/2017 |
| WO | WO 2017/042833 A1 | 3/2017 |
| WO | WO 2017/062412 A1 | 4/2017 |
| WO | WO 2017/069717 A1 | 4/2017 |
| WO | WO2017062412 * | 4/2017 |
| WO | WO 2017/085235 A1 | 5/2017 |
| WO | WO 2017/112827 | 6/2017 |
| WO | WO 2017/203440 A1 | 11/2017 |
| WO | WO 2018/081543 | 5/2018 |
| WO | WO 2018/132774 A1 | 7/2018 |
| WO | WO 2018/133774 A1 | 7/2018 |
| WO | WO 2019/032926 A1 | 2/2019 |
| WO | WO 2019/084342 A1 | 5/2019 |
| WO | WO 2019/140125 A1 | 7/2019 |
| WO | WO 2020/006064 A2 | 1/2020 |
| WO | WO 2020/006246 A1 | 1/2020 |
| WO | WO 2020/014498 A1 | 1/2020 |
| WO | WO 2020/023630 A1 | 1/2020 |
| WO | WO 2020/061363 A1 | 3/2020 |
| WO | WO 2020/092940 A1 | 5/2020 |
| WO | WO 2020/118111 A1 | 6/2020 |
| WO | WO 2020/146372 A1 | 7/2020 |
| WO | WO 2020/163251 A1 | 8/2020 |
| WO | WO 2020/190363 A1 | 9/2020 |
| WO | WO 2020/191201 A1 | 9/2020 |
| WO | WO 2020/219893 A1 | 10/2020 |
| WO | WO 2020/219932 A1 | 10/2020 |
| WO | WO 2021/113352 A1 | 6/2021 |
| WO | WO 2021/146209 A1 | 7/2021 |

OTHER PUBLICATIONS

Temme, et al. (Proceedings of the National Academy of Sciences 109.18 (2012): 7085-7090). (Year: 2012).*
Lowman et al. (Plant and soil 405 (2016): 47-63). (Year: 2016).*
Bennet et al. "Engineering nitrogenases for synthetic nitrogen fixation: From pathway engineering to directed evolution." BioDesign Research 5 (2023): 0005. (Year: 2023).*
International Search Report and Written Opinion for PCT/US2020/014083, mailed on Jul. 20, 2020.
Invitation to Pay Additional Fees for PCT/US2020/014083, mailed May 28, 2020.
Fox et al., Major cereal crops benefit from biological nitrogen fixation when inoculated with the nitrogen-fixing bacterium Pseudomonas protegens Pf-5 X940. Environ Microbiol. Oct. 2016;18(10):3522-3534. doi: 10.1111/1462-2920.13376. Epub Jun. 27, 2016. PMID: 27198923.
Lowman et al., Strategies for enhancement of switchgrass (*Panicum virgatum* L.) performance under limited nitrogen supply based on utilization of N-fixing bacterial endophytes. Plant and soil. 2016;405, No. 1-2:47-63. doi: 10.1007/s11104-015-2640-0.
Ryu et al., Control of nitrogen fixation in bacteria that associate with cereals. Nat Microbiol. Feb. 2020;5(2):314-330. doi: 10.1038/s41564-019-0631-2. Epub Dec. 16, 2019. PMID: 31844298.
Setten et al., Engineering Pseudomonas protegens Pf-5 for nitrogen fixation and its application to improve plant growth under nitrogen-deficient conditions. PLoS One. May 13, 2013;8(5):e63666. doi: 10.1371/journal.pone.0063666. Erratum in: PLoS One. 2013;8(10). doi: 10.1371/annotation/279fe0d7-d9b1-4d05-a45a-5ff00b4606b7. PMID: 23675499; PMCID: PMC3652814.
Temme et al., Refactoring the nitrogen fixation gene cluster from Klebsiella oxytoca. Proc Natl Acad Sci U S A. May 1, 2012;109(18):7085-90. doi: 10.1073/pnas.1120788109. Epub Apr. 16, 2012. PMID: 22509035; PMCID: PMC3345007.
Yu et al., Recombineering Pseudomonas protegens CHA0: An innovative approach that improves nitrogen fixation with impressive bactericidal potency. Microbiol Res. Jan. 2019;218:58-65. doi: 10.1016/j.micres.2018.09.009. Epub Oct. 6, 2018. PMID: 30454659.
US 8,476,226, 11/1999, Koenck (withdrawn)
[No Author Listed] cera-gmc.org [online], GM Crop Database. Center for Environmental Risk Assessment (CERA), 2010, retrieved from <http://ucbiotech.org/biotech_info/PDFs/Center_for_Environmental_Risk_Assessment_CERA_2011_GM_Crop_Database.pdf>, 1 page.
[No Author Listed] Emboss. Emboss Needle: Pairwise Sequence Alignment (Nucleotide). Available at URL<http://www.ebi.ac.uk/Tools/psa/emboss_needle/nucleotide.html>, Accessed on Oct. 10, 2016, 1 page.

(56) References Cited

OTHER PUBLICATIONS

[No Author Listed], "T7 RNA Polymerase Expression System for Bacillus megaterium," T7 RNAP Expression System Handbook, Jan. 2010, © MoBiTec GmbH, 18 pages.

[No Author Listed], 40 CFR 725.3 U.S. Government Publishing Office (Jul. 1, 2010) https://www.gpo.gov/fdsys/pkg/CFR-2010-title40-vol30/pdf/CFR-2010-title40-vol30-sec725-3.pdf (Year: 2010), 3 pages.

Aita et al., Adaptive Walks by the Fittest among Finite Random Mutants on a Mt. Fuji-type Fitness Landscape. J Theor Biol. Aug. 7, 1998;193(3):383-405. doi: 10.1006/jtbi.1998.0709.

Alper et al., Tuning genetic control through promoter engineering. Proc Natl Acad Sci U S A. Sep. 6, 2005;102(36):12678-83. Epub Aug. 25, 2005. Erratum in: Proc Natl Acad Sci U S A. Feb. 21, 2006;103(8):3006.

Altschul et al. Basic local alignment search tool. J Mol Biol 215(3):403-410 (1990).

Altschul et al., "BLAST. Basic local alignment search tool," 2021, retrieved on Apr. 8, 2021, retrieved from URL<https://blast.ncbi.nlm.nih.gov/Blast.cgi>, 3 pages.

Altschul et al., "Gapped BLAST and PSI-BLAST: a new generation of protein database search programs," Nucleic Acids Res., 1997, 25:3389-3402.

Amalraj et al., Effect of Polymeric Additives, Adjuvants, Surfactants on Survival, Stability and Plant Growth Promoting Ability of Liquid Bioinoculants. J. Plant Physiol Pathol, 2013, 1:2, 6 pages.

Ambrosio et al., "Metabolic engineering of a diazotrophic bacterium improves ammonium release and biofertilization of plants and microalgae," Metab Eng., Mar. 2017, 40:59-68.

An et al., "Constitutive expression of the nifA gene activates associative nitrogen fixation of Enterobacter gergoviae 57-7, an opportunistic endophytic diazotroph," Journal of Applied Microbiology, 2007, 103(3):613-620.

Andersen et al., "Energetics of biological nitrogen fixation: determination of the ratio of formation of H2 to NH4+ catalysed by nitrogenase of Klebsiella pneumoniae in vivo," J Gen Microbial., Nov. 1977, 103(1):107-22.

Andersen et al., "Herpesvirus-mediated gene delivery into the rat brain: specificity and efficiency of the neuron-specific enolase promoter," Cell. Mol. Neurobiol., 1993, 13:503-515.

Anderson et al., "BglBricks: A flexible standard for biological part assembly," Journal of Biological Engineering, 2010, 4:1, 12 pages.

Andrews et al., "Use of Nitrogen Fixing Bacteria Inoculants as a Substitute for Nitrogen Fertiliser for Dryland Graminaceous Crops: Progress Made, Mechanisms of Action and Future Potential," Symbiosis, 2003, 34:21 pages.

Andrianantoandro et al., Synthetic biology: new engineering rules for an emerging discipline. Mol Syst Biol. 2006;2:2006.0028. doi: 10.1038/msb4100073. Epub May 16, 2006.

Arbuthnot et al., In vitro and in vivo hepatoma cell-specific expression of a gene transferred with an adenoviral vector. Hum Gene Ther. Aug. 20, 1996;7(13): 1503-14. doi: 10.1089/hum.1996.7.13-1503.

Arnold et al., Nucleotide sequence of a 24,206-base-pair DNA fragment carrying the entire nitrogen fixation gene cluster of Klebsiella pneumoniae. J Mol Biol. Oct. 5, 1988;203(3):715-38. doi: 10.1016/0022-2836(88)90205-7.

Arriel-Elias et al., Shelf life enhancement of plant growth promoting rhizobacteria using a simple formulation screening method. African J Microbiology Research, Feb. 2018, 12(5):115-126.

Arsene et al., "Modulation of NifA activity by PII in Azospirillum brasilense: Evidence for a Regulatory role of the NifA N-Terminal Domain," Journal of Bacteriology, Aug. 1996, 178(16):4830-4838.

Austin et al. "Characterisation of the Klebsiella pneumoniae nitrogen-fixation regulatory proteins NIFA and NIFL in vitro," Eur J Biochem., 1990, 187(2):353-360.

Ausubel et al., "Glutamine Synthetase Mutations Which Affect Expression of Nitrogen Fixation Genes in Klebsiella pneumoniae," J Bacteriol, Nov. 1979, 140(2):597-606.

Bageshwar et al., "An Environmentally Friendly Engineered Azotobacter Strain That Replaces a Substantial Amount of Urea Fertilizer while Sustaining the Same Wheat Yield," Appl Environ Microbial., Aug. 2017, 83(15):e00590-17.

Bali et al., "Excretion of Ammonium by a nifL Mutant of Azotobacter vinelandii fixing Nitrogen," Applied and Environmental Microbiology, May 1992, 58(5):1711-1718.

Barney et al., "Transcriptional analysis of an Ammonium-excreting stain of azotobacter vinelandii deregulated for nitrogen fixation," Appl. Environ. Microbial. Jul. 2017, 83(20):1-22.

Barney et al., Gene deletions resulting in increased nitrogen release by azotobacter vinelandii: application of a novel nitrogen biosensor. Appl. Environ. Microbiol. 2015; 81(13):4316-4328. Published online Apr. 17, 2015.

Barrango et al., "Exploiting CRISPR-Cas immune systems for genome editing in bacteria," Curr. Opin. Biotechnol., Nov. 2016, 37:61-68.

Batista et al., Manipulating nitrogen regulation in diazotrophic bacteria for agronomic benefit. Biochem Soc Trans. Apr. 1, 2019;47(2):603-14.

Batzer et al., Enhanced evolutionary PCR using oligonucleotides with inosine at the 3'- terminus. Nucleic Acids Res. Sep. 25, 1991;19(18):5081. doi: 10.1093/nar/19.18.5081.

Baum et al., "Control of coleopteran insect pests through RNA interference," Nature Biotechnology, Nov. 2007, 25(11):1322-1326.

Bayer et al., Synthesis of methyl halides from biomass using engineered microbes. J Am Chem Soc. May 13, 2009;131(18):6508-15. doi: 10.1021/ja809461u.

Bender et al., "Regulatory mutations in the Klebsiella aerogenes structural gene for glutamine synthetase," J Bacteriol., Oct. 1977, 132(1):100-105.

Benyon et al., The nif promoters of Klebsiella pneumoniae have a characteristic primary structure. Cell. Sep. 1983;34(2):665-71. doi: 10.1016/0092-8674(83)90399-9.

Beringer et al., "Genetic engineering and nitrogen fixation," Biotech. Gen. Eng. Rev., Feb. 1984, 1(1):65-88.

Beringer et al., Maintenance and assessment of cell viability in formulation of non-sporulating bacterial inoculants. Microb. Biotechnol., Mar. 2018, 11(2):277-301 (2018); doi: 10.1111/1751-7915.12880.

Biggins et al., Metabolites from the induced expression of cryptic single operons found in the genome of Burkholderia pseudomallei. J Am Chem Soc. Feb. 16, 2011;133(6):1638-41. doi: 10.1021/ja1087369. Epub Jan. 19, 2011.

Bikard et al., The synthetic integron: an in vivo genetic shuffling device. Nucleic Acids Res. Aug. 2010;38(15):e153. doi:10.1093/nar/gkq511. Epub Jun. 9, 2010.

Bilitchenko et al., Eugene-a domain specific language for specifying and constraining synthetic biological parts, devices, and systems. PLoS One. Apr. 29, 2011;6(4):e18882. doi: 10.1371/journal.pone.0018882. 12 pages.

Bittner et al., "RpoS and RpoN are involved in the growth-dependent regulation of rfaH transcription and O antigen expression in *Salmonella enterica* serovar typhi." Microbial Pathogenesis, Jan. 2004, 36(1): 19-24.

Blanco et al., "Sequence and molecular analysis of the nifL gene of Azotobacter vine landii." Mol Microbial. Aug. 1993, 9(4):869-79.

Bloch et al., Biological nitrogen fixation in maize: optimizing nitrogenase expression in a rootassociated diazotroph. J Experimental Botany, Jul. 2020, 71(15):4591-4603.

Bonde et al., MODEST: a web-based design tool for oligonucleotide-mediated genome engineering and recombineering. Nucleic Acids Res. Jul. 2014;42(Web Server issue):W408-15. doi: 10.1093/nar/gku428. Epub May 16, 2014.

Boshart et al., A very strong enhancer is located upstream of an immediate early gene of human cytomegalovirus. Cell. Jun. 1985;41(2):521-30. doi: 10.1016/s0092-8674(85)80025-8.

Bosmans et al., "Sea anemone venom as a source of insecticidal peptides acting on voltage-gated Na+ channels," Toxicon, Mar. 2007, 49(4):550-560.

Bosworth, et al. Alfalfa yield response to inoculation with recombinant strains of Rhizobium meliloti with an extra copy of dctABD and/or modified nifA expression. Appl Environ Microbiol. Oct. 1994;60(10):3815-32.

(56) References Cited

OTHER PUBLICATIONS

Boyle et al., Tools for genome-wide strain design and construction. Curr Opin Biotechnol. Oct. 2012;23(5):666-71.
Brandl et al., *Salmonella* interactions with plants and their associated microbiota. Phytopathology. Apr. 2013;103(4):316-25. doi: 10.1094/PHYTO-11-12-0295-RVW.
Brewin et al., "The Basis of Ammonium release in nifL Mutants of Azotobacter vinelandii," Journal of Bacteriology, Dec. 1999, 181(23):7356-7362.
Buchanan-Wollaston et al., "Role of the nifA gene product in the regulation of nif expression in Klebsiella pneumoniae," Nature., Dec. 1981, 294(5843):776-8.
Buck et al., Frameshifts close to the Klebsiella pneumoniae nifH promoter prevent multicopy inhibition by hybrid nifH plasmids. Mol Gen Genet. May 1987;207(2-3):492-8. doi: 10.1007/BF00331620.
Buckley et al., NifH Sequence Database. Retrieved from <https://blogs.cornell.edu/buckley/nifh-sequence-database/>. Buckley Lab. Available on or before Jan. 10, 2018. 2 pages.
Buddrus-Schiemann et al., "Root colonization by *Pseudomonas* sp. DSMZ 13134 and impact on the indigenous rhizosphere bacterial community of barley." Microb Ecol. Aug. 2010, 60(2):381-393.
Burris, Nitrogenases. J Biol Chem. May 25, 1991;266(15):9339-42.
Cardinale, S., & Arkin, A.P. Contextualizing context for synthetic biology identifying causes of failure of synthetic biological systems. Biotechnol. J. 7:856-866 (2012).
Carr et al., "Enhanced multiplex genome engineering through co-operative oligonucleotide coselection," Nucleic Acids Res., 2012, 40(17):e132.
Chakroun et al., "Bacterial Vegetative Insecticidal Proteins (Vip) from Entomopathogenic Bacteria," Microbiol Mol Biol Rev., Mar. 2016, 80(2):329-50.
Chan et al., "Refactoring bacteriophage T7," Molecular Systems Biology, 2005, 1(1):E1-E10.
Chen et al., "Characterization of 582 natural and synthetic terminators and quantification of their design constraints," Nat. Methods, 2013, 10:659-664.
Chen et al., "Complete genome sequence of Kosakonia sacchari type strain SP1 T," Stand Genomic Sci., Jun. 15, 2014, 9(3):1311-1318.
Chen et al., "Expression of rat bone sialoprotein promoter in transgenic mice," J Bone Miner Res., May 1996, 11(5):654-64.
Chiang et al., "Mutagenic Oligonucleotide-directed PCR Amplification (Mod-PCR): An Efficient Method for Generating Random Base Substitution Mutations in a DNA sequence element," PCR methods and applications, 1993, 2:210-217.
Chin JW "Programming and engineering biological networks," Curr Opin Struct Biol 16: 551-556 (2006).
Choi et al., "A Tn7-based broad-range bacterial cloning and expression system," Nat Methods, Jun. 2005, 2(6):443-8.
Choudhary et al., "Interactions of *Bacillus* spp. and Plants—With Special Reference to Induced Systemic Resistance (ISR)," Microbiological Research, 2009, 164(5):493-513.
Clancy et al., "The domains carrying the opposing activities in adenylyltransferase are separated by a central regulatory domain," FEBS Journal, 2007, 274(11):2865-2877.
Cobb et al., Directed evolution: an evolving and enabling synthetic biology tool. Curr Opin Chem Biol. Aug. 2012;16(3-4):285-91. doi:10.1016/j.cbpa.2012.05.186. Epub Jun. 4, 2012.
Cohen, "In vitro Tomato Fruit Cultures Demonstrate a Role for Indole-3-acetic Acid in Regulating Fruit Ripening," J. Amer. Soc. Hort. Sci., 1996, 121(3):520-524.
Colby, Calculating Synergistic and Antagonistic Responses of Herbicide Combinations. Weeds, Jan. 1967, 15(1):20-22, 4 pages.
Colebatch et al., "Symbiotic nitrogen fixation research in the postgenomics era," New Phytologist., 2002, 153(1):37-42.
Colnaghi et al., "Lethality of glnD null mutations in Azotobacter vinelandii is suppressible by prevention of glutamine synthetase adenylylation," Microbiology, May 2001, 147(Pt 5):1267-76.
Colnaghi et al., "Strategies for increased ammonium production in free-living or plant associated nitrogen fixing bacteria," Plant and Soil, Nov. 1997, 194:145-154.
Compant et al., "A review on the plant microbiome: Ecology, functions, and emerging trends in microbial application," Journal of Advanced Research, Sep. 2019, 19:29-37.
Conniff, "Microbes Help Grow Better Crops," (Sep. 1, 2013) Scientific American. Retrieved from URL <https://www.scientificamerican.com/article/microbes-helpgrow-better-crops/>, (Year: 2013), 7 pages.
Contreras et al., "The product of the nitrogen fixation regulatory gene nfrX of Azotobacter vinelandii is functionally and structurally homologous to the uridylyltransferase encoded by glnD in enteric bacteria." J Bacteriol. Dec. 1991, 173(24):7741-7749.
Cornelis, The type III secretion injectisome. Nat Rev Microbiol. Nov. 2006;4(11):811-25. doi: 10.1038/nrmicro1526.
Costerton et al., Microbial Biofilms. Annu. Rev. Microbial., Oct. 1995, 49:711-745.
Crameri et al., "Molecular evolution of an arsenate detoxification pathway by DNA shuffling," Nat. Biotechnol., 1997, 15:436-438.
Crickmore et al., "Revision of the Nomenclature for the Bacillus thuringiensis Pesticidal Crystal Proteins," Microbiol Mol Biol Rev., Sep. 1998, 62(3):807-813.
Crook et al., "Re-engineering multicloning sites for function and convenience," Nucl. Acids Res., 2011, 39:e92, 10 pages.
Curatti et al., "Genes required for rapid expression of nitrogenase activity in Azotobacter vinelandii," PNAS, May 2005, 102(18):6291-6296.
Czar et al., "Gene synthesis demystified," Trends Biotechnol, 2009, 27(2):63-72.
Da Silva et al., Survival of endophytic bacteria in polymer-based inoculants and efficiency of their aplication to sugarcane/Plant Soil, May 2012, 356:231-243.
Dandekar et al., "Conservation of gene order: a fingerprint of proteins that physically interact," Trends Biochem. Sci., 1998, 23:324-328.
Das et al., "Microbial assay of N2 fixation rate, a simple alternate for acetylene reduction assay," MethodsX, 2018, 5:909-914.
Datsenko et al., "One-step inactivation of chromosomal genes in *Escherichia coli* K-12 using PCR products," PNAS, Jun. 2000, 97(12):6640-6645.
Davin-Regli et al., "Enterobacter aerogenes and Enterobacter cloacae; versatile bacterial pathogens confronting antibiotic treatment," Front Microbiol, 2015, 6:392, 10 pages.
De Bruijn et al., "The Cloning and characterization of the glnF (ntrA) Gene of Klebsiella pneumoniae: Role of glnF (ntrA) in the Regulation of Nitrogen Fixation (nif) and other Nitrogen assimilation genes," Mol. Genet., Aug. 1983, 192:342-353.
De Freitas, "Yield and N assimilation of winter wheat (*Triticum aestivum* L., var. Norstar) inoculated with rhizobacteria," Pedobiologia, Jan. 2000, 44(2):97-104.
De Raad et al., "A solid-phase platform for combinatorial and scarless multipart gene assembly," ACS Synth. Biol., 2013, 2:316-326.
Delaux et al., Tracing the evolutionary path to nitrogen-fixing crops. Curr Opin Plant Biol. 2015;26:95-9.
Dent et al., Establishing symbiotic nitrogen fixation in cereals and other non-legume crops: The greener nitrogen revolution. Agric & Food Secur. 2017;6(7):1-9.
Desnoues et al., "Nitrogen fixation genetics and regulation in a Pseudomonas stutzeri strain associated with rice," Microbiology, May 2003, 149:2251-2262.
Dixon et al., "Genetic regulation of biological nitrogen fixation," Nature Reviews, Aug. 2004, 2:621-631.
Dixon et al., "Genetic transfer of nitrogen fixation from Klebsiella pneumoniae to *Escherichia coli*," Nature, 1972, 237(5350): 102-103.
Dong et al., "Kinetics and Strain Specificity of Rhizosphere and Endophytic Colonization by Enteric Bacteria on Seedlings of Medicago sativa and Medicago truncatula," Appl Environ Microbial., Mar. 2003, 69(3):1783-1790.

(56) References Cited

OTHER PUBLICATIONS

Dos Santos et al., "Distribution of nitrogen fixation and nitrogenase-like sequences amongst microbial genomes," BMC Genomics, Dec. 2012, 13(1):162, 12 pages.
Du et al., "Customized optimization of metabolic pathways by combinatorial transcriptional engineering," Nucleic Acids Res., Oct. 2012, 40(18):e142, 10 pages.
Dunican et al., Genetic transfer of nitrogen fixation from Rhizobium trifolii to Klebsiella aerogenes. Biochem Biophys Res Commun. Mar. 15, 1974;57(1):62-72.
Dykxhoorn et al., "A set of compatible tac promoter expression vectors," Gene, 1996, 177(1-2):133-136.
Easter et al., "Role of the parCBA Operon of the Broad-Host-Range Plasmid RK2 in Stable Plasmid Maintenance," Journal Of Bacteriology, 1998, 180(22):6023-6030.
Egener et al., "Identification of NifL-like protein in a diazotroph of the b-subgroup of the proteobacteria, azoarcus sp. strain BH72," Microbiology, Oct. 2002, 148(10):3203-3212.
Endy et al., "Foundations for engineering biology," Nature, 2005, 438:449-453.
Engler, et al. A one pot, one step, precision cloning method with high throughput capability. PLoS One. 2008;3(11):e3647. doi: 10.1371/journal.pone.0003647. Epub Nov. 5, 2008. 7 pages.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009. 9 pages.
Enkh-Amgalan et al., "Molecular evolution of the nif gene cluster carrying nifl1 and nifl2 genes in the Gram-positive phototrophic bacterium Heliobacterium chlorum," International Journal of Systematic and Evolutionary Microbiology, 2006, 56:65-74.
Estrem et al., "Identification of an UP element consensus sequence for bacterial promoters," PNAS, 1998, 95(11):9761-9766.
Eyraud et al., "Expression and Biological Activity of the Cystine Knot Bioinsecticide PA1b (Pea Albumin 1 Subunit b)," PLOS One, Dec. 2013, 8(12):e81619, 9 pages.
Fani et al., "Molecular evolution of nitrogen fixation: the evolutionary history of the niID, nifK, nifE, and nifN gene," J Mol Evol., 2000, 51(1):1-11.
Feher et al. "In the fast lane: large-scale bacterial genome engineering," J Biotechnol., Jul. 2012, 160(1-2):72-9.
Ferrières et al., "The yjbEFGH locus in *Escherichia coli* K-12 is an operon encoding proteins involved in exopolysaccharide production," Microbiology, Apr. 2007, 153(Pt 4):1070-80.
Fischbach et al., "The evolution of gene collectives: how natural selection drives chemical innovation," Proc. Natl. Acad. Sci. USA, 2008, 105:4601-4608.
Fischbach et al., Prokaryotic gene clusters: A rich toolbox for synthetic biology. Biotechnol J. 2010;15(12):1277-96.
Fontana et al., "RNA folding and combinatory landscapes," Phys. Rev. E., 1993, 47:2083-2099.
Forner et al., "Treatment of hepatocellular carcinoma," Crit Rev Oncol Hematol., Nov. 2006, 60(2):89-98.
Fox et al., Major cereal crops benefit from biological nitrogen fixation when inoculated with the nitrogen-fixing bacterium Pseudomonas protegens Pf-5 X940. Environ Microbiol. 2016;18(10):3522-34.
Frasch et al., Design-based re-engineering of biosynthetic gene clusters: plug-and-play in practice. Curr Opin Biotechnol. Dec. 2013;24(6):1144-50. doi: 10.1016/j.copbio.2013.03.006. Epub Mar. 27, 2013.
Gaby et al., "A comprehensive aligned nifH gene database: a multipurpose tool for studies of nitrogen-fixing bacteria," Database, 2014, 2014:bau001, 8 pages.
Gamer et al., "A T7 RNA polymerase-dependent gene expression system for Bacillus megaterium," Appl Micro Biol Biotechnol., Apr. 2009, 82(6):1195-203.
Gebeyehu et al., "Novel biotinylated nucleotide-analogs for labeling and colorimetric detection of DNA," Nucl. Acids Res., 1987, 15:4513, 22 pages.

Geddes et al., Use of plant colonizing bacteria as chassis for transfer of N2-fixation to cereals. Curr Opin Biotechnol. 2015;32:216-22.
GenBank Accession No. CP007215.3, "Kosakonia sacchari SP1 chromosome, complete genome," Sep. 19, 2017, 729 pages.
Georg et al., "cis-antisense RNA, another level of gene regulation in bacteria," Microbiol Mol Biol Rev, 2011, 75(2):286-300.
Gibson et al., "Chemical synthesis of the mouse mitochondrial genome," Nat. Methods, 2010, 7:901-903.
Gibson et al., "Enzymatic assembly of DNA molecules up to several hundred kilobases," Nat Methods, 2009, 6(5):343-345.
Gibson, "Physical Environment and Symbiotic Nitrogen Fixation," Australian Journal of Biological Sciences, 1963, 16(1):28-42.
Gosink et al., "The product of the Klebsiella pneumoniae nifX gene is a negative regulator of the nitrogen fixation (nit) regulon," J Bacteriology, 1990, 172(3):1441-1447.
Gossen et al., "Tight control of gene expression in mammalian cells by tetracycline-responsive promoters," PNAS USA, 1992, 89(12):5547-5551.
Gossen et al., "Transcriptional activation by tetracyclines in mammalian cells," Science, 1995, 268(5218):1766-1769.
Gottelt et al., "Deletion of a regulatory gene within the cpk gene cluster reveals novel antibacterial activity in Streptomyces coelicolor A3(2)," Microbiology, 2010, 156:2343-2353.
Govantes et al., "Mechanism of coordinated synthesis of the antagonistic regulatory proteins NifL and NifA of Klebsiella pneumoniae," J Bacteriol. Dec. 1996, 178(23):6817-6823.
Guell et al., "Bacterial transcriptomics: what is beyond the RNA horiz-ome?," Nature reviews Microbiology, 2011, 9(9):658-669.
Guell et al., "Transcriptome complexity in a genome-reduced bacterium," Science, 2009, 326:1268-1271.
Guo et al., "Discovery of Reactive Microbiota-Derived Metabolites that Inhibit Host Proteases," Cell, Jan. 2017, 168(3):517-526, e18.
Haapalainen et al., "Soluble plant cell signals induce the expression of the type Ill secretion system of Pseudomonas syringae and upregulate the production of pilus protein HrpA," Mol. Plant Microbe Interact., 2009, 22:282-290.
Hale et al., "An efficient stress-free strategy to displace stable bacterial plasmids," BioTechniques, Mar. 2010, 48:223-228.
Hansal et al., "Cutting Edge: Induction of antigen-specific hyporesponsiveness by transplantation of hemopoietic cells containing an MHC class I transgene regulated by a lymphocyte-specific promoter," J Immunol., Aug. 1998, 161(3):1063-8.
Harvey et al., "Inducible control of gene expression: prospects for gene therapy," Curr Opin Chem Biol., Aug. 1998, 2(4):512-8.
Herlache et al., "Characterization of the Agrobacterium vitis pehA gene and comparison of the encoded polygalacturonase with the homologous enzymes from Erwinia carotovora and Ralstonia solanacearum," Appl Environ Microbial., Jan. 1997, 63(1):338-346.
Hernandez et al., "Biochemical analysis of the recombinant Fur (ferric uptake regulator) protein from Anabaena PCC 7119: factors affecting its oligomerization state," Biochem J., 2002, 366:315-322.
Hidaka et al., Promotion of the Growth of Rice by Inoculation of Nitrogen-Fixing-Activity-Enhanced Bacteria to the Rhizosphere. Curr Plant Sci Biotechnol Agri. 1999;38:445.
Hoeschle-Zeledon et al., Regulatory challenges for biological control. The CGIAR Systemwide Program on Integrated Pest Management, Jan. 2013, SP-IPM Secretariat, International Institute Tropical Agriculture (IITA), Ibadan, Nigeria, 56 pages.
Holden et al., "Colonization outwith the colon: plants as an alternative environmental reservoir for human pathogenic enterobacteria," FEMS Microbiol. Rev., 2009, 33:689-703.
Hu et al., "Assembly of nitrogenase MoFe protein," Biochemistry, 2008, 47(13):3973-3981.
Hunter, "'Genetically Modified Lite' placates public but not activists," EMBO Reports, Jan. 2014, 15(2):138-141.
Huynen et al., "Smoothness within ruggedness: the role of neutrality in adaptation," Proc. Natl. Acad. Sci. USA, 1996, 93:397-401.
Iber, "A quantitative study of the benefits of co-regulation using the spoIIA operon as an example," Mol. Sys. Biol., 2006, 2:1-6.
Idalia et al., "*Escherichia coli* as a model organism and its application in biotechnology," Recent Advances on Physiology, Pathogenesis, and Biotechnological Applications, Chapter 13, 2017, pp. 253-274.

(56) References Cited

OTHER PUBLICATIONS

Iniguez et al., Nitrogen Fixation in Wheat Provided by Klebsiella pneumoniae 342. MPMI. 2004;17(10):1078-85.

Ishihama, "Prokaryotic genome regulation: multifactor promoters, multitarget regulators and hierarchic networks," FEMS Microbial Rev, 2010, 34(5):628-645.

Ivanova et al., "Artificial Regulation of Genes, Of the coding proteins of the nitrogenase complex Rhizobial bacteria," Natural Sciences, 2014, 13(174):36-39 (Machine Translation).

Izquierdo et al., "Distribution of Extensive nifH Gene Diversity Across Physical Soil Microenvironments," Microbial Ecology, 2006, 51(4):441-452.

Jacob et al., "Solid-state NMR studies of Klebsiella pneumoniae grown under nitrogen-fixing conditions," J Biol Chem, 1987, 262(1):254-259.

Jacoby et al., "The Role of Soil Microorganisms in Plant Mineral Nutrition-Current Knowledge and Future Directions," Frontiers in Plant Scients, 2017, 8(19):1-19.

Jahn et al., Extraction of Extracellular Polymeric Substances (EPS) from Biofilms Using a Cation Exchange Resin. Wat. Sci. Tech., 1995, 32(8):157-164.

Janczarek et al., "Multiple copies of rosR and pssA genes enhance exopolysaccharide production, symbiotic competitiveness and clover nodulation in Rhizobium leguminosarum bv. *trifolii*," Antonie Van Leeuwenhoek, Nov. 2009, 96(4):471-86.

Jashke et al., "A fully decompressed synthetic bacteriophage 0X174 genome assembled and archived in yeast," Virology, 2012, 434:278-284.

Jensen, "The *Escherichia coli* K-12 "wild types" W3110 and MG1655 have an rph frameshift mutation that leads to pyrimidine starvation due to low pyre expression levels," J. Bacteriol., 1993, 175:3401-3407.

Johnson et al., "Properties of overlapping genes are conserved across microbial genomes," Genome Res, 2004, 14(11):2268-2272.

Joseph et al., "Recent developments of the synthetic biology toolkit for Clostridum," Frontiers in microbology, 2018, 9(154):1-13.

Kabaluk et al., The use and regulation of microbial pesticides in representative jurisdictions Worldwide. IOBC Global, 2010, 99 pages.

Kalir et al., "Ordering genes in a flagella pathway by analysis of expression kinetics from living bacteria," Science, 2001, 292(5524):2080-2083.

Kaneko et al., "Complete genomic structure of the cultivated rice endophyte *Azospirillum* sp. B510," DNA Res., 2010, 17:37-50.

Kant et al., "Understanding plant response to nitrogen limitation for the improvement of crop nitrogen use efficiency," Journal of Experimental Botany, 2011, 62(4):1499-1509.

Karlin et al., "Applications and statistics for multiple high-scoring segments in molecular sequences," Proc Natl Acad Sci USA, Jun. 1993, 90(12):5873-7.

Karlin et al., "Methods for assessing the statistical significance of molecular sequence features by using general scoring schemes," Proc Natl Acad Sci USA, Mar. 1990, 87(6):2264-8.

Katsnelson, "Engineered bacteria could boost corn yields: Gene-edited microbe offer continuous nitrogen fixation," Chemical & Engineering News, Dec. 28, 2021, retrieved from URL https://cen.acs.org/food/agriculture/Engineered-bacteria-boost-corn-yields/99/web/2021/12>, 3 pages.

Kececiglu et al., "Of mice and men: Algorithms for evolutionary distances between genomes with translocation," SODA: Proceedings of the sixth annual ACM-SIAM symposium on Discrete algorithms, 1995, 10 pages.

Kelly et al., "Measuring the activity of BioBrick promoters using an in vivo reference standard," J Biol Eng, 2009, 3:4, 13 pages.

Kent et al., A transposable partitioning locus used to stabilize plasmid-borne hydrogen oxidation and trifolitoxin production genes in a sinorhizobium strain. Appl Environ Microbiol. May 1998;64(5):1657-62.

Kerby et al., "Photoproduction of ammonium by immobilized mutant strains of Anabaena variabilis," Applied Microbiology and Biotechnology, Apr. 1986, 24(1):42-46.

Kim et al., "A 20 nucleotide upstream element is essential for the nopaline synthase (nos) promoter activity," Plant Mol Biol., Jan. 1994, 24(1):105-17.

Kim et al., "Constitutive expression of nitrogenase system in Klebsiella oxytoca by gene targeting mutation to the chromosomal nifLA operon," Journal of Biotechnology, Jun. 1989, 10(3-4):293-301.

King et al., "Spider-Venom Peptides: Structure, Pharmacology, and Potential for Control of Insect Pests," Annu. Rev. Entomol., 2013, 58:475-96.

Kingsford et al., "Rapid, accurate, computational discovery of Rho-independent transcription terminators illuminates their relationship to DNA uptake," Genome Bio. 2007, 8(2):R22, 12 pages.

Kitano, "Systems biology: a brief overview," Science, 2002, 295(5560): 1662-1664.

Klose et al., "Glutamate at the site of phosphorylation of nitrogen-regulatory protein NTRC mimics aspartyl-phosphate and activates the protein," J Mol Biol., Jul. 1993, 232(1):67-78.

Knight, "Idempotent Vector Design for Standard Assembly of Biobricks," MIT Artificial Intelligence Laboratory, The TTL Data Book for Design Engineers, 2003, 11 pages.

Kovacs et al., "Stochasticity in protein levels drives colinearity of gene order in metabolic operons of *Escherichia coli*," PLoS Biol, 2009, 7(5):e1000115, 9 pages.

Kranz et al., "Ammonia-constitutive nitrogen fixation mutants of Rhodobacter capsulatus," Gene, Nov. 1988, 71(1):65-74.

Kumar et al., "Metabolic regulation of *Escherichia coli* and its gdhA, glnL, gltB, D mutants under different carbon and nitrogen limitations in the continuous culture," Microbial Cell Factories, Jan. 2010, 9(8):1-17.

Kurzweil, Plant Bacteria breakthrough enables crops worldwide to take nitrogen from the air. Plant Bacteria Breakthrough Enables Crops Worldwide Take Nitrogen From Air. Aug. 1, 2013. 4 pages.

Kutter et al., "Colonization of barley (*Hordeum vulgare*) with *Salmonella enterica* and *Listeria* spp," FEMS Microbial. Ecol., 2006, 56, 262-271.

Lauritsen et al., "A versatile one-step CRISPR-Cas9 based approach to plasmid-curing." Microb Cell Fact, 2017, 16(135):1-10.

Leang et al., Genome-wide analysis of the RpoN regulon in Geobacter sulfurreducens. BMC Genomics. Jul. 22, 2009;10:331. doi: 10.1186/1471-2164-10-331.

Lee et al., The class IId bacteriocin thuricin-17 increases plant growth. Planta. Mar. 2009;229(4):747-55. doi: 10.1007/s00425-008-0870-6. Epub Dec. 13, 2008.

Lenski et al., "Effects of Segregation and Selection on Instability of Plasmid pACYC184 in *Escherichia coli* B," Journal of Bacteriology, Nov. 1987, 169(11):5314-5316.

Levican et al., "Comparative genomic analysis of carbon and nitrogen assimilation mechanisms in three indigenous bioleaching bacteria: predictions and validations," BMC Genomics, 2008, 9:581, 19 pages.

Levin-Karp et al., "Quantifying translational coupling in *E. coli* synthetic operons using RBS modulation and fluorescent reporters," ACS Synth. Biol., 2013, 2:327-336.

Li et al., "Human Enhancers Are Fragile and Prone to Deactivating Mutations," Mol Biol Evol., Aug. 2015, 32(8):2161-80.

Liang et al., "Minimal effect of gene clustering on expression in *Escherichia coli*," Genetics, Feb. 2013, 193(2):453-65.

Lim et al., Fundamental relationship between operon organization and gene expression. PNAS USA. Jun. 28, 2011;108(26):10626-31. doi: 10.1073/pnas.1105692108. Epub Jun. 13, 2011.

Lin et al., "PC, a Novel Oral Insecticidal Toxin from Bacillus bombysepticus Involved in Host Lethality via APN and BtR-175," Scientific Reports, Jun. 2015, 5:11101, 14 pages.

Liu et al., "Phenazine-1-carboxylic acid biosynthesis in Pseudomonas Chlororaphis GP72 is positively regulated by the sigma factor RpoN," World Journal of Microbiology and Biotechnology, Jan. 2008, 24(9):1961-1966.

(56) References Cited

OTHER PUBLICATIONS

Liu et al., "Whole genome analysis of halotolerant and alkalotolerant plant growth-promoting rhizobacterium *Klebsiella* sp. D5A," Sci Rep., May 2016, 6:1-10.
Lombo et al., "The mithramycin gene cluster of Streptomyces argillaceus contains a positive regulatory gene and two repeated DNA sequences that are located at both ends of the cluster," J. Bacterial., 1999, 181:642-647.
Lowman et al., Strategies for enhancement of switchgrass (*Panicum virgatum* L.) performance under limited nitrogen supply based on utilization of N-fixing bacterial endophytes. Plant and Soil, Aug. 2016, 405(1):47-63, 17 pages.
Lucks et al., "Toward scalable parts families for predictable design of biological circuits," Curr. Opin. Microbiol., 2008, 11:567-573.
Ma et al., "Effect of nicotine from tobacco root exudates on chemotaxis, growth, biocontrol efficiency, and colonization byPseudomonas aeruginosaNXHG29," Antonie van Leeuwenhoek, 2018, 111(7):1237-1257.
Mabrouk et al., "Chapter 6: Potential of Rhizobia in Improving Nitrogen Fixation and Yields of Legumes," Symbiosis, May 30, 2018, IntechOpen, pp. 1-16, retrieved on Jan. 12, 2021, retrieved from URL<https://www.intechopen.com/books/symbiosis/potential-of-rhizobia-in-improving- B351nitrogen-fixation-and-yields-of-legumes> 2 pages, Abstract.
MacNeil et al., "Fine-structure mapping and complementation analysis of nif (nitrogen fixation) genes in Klebsiella pneumoniae," J Bacterial. Oct. 1978, 136(1):253-266.
MacNeil et al., "Mutations in nif genes that cause Klebsiella pneumoniae to be derepressed for nitrogenase synthesis in the presence of ammonium," J Bacterial, Nov. 1980, 144(2):744-751.
Magari et al., "Pharmacologic control of a humanized gene therapy system implanted into nude mice," J Clin Invest., Dec. 1997, 100(11):2865-2872.
Magasanik, "Genetic control of nitrogen assimilation in bacteria," Ann. Rev. Genet, 1982, 16:135-68.
Mandal et al., "Gene regulation by riboswitches," Nat Rev Mol Cell Biol, 2004, 5(6):451-463.
Mao et al., Silencing a cotton bollworm P450 monooxygenase gene by plant-mediated RNAi impairs larval tolerance of gossypol. Nature Biotechnology, Nov. 2007, 25(11): 1307-1313.
Marroqui et al., Enhanced Symbiotic Performance by Rhizobium tropici Glycogen Synthase Mutants. J Bacteriol. Feb. 2001;183(3):854-64.
Martinelli et al., "Structure-function studies on jaburetox, a recombinant insecticidal peptide derived from jack bean (*Canavalia ensiformis*) urease," Biochimica et Biophysica Acta, Mar. 2014, 1840(3):935-44.
Martinez-Noel et al., NifB and NifEN protein levels are regulated by ClpX2 under nitrogen fixation conditions in Azotobacter vinelandii. Mol Microbiol. Mar. 2011;79(5):1182-93. doi: 10.1111/j.1365-2958.2011.07540.x. Epub Jan. 25, 2011.
Marx et al., "Broad-host-range ere-lox system for antibiotic marker recycling in gram-negative bacteria," Biotechniques, Nov. 2002, 33(5):1062-7.
Masepohl et al., "Organization and regulation of genes encoding the molybdenum nitrogenase and the alternative nitrogenase in Rhodobacter capsulatus," Arch. Microbial., Sep. 1996, 165:80-90.
Mason et al., "Cryptic Growth in Klebsiella-Pneumoniae," Appl Microbiol Biot, 1987, 25(6):577-584.
Matsubayashi et al., "Peptide hormones in plants," Annu Rev Plant Biol., 2006, 57:649-74.
Medema et al., "Exploiting plug-and-play synthetic biology for drug discovery and production in microorganisms," Nat. Rev. Microbiol., 2011, 9:131-137.
Medema et al., Computational tools for the synthetic design of biochemical pathways. Nat Rev Microbiol. Jan. 23, 2012;10(3):191-202. doi: 10.1038/nrmicro2717.
Mengel, Roots, growth and nutrient uptake. Purdue Univ. Dept of Agronomy.May 1995. Publication No. AGRY-95-08. 8 pages.

Mirsky, Refactoring the *Salmonella* Type Ill Secretion System. University of California, San Francisco Dissertation. Doctor of Philosophy in Biophysics. Apr. 12, 2012. 59 pages.
Mirzahoseini et al., "Heterologous Proteins Production in *Escherichia coli*: An Investigation on the Effect of Codon Usage and Expression Host Optimization," Cell Journal (Yakhteh), Dec. 2011, 12(4):453, 7 pages.
Mitra, "Regulation of nifLA operon in Azotobacter vinelandii," Thesis submitted to the Jawaharlal Nehru University, New Delhi, for the degree of doctor of philosophy, 2000, 153 pages.
Miyazaki, "Creating random mutagenesis libraries by megaprimer PCR of whole plasmid (Mega Whop)," Methods Mol Biol, 2003, 231:23-28.
Moon et al., "Genetic programs constructedfrom layered logic gates in single cells," Nature, Nov. 2012, 491(7423):249-53.
Mueller et al., "Closing yield gaps through nutrient and water management," Nature, 2012, 490:254-257.
Mus et al., "Diazotrophic Growth Allows Azotobacter vinelandii To Overcome the Deleterious Effects of a glnE Deletion," Appl Environ Microbiol., Jun. 2017, 83(13):e00808-17.
Mus et al., "Symbiotic Nitrogen Fixation and the Challenges to Its Extension to Nonlegumes," Appl Environ Microbial., Jul. 2016, 82(13):3698-3710.
Muse et al., "The nac (Nitrogen Assimilation Control) Gene from *Escherichia coli*," J Bacteriology, Mar. 1998, 180(5):1166-1173.
Mutalik et al., "Quantitative estimation of activity and quality for collections of functional genetic elements," Nat. Methods, 2013, 10:347-353.
Nagy et al., Nanofibrous solid dosage form of living bacteria prepared by electrospinning. eXPRESS Polymer Letters, 2014, 8(5):352-361.
Naimov et al., "Solubilization, Activation, and Insecticidal Activity of Bacillus thuringiensis Serovar thompsoni HD542 Crystal Proteins," Applied and Environmental Microbiology, Dec. 2008, 74(23):7145-7151.
Nassar et al., "Promotion of plant growth by an auxin-producing isolate of the yeast *Williopsis saturnus* endophytic in maize (*Zea mays* L.) roots," Biology and Fertility of Soils, 2005, 42:97-108.
Nelissen et al., "Translational research:from pot to plot," Plant Biotechnology Journal, Jan. 2014, 12:277-285.
Nestmann, "Mutagenesis by nitrosoguanidine, ethyl methanesulfonate, and mutator gene mutH in continuous cultures of *Escherichia coli*," Science Direct, Jun. 1975, 28(3):323-330.
Nichkawade, "Studies on upstream regulatory sequence of the nifLA promoter of Klebsiella pnuemoniae," Thesis submitted to the Jawaharlal Nehru University, New Delhi, for the degree of doctor of philosophy, 1996, 166 pages.
Nielsen et al., Conceptual model for production and composition of exopolymers in biofilms. Wat. Sci. Tech., 1997, 36(1): 11-19.
Nielsen et al., Extraction of EPS. Wingender et al. (eds.), Microbial Extracellular Polymeric Substances, 1999, 24 pages.
Nielsen, "Transgenic organisms—time for conceptual diversification?," Nature Biotechnology, 2003, 21:227-228.
No et al., "Ecdysone-inducible gene expression in mammalian cells and transgenic mice," Proc. Natl. Acad. Sci. USA, Apr. 1996, 93(8):3346-3351.
Noskov et al., "Assembly of large, high G+C bacterial DNA fragments in yeast," ACS Synth. Biol., 2012, 1:267-273.
Ohta et al., Associative N2-fixation of rice with soiol microorganisms. Soil and Microorganisms. 1985;27:17-27.
Ohtsuka et al., "An alternative approach to deoxyoligonucleotides as hybridization probes by insertion of deoxyinosine at ambiguous codon positions," J. Biol. Chem., 1985, 260:2605-2608.
Okubo et al., "Effects of Elevated Carbon Dioxide, Elevated Temperature, and Rice Growth Stage on the Community Structure of Rice Root-Associated Bacteria," Microbes Environ., Jun. 2014, 29(2):184-190.
Orme-Johnson, "Molecular basis of biological nitrogen fixation," Annu Rev Biophys Biophys Chem, 1985, 14:419-459.
Ortiz-Marquez et al., "Association with an Ammonium-excreting bacterium allows diazotrophic culture of oil-rich Eukaryotic microalgae," Appl. Microbial., 2012, 78(7):2345-2352.

(56) References Cited

OTHER PUBLICATIONS

Pakula et al., "Genetic analysis of protein stability and function," Annu Rev Genet, 1989, 23:289-310.
Parker et al., "Pore-forming protein toxins: from structure to function," Progress in Biophysics & Molecular Biology, 2005, 88:91-142.
Patil et al., Liquid formulations of Acetobacter diazotrophicus L 1 and Herbaspirillum seropedicae J24 and their field trials on wheat. International J Environmental Science, 2012, 3(3):1116-1129, 4 pages (Abstract Only).
Pfleger et al., "Combinatorial engineering of intergenic regions in operons tunes expression of multiple genes," Nature Biotechnology, 2006, 24(8):1027-1031.
Philippe et al., "Improvement of pCVD442, a suicide plasmid for gene allele exchange in bacteria," Plasmid, 2004, 51(3):246-255.
Piccioli et al. "Neuroantibodies: ectopic expression of a recombinant anti-substance P antibody in the central nervous system of transgenic mice," Neuron., Aug. 1995, 15(2):373-84.
Piccioli et al., "Neuroantibodies: molecular cloning of a monoclonal antibody against substance P for expression in the central nervous system," Proc Natl Acad Sci USA, Jul. 1991, 88(13):5611-5615.
Pickens et al., "Metabolic engineering for the production of natural products," Annu. Rev. Chem. Biomol. Eng., 2011, 2:211-236.
Plotnikova et al., "Pathogenesis of the human opportunistic pathogen Pseudomonas aeruginosa PA14 in *Arabidopsis*," Plant Physiol., 2000, 124:1766-1774.
Poliner et al., "Nontransgenic Marker-Free Gene Disruption by an Episomal CRISPR System in the Oleaginous Microalga, Nannochloropsis oceanica CCMP1779," ACS Synth. Biol., 2018, 7(4):962-968.
Price et al., "Operon formation is driven by coregulation and not by horizontal gene transfer," Genome Res., 2005, 15:809-819.
Price et al., "The life-cycle of operons," PLoS Genet., 2006, 2:e96, 15 pages.
Purcell et al., "Cholesterol oxidase: a potent insecticidal protein active against boll weevil larvae," Biochem Biophys Res Commun, Nov. 1993, 196(3):1406-13.
Purnick et al., "The second wave of synthetic biology: from modules to systems," Nat Rev Mol Cell Biol, 2009, 10(6):410-422.
Pyne et al., "Coupling the CRISPR/Cas9 System with Lambda Red Recombineering Enables Simplified Chromosomal Gene Replacement in *Escherichia coli*," Applied and Environmental Microbioloy, Aug. 2015, 81(15):5103-5144.
Qaim et al., "Yield Effects of Genetically Modified Crops in Developing Countries," Science, Feb. 2003, 299(5608):900-2.
Qiu et al., "Construction of genetically engineered strains of Enterobacter cloacae (nifl~(-)A~(c))," Acta Phytophysiologica Sinica, Jan. 1999, 25(3):269-273.
Rakhee et al., Extracellular polymeric substances of the marine fouling diatom amphora rostrata Wm.Sm. Biofouling, 2001, 17(2):117-127, 12 pages.
Ramirez et al., "Burkholderia and Paraburkholderia are Predominant Soybean Rhizobial Genera in Venezuelan Soils in Different Climatic and Topographical Regions," Microbes and Environments, Mar. 2019, 34(1):43-58.
Ramon et al., "Single-step linker-based combinatorial assembly of promoter and gene cassettes for pathway engineering," Biotechnol. Lett., 2011, 33:549-555.
Ran et al., "Genome erosion in a nitrogen-fixing vertically transmitted endosymbiotic multicellular cyanobacterium," PLoS One, Jul. 2010, 5(7):e11486, 11 pages.
Resendis-Antonio et al., "Systems biology of bacterial nitrogen fixation: High-throughput technology and its integrative description with constraint-based modeling," BMC Syst Biol., 2011, 5:120, 15 pages.
Riedel et al., "Nitrogen fixation by Klebsiella pneumoniae is inhibited by certain multicopy hybrid nif plasmids," J Bacterial, 1983, 153(1):45-56.
Roberts et al., "Regulation and characterization of protein products coded by the nif (nitrogen fixation) genes of Klebsiella pneumoniae," J Bacterial., Oct. 1978, 136(1): 267-279.
Robledo et al., "Rhizobium cellulase CelC2 is essential for primary symbiotic infection of legume host roots," Proc Natl Acad Sci USA, May 2008, 105(19):7064-9.
Robledo et al., "Role of Rhizobium endoglucanase CelC2 in cellulose biosynthesis and biofilm formation on plant roots and abiotic surfaces," Microb Cell Fact., Sep. 2012, 11:125, 12 pages.
Robson et al., 2015. Azotobacter Genomes: The Genome of Azotobacter chroococcam NCIMB 8003 (ATCC 4412). PLoS One, 10(6): e0127997.
Rogers et al., Synthetic biology approaches to engineering the nitrogen symbiosis in cereals. J Exper Botany. 2014;65(8):1939-46.
Rojas-Tapias et al., Preservation of Azotobacter chroococcum vegetative cells in dry polymers. Univ. Sci., 2015, 20(2):201-207.
Rommens et al., "Intergeneric transfer and functional expression of the tomato disease resistance gene Pto," Plant Cell, Oct. 1995, 7(10):1537-1544.
Roncato-Maccari et al., "Endophytic Herbaspirillum seropedicae expresses nif genes in gramineous plants," FEMS Microbiology Ecology, 2003, 45:39-47.
Rong et al., "Promoter specificity determinants of T7 RNA polymerase," Proc. Natl. Acad. Sci. USA, 1998, 95(2):515-519.
Rosenblueth et al., Bacterial Endophytes and Their Interaction with Hosts. Mol Plant Microbe Interact. Aug. 2006;19(8):827-37.
Rosenblueth et al., Nitrogen Fixation in Cereals. Frontiers in Microbiol. Aug. 9, 2018;9:1794, 13 pages.
Rossolini et al., "Use of Deoxyinosine-Containing Primers vs Degenerate Primers for Polymerase Chain Reaction Based on Ambiguous Sequence Information," Mol. Cell. Probes, 1994, 8:91-98.
Rubio et al., "Maturation of Nitrogenase: a Biochemical Puzzle," J. Bacteriology, 2005, 187(2):405-414.
Ryu et al., Control of nitrogen fixation in bacteria that associate with cereals. Nat. Microbiol., Feb. 2020, 5(2):314-330, 31 pages.
Saikia et al., Biological nitrogen fixation with non-legumes: An achievable target or a dogma? Curr Sci. 2007;92(3):317-22.
Saleh et al., "Involvement of gacS and rpoS in enhancement of the plant growth-promoting capabilities of Enterobacter cloacae CAL2 and UW4," Canadian Journal of Microbiology, Aug. 2001, 47(8):698-705.
Salis et al., "Automated design of synthetic ribosome binding sites to control protein expression," Nat Biotechnol, 2009, 27(10):946-950.
Sanahuja et al., "Bacillus thuringiensis: a century of research, development and commercial applications," Plant Biotechnology Journal, Apr. 2011, 9(3):283-300.
Sandoval et al., "Strategy for directing combinatorial genome engineering in *Escherichia coli*," Proc Natl Acad Sci USA, Jun. 2012, 109(26):10540-5.
Sanjuan et al., Multicopy plasmids carrying the klebsiella pneumoniae nifA gene enhance rhizobium meliloti nodulation competitiveness on alfalfa. Mol Plant Microbe Int. 1991;4(4):365-9.
Santi et al., "Biological nitrogen fixation in non-legume plants," Annals of Botany, Jan. 2013, 111:743-767.
Sanyal et al., "The etiology of hepatocellular carcinoma and consequences for treatment," Oncologist, 2010, 15(Suppl 4):14-22.
Schmidt-Dannert et al., "Molecular breeding of carotenoid biosynthetic pathways," Nat. Biotechnol., 2000, 18:750-753.
Schmitz et al., "Iron is required to relieve inhibitory effects on Nifl on transcriptional activation by NifA in Klebsiella pneumoniae," J Bacterial, Aug. 1996, 178(15):4679-4687.
Schouten et al., "Do cisgenic plants warrant less stringent oversight?," Nature Biotechnology, Jul. 2006, 24(7):753.
Schuler et al., "Insect-resistant transgenic plants," Trends in Biotechnology, Apr. 1998, 16(4):168-175.
Schuler et al., Potential side effects of insect-resistant transgenic plants on arthropod natural Enemies. Trends Biotechnol., May 1999, 17(5):210-216.
Service, "Genetically engineered microbes make their own fertilizer, could feed the world's poorest," Science, Apr. 2017, 2 pages.

(56) References Cited

OTHER PUBLICATIONS

Setten et al., "Engineering Pseudomonas protegens Pf-5 for Nitrogen Fixation and its application to improve plant growth under nitrogen-deficient conditions," PLOS One, 2013, 8(5):1-14.
Shamseldin, The role of different genes involved in symbiotic nitrogen fixation—review. Global J Biotechnol Biochem. 2013;8(4):84-94.
Shetty et al., "Engineering BioBrick vectors from BioBrick parts," J Biol Eng, 2008, 2:5, 12 pages.
Sibold et al., "A nif mutant of Klebsiella pneumoniae fixing nitrogen in the presence of ammonia," FEMS Microbiology Letters, Jan. 1981, 10(1):37-41.
Sibold et al., "Constitutive expression of nitrogen fixation (nif) genes of Klebsiella pneumoniae due to a DNA duplication," Embo J., 1982, 1(12):1551-8.
Siddavattam et al., "Regulation of nif Gene expression in Enterobacter agglomerans: Nucleotide sequence of the nifLA operon and influence of temperature and ammonium on its transcription," Molecular and general genetics, Dec. 1995, 249(6):629-636.
Simon et al., "Perturbation of niff expression in Klebsiella pneumoniae has limited effect on nitrogen fixation," J Bacteriol, 1996, 178(10):2975-2977.
Singer et al., "Genes and Genomes," Moscow: Mir, 1998, 1:33, 4 pages (with machine translation).
Singh et al., "An L-methionine-D,L-sulfoximine-resistant mutant of the cyanobacterium Nostoc muscorum showing inhibitor-resistant y- glutamyl-transferase, defective glutamine synthetase and producing extracellular ammonia during N2 fixation," FESS Letters, Apr. 1983, 154(1):10-14.
Sivaraman et al., "Codon choice in genes depends on flanking sequence information—implications for theoretical reverse translation," Nucleic Acids Res, 2008, 36(3):e16, 8 pages.
Sleight et al., "Randomized BioBrick assembly: a novel DNA assembly method for randomizing and optimizing genetic circuits and metabolic pathways," ACS Synth. Biol., 2013, 2(9):506-518.
Sleight et al., Designing and engineering evolutionary robust genetic circuits. J Biol Engin. 2010;4(12):1-20.
Smanski et al., "Engineered Streptomyces platensis strains that overproduce antibiotics platensimycin and platencin," Antimicrob. Agents Chemother., 2009, 53:1299-12304.
Smanski et al., Synthetic biology to access and expand nature's chemical diversity. Nat Rev Microbiol. Mar. 2016;14(3):135-49. doi: 10.1038/nrmicro.2015.24.
Smanski, et al. Functional optimization of gene clusters by combinatorial design and assembly. Nat Biotechnol. Dec. 2014;32(12):1241-9. doi: 10.1038/nbt.3063. Epub Nov. 24, 2014, 12 pages.
Sorek et al., "Prokaryotic transcriptomics: a new view on regulation, physiology, and pathogenicity," Nat. Rev. Genet., 2010, 11:9-16.
Souza et al., "The N-Terminus of the NIFA protein of herbaspirillum seropedicae is probably involved in sensing of ammonia," In Tikhonovich et al. (Eds.) Proceedings of the 10th International Congress on Nitrogen Fixation, St. Petersburg, Russia, May 28-Jun. 3, 1995 (p. 260) Dordrecht: Kluwer.
Spiller et al., "Isolation and characterization of nitrogenase-derepressed mutant strains of cyanobacterium Anabaena variabilis," J Bacteriol. Feb. 1986, 165(2):412-419.
Staron et al., "The Third Pillar of Bacterial Signal Transduction: Classification of the Extracytoplasmic Function (ECF) Sigma Factor Protein Family," Mol Microbiol, 2009, 14(3):557-81.
Steenhoudt et al., "Azospirillum, a free-living nitrogen-fixing bacterium closely associated with grasses: genetic, biochemical and ecological aspects," FEMS Microbial. Rev., 2000, 24:487-506.
Stein et al., "The osteocalcin gene: a model for multiple parameters of skeletal-specific transcriptional control," Mol Biol Rep., Aug. 1997, 24(3):185-96.
Stemmer, "DNA shuffling by random fragmentation and reassembly: In vitro recombination for molecular evolution," Proc. Natl. Acad. Sci. USA, Oct. 1994, 91:10747-10751.
Stemple, Tilling—a high-throughput harvest for functional genomics. Nat Rev Genet. Feb. 2004;5:145-50. doi:10.1038/nrg1273.
Stephanopoulos, "Challenges in engineering microbes for biofuels production," Science, Feb. 2007, 315(5813):801-4.
Stewart et al., "In situ studies on nitrogen fixation with the acetylene reduction technique," Science, 1967, 158(3800):536.
Stucken et al., "The smallest known genomes of multicellular and toxic cyanobacteria: comparison, minimal gene sets for linked traits and the evolutionary implications," PLoS One, 2010, 5:e9235, 15 pages.
Subtil et al., "Secretion of Predicted Inc Proteins of Chlamydia pneumoniae by a Heterologous Type Ill Machinery," Molecular Microbiology, Feb. 2001, 39(3):792-800.
Suh et al., "Functional expression of the FeMo-cofactor-specific biosynthetic genes nifEN as a NifE-N fusion protein synthesizing unit in Azotobacter vinelandii," Biochem. Biophys. Res. Comm., 2002, 299:233-240.
Suzuki et al., "Immune-mediated motor polyneuropathy after hematopoietic stem cell transplantation," Bone Marrow Transplant., Aug. 2007, 40(3):289-91.
Swain et al., "Nitrogen fixation and its improvement through genetic engineering," J. Global Biosciences, 2013, 2(5): 98-112.
Tamsir et al., "Robust multicellular computing using genetically encoded NOR gates and chemical 'wires'," Nature, 2011, 469(7329):212-215.
Tan, "A synthetic biology challenge: making cells compute," Mol Biosyst, 2007, 3:343-353.
Temme et al., "Induction and relaxation dynamics of the regulatory network controlling the type III secretion system encoded within Salmonella pathogenicity island 1," J Mol Biol, 2008, 377(1):47-61.
Temme et al., Modular control of multiple pathways using engineered orthogonal T7 polymerases. Nucleic Acids Res. Sep. 1, 2012;40(17):8773-81. Epub Jun. 28, 2012.
Temme, Designing and Engineering Complex Behavior in Living Machines. University of California, San Francisco Dissertation. Doctor of Philosophy in Bioengineering. Oct. 1, 2011. 74 pages.
Temme, et al., Refactoring the nitrogen fixation gene cluster from Klebsiella oxytoca. PNAS, May 1, 2012;109(18):7085-90.
Thiel et al., "Characterization of genes for a second Modependent nitrogenase in the cyanobacterium Anabaena variabilis," J. Bact., 1997, 179:5222-5225.
Thomas et al., "Ammonium Excretion by an I-Methionine-dl-Sulfoximine-Resistant Mutant of the Rice Field Cyanobacterium Anabaena siamensis," Appl Environ Microbiol., Nov. 1990, 56(11):3499-3504.
Tijssen, "Laboratory Techniques In Biochemistry And Molecular Biology," Elsevier, 1993, 24:65 pages.
Tilman et al., "Global food demand and the sustainable intensification of agriculture," PNAS, 2011, 108:20260-20264.
Triplett, "Diazotrophic endophytes: progress and prospects for nitrogen fixation in monocots," Plant and Soil, 1996, 186:29-38.
Tritt et al., "An Integrated Pipeline for de Novo Assembly of Microbial Genomes," PLoS One, Sep. 2012, 7(9):e42304, 9 pages.
Troisfontaines et al., Type III secretion: more systems than you think. Physiology (Bethesda). Oct. 2005;20:326-39.
Ueda et al., "Remarkable N2-Fixing Bacterial Diversity Detected in Rice Roots by Molecular Evolutionary Analysis of nifH Gene Sequences," Journal of Bacteriology, Mar. 1995, 177:1414-1417.
Uozumi et al., "Cloning and Expression of the nif A Gene of Klebsiella oxytoca in K. pneumoniae and Azospirillum lipoferum," Agricultural and Biological Chemistry, 1986, 50(6):1539-1544.
Van Dongen, "Performance criteria for graph clustering and Markov cluster experiments," CWI, 2000, 36 pages.
Van Heeswijk et al., "Nitrogen Assimilation in *Escherichia coli*: Putting Molecular Data into a Systems Perspective," Microbiology and Molecular Biology Reviews, Dec. 2013, 77(4):628-695.
Vernon et al., "Analysis of 16S rRNA gene sequences and circulating cell-free DNA from plasma of chronic fatigue syndrome and non-fatigued subjects," BMC Microbiology, 2002, 2:39, 6 pages.
Villa et al., "Azotobacter vinelandii siderophore can provide nitrogen to support the culture of the green algae neochloris oleoabundans and scenedesmus," FEMS Microbial. Lett., 2014, 351(1):70-77.
Villalobos et al., "Gene Designer: a synthetic biology tool for constructing artificial ONA segments," BMC Bioinformatics, 2006, 7:285, 8 pages.

(56) References Cited

OTHER PUBLICATIONS

Voigt et al., Genetic parts to program bacteria. Curr Opin Biotechnol. 2006;17(5):548-57.
Voigt, Gaining Access: Rebuilding Genetics from the Ground Up. MIT. Department of Biological Engineering. Mar. 14, 2011. Retrieved from URL<iom.edu//media/Files/ActivityFiles/PublicHealth/MicrobialThreats/2011-MAR-14Noigt.pdf, 82 pages.
Wang et al., "A minimal nitrogen fixation gene cluster from *paenibacillus* sp. WLY78 enables expression of active nitrogenase in *Escheichia coli*," Plos Genetics, 2013, 9(10):1-11.
Wang et al., "Ligand-inducible and liver-specific target gene expression in transgenic mice," Nat Biotechnol., Mar. 1997, 15(3):239-43.
Wang et al., "Positive and negative regulation of gene expression in eukaryotic cells with an inducible transcriptional regulator," Gene Ther., May 1997, 4(5):432-441.
Wang et al., "Programming cells by multiplex genome engineering and accelerated evolution," Nature, Aug. 2009, 460(7257):894-8.
Wang et al., "Roles of poly-3-hydroxybutyrate (PHB) and glycogen in symbiosis of Sinorhizobium meliloti with *Medicago* sp.," Microbiology, Feb. 2007, 153(2):388-398.
Wang et al., Biofilm formation enables free-living nitrogen-fixing rhizobacteria to fix nitrogen under aerobic conditions. The ISME Journal, Jul. 2017, 11:1602-1613.
Wang et al., Using Synthetic biology to distinguish and overcome regulatory and functional barriers related to nitrogen fixation. PLoS One. 2013;8(7):e68677. 11 pages.
Watanabe et al., "Chapter 15. Plasmid-borne gene cluster assemblage and heterologous biosynthesis of nonribosomal peptides in *Escherichia coli*," Methods Enzymol., 2009, 458:379-99.
Watanabe et al., "Total biosynthesis of antitumor nonribosomal peptides in *Escherichia coli*," Nature Chemical Biology, 2006, 2:423-428.
Weber et al., A modular cloning system for standardized assembly of multigene constructs. PLoS One. Feb. 18, 2011;6(2):e16765, 11 pages. doi: 10.1371/journal.pone.0016765.
Wei et al., "Endophytic nitrogen-fixing Klebsiella variicola strain DX120E promotes sugarcane growth," Biology and fertility of soils, 2014, 50:657-666.
Welch et al., Design Parameters to Control Synthetic Gene Expression in *Escherichia coli*. PLoS One. Sep. 2009;4(9):e7002, 10 pages.
Wells, "Additivity of mutational effects in proteins," Biochemistry, 1990, 29:8509-8517.
Wen et al., "Enabling Biological Nitrogen Fixation for Cereal Crops in Fertilized Fields," ACS Synth. Biol., Dec. 2021, 10(12):3264-3277.
Wenzel et al., "Recent developments towards the heterologous expression of complex bacterial natural product biosynthetic pathways," Curr Opin Biotechnol, 2005, 16(6):594-606.
Werner et al., Fast track assembly of multigene constructs using Golden Gate cloning and the MoClo system. Bioeng Bugs. Jan. 1, 2012;3(1):38-43. doi: 10.1371/journal.pone.0016765. Epub Jan. 1, 2012.
Widmaier et al., "Engineering the *Salmonella* type III secretion system to export spider silk monomers," Mol. Syst. Biol., 2009, 5:309, 9 pages.
Wimpenny et al., Community structure and co-operation in biofilms. 59th Symposium of the Society for General Microbiology, Allison et al. (eds.), Sep. 2000, 23 pages.
Witkowski et al., "Conversion of a β-Ketoacyl synthase to a malonyl decarboxylase by replacement of the active-site cysteine with glutamine," Biochemistry, Sep. 1999, 38(36):11643-50.
Woolbright et al., "Novel insight into mechanisms of cholestatic liver injury," World J Gastroenterol., Sep. 2012, 18(36):4985-93.
Wootton et al., "Statistics of local complexity in amino acid sequences and sequence databases," Computers & Chemistry, Jun. 1993, 17(2):149-163.
Wu et al., "Effects of biofertilizer containing N-fixer, P and K solubilizers and AM fungi on maize growth: a greenhouse trial," Geoderma, Mar. 2005, 125(1-2):155-166.
Wu et al., "Multivariate modular metabolic engineering of *Escherichia coli* to produce resveratrol from L-tyrosine," J. Biotechnol., 2013, 167:404-411.
Xie et al., "Interaction between NifL and NifA in the nitrogen-fixing Pseudomonas stutzeri A1501," Microbiology (Reading), Dec. 2006, 152(Pt 12):3535-3542.
Xu et al., "ePathBrick: a synthetic biology platform for engineering metabolic pathways in *E. coli*.," ACS Synth. Biol., 2012, 1:256-266.
Yan et al., "Global transcriptional analysis of nitrogen fixation and ammonium repression in rootassociated Pseudomonas stutzeri A1501," BMC Genomics, Jan. 2010, 11(11):1-13.
Yao et al., "Complementation analysis of heterologous nifA genes to nifA mutants of Sinorhizobium pallida," Chinese Science Bulletin, Oct. 2006, 51(19):2258-2264, 2 pages (English abstract only).
Yarza et al., "Uniting the classification of cultured and uncultured bacteria and archaea using 16S rRNA gene sequences," Nature Rev. Micro., 2014, 12:635-345.
Ye et al., "Primer-BLAST: a tool to design target-specific primers for polymerase chain reaction," BMC Bioinformatics., Jun. 2012, 13(134):1-11.
Yokobayashi et al, "Directed evolution of a genetic circuit," Proc Natl Acad Sci USA, 2002, 99(26):16587-16591.
Yoshida et al., "Atmospheric dinitrogen fixation in the flooded rice rhizosphere as determined by the N-15 isotope technique," Soil Science and Plant Nutrition, Dec. 1980, 26(4):551-559.
Young et al., Relationships between corn plants and nitrogen fixing bacteria on an organic farm. Ceres Trust. Dec. 31, 2012. 9 pages.
Yu et al., Recombineering Pseudomonas protegens CHA0: An innovative approach that improves nitrogen fixation with impressive bactericidal potency.Microbiological Research, Jan. 2019,218:58-65.
Zaslaver et al., "Optimal gene partition into operons correlates with gene functional order," Phys Biol, 2006, 3(3):183-189.
Zazopoulos et al., "A genomics-guided approach for discovering and expressing cryptic metabolic pathways," Nat Biotechnol, 2003, 21(2):187-190.
Zehr et al., "New Nitrogen-Fixing Microorganisms Detected in Oligotrophic Oceans by Amplification of Nitrogenase (nifH) Genes," Appl Environ Microbiol., Sep. 1998, 64(9):3444-3450.
Zehr Lab NifH database, retrieved from URL <https://wwwzehr.pmc.ucsc.edu/nifH_Database_Public/>, Apr. 4, 2014, 1 page.
Zhang et al., "GlnD Is Essential for NifA Activation, NtrB/NtrC-Regulated Gene Expression, and Posttranslational Regulation of Nitrogenase Activity in the Photosynthetic, Nitrogen-Fixing Bacterium Rhodospirillum rubrum," J. Bacteriol., Februray 2005, 187(4): 1254-1265.
Zhang et al., "Mutagenesis and functional characterization of the four domains of GlnD, a bifunctional nitrogen sensor protein," J Bacteriology, Jun. 2010, 192(11):2711-2721.
Zhang et al., "Mutagenesis and Functional Characterization of the glnB, glnA, and nifA Genes from the Photosynthetic Bacterium Rhodospirillum rubrum," Journal of Bacteriology, Feb. 2000, 182(4):983-992.
Zhang et al., Influence of different factors on the nitrogenase activity of the engineered *Escherichia coli* 78-7. World J Microbiol Biotechnol. 2015;31:921-7. doi: 10.1007/s11274-015-1846-x.
Zhang et al., Involvement of the ammonium transporter AmtB in nitrogenase regulation and ammonium excretion in Pseudomonas stutzeri A 1501. Res Microbial. 2012;163:332-9.
Zhao et al., "Evidence for nifU and nifS participation in the biosynthesis of the iron-molybdenum cofactor of nitrogenase," J. Biol. Chem., 2007, 282(51):37016-37025.
Zomer, "PPP: Perform Promoter Prediction," retrieved from URL <http://bioinformatics.biol.rug.nl/websoftware/ppp/ppp_start.php>, 2011, 2 pages.
U.S. Appl. No. 17/204,219, filed Mar. 17, 2021, Zhao et al..
U.S. Appl. No. 17/822,740, filed Aug. 26, 2022, Voigt et al.
U.S. Appl. No. 17/440,618, filed May 26, 2022, Voigt et al.
Biswas et al., Rhizobia inoculation improves nutrient uptake and growth of lowland rice. Soil Sci Soc Am J 2000; 64:1644-50.
Biswas et al., Rhizobial inoculation influences seedling vigor and yield of rice. Agronom J. 2000; 92: 880-6.

(56) References Cited

OTHER PUBLICATIONS

Cannon et al., Chromosomal integration of Klebsiella nitrogen fixation genes in *Escherichia coli*. J Gen Microbiol. Jan. 1974;80(1):227-39.

Cannon et al., Plasmids formed in nitrogen-fixing *Escherichia coli*-Klebsiella pneumoniae hybrids. J Gen Microbiol. Jan. 1974;80(1):241-51.

Delmotte et al., An integrated proteomics and transcriptomics reference data set provides new insights into the Bradyrhizobium japonicum bacteroid metabolism in soybean root nodules. Proteomics. Apr. 2010;10(7):1391-400.

Edgar, Muscle: multiple sequence alignment with high accuracy and high throughput. Nucleic Acids Res. Mar. 19, 2004;32(5):1792-7.

Ferri et al., Plasmid electroporation of Sinorhizobium strains: The role of the restriction gene hsdR in type strain Rm1021. Plasmid. May 2010;63(3):128-35. doi: 10.1016/j.plasmid.2010.01.001. Epub Jan. 22, 2010.

Geddes et al., Use of plant colonizing bacteria as chassis for transfer of $N_2$-fixation to cereals. Curr Opin Biotechnol. Apr. 2015;32:216-222. doi: 10.1016/j.copbio.2015.01.004. Epub Jan. 24, 2015.

Gorochowski et al., Genetic circuit characterization and debugging using RNA-seq. Mol Syst Biol. Nov. 9, 2017;13(11):952.

Gutierrez-Zamora et al., Natural endophytic association between Rhizobium etli and maize (*Zea mays* L.). J Biotechnol. Oct. 4, 2001;91(2-3):117-26.

Hoover et al., Homocitrate is a component of the iron-molybdenum cofactor of nitrogenase. Biochemistry. Apr. 4, 1989;28(7):2768-71.

Igiehon et al., Rhizosphere Microbiome Modulators: Contributions of Nitrogen Fixing Bacteria towards Sustainable Agriculture. Int J Environ Res Public Health. Mar. 23, 2018;15(4):574.

Jones et al., Soil microbial community analysis using two-dimensional polyacrylamide gel electrophoresis of the bacterial ribosomal internal transcribed spacer regions. J Microbiol Methods. May 2007;69(2):256-67. doi: 10.1016/j.mimet.2006.12.024. Epub Jan. 18, 2007.

Kechris et al., Quantitative exploration of the occurrence of lateral gene transfer by using nitrogen fixation genes as a case study. Proc Natl Acad Sci U S A. Jun. 20, 2006;103(25):9584-9. doi: 10.1073/pnas.0603534103. Epub Jun. 12, 2006.

Kornberg, "DNA Replication," W. H. Freeman & Co., San Francisco, 1980, pp. 75-77.

Li et al., Using synthetic biology to increase nitrogenase activity. Microb Cell Fact. Feb. 20, 2016;15:43.

Li et al., The anti-Shine-Dalgarno sequence drives translational pausing and codon choice in bacteria. Nature. Mar. 28, 2012;484(7395):538-41.

Mahmood et al., Seed biopriming with plant growth promoting rhizobacteria: a review. FEMS Microbiol Ecol Aug. 2016; 92(8): fiw112.

Malik et al., Association of nitrogen-fixing, plant-growth-promoting rhizobacteria (PGPR) with kallar grass and rice. Plant and Soil. 1997; 194: 37-44.

No et al., Ecdysone-inducible gene expression in mammalian cells and transgenic mice. Proc Natl Acad Sci U S A. Apr. 16, 1996;93(8):3346-51.

Oh et al., "Organization of nif gene cluster in *Frankia* sp. EuIK1 strain, a symbiont of Elaeagnus umbellata," Arch. Microbiol., 2012, 194:29-34.

Pascuan et al., Exploring the Ancestral Mechanisms of Regulation of Horizontally Acquired Nitrogenases. J Mol Evol. Oct. 2015;81(3-4):84-9. doi: 10.1007/s00239-015-9698-4. Epub Sep. 15, 2015.

Perrine-Walker et al., Infection process and the interaction of rice roots with rhizobia. J Exp Bot. 2007;58(12):3343-50. doi: 10.1093/jxb/erm181. Epub Oct. 8, 2007.

Sandig et al., HBV-derived promoters direct liver-specific expression of an adenovirally transduced LDL receptor gene. Gene therapy. Nov. 1, 1996;3(11):1002-9.

Shanks et al., *Saccharomyces cerevisiae*-based molecular tool kit for manipulation of genes from gram-negative bacteria. Appl Environ Microbiol. Jul. 2006;72(7):5027-36.

Thony et al., Dual control of the Bradyrhizobium japonicum symbiotic nitrogen fixation regulatory operon fixR nifA: analysis of cis- and trans-acting elements. J Bacteriol. Aug. 1989;171(8):4162-9.

Tsukada et al., Comparative genome-wide transcriptional profiling of Azorhizobium caulinodans ORS571 grown under free-living and symbiotic conditions. Appl Environ Microbiol. Aug. 2009;75(15):5037-46. doi: 10.1128/AEM.00398-09. Epub Jun. 19, 2009.

Yan et al., Nitrogen fixation island and rhizosphere competence traits in the genome of root-associated Pseudomonas stutzeri A1501. PNAS. May 2008; 105(21): 7564-9.

Zhang et al., Expression of the N2 fixation gene operon of *Paenibacillus* sp. WLY78 under the control of the T7 promoter in *Escherichia coli* BL21. Biotechnol Lett. Oct. 2015;37(10):1999- 2004. doi: 10.1007/s10529-015-1874-5. Epub Jun. 9, 2015.

\* cited by examiner

FIG. 22

SEQUENCE LISTING

<160> NUMBER OF SEQ ID NOS: 293

<210> SEQ ID NO 1
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by /5rApp/
<220> FEATURE:
<221> NAME/KEY: misc_feature
<222> LOCATION: (17)..(17)
<223> OTHER INFORMATION: may be modified by /3ddc/

<400> SEQUENCE: 1
ctgtaggcac catcaat                                                      17

<210> SEQ ID NO 2
<211> LENGTH: 33
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by /5Phos/
<220> FEATURE:
<221> NAME/KEY: misc_feature
<222> LOCATION: (33)..(33)
<223> OTHER INFORMATION: may be modified by /iSp18/

<400> SEQUENCE: 2
agatcggaag agcgtcgtgt agggaaagag tgt                                    33

<210> SEQ ID NO 3
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: may be modified by /iSp18/

<400> SEQUENCE: 3
caagcagaag acggcatacg agatattgat ggtgcctaca g                           41

<210> SEQ ID NO 4
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 4
caagcagaag acggcatacg a                                                 21

<210> SEQ ID NO 5
<211> LENGTH: 85
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (63)..(68)
<223> OTHER INFORMATION: n is a, c, g, or t

<400> SEQUENCE: 5
aatgatacgg cgaccaccga gatctacacg atcggaagag cacacgtctg aactccagtc       60
acnnnnnnac actctttccc tacac                                             85

<210> SEQ ID NO 6
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 6
cgacaggttc agagttctac agtccgacga tc                                     32

<210> SEQ ID NO 7
<211> LENGTH: 32
<212> TYPE: DNA
<213> ORGANISM: Artificial Sequence
<220> FEATURE:
```

```
<223> OTHER INFORMATION: Synthetic polynucleotide

<400> SEQUENCE: 7
cgacaggttc agagttctac agtccgacga tc                                    32

<210> SEQ ID NO 8
<211> LENGTH: 68
<212> TYPE: DNA
<213> ORGANISM: Klebsiella oxytoca

<400> SEQUENCE: 8
cgtagggcgc attaatgcag ctggcacgac aggtgaattc tagactgctg gatacgctgc      60
ttaaggtc                                                               68

<210> SEQ ID NO 9
<211> LENGTH: 24
<212> TYPE: DNA
<213> ORGANISM: Klebsiella oxytoca

<400> SEQUENCE: 9
tacgctgttt gagctggcaa acct                                             24

<210> SEQ ID NO 10
<211> LENGTH: 74
<212> TYPE: DNA
<213> ORGANISM: Pseudomonas stutzeri

<400> SEQUENCE: 10
gcccggagag caagcccgta gggcgcatta atgcagctgg cacgacaggt gttaggttgg      60
cctgaattcg gtgt                                                        74

<210> SEQ ID NO 11
<211> LENGTH: 48
<212> TYPE: DNA
<213> ORGANISM: Pseudomonas stutzeri

<400> SEQUENCE: 11
ggctcacttc gatttcgtcc gcggtgcgtg ccctgctagt gatgcgta                   48

<210> SEQ ID NO 12
<211> LENGTH: 25
<212> TYPE: DNA
<213> ORGANISM: Pseudomonas stutzeri

<400> SEQUENCE: 12
cgcctgattt cgcctgatga acagg                                            25

<210> SEQ ID NO 13
<211> LENGTH: 20
<212> TYPE: DNA
<213> ORGANISM: Pseudomonas stutzeri

<400> SEQUENCE: 13
tgacgctgtt gaccaccgcc                                                  20

<210> SEQ ID NO 14
<211> LENGTH: 23
<212> TYPE: DNA
<213> ORGANISM: Pseudomonas stutzeri

<400> SEQUENCE: 14
atggaagtgg tcggcaccgg cta                                              23
```

<210> SEQ ID NO 15
<211> LENGTH: 22
<212> TYPE: DNA
<213> ORGANISM: Pseudomonas stutzeri

<400> SEQUENCE: 15
cgcaacggtt ggggtaggtt gg                                            22

<210> SEQ ID NO 16
<211> LENGTH: 23
<212> TYPE: DNA
<213> ORGANISM: Pseudomonas stutzeri

<400> SEQUENCE: 16
gacgtccatc gcttcggctt cga                                           23

<210> SEQ ID NO 17
<211> LENGTH: 37
<212> TYPE: DNA
<213> ORGANISM: Pseudomonas stutzeri

<400> SEQUENCE: 17
ctgcgaaatc gacgctgtcg agcatcatcg cggttca                            37

<210> SEQ ID NO 18
<211> LENGTH: 101
<212> TYPE: DNA
<213> ORGANISM: Azotobacter vinelandii

<400> SEQUENCE: 18
atccattctc aggctgtctc gtctcgtctc tacgtacgcg gatcccaggc aacgtcttcg   60
tactgcggta ccgggttgcg ggggcagcca gtggaaaaag g                      101

<210> SEQ ID NO 19
<211> LENGTH: 21
<212> TYPE: DNA
<213> ORGANISM: Azotobacter vinelandii

<400> SEQUENCE: 19
ctacggcacg ccctggttcg a                                             21

<210> SEQ ID NO 20
<211> LENGTH: 22
<212> TYPE: DNA
<213> ORGANISM: Azotobacter vinelandii

<400> SEQUENCE: 20
gctcggaaag tgctggagaa ac                                            22

<210> SEQ ID NO 21
<211> LENGTH: 24
<212> TYPE: DNA
<213> ORGANISM: Azotobacter vinelandii

<400> SEQUENCE: 21
aaatcagaca ttcatggcca cagg                                          24

<210> SEQ ID NO 22
<211> LENGTH: 22
<212> TYPE: DNA
<213> ORGANISM: Azotobacter vinelandii

```
<400> SEQUENCE: 22
tctaccatgg cgtgactctc gg                                              22

<210> SEQ ID NO 23
<211> LENGTH: 43
<212> TYPE: DNA
<213> ORGANISM: Azotobacter vinelandii

<400> SEQUENCE: 23
actcgtcttc tgtccgttta aactcccgga actctaccac cgc                       43

<210> SEQ ID NO 24
<211> LENGTH: 21
<212> TYPE: DNA
<213> ORGANISM: Azotobacter vinelandii

<400> SEQUENCE: 24
cttggataga cgaggcacag c                                               21

<210> SEQ ID NO 25
<211> LENGTH: 36
<212> TYPE: DNA
<213> ORGANISM: Azotobacter vinelandii

<400> SEQUENCE: 25
gccggctcct gcaacctgaa ggggccgagg atgatg                               36

<210> SEQ ID NO 26
<211> LENGTH: 30
<212> TYPE: DNA
<213> ORGANISM: Paenibacillus polymyxa

<400> SEQUENCE: 26
gaattgagga taaatgtcag ggatttcatg                                      30

<210> SEQ ID NO 27
<211> LENGTH: 24
<212> TYPE: DNA
<213> ORGANISM: Paenibacillus polymyxa

<400> SEQUENCE: 27
ccaagcattt tgagatcgcg gatg                                            24

<210> SEQ ID NO 28
<211> LENGTH: 21
<212> TYPE: DNA
<213> ORGANISM: Paenibacillus polymyxa

<400> SEQUENCE: 28
cggaggtgcc ggtatgagcg a                                               21

<210> SEQ ID NO 29
<211> LENGTH: 22
<212> TYPE: DNA
<213> ORGANISM: Paenibacillus polymyxa

<400> SEQUENCE: 29
gaagtttgca gcgaaagagg cg                                              22

<210> SEQ ID NO 30
<211> LENGTH: 23
<212> TYPE: DNA
<213> ORGANISM: Paenibacillus polymyxa
```

```
<400> SEQUENCE: 30
gggatgatgc agaatacatc ccg                                              23

<210> SEQ ID NO 31
<211> LENGTH: 26
<212> TYPE: DNA
<213> ORGANISM: Paenibacillus polymyxa

<400> SEQUENCE: 31
ggtgacctgg atgatgcaga ggagag                                           26

<210> SEQ ID NO 32
<211> LENGTH: 118
<212> TYPE: DNA
<213> ORGANISM: Unknown
<220> FEATURE:
<223> OTHER INFORMATION: Cyanothece

<400> SEQUENCE: 32
ggcccgcgtt aggttggcct gaattcggtg tgtatccccc ggagatacgt aaaaaaaaaa      60
accccgccct gtcaggggcg gggttttttt ttgataagtc aagctatcag aaccgatc       118

<210> SEQ ID NO 33
<211> LENGTH: 48
<212> TYPE: DNA
<213> ORGANISM: Unknown
<220> FEATURE:
<223> OTHER INFORMATION: Cyanothece

<400> SEQUENCE: 33
taattcccat aacatctgca tgcataataa ggtggggaaa gtctcagc                   48

<210> SEQ ID NO 34
<211> LENGTH: 24
<212> TYPE: DNA
<213> ORGANISM: Unknown
<220> FEATURE:
<223> OTHER INFORMATION: Cyanothece

<400> SEQUENCE: 34
aatgtatttc tgatcgatgc gacg                                             24

<210> SEQ ID NO 35
<211> LENGTH: 24
<212> TYPE: DNA
<213> ORGANISM: Unknown
<220> FEATURE:
<223> OTHER INFORMATION: Cyanothece

<400> SEQUENCE: 35
gttatctggc tgatgtttgt ggtg                                             24

<210> SEQ ID NO 36
<211> LENGTH: 24
<212> TYPE: DNA
<213> ORGANISM: Unknown
<220> FEATURE:
<223> OTHER INFORMATION: Cyanothece

<400> SEQUENCE: 36
gtcaaactgt cttgtttaaa gccg                                             24

<210> SEQ ID NO 37
```

```
<211> LENGTH: 104
<212> TYPE: DNA
<213> ORGANISM: Azospirillum brasilense

<400> SEQUENCE: 37
ttaaggtcat gcagcaggag aactaaaggc ccgcgttagg ttggtaataa aaaagccccc      60
ggaatgatct tccggggggcc ctgcgcaaat acaacatcga gatc                    104

<210> SEQ ID NO 38
<211> LENGTH: 26
<212> TYPE: DNA
<213> ORGANISM: Azospirillum brasilense

<400> SEQUENCE: 38
gacgactgaa taaggatcgc ggaatg                                          26

<210> SEQ ID NO 39
<211> LENGTH: 23
<212> TYPE: DNA
<213> ORGANISM: Azospirillum brasilense

<400> SEQUENCE: 39
tatgtcacag gcccgacaaa gcg                                             23

<210> SEQ ID NO 40
<211> LENGTH: 23
<212> TYPE: DNA
<213> ORGANISM: Azospirillum brasilense

<400> SEQUENCE: 40
gattgtcggg tatcgcacac gag                                             23

<210> SEQ ID NO 41
<211> LENGTH: 25
<212> TYPE: DNA
<213> ORGANISM: Azospirillum brasilense

<400> SEQUENCE: 41
cgaaggagtt cgccccagtc tattc                                           25

<210> SEQ ID NO 42
<211> LENGTH: 68
<212> TYPE: DNA
<213> ORGANISM: Rhodopseudomonas palustris

<400> SEQUENCE: 42
aatacgatcg catgtcctag gtaatacgac tcactatagg gagaggtaat cagtggtgga      60
tttgatgt                                                              68

<210> SEQ ID NO 43
<211> LENGTH: 20
<212> TYPE: DNA
<213> ORGANISM: Rhodopseudomonas palustris

<400> SEQUENCE: 43
ccaagcaaag gaccaccctc                                                 20

<210> SEQ ID NO 44
<211> LENGTH: 22
<212> TYPE: DNA
<213> ORGANISM: Rhodopseudomonas palustris

<400> SEQUENCE: 44
```

```
agcttcgata tcatccgctg at                                              22

<210> SEQ ID NO 45
<211> LENGTH: 23
<212> TYPE: DNA
<213> ORGANISM: Rhodopseudomonas palustris

<400> SEQUENCE: 45
ttgttcatgt cggacctaac cga                                             23

<210> SEQ ID NO 46
<211> LENGTH: 67
<212> TYPE: DNA
<213> ORGANISM: Rhodobacter sphaeroides

<400> SEQUENCE: 46
caatacgatc gcatgtccta ggtaatacga ctcactatag ggagatgcat ttcacgcttc     60
gcgattc                                                               67

<210> SEQ ID NO 47
<211> LENGTH: 20
<212> TYPE: DNA
<213> ORGANISM: Rhodobacter sphaeroides

<400> SEQUENCE: 47
ccgccttcac cagagacacc                                                 20

<210> SEQ ID NO 48
<211> LENGTH: 23
<212> TYPE: DNA
<213> ORGANISM: Rhodobacter sphaeroides

<400> SEQUENCE: 48
atcgagaagt tctacgatgc cgt                                             23

<210> SEQ ID NO 49
<211> LENGTH: 68
<212> TYPE: DNA
<213> ORGANISM: Rhodobacter sphaeroides

<400> SEQUENCE: 49
gcaaaaaaaa accccgcccc tgacagggcg gggttttttt tttcaattgg acctggatgg     60
gcagcaag                                                              68

<210> SEQ ID NO 50
<211> LENGTH: 106
<212> TYPE: DNA
<213> ORGANISM: Azorhizobium caulinodans

<400> SEQUENCE: 50
ctcgcatcca ttctcaggct gtctcgtctc gtctctctag agtcggagct cttggggcct     60
ctaaacgggt cttgaggggt ttttgttgt cttcgacgcg aagctc                    106

<210> SEQ ID NO 51
<211> LENGTH: 53
<212> TYPE: DNA
<213> ORGANISM: Azorhizobium caulinodans

<400> SEQUENCE: 51
ataggcaata cgatcgcatg tccgtttaaa ctgataagga cggcactggc tgg            53
```

<210> SEQ ID NO 52
<211> LENGTH: 19
<212> TYPE: DNA
<213> ORGANISM: Azorhizobium caulinodans

<400> SEQUENCE: 52
cgatgccgtc cagcacctc                                            19

<210> SEQ ID NO 53
<211> LENGTH: 21
<212> TYPE: DNA
<213> ORGANISM: Azorhizobium caulinodans

<400> SEQUENCE: 53
ctgccacggt tcccaaggtt c                                         21

<210> SEQ ID NO 54
<211> LENGTH: 62
<212> TYPE: DNA
<213> ORGANISM: Azorhizobium caulinodans

<400> SEQUENCE: 54
taaaaaagcg gctaaccacg ccgctttttt tacgtctgca gtgttgtcga agcttgatgc    60
gc                                                                  62

<210> SEQ ID NO 55
<211> LENGTH: 60
<212> TYPE: DNA
<213> ORGANISM: Azorhizobium caulinodans

<400> SEQUENCE: 55
cgctgcttaa ggtcatgcag caggagaact aaaggcccgc tctgcgaaag gaatagcgtc    60

<210> SEQ ID NO 56
<211> LENGTH: 19
<212> TYPE: DNA
<213> ORGANISM: Azorhizobium caulinodans

<400> SEQUENCE: 56
ctatcgccgc cacctgacc                                            19

<210> SEQ ID NO 57
<211> LENGTH: 30
<212> TYPE: DNA
<213> ORGANISM: Azorhizobium caulinodans

<400> SEQUENCE: 57
cgtcagaacg gctctgacgc atcagggaga                                30

<210> SEQ ID NO 58
<211> LENGTH: 32
<212> TYPE: DNA
<213> ORGANISM: Azorhizobium caulinodans

<400> SEQUENCE: 58
agtaatattg cggatcggcc agcagcgagg aa                             32

<210> SEQ ID NO 59
<211> LENGTH: 25
<212> TYPE: DNA
<213> ORGANISM: Azorhizobium caulinodans

<400> SEQUENCE: 59

```
ggtggtcatt ggcaacggtt cgaag                                           25

<210> SEQ ID NO 60
<211> LENGTH: 31
<212> TYPE: DNA
<213> ORGANISM: Azorhizobium caulinodans

<400> SEQUENCE: 60
tccccaagag cccaaccgtt ccgggagcga a                                    31

<210> SEQ ID NO 61
<211> LENGTH: 99
<212> TYPE: DNA
<213> ORGANISM: Gluconacetobacter diazotrophicus

<400> SEQUENCE: 61
ttaaggtcat gcagcaggag aactaaaggc ccgcgttagg ttggtaataa aaaagccccc    60
ggaatgatct tccgggggcc gatcgaggaa atcgacgtg                            99

<210> SEQ ID NO 62
<211> LENGTH: 28
<212> TYPE: DNA
<213> ORGANISM: Gluconacetobacter diazotrophicus

<400> SEQUENCE: 62
atattccgga tacggctggt gaggtgga                                        28

<210> SEQ ID NO 63
<211> LENGTH: 24
<212> TYPE: DNA
<213> ORGANISM: Gluconacetobacter diazotrophicus

<400> SEQUENCE: 63
cgccacgtcg tcaatgccta taac                                            24

<210> SEQ ID NO 64
<211> LENGTH: 21
<212> TYPE: DNA
<213> ORGANISM: Gluconacetobacter diazotrophicus

<400> SEQUENCE: 64
tgaccaccgt gcagaagatc c                                               21

<210> SEQ ID NO 65
<211> LENGTH: 23
<212> TYPE: DNA
<213> ORGANISM: Klebsiella oxytoca

<400> SEQUENCE: 65
gtgacgctcg cgtatcaggt ttg                                             23

<210> SEQ ID NO 66
<211> LENGTH: 69
<212> TYPE: DNA
<213> ORGANISM: Klebsiella oxytoca

<400> SEQUENCE: 66
atcaggcgca tatttgaatg tatttactgc agcggccgct tctagagtga ccaaaagctt    60
ccgcaaccc                                                             69

<210> SEQ ID NO 67
```

```
<211> LENGTH: 48
<212> TYPE: DNA
<213> ORGANISM: Pseudomonas stutzeri

<400> SEQUENCE: 67
actacgcatc actagcaggg cacgcaccgc ggacgaaatc gaagtgag           48

<210> SEQ ID NO 68
<211> LENGTH: 22
<212> TYPE: DNA
<213> ORGANISM: Pseudomonas stutzeri

<400> SEQUENCE: 68
ttgtcgactc ccggggtctg ac                                      22

<210> SEQ ID NO 69
<211> LENGTH: 23
<212> TYPE: DNA
<213> ORGANISM: Pseudomonas stutzeri

<400> SEQUENCE: 69
ggctttaacg gcatgttccg ggt                                     23

<210> SEQ ID NO 70
<211> LENGTH: 24
<212> TYPE: DNA
<213> ORGANISM: Pseudomonas stutzeri

<400> SEQUENCE: 70
gtagtcgtcg ttgtggccga actc                                    24

<210> SEQ ID NO 71
<211> LENGTH: 22
<212> TYPE: DNA
<213> ORGANISM: Pseudomonas stutzeri

<400> SEQUENCE: 71
aaagcatcat ctcgggtcgg gc                                      22

<210> SEQ ID NO 72
<211> LENGTH: 21
<212> TYPE: DNA
<213> ORGANISM: Pseudomonas stutzeri

<400> SEQUENCE: 72
cgtcgagcga caacgcctcg a                                       21

<210> SEQ ID NO 73
<211> LENGTH: 25
<212> TYPE: DNA
<213> ORGANISM: Pseudomonas stutzeri

<400> SEQUENCE: 73
ctatgagctg gactgaaccg cgatg                                   25

<210> SEQ ID NO 74
<211> LENGTH: 74
<212> TYPE: DNA
<213> ORGANISM: Pseudomonas stutzeri

<400> SEQUENCE: 74
gaaaataccg catcaggcgc atatttgaat gtatttactg cagcggccgc tggcgaatct    60
ccttcctcgg ttcg                                               74
```

<210> SEQ ID NO 75
<211> LENGTH: 22
<212> TYPE: DNA
<213> ORGANISM: Azotobacter vinelandii

<400> SEQUENCE: 75
gccttcgaac atgttgtccc ag                                    22

<210> SEQ ID NO 76
<211> LENGTH: 24
<212> TYPE: DNA
<213> ORGANISM: Azotobacter vinelandii

<400> SEQUENCE: 76
tcgagttcga gcagtttctc cagc                                  24

<210> SEQ ID NO 77
<211> LENGTH: 20
<212> TYPE: DNA
<213> ORGANISM: Azotobacter vinelandii

<400> SEQUENCE: 77
agcgaacaat acctgtggcc                                       20

<210> SEQ ID NO 78
<211> LENGTH: 21
<212> TYPE: DNA
<213> ORGANISM: Azotobacter vinelandii

<400> SEQUENCE: 78
tggcgcttgc ccttgttcca a                                     21

<210> SEQ ID NO 79
<211> LENGTH: 54
<212> TYPE: DNA
<213> ORGANISM: Azotobacter vinelandii

<400> SEQUENCE: 79
gcgcggtggt agagttccgg gagtttaaac ggacagaaga cgagtcgtgc gggc    54

<210> SEQ ID NO 80
<211> LENGTH: 20
<212> TYPE: DNA
<213> ORGANISM: Azotobacter vinelandii

<400> SEQUENCE: 80
ttgctcaggg tcgggttggc                                       20

<210> SEQ ID NO 81
<211> LENGTH: 39
<212> TYPE: DNA
<213> ORGANISM: Azotobacter vinelandii

<400> SEQUENCE: 81
catcatcctc ggcccctcca ggttgcagga gccggcttg                  39

<210> SEQ ID NO 82
<211> LENGTH: 21
<212> TYPE: DNA
<213> ORGANISM: Azotobacter vinelandii

<400> SEQUENCE: 82

```
gcaagccact ccactgacga a                                              21

<210> SEQ ID NO 83
<211> LENGTH: 22
<212> TYPE: DNA
<213> ORGANISM: Paenibacillus polymyxa

<400> SEQUENCE: 83
acaggttccg cagttcacaa gc                                             22

<210> SEQ ID NO 84
<211> LENGTH: 25
<212> TYPE: DNA
<213> ORGANISM: Paenibacillus polymyxa

<400> SEQUENCE: 84
gctgattgtg atcgacaata ttcgg                                          25

<210> SEQ ID NO 85
<211> LENGTH: 22
<212> TYPE: DNA
<213> ORGANISM: Paenibacillus polymyxa

<400> SEQUENCE: 85
gaaagcctac acgaagcaaa gg                                             22

<210> SEQ ID NO 86
<211> LENGTH: 22
<212> TYPE: DNA
<213> ORGANISM: Paenibacillus polymyxa

<400> SEQUENCE: 86
cttgagaatc tgccgggcgc ct                                             22

<210> SEQ ID NO 87
<211> LENGTH: 22
<212> TYPE: DNA
<213> ORGANISM: Paenibacillus polymyxa

<400> SEQUENCE: 87
atccacaaat caacaccctg cg                                             22

<210> SEQ ID NO 88
<211> LENGTH: 22
<212> TYPE: DNA
<213> ORGANISM: Paenibacillus polymyxa

<400> SEQUENCE: 88
aaagcgttcc agtcacggtc ac                                             22

<210> SEQ ID NO 89
<211> LENGTH: 48
<212> TYPE: DNA
<213> ORGANISM: Unknown
<220> FEATURE:
<223> OTHER INFORMATION: Cyanothece

<400> SEQUENCE: 89
gagactttcc ccaccttatt atgcatgcag atgttatggg aattaacg                 48

<210> SEQ ID NO 90
<211> LENGTH: 23
<212> TYPE: DNA
<213> ORGANISM: Unknown
```

```
<220> FEATURE:
<223> OTHER INFORMATION: Cyanothece

<400> SEQUENCE: 90
accttgacaa tcattacaca gcg                                              23

<210> SEQ ID NO 91
<211> LENGTH: 28
<212> TYPE: DNA
<213> ORGANISM: Unknown
<220> FEATURE:
<223> OTHER INFORMATION: Cyanothece

<400> SEQUENCE: 91
caaatataat gatcgacatt ttcaccac                                         28

<210> SEQ ID NO 92
<211> LENGTH: 24
<212> TYPE: DNA
<213> ORGANISM: Unknown
<220> FEATURE:
<223> OTHER INFORMATION: Cyanothece

<400> SEQUENCE: 92
cgttaacttt gtcgcaaaac ttcg                                             24

<210> SEQ ID NO 93
<211> LENGTH: 102
<212> TYPE: DNA
<213> ORGANISM: Unknown
<220> FEATURE:
<223> OTHER INFORMATION: Cyanothece

<400> SEQUENCE: 93
accaaggcga atctccttcc tcggttcgcg atcacgctac tccgccaata aaaaagcccc      60
cggaatgatc ttccgggggc cagattcagg taactgctca ag                        102

<210> SEQ ID NO 94
<211> LENGTH: 23
<212> TYPE: DNA
<213> ORGANISM: Azospirillum brasilense

<400> SEQUENCE: 94
tgcgtcttct tcgggcatcg tca                                              23

<210> SEQ ID NO 95
<211> LENGTH: 23
<212> TYPE: DNA
<213> ORGANISM: Azospirillum brasilense

<400> SEQUENCE: 95
agaaaattga ttgcggacga gcg                                              23

<210> SEQ ID NO 96
<211> LENGTH: 27
<212> TYPE: DNA
<213> ORGANISM: Azospirillum brasilense

<400> SEQUENCE: 96
ttcaataagt taagcagatc ggcctcg                                          27

<210> SEQ ID NO 97
<211> LENGTH: 33
<212> TYPE: DNA
```

```
<213> ORGANISM: Azospirillum brasilense

<400> SEQUENCE: 97
cggtgttacg aataaatatt tctacgaata gac                                   33

<210> SEQ ID NO 98
<211> LENGTH: 68
<212> TYPE: DNA
<213> ORGANISM: Azospirillum brasilense

<400> SEQUENCE: 98
gctccaaaag gagcctttaa ttgtatcggt ttatcagctt gctttgttcc gcgggtctcg     60
atacaacg                                                              68

<210> SEQ ID NO 99
<211> LENGTH: 22
<212> TYPE: DNA
<213> ORGANISM: Rhodopseudomonas palustris

<400> SEQUENCE: 99
ggtcttgcgg atcatcactt tc                                              22

<210> SEQ ID NO 100
<211> LENGTH: 20
<212> TYPE: DNA
<213> ORGANISM: Rhodopseudomonas palustris

<400> SEQUENCE: 100
gacggtcagg tggtccgaac                                                 20

<210> SEQ ID NO 101
<211> LENGTH: 23
<212> TYPE: DNA
<213> ORGANISM: Rhodopseudomonas palustris

<400> SEQUENCE: 101
ggtgagaatg atcatgatcg gcc                                             23

<210> SEQ ID NO 102
<211> LENGTH: 67
<212> TYPE: DNA
<213> ORGANISM: Rhodopseudomonas palustris

<400> SEQUENCE: 102
ctccaaaagg agcctttaat tgtatcggtt tatcagcttg ctttgacgac aagtggagaa     60
gggatag                                                               67

<210> SEQ ID NO 103
<211> LENGTH: 22
<212> TYPE: DNA
<213> ORGANISM: Rhodobacter sphaeroides

<400> SEQUENCE: 103
tcccatggtc atgtcctttg cg                                              22

<210> SEQ ID NO 104
<211> LENGTH: 21
<212> TYPE: DNA
<213> ORGANISM: Rhodobacter sphaeroides

<400> SEQUENCE: 104
gtgcgctttt ccacgaggag c                                               21
```

```
<210> SEQ ID NO 105
<211> LENGTH: 66
<212> TYPE: DNA
<213> ORGANISM: Rhodobacter sphaeroides

<400> SEQUENCE: 105
aattgaaaaa aaaaaccccg ccctgtcagg ggcggggttt tttttgcag cgcccattcc    60 gtcttc                                                              66

<210> SEQ ID NO 106
<211> LENGTH: 66
<212> TYPE: DNA
<213> ORGANISM: Rhodobacter sphaeroides

<400> SEQUENCE: 106
gctccaaaag gagcctttaa ttgtatcggt ttatcagctt gctttggaga aagcctgcgc    60
ggctag                                                              66

<210> SEQ ID NO 107
<211> LENGTH: 65
<212> TYPE: DNA
<213> ORGANISM: Azorhizobium caulinodans

<400> SEQUENCE: 107
gcccccggaa ggtgatcttc cggggcttt ctcatgcgtt gacagccttg agatagatca    60
agtgc                                                               65

<210> SEQ ID NO 108
<211> LENGTH: 20
<212> TYPE: DNA
<213> ORGANISM: Azorhizobium caulinodans

<400> SEQUENCE: 108
ctgatccagg ccttcatcgg                                               20

<210> SEQ ID NO 109
<211> LENGTH: 23
<212> TYPE: DNA
<213> ORGANISM: Azorhizobium caulinodans

<400> SEQUENCE: 109
gacatgtctg gtctccttgg aac                                           23

<210> SEQ ID NO 110
<211> LENGTH: 42
<212> TYPE: DNA
<213> ORGANISM: Azorhizobium caulinodans

<400> SEQUENCE: 110
ttctggaatt tggtaccgag tcagtaacgt gccacagcct cg                      42

<210> SEQ ID NO 111
<211> LENGTH: 117
<212> TYPE: DNA
<213> ORGANISM: Azorhizobium caulinodans

<400> SEQUENCE: 111
atcaggcgca tatttgaatg tatttactgc agcggccgct acgtacttgt ggggtcagtt    60
ccggctgggg gttcagcagc cacctgcagt taattaaggc gctcctttcc tgattcg     117
```

```
<210> SEQ ID NO 112
<211> LENGTH: 20
<212> TYPE: DNA
<213> ORGANISM: Azorhizobium caulinodans

<400> SEQUENCE: 112
gctgctgtgt ggagagatcg                                              20

<210> SEQ ID NO 113
<211> LENGTH: 22
<212> TYPE: DNA
<213> ORGANISM: Azorhizobium caulinodans

<400> SEQUENCE: 113
gtcggtgaga ttgatcatgg cc                                           22

<210> SEQ ID NO 114
<211> LENGTH: 20
<212> TYPE: DNA
<213> ORGANISM: Azorhizobium caulinodans

<400> SEQUENCE: 114
tgcatgtccg ttcctcgctg                                              20

<210> SEQ ID NO 115
<211> LENGTH: 24
<212> TYPE: DNA
<213> ORGANISM: Azorhizobium caulinodans

<400> SEQUENCE: 115
acatgtcttg aattccttcg aacc                                         24

<210> SEQ ID NO 116
<211> LENGTH: 18
<212> TYPE: DNA
<213> ORGANISM: Azorhizobium caulinodans

<400> SEQUENCE: 116
tgcattgcgt tcgctccc                                                18

<210> SEQ ID NO 117
<211> LENGTH: 19
<212> TYPE: DNA
<213> ORGANISM: Azorhizobium caulinodans

<400> SEQUENCE: 117
tgtcagggca ggcagggcc                                               19

<210> SEQ ID NO 118
<211> LENGTH: 41
<212> TYPE: DNA
<213> ORGANISM: Gluconacetobacter diazotrophicus

<400> SEQUENCE: 118
tcaccagccg tatccggaat atgtcaggat catgacatcc c                      41

<210> SEQ ID NO 119
<211> LENGTH: 20
<212> TYPE: DNA
<213> ORGANISM: Gluconacetobacter diazotrophicus

<400> SEQUENCE: 119
acgatttcca tgcccaggtc                                              20
```

<210> SEQ ID NO 120
<211> LENGTH: 20
<212> TYPE: DNA
<213> ORGANISM: Gluconacetobacter diazotrophicus

<400> SEQUENCE: 120
cctccagcac ctcttcgatg                                                 20

<210> SEQ ID NO 121
<211> LENGTH: 67
<212> TYPE: DNA
<213> ORGANISM: Gluconacetobacter diazotrophicus

<400> SEQUENCE: 121
gctccaaaag gagcctttaa ttgtatcggt ttatcagctt gctttgggca atacctgaga     60
cgtttca                                                               67

<210> SEQ ID NO 122
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 122
agagtgttga cttgtgagcg gataacaatg atacttagat tcaattgtga gcggataaca     60
atttcacaca                                                            70

<210> SEQ ID NO 123
<211> LENGTH: 2652
<212> TYPE: DNA
<213> ORGANISM: Artificial Sequence
<220> FEATURE:
<223> OTHER INFORMATION: Synthetic polynucleotide

<400> SEQUENCE: 123
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagccg tagcgtacat caccattaag    360
accactctgg cttgcctaac cagtgctgac aatacaaccg ttcaggctgt agcaagcgca    420
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctacttgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960

| | |
|---|---|
| aacattgcgc aaaacaccgc atggaaaatc aacaagaaag tcctagcggt cgccaacgta | 1020 |
| atcaccaagt ggaagcattg tccggtcgag gacatccctg cgattgagcg tgaagaactc | 1080 |
| ccgatgaaac cggaagacat cgacatgaat cctgaggctc tcaccgcgtg gaaacgtgct | 1140 |
| gccgctgctg tgtaccgcaa ggacaaggct cgcaagtctc gccgtatcag ccttgagttc | 1200 |
| atgcttgagc aagccaataa gtttgctaac cataaggcca tctggttccc ttacaacatg | 1260 |
| gactggcgcg tcgtgtttta cgctgtgtca atgttcaacc cgcaaggtaa cgatatgacc | 1320 |
| aaaggactgc ttacgctggc gaaaggtaaa ccaatcggta aggaaggtta ctactggctg | 1380 |
| aaaatccacg gtgcaaactg tgcgggtgtc gacaaggttc cgttccctga gcgcatcaag | 1440 |
| ttcattgagg aaaaccacga gaacatcatg gcttgcgcta agtctccact ggagaacact | 1500 |
| tggtgggctg agcaagattc tccgttctgc ttccttgcgt tctgctttga gtacgctggg | 1560 |
| gtacagcacc acggcctgag ctataactgc tcccttccgc tggcgtttga cgggtcttgc | 1620 |
| tctggcatcc agcacttctc cgcgatgctc cgagatgagg taggtggtcg cgcggttaac | 1680 |
| ttgcttccta gtgaaaccgt tcaggacatc tacgggattg ttgctaagaa agtcaacgag | 1740 |
| attctacaag cagacgcaat caatgggacc gataacgaag tagttaccgt gaccgatgag | 1800 |
| aacactggtg aaatctctga gaaagtcaag ctgggcacta aggcactggc tggtcaatgg | 1860 |
| ctggcttacg gtgttactcg cagtgtgact aagcgttcag tcatgacgct ggcttacggg | 1920 |
| tccaaagagt tcggcttccg tcaacaagtg ctggaagata ccattcagcc agctattgat | 1980 |
| tccggcaagg gtctgatgtt cactcagccg aatcaggctg ctggatacat ggctaagctg | 2040 |
| atttgggaat ctgtgagcgt gacggtggta gctgcggttg aagcaatgaa ctggcttaag | 2100 |
| tctgctgcta agctgctggc tgctgaggtc aaagataaga agactggaga gattcttcgc | 2160 |
| aagcgttgcg ctgtgcattg ggtaactcct gatggtttcc ctgtgtggca ggaatacaag | 2220 |
| aagcctattc agacgcgctt gaacctgatg ttcctcggtc agttccgctt acagcctacc | 2280 |
| attaacacca caaagatag cgagattgat gcacacaaac aggagtctgg tatcgctcct | 2340 |
| aactttgtac acagccaaga cggtagccac cttcgtaaga ctgtagtgtg ggcacacgag | 2400 |
| aagtacggaa tcgaatcttt tgcactgatt cacgactcct tcggtacgat tccggctgac | 2460 |
| gctgcgaacc tgttcaaagc agtgcgcgaa actatggttg acacatatga gtcttgtgat | 2520 |
| gtactggctg atttctacga ccagttcgct gaccagttgc acgagtctca attggacaaa | 2580 |
| atgccagcac ttccggctaa aggtaacttg aacctccgtg acatcttaga gtcggacttc | 2640 |
| gcgttcgcgt aa | 2652 |

<210> SEQ ID NO 124
<211> LENGTH: 51
<212> TYPE: DNA
<213> ORGANISM: A. caulinodans

<400> SEQUENCE: 124

| | |
|---|---|
| cgaatggtgc aaaacctttc gcggtatggc atgatagcgc ccggaagaga g | 51 |

<210> SEQ ID NO 125
<211> LENGTH: 1545
<212> TYPE: DNA
<213> ORGANISM: Artificial Sequence
<220> FEATURE:
<223> OTHER INFORMATION: Synthetic polynucleotide

<400> SEQUENCE: 125

| | |
|---|---|
| atggcgatga gcccaaagat ggagttccgc cagagccagt ctctggtgat gacgccgcag | 60 |

```
ctgatgcagg ccatcaagct gctgcagctc tccaatctcg aactggtcgc ctatgtggag    120
gccgagctcg aacgcaatcc gctgctggag cgggcgagcg agccggaaag ccccgagcac    180
gatccgccga acccgcagga agaggcaccc accccgcctg acagtggcgc gccggtgtcc    240
ggcgactgga tggaaagcga catgggctcg agccgcgagg ccatcgagac ccggctggac    300
accgacctcg gcaatgtctt tcccgatgat gcgccggccg agcgcatcgg cgcgggcagc    360
ggcagcggct cgtccatcga atggggctcg ggcggcgacc ggggcgagga ctacaatccg    420
gaagccttcc tcgctgccga gacgacgctg gccgaccatc tggaagccca gctctccgtg    480
gcggagcccg atccgcgcg ccgcctcatc ggcctcaacc tcatcggcct catcgacgag    540
acgggttatt tctccggcga cctcgatgcg gtggccgagc aactgggcgc cacccacgat    600
caggtggccg acgtgctgcg cgtcatccag agcttcgagc cgtccggcgt cggcgcacgg    660
tcgctcagcg aatgcctggc cctgcaattg cgcgacaagg atcgctgcga tcccgccatg    720
caggcgctgc tcgacaatct ggaactcctc gcccgccacg accgcaacgc gctgaagcgc    780
atctgcgggg tggacgcgga agacctcgcg gacatgatcg gcgagatccg ccgcctcgat    840
ccgaagcccg gcctcgccta tggcggcggc gtcgtccacc cgctggtgcc ggacgtgttc    900
gtgcgcgagg gctccgacgg cagctggatc gtggaactga attccgagac gctgccgcgc    960
gtgctggtga accagaccta tcacgcgacg gtggccaagg cggcgcgctc ggccgaggaa   1020
aagaccttcc tcgccgactg cctccagagc gcctcctggc ttacccgctc gctcgaccag   1080
cgggctcgca ccatcctcaa ggtggcgagc gagatcgtgc ccagcagga cgccttcctc    1140 gtgcacggcg tgcggcacct cgcccctg aacctgcgca cggtggcgga tgccatcggc   1200
atgcacgaat ccaccgtctc gcgggtgacc tcgaacaagt acatctccac cccgcgcggg   1260
gtgctggaga tgaagttctt cttctcctcc tccatcgctt cctcgggtgg tggcgaggcc   1320
catgcggcgg aggcggtgcg ccaccgcatc aagagcctca tcgaggccga gagtgcggac   1380
gacgtgctgt ccgacgacac gctggtgcag aagctgaagg acgacggcat cgatatcgcc   1440
cgccgaacgg tcgcgaaata tcgcgagagc atgaacatcc cgtcctcggt ccagcgccgc   1500
cgcgaaaagc aggccctgcg cagcgacgcc gccgccgccg gctga                   1545
```

<210> SEQ ID NO 126
<211> LENGTH: 1083
<212> TYPE: DNA
<213> ORGANISM: Artificial Sequence
<220> FEATURE:
<223> OTHER INFORMATION: Synthetic polynucleotide

<400> SEQUENCE: 126

```
gtgaaaccag taacgttata cgatgtcgca gagtatgccg gtgtctctta tcagaccgtt     60
tcccgcgtgg tgaaccaggc cagccacgtt tctgcgaaaa cgcgggaaaa agtggaagcg    120
gcgatggcgc agctgaatta cattcccaac cgcgtggcac aacaactggc gggcaaacag    180
tcgttgctga ttggcgttgc cacctccagt ctggccctgc acgcgccgtc gcaaattgtc    240
gcggcgatta atctcgcgc cgatcaactg ggtgccagcg tggtggtgtc gatggtagaa    300
cgaagcggcg tcgaagcctg taaagcgcg gtgcacaatc ttctcgcgca acgcgtcagt    360
gggctgatca ttaactatcc gctggatgac caggatgcca ttgctgtgga agctgcctgc    420
actaatgttc cggcgttatt tcttgatgtc tctgaccaga cacccatcaa cagtattatt    480
ttctcccatg aagacggtac gcgactgggc gtggagcatc tggtcgcatt gggtcaccag   540
```

| | |
|---|---|
| caaatcgcgc tgttagcggg cccattaagt tctgtctcgg cgcgtctgcg tctggctggc | 600 |
| tggcataaat atctcactcg caatcaaatt cagccgatag cggaacggga aggcgactgg | 660 |
| agtgccatgt ccggttttca acaaaccatg caaatgctga atgagggcat cgttcccact | 720 |
| gcgatgctgg ttgccaacga tcagatggcg ctgggcgcaa tgcgcgccat taccgagtcc | 780 |
| gggctgcgcg ttggtgcgga tatctcggta gtgggatacg acgataccga agacagctca | 840 |
| tgttatatcc cgccgttaac caccatcaaa caggattttc gcctgctggg gcaaaccagc | 900 |
| gtggaccgct tgctgcaact ctctcagggc caggcggtga agggcaatca gctgttgccc | 960 |
| gtctcactgg tgaaaagaaa aaccacccctg gcgcccaata cgcaaaccgc ctctccccgc | 1020 |
| gcgttggccg attcattaat gcagctggca cgacaggttt cccgactgga aagcgggcag | 1080 |
| tga | 1083 |

<210> SEQ ID NO 127
<211> LENGTH: 717
<212> TYPE: DNA
<213> ORGANISM: Artificial Sequence
<220> FEATURE:
<223> OTHER INFORMATION: Synthetic polynucleotide

<400> SEQUENCE: 127

| | |
|---|---|
| atgagtaaag gagaagaact tttcactgga gttgtcccaa ttcttgttga attagatggt | 60 |
| gatgttaatg ggcacaaatt ttctgttagt ggagagggtg aaggtgatgc aacatacgga | 120 |
| aaacttaccc ttaaatttat ttgcactact ggaaaactac ctgttccatg gccaacactt | 180 |
| gtcactactt tcggttatgg tgttcaatgc tttgcgagat acccagatca tatgaaacag | 240 |
| catgactttt tcaagagtgc catgcccgaa ggttatgtac aggaaagaac tatatttttc | 300 |
| aaagatgacg ggaactacaa gacacgtgct gaagtcaagt ttgaaggtga taccttgtt | 360 |
| aatagaatcg agttaaaagg tattgatttt aagaagatg gaaacattct tggacacaaa | 420 |
| ttggaataca actataactc acacaatgta tacatcatgg cagacaaaca aaagaatgga | 480 |
| atcaaagtta acttcaaaat tagacacaac attgaagatg aagcgttca actagcagac | 540 |
| cattatcaac aaaatactcc aattggcgat ggccctgtcc ttttaccaga caaccattac | 600 |
| ctgtccacac aatctgccct ttcgaaagat cccaacgaaa agagagacca catggtcctt | 660 |
| cttgagtttg taacagctgc tgggattaca catggcatgg atgaactata caaatag | 717 |

<210> SEQ ID NO 128
<211> LENGTH: 717
<212> TYPE: DNA
<213> ORGANISM: Artificial Sequence
<220> FEATURE:
<223> OTHER INFORMATION: Synthetic polynucleotide

<400> SEQUENCE: 128

| | |
|---|---|
| atgcgtaaag gcgaagagct gttcactggt gtcgtcccta ttctggtgga actggatggt | 60 |
| gatgtcaacg gtcataagtt ttccgtgcgt ggcgagggtg aaggtgacgc aactaatggt | 120 |
| aaactgacgc tgaagttcat ctgtactact ggtaaactgc cggtaccttg gccgactctg | 180 |
| gtaacgacgc tgacttatgg tgttcagtgc tttgctcgtt atccggacca tatgaagcag | 240 |
| catgactttt tcaagtccgc catgccggaa ggctatgtgc aggaacgcac gatttccttt | 300 |
| aaggatgacg gcacgtacaa aacgcgtgcg gaagtgaaat ttgaaggcga taccctggta | 360 |
| aaccgcattg agctgaaagg cattgacttt aagaagacg gcaatatcct gggccataag | 420 |
| ctggaataca attttaacag ccacaatgtt tacatcaccg ccgataaaca aaaaaatggc | 480 |

```
attaaagcga attttaaaat tcgccacaac gtggaggatg gcagcgtgca gctggctgat    540
cactaccagc aaaacactcc aatcggtgat ggtcctgttc tgctgccaga caatcactat    600
ctgagcacgc aaagcgttct gtctaaagat ccgaacgaga aacgcgatca tatggttctg    660
ctggagttcg taaccgcagc gggcatcacg catggtatgg atgaactgta caaatga      717
```

<210> SEQ ID NO 129
<211> LENGTH: 678
<212> TYPE: DNA
<213> ORGANISM: Artificial Sequence
<220> FEATURE:
<223> OTHER INFORMATION: Synthetic polynucleotide

<400> SEQUENCE: 129

```
atggcttcct ccgaagacgt tatcaaagag ttcatgcgtt tcaaagttcg tatggaaggt     60
tccgttaacg gtcacgagtt cgaaatcgaa ggtgaaggtg aaggtcgtcc gtacgaaggt    120
acccagaccg ctaaactgaa agttaccaaa ggtggtccgc tgccgttcgc ttgggacatc    180
ctgtccccgc agttccagta cggttccaaa gcttacgtta acacccggc tgacatcccg     240 gactacctga actgtccctt cccggaaggt ttcaaatggg aacgtgttat gaacttcgaa    300
gacggtggtg ttgttaccgt tacccaggac tcctccctgc aagacggtga gttcatctac    360
aaagttaaac tgcgtggtac caacttcccg tccgacggtc cggttatgca gaaaaaaacc    420
atgggttggg aagcttccac cgaacgtatg tacccggaag acggtgctct gaaaggtgaa    480
atcaaaatgc gtctgaaact gaaagacggt ggtcactacg acgctgaagt taaaaccacc    540
tacatggcta aaaaaccggt tcagctgccg ggtgcttaca aaaccgacat caaactggac    600
atcacctccc acaacgaaga ctacaccatc gttgaacagt acgaacgtgc tgaaggtcgt    660
cactccaccg gtgcttaa                                                 678
```

<210> SEQ ID NO 130
<211> LENGTH: 711
<212> TYPE: DNA
<213> ORGANISM: Artificial Sequence
<220> FEATURE:
<223> OTHER INFORMATION: Synthetic polynucleotide

<400> SEQUENCE: 130

```
atggtttcga agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc cctcagttc atgtacggct ccaaggccta cgtgaagcac     240
cccgccgaca tccccgacta cttgaagctg tccttccccg agggcttcaa gtgggagcgc    300
gtgatgaact tcgaggacgg cggcgtggtg accgtgaccc aggactcctc cttgcaggac    360
ggcgagttca tctacaaggt gaagctgcgc ggcaccaact cccctccga cggcccgta    420 atgcagaaga agacgatggg ctgggaggcc tcctccgagc ggatgtaccc cgaggacggc    480
gccctgaagg gcgagatcaa gcagaggctg aagctgaagg acggcggcca ctacgacgct    540
gaggtcaaga ccacctacaa ggccaagaag cccgtgcagc tgcccggcgc ctacaacgtc    600
aacatcaagt tggacatcac ctcccacaac gaggactaca ccatcgtgga acagtacgaa    660
cgcgccgagg gccgccactc caccggcggc atggacgagc tgtacaagta a             711
```

<210> SEQ ID NO 131

```
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 131
taatacgact cactataggg aga                                              23

<210> SEQ ID NO 132
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 132
taatacgact cactacaggc aga                                              23

<210> SEQ ID NO 133
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 133
taatacgact cactagagag aga                                              23

<210> SEQ ID NO 134
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 134
taatacgact cactaatggg aga                                              23

<210> SEQ ID NO 135
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 135
taatacgact cactaaaggg aga                                              23

<210> SEQ ID NO 136
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 136
taatacgact cactataggt aga                                              23

<210> SEQ ID NO 137
<211> LENGTH: 23
<212> TYPE: DNA
<213> ORGANISM: A. caulinodans

<400> SEQUENCE: 137
taatacgact cactattggg aga                                              23
```

<210> SEQ ID NO 138
<211> LENGTH: 1221
<212> TYPE: DNA
<213> ORGANISM: K. oxytoca

<400> SEQUENCE: 138

| | | | | | |
|---|---|---|---|---|---|
| gtgttccgtg | ggaggcctgc | catgctcgcc | aagacacccg | caaaccccgc | gccgcttcag | 60 |
| cggacggcgt | tcctgaacga | caccacgctg | cgcgacggcg | agcaggcgcc | gggtgtcgcc | 120 |
| ttcacccgca | aggagaagat | cgagatcgcc | gccgcccttg | ccgccgccgg | tgtcccggag | 180 |
| atcgaggcgg | gaacgcccgc | catgggcgac | gaagaggtgg | aaaccatccg | ctccatcgtc | 240 |
| tcgctgaacc | tcccgacgcg | cgtcatggcc | tggtgccgca | tgagcgagga | cgacctgatg | 300 |
| gccgccgtcg | cggcgggcgt | gaagatcgtc | aatgtctcca | ttcccacctc | cgaccggcaa | 360 |
| ctggccggca | agctcggcaa | ggatcgcgcc | tgggcgctcg | gccgtgtggc | ggaggtggtg | 420 |
| acactggcgc | gtcggctcgg | ctttgaggtg | cggtagggg | gcgaggattc | ctcgcgggcc | 480 |
| gatcccgatt | ttctctgccg | tctcgcggag | acggcgaagg | cggcgggcgc | ctttcgcctg | 540 |
| cggctggccg | acacgcttgg | cgtgcttgac | cccttcggca | cctatgcatt | ggtgcgccgg | 600 |
| gtggccgcca | ccaccgacat | cgagcttgag | ttccacgccc | atgacgatct | cggccttgcc | 660 |
| accgccaata | cgctggcggc | ggtgatgggc | ggagcgcgtc | acgccagcgt | caccgtcgcc | 720 |
| gggctcggcg | agcgcgcggg | caatgccgcg | ctggaggaag | tggccatcgc | cctgcgccag | 780 |
| acggcgcggg | cggagaccgg | catcgctccg | gccgcgctga | gccgctggc | cgaactagtg | 840 |
| tgcggcgccg | ccgcccgtcc | ggtgccgcgc | ggcaaggcca | tcgtcggcgc | ggatgtgttc | 900 |
| acccacgagt | cgggcatcca | tgtctccggc | ctgctcaagg | accgggccac | ctatgaagct | 960 |
| ctgaatccgg | aactgttcgg | gcgtggccac | acggtggtgc | tcggaaagca | ttccggtctt | 1020 |
| gcggcggtgg | agaaggcgct | ggccgacgag | ggcatcaccg | tggatgcggt | gcgcgggcgc | 1080 |
| gccattctcg | accgggtgcg | ggcttttgct | gtccgcacca | aggagaatgt | tcccgcgag | 1140 |
| acgctgctgc | gcttctatca | ggacagcttc | accgagtccg | cgctgcgtct | gcggcgggcc | 1200 |
| gccgtggaag | gcgcaatctg | a | | | | 1221 |

<210> SEQ ID NO 139
<211> LENGTH: 323
<212> TYPE: DNA
<213> ORGANISM: P. stutzeri

<400> SEQUENCE: 139

| | | | | | |
|---|---|---|---|---|---|
| tgttgcctca | agcacagcct | gtgccagctc | gcggatgaca | gaagagttag | cgcgaattca | 60 |
| acgcgttatg | aagagagtcg | ccgcgcagcg | cgccaagaga | ttgcgtggaa | taagacacag | 120 |
| ggggcgacaa | gctgttgaac | aggcgacaaa | gcgccaccat | ggccccggca | ggcgcaattg | 180 |
| ttctgttttcc | cacatttggt | cgccttattg | tgccgttttg | ttttacgtcc | tgcgcggcga | 240 |
| caaataacta | acttcataaa | aatcataaga | atacataaac | aggcacggct | ggtatgttcc | 300 |
| ctgcacttct | ctgctggcaa | aca | | | | 323 |

<210> SEQ ID NO 140
<211> LENGTH: 233
<212> TYPE: DNA
<213> ORGANISM: A. vinelandii

<400> SEQUENCE: 140

```
tgtcatgttc gcaacagttg ccgaaagtgt ggaaaaccgg cgcttggccc ggccgatctt      60
tttgtcgcca ttgcaacagt caggcctgtc ggttgttaac tatcgaaccg ccgaaggatg     120
ttgctagtaa ttaaattatt ctaattaaaa caagtgctta gattatttta gaaacgctgg     180
cacaaaggct gctattgccc tgttgcgcag gcttgttcgt gcctatagcc cac            233
```

<210> SEQ ID NO 141
<211> LENGTH: 256
<212> TYPE: DNA
<213> ORGANISM: Unknown
<220> FEATURE:
<223> OTHER INFORMATION: R. sp. IRBG74

<400> SEQUENCE: 141

```
tgtcagtttt gtcacagggg gccggaccag gatggtggac gctcgatggg gatgtcgggc      60
cattgttcgg ttgtagcaat tacaacagtc ggagtagggg gattgtaggg ggattgttgt     120
gtatcagacc gccctgcagc tcccgtcgat ggataattaa tcatttaaaa tcaatggttt     180
atttatgtgt tgcgggtgct ggcacagacg ctgcattacc tttggtgcgc ggagttgttc     240
gggcttacgg ccgaac                                                     256
```

<210> SEQ ID NO 142
<211> LENGTH: 294
<212> TYPE: DNA
<213> ORGANISM: A. caulinodans

<400> SEQUENCE: 142

```
ttgacaaagc ctccgagaag agcgccccct aaccctcct cagccctgat cggcagtatc       60
atcttgtcga atcctaacgt ctgataggca acgctatacg acaaacgctg gttacaattg     120
tcggttccgc gacaagaatt tgctttgtct ggcgggtggt ctattttgag ctaagtagct     180
gagaaatcag gaaaacaaaa ctctattcgg tctacccgac gagttggcac gggtcttgta     240
accatccttg cgcaggcggc gaaagccacc ggcgatattc atgttgcggg caac           294
```

<210> SEQ ID NO 143
<211> LENGTH: 215
<212> TYPE: DNA
<213> ORGANISM: K. oxytoca

<400> SEQUENCE: 143

```
tgtcgcgttt gaaacacggg gcttttggaa ccgttcgatt ctgcaatgca ctgattttac      60
ttgattaatt cgaccacacg accactggca cacccgttgc aaaaccccttt ggtgcaggcg    120 acgggttgcc ggtctggttc gcggatctcc tcgatccccg gctaccgacc cgcctccgaa     180
aagtccggtc ccgatccagt tcggcggggc cacac                                215
```

<210> SEQ ID NO 144
<211> LENGTH: 1575
<212> TYPE: DNA
<213> ORGANISM: P. stutzeri

<400> SEQUENCE: 144

```
atgatccata aatccgattc ggacaccacc gtcagacgtt tcgatctctc ccagcagttt      60
accgccatgc agcggataag cgtggtcctg agtcgcgcca ccgaagcgag caaaaccctg     120
caggaggttc tgagcgtgct acataacgat gcctttatgc agcacgggat gatttgcctg     180
tacgacagcc agcaggagat cctgagcatc gaagcgctgc agcaaacgga agatcagacg     240
ctgcccggca gtacgcaaat tcgctaccgg ccggggggaag gattagtcgg taccgtgctg    300
```

```
gcgcagggcc agtcgctggt gctgccgcgc gtcgccgacg accagcgttt tctcgatcgt    360
ctgagcctgt acgactatga cctgccgttt atcgccgttc cgctgatggg cccccactcc    420
cggcccatcg gcgtactggc ggcgcagccg atggcgcgtc aggaagagcg gctgcccgcc    480
tgcacgcgct ttctcgaaac cgtcgccaat ctgatcgccc agacgattcg cctgatgatc    540
ctgccaacct ccgccgcgca ggcgccgcag cagagcccca aatagagcg cccgcgcgcc    600 tgtacccctt cgcgcggttt cggcctggaa aatatggtcg gtaaaagccc ggcgatgcgg    660
cagattatgg atattattcg tcaggtttcc cgctgggata ccacggtgct ggtacgcggc    720
gagagcggca ccgggaaaga gctcatcgcc aacgccatcc accataattc ccgcgcgcc     780 gccgcggcgt tcgtcaaatt taactgcgcg gcgctgccgg acaacctgct ggagagcgag    840
ctgtttggtc atgagaaagg cgcgtttacc ggcgcggtgc gccagcggaa aggccgcttt    900
gagctggcgg acggcggcac cttattcctc gatgagatcg gcgaaagcag cgcctcgttt    960
caggctaagc tactgcgtat tctgcaagag ggggagatga agcgcgtcgg cggcgacgaa   1020
accctgcggg tcaacgtgcg cattatcgcg gcgaccaacc gccatctgga agaggaggtg   1080
cggctgggtc atttccgcga ggatctatac taccgcctga acgtaatgcc tatcgcgctg   1140
ccgccgctgc gcgagcgcca ggaggatatc gccgagctgg cgcactttct ggtgcgaaaa   1200
atcgcccaca gccaggggcg aacgctgcgc atcagcgatg gggcgattcg cctgctgatg   1260
gagtacagct ggccgggaaa cgtgcgcgaa ctggaaaact gtctcgaacg ttcggcggtg   1320
ctgtcggaaa gcggcctgat agaccgggac gtgattctgt tcaaccatcg cgataacccg   1380
ccgaaagcgc tcgccagcag cggcccggcg gaggacggct ggctcgataa cagcctcgac   1440
gagcgccagc ggctgatcgc cgccctggaa aaagcgggct gggtgcaggc caaagcggcg   1500
cggctgctcg gcatgacccc gcgccaggtg gcgtatcgca ttcagattat ggatatcacc   1560
atgccgcgac tgtga                                                     1575
```

<210> SEQ ID NO 145  
<211> LENGTH: 1566  
<212> TYPE: DNA  
<213> ORGANISM: A. vinelandii

<400> SEQUENCE: 145

```
atgaacgcca cattcgccga acgccccagc gcgccaaccc gcaacgaact gctggatgcc     60
caactgcagg cgctggcgca gatcgcccgc atccttaacc gcggccggcc catcgaggaa    120
ctgctggccg agatcctcgc cgtgctgcac gaagacctcg gcctgctgca cgggctggtc    180
tccatctgca acccgaagga cggcagcctg caggtgggcg ccgtgcacag cgactccgaa    240
accgtggtac gggcctgcga aagcaccgc taccgcatcg gcgaaggcgt gttcggcaac    300
atcctcaagc atggcaacag cgtggtgctc gggcgtatcg acgccgaacc gcgctttctc    360
gaccgactgg cgctgtacga catggacctg cccttcatcg ccgtgccgat caaggccgtc    420
gacggcacca ccatcggcgt gctggctgcc cagcccgacc gccgcgccga cgagctgatg    480
cccgaacgca cccgtttgat ggaaatcgtc gcccgcctac tggcgcagac cgtgcgcctg    540
gtggtgaacc tcgaggacgg ccaggaagtg gtcgacgagc gcgacgagct acgccgcgaa    600
gtccgcgcca agtacggctt cgagaacatg gtggtgggcc acaccgcctc catgcgccgg    660
gttttcgacc aggttcgacg ggtcgccaag tggaacagca ccgtgctgat cctcggcgaa    720
tccggcaccg gcaaggagct gatcgccagc gccatccact acaactcacc gcgcgctcac    780
```

```
cagccgctgg tacgcctgaa ctgcgccgcg ctaccggaaa ccctgctcga atcggaactg    840
ttcggtcacg agaaaggcgc cttcaccggc gccgtgaagc agcgcaaggg acgtttcgaa    900
caggccgacg gcggcaccct gttcctcgac gagatcggcg agatctcgcc gatgttccag    960
gccaagctgc tgcgcgtgct gcaggaaggc gagctgagc gcgtcggcgg cagccagacg    1020
gtgaaggtca acgtgcgcat cgtcgccgcc accaaccgcg acctggagca cgaggtggag    1080
caaggcaagt tccgcgaaga cctctactac cgcctcaacg tcatggccat ccgcgtcccg    1140
ccgctgcgcg agcgcagcgc cgacatcccg gaactggccg aattcctcct cgacaagatc    1200
gcccgccagc agggtcgcaa actcaagctg accgacagcg ccctgcgtct gctgatgagc    1260
caccgctggc cgggcaacgt gcgcgaactg gaaaactgcc tggaacgctc ggccatcatg    1320
agcgaggatg gcaccatcag ccgcgacgtg gtctccctca ccggcctcga ccacgacgcc    1380
acgccgctgg cgccggtccc cgaagtcgac ctcgccgacg acagcctcga cgaccgcgag    1440
cgcgtcatcg ccgcgctgga acaggccggc tgggtccagg ccaaggccgc ccgcctgctc    1500
ggcatgacgc cccggcagat cgcctaccga gtgcagacgc tgaacattca tatgcgcaag    1560
atctga                                                                1566

<210> SEQ ID NO 146
<211> LENGTH: 1569
<212> TYPE: DNA
<213> ORGANISM: Unknown
<220> FEATURE:
<223> OTHER INFORMATION: R. sp. IRBG74

<400> SEQUENCE: 146
atgaatgcaa ccatccctca gcgctcggcc aaacagaacc cggtcgaact ctatgacctg    60
caattgcagg ccctggcgag catcgcccgc acgctcagcc gcgaacaaca gatcgacgaa    120
ctgctcgaac aggtcctggc cgtactgcac aatgacctcg gcctgctgca tggcctggtg    180
accatttccg acccggaaca cggcgccctg cagatcggcg ccatccacac cgactcggaa    240
gcggtggccc aggcctgcga aggcgtgcgc tacagaagcg gcgaaggcgt gatcggcaac    300
gtgctcaagc acggcaacag cgtggtgctc gggcgcatct ccgccgaccc cgcctttctc    360
gaccgcctgg cgctgtacga cctggaaatg ccgttcatcg ccgtgccgat caagaacccc    420
gagggcaaca ccatcggcgt gctggcggcc cagccggact gccgcgccga cgagcacatg    480
cccgcgcgca cgcgccttct ggagatcgtc gccaacctgc tggcgcagac cgtgcgcctg    540
gtggtgaaca tcgaggacgg ccgcgaggcg ccgacgagc gcgacgaact cgtcgcgag    600 gtgcgcggca agtacggctt cgagaacatg gtggtgggcc acacccccac catgcgccgg    660
gtgttcgatc agatccgccg ggtcgccaag tggaacagca ccgtactggt cctcggcgag    720
tccggtaccg gcaaggaact gatcgccagc gccatccact acaactcgcc gcgcgcgcac    780
cgccccttcg tgcgcctgaa ctgcgccgcg ctgccggaaa ccctgctcga gtccgaactc    840
ttcggccacg agaagggcgc cttcaccggc gcggtgaagc agcgcaaggg gcgtttcgag    900
caggccgacg gcggcaccct gttcctcgac gagatcggcg agatctcgcc gatgttccag    960
gccaagctgc tgcgcgtgct gcaggaaggc gagttcgagc gggtcggcgg caaccagacg    1020
gtgcgggtca acgtgcgcat cgtcgccgcc accaaccgcg acctggaaag cgaggtggaa    1080
aagggcaagt tccgcgagga cctctactac cgcctgaacg tcatggccat ccgcattccg    1140
ccgctgcgcg agcgtaccgc cgacattccc gaactggcgg aattcctgct cggcaagatc    1200
ggccgccagc agggccgccc gctgaccgtc accgacagcg ccatccgcct gctgatgagc    1260
```

```
caccgctggc cgggcaacgt gcgcgaactg gagaactgcc tggagcgctc ggcgatcatg      1320
agcgaggacg gcaccatcac ccgcgacgtg gtctcgctga ccggggtcga caacgagagc      1380
ccgccgctcg ccgcgccgct gcccgaggtc aacctggccg acgagaccct ggacgaccgc      1440
gaacgggtga tcgccgccct cgaacaggcc ggctgggtgc aggccaaggc cgcgcggctg      1500
ctgggcatga cgccgcggca gatcgcctac cgcatccaga ccctcaacat ccacatgcgc      1560
aagatctga                                                              1569

<210> SEQ ID NO 147
<211> LENGTH: 1695
<212> TYPE: DNA
<213> ORGANISM: A. caulinodans

<400> SEQUENCE: 147
atgctgcaca atgggctcaa tgagggtatg actgaacgat ccgctcaaac catccacaaa       60
ccggatttct gggcagcgg tatctatcgg atatcgaaag ttttgattgg tccagacagt      120
ctcgagacga agcttgccaa tgtcattaac gccctctcag taattctccc aatgcggcgc      180
ggcgcaatcg tcgttctaaa tgttaaagga gagcccgaga tggttgcaat gctgggccta      240
gagcaagcat ctcaaggcgc ccgctccatt ccggcggagg ctgcgataga tagaatcgtc      300
gccaaaggcg cgccgctggt cgtaccggac atttgcaagt cggacctgtt ccaggcggag      360
ctccaaacca actcgaacgc cacaggccca gccacgttcg ttggcgtccc gatgaaggtc      420
gaaaaagaaa cgcttggaac actatggatc gaccgcgcca agatggcag cactaggatc      480 caatttgagg aagaggtgcg cttcctctcc atggtcgcca acctttcggc ccgggccatt      540
tggctggatc gccaccagag ccgcgatggt cagccaatcg tgggcgagga aggaactcgc      600
aagactagtt caggcgacaa ggaactgccc gaatctgccc gacaaaggcc cacaaaaatc      660
gattggattg tcggggaaag ccctgccctc aagcaggtgg ttgaaagcgt caaagtcgtt      720
gcaacaacca attctgcggt gcttctcagg ggcgaaagcg gcacgggcaa ggagttcttt      780
gcaaaggcca tccacgagct ttcataccgg aaaaagaagc ccttcgtgaa gttgaactgc      840
gccgcgctgt ctgcaggcgt tttggaatcg gaattgtttg acatgaaaaa gggcgccttc      900
acggggccca tctctcagcg cgcaggccgc ttcgaactcg cagacggcgg aacgctgctg      960
ctcgatgaga tcgcgacat tcgccgggc ttccaagcga aactgttgcg cgtcttgcag     1020
gaaggtgagc ttgagcgagt cggcggcaca aaaacactca agtggacgt tcgactcata     1080 tgcgccacga acaaagacct agaagcggca gtcgcggatg gggagttcag gccgaccttt     1140
tattaccgga tcaatgtggt gccctatttt ctgccgcctc tccgggagcg aaatggggat     1200
attccacgcc ttgcgagagt tttcctcggc cgattcaaca gggaaaacaa tcgcgatctc     1260
gcgttcgcgc cggctgcgct cgagctcttg tcaaaatgca actttcccgg caacgtccga     1320
gagcttgaaa actgcgtccg caggaccgcc actctcgcgc gttcggagac gatcgttcca     1380
tcagatttct cctgcctgaa gaaccagtgc ttttcttcaa tgctctggaa accggtgac      1440 cgtccacttg gggatacgct caatggggttg gccatgcgta agagtttgtc ggtcgaatcg     1500
ccgatcagcc tcggttactc caatggaccg gccggcttaa cggtggcacc acatctaacg     1560
gaccgcgagc tgctaatcag tgcgatggag aaggccggtt gggttcaggc aaaggcagct     1620
cggatcctcg gcctcacacc gcgacaggtc ggctatgctt tacgtaggca tcgtatacag     1680
gtgaagaaaa tctaa                                                      1695
```

<210> SEQ ID NO 148
<211> LENGTH: 1848
<212> TYPE: DNA
<213> ORGANISM: Artificial Sequence
<220> FEATURE:
<223> OTHER INFORMATION: Synthetic polynucleotide

<400> SEQUENCE: 148

| | | | | | |
|---|---|---|---|---|---|
| atgccaatga | ccgacgcctt | ccaggtccgc | gtacctcggg | tttcgtcgag | caccgccgga | 60 |
| gacatcgccg | cgtcatccat | caccacgcgg | ggcgcgctgc | cgcgcccggg | agggatgcct | 120 |
| gtgtccatgt | cgcggggggac | ctcgcccgag | gtggcactca | tcggggtcta | tgagatatcg | 180 |
| aagatcctga | cggcgccccg | gcgcctcgaa | gtcacgctcg | ccaatgtggt | gaacgtgctc | 240 |
| tcctccatgc | tgcagatgcg | gcatggcatg | atctgcatcc | tcgacagcga | gggcgatccc | 300 |
| gacatggtgg | ccaccaccgg | ctggacgcct | gagatggcgg | ccagatccg | cgcgcatgtg | 360 |
| ccccagaagg | ccatcgacca | gatcgtcgcc | acgcagatgc | cgctggtggt | gcaggacgtg | 420 |
| acggccgatc | cgctcttcgc | cggtcacgag | gatctgttcg | gcccgcctga | ggaggccacc | 480 |
| gtctccttca | tcggcgtgcc | gatcaaggcc | gaccaccatg | tgatgggcac | cctctccatc | 540 |
| gaccgcatct | gggacggcac | cgcccgtttc | cgcttcgacg | aggacgtgcg | cttcctcacc | 600 |
| atggtggcca | atctcgtcgg | ccagaccgtg | cgcctgcaca | agctggtggc | gagcgaccgc | 660 |
| gaccggctga | tcgcccagac | gcaccgcctc | gaaaaggcgc | tgcgggaaga | aaatccggg | 720 |
| gccgagccgg | aggtggccga | ggccgccaac | ggatccgcca | tgggcatcgt | gggcgatagc | 780 |
| ccgctggtga | aacgcctgat | cgcgaccgcg | caagtggtcg | cccgctcaaa | ctccaccgtg | 840 |
| ctgctgcgcg | gggagagcgg | caccggcaag | gagttgttcg | cccgtgccat | ccacgaactg | 900 |
| tcgccccgca | agggcaagcc | cttcgtgaag | gtgaactgcg | ccgccctccc | ggaatcggtg | 960 |
| ctggaatcgg | aactgttcgg | ccatgagaag | ggcgccttca | ccggtgcgct | gaacatgcgc | 1020 |
| cagggccgct | cgagctggc | gcacggcggc | acgctcttcc | ttgacgagat | cggcgagatc | 1080 |
| accccgcctt | ccaggccaa | gctgctgcgc | gtgctgcagg | aaggcgagtt | cgagcgggtc | 1140 |
| ggcggcaatc | gcacgctgaa | ggtggatgtg | cggctcgtgt | gcgccaccaa | caagaatctg | 1200 |
| gaagaggcgg | tctccaaggg | cgagttccgg | gccgatctct | actaccgcat | ccatgtggtg | 1260 |
| ccgctgatcc | tgccgccgct | gcgcgaacgg | ccgggcgaca | ttcccaagct | cgcgaagaac | 1320 |
| ttcctcgacc | gcttcaacaa | ggaaaacaag | ctccacatga | tgctctcggc | gccggccatc | 1380 |
| gacgtgctgc | ggcgctgcta | tttcccgggc | aacgtgcgcg | agctggagaa | ctgtatccgg | 1440 |
| cggacggcaa | cgctcgccca | cgatgccgtc | atcacccccc | atgacttcgc | ctgcgacagc | 1500 |
| ggccagtgcc | tctcggccat | gctctggaag | ggctcggccc | cgaagcctgt | gatgccgcac | 1560 |
| gtgccgccgg | cgcccacgcc | gctgactccg | ctctcccctg | ctccgctcgc | gaccgcagcg | 1620 |
| cccgctgcgg | cgagcccggc | gccggcggcc | gacagcctgc | cggtcacttg | ccccggcacc | 1680 |
| gaggcctgtc | ccgcggtgcc | ccccgccag | agcgaaaagg | agcagttgct | ccaggccatg | 1740 |
| gagcgctccg | gctgggtgca | ggcgaaggcc | gcgcgcctcc | tcaacctcac | gccgcgccag | 1800 |
| gtgggttatg | cgctgcgcaa | atatgacatc | gacatcaagc | gcttctga | | 1848 |

<210> SEQ ID NO 149
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 149
taggtgttga cggctagctc agtcctaggt acagtgctag ctctaga                        47

<210> SEQ ID NO 150
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 150
taggtgttta cagctagctc agtcctaggt attatgctag ctctaga                        47

<210> SEQ ID NO 151
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 151
taggtgttga cagctagctc agtcctaggt actgtgctag ctctaga                        47

<210> SEQ ID NO 152
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 152
taggtgctga tagctagctc agtcctaggg attatgctag ctctaga                        47

<210> SEQ ID NO 153
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 153
taggtgttga cagctagctc agtcctaggt attgtgctag ctctaga                        47

<210> SEQ ID NO 154
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 154
taggtgttta cggctagctc agtcctaggt actatgctag ctctaga                        47

<210> SEQ ID NO 155
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 155
taggtgttta cggctagctc agtcctaggt atagtgctag ctctaga                        47

<210> SEQ ID NO 156

```
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 156
taggtgttta cggctagctc agccctaggt attatgctag ctctaga        47

<210> SEQ ID NO 157
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 157
taggtgctga cagctagctc agtcctaggt ataatgctag ctctaga        47

<210> SEQ ID NO 158
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 158
taggtgttta cagctagctc agtcctaggg actgtgctag ctctaga        47

<210> SEQ ID NO 159
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 159
taggtgttta cggctagctc agtcctaggt acaatgctag ctctaga        47

<210> SEQ ID NO 160
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 160
taggtgttga cggctagctc agtcctaggt atagtgctag ctctaga        47

<210> SEQ ID NO 161
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 161
taggtgctga tagctagctc agtcctaggg attatgctag ctctaga        47

<210> SEQ ID NO 162
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 162
```
taggtgctga tggctagctc agtcctaggg attatgctag ctctaga    47

<210> SEQ ID NO 163
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 163
taggtgttta tggctagctc agtcctaggt acaatgctag ctctaga    47

<210> SEQ ID NO 164
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 164
taggtgttta tagctagctc agcccttggt acaatgctag ctctaga    47

<210> SEQ ID NO 165
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 165
taggtgttga cagctagctc agtcctaggg actatgctag ctctaga    47

<210> SEQ ID NO 166
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 166
taggtgttga cagctagctc agtcctaggg attgtgctag ctctaga    47

<210> SEQ ID NO 167
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 167
taggtgttga cggctagctc agtcctaggt attgtgctag ctctaga    47

<210> SEQ ID NO 168
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 168
taggtgttga cagctagctc agtcctaggt ataatgctag ctctaga    47

<210> SEQ ID NO 169
<211> LENGTH: 47
<212> TYPE: DNA

```
<213> ORGANISM: Artificial Sequence
<220> FEATURE:
<223> OTHER INFORMATION: Synthetic polynucleotide

<400> SEQUENCE: 169
taggtgttga cattattcca tcgaactagt taactagtac gaaagtt        47

<210> SEQ ID NO 170
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 170
tagcataacc ccttggggcc tctaaacggg tcttgagggg ttttttgt        48

<210> SEQ ID NO 171
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 171
tactcgaacc cctagcccgc tcttatcggg cggctagggg ttttttgt        48

<210> SEQ ID NO 172
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 172
tacatatcgg gggggtaggg gtttttttgt        29

<210> SEQ ID NO 173
<211> LENGTH: 80
<212> TYPE: DNA
<213> ORGANISM: Artificial Sequence
<220> FEATURE:
<223> OTHER INFORMATION: Synthetic polynucleotide

<400> SEQUENCE: 173
ccaggcatca aataaaacga aaggctcagt cgaaagactg ggcctttcgt tttatctgtt        60
gtttgtcggt gaacgctctc                                                 80

<210> SEQ ID NO 174
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 174
ctcggtacca aattccagaa aagaggcctc ccgaaagggg ggcctttttt cgttttggtc        60
c                                                                      61

<210> SEQ ID NO 175
<211> LENGTH: 146
<212> TYPE: DNA
<213> ORGANISM: Artificial Sequence
<220> FEATURE:
<223> OTHER INFORMATION: Synthetic polynucleotide
```

<400> SEQUENCE: 175
ctcggtacca aattccagaa aagacacccg aaagggtgtt ttttcgtttt ggtcctcctt    60
ggccctccat ccttagatag cagataaaaa aaatccttag ctttcgctaa ggatgatttc   120
ttcataggca atacgatcgc atgtcc                                        146

<210> SEQ ID NO 176
<211> LENGTH: 129
<212> TYPE: DNA
<213> ORGANISM: Artificial Sequence
<220> FEATURE:
<223> OTHER INFORMATION: Synthetic polynucleotide

<400> SEQUENCE: 176
ccaggcatca ataaaacga aaggctcagt cgaaagactg ggcctttcgt tttatctgtt     60
gtttgtcggt gaacgctctc tactagagtc acactggctc accttcgggt gggcctttct  120
gcgtttata                                                           129

<210> SEQ ID NO 177
<211> LENGTH: 129
<212> TYPE: DNA
<213> ORGANISM: Artificial Sequence
<220> FEATURE:
<223> OTHER INFORMATION: Synthetic polynucleotide

<400> SEQUENCE: 177
ccaggcatca ataaaacga aaggctcagt cgaaagactg ggcctttcgt tttatctgtt     60
gtttgtcggt gaacgctctc tactagagtc acactggctc accttcgggt gggcctttct  120
gcgtttata                                                           129

<210> SEQ ID NO 178
<211> LENGTH: 168
<212> TYPE: DNA
<213> ORGANISM: Artificial Sequence
<220> FEATURE:
<223> OTHER INFORMATION: Synthetic polynucleotide

<400> SEQUENCE: 178
ggtcttgtcc actaccttgc agtaatgcgg tggacaggat cggcggtttt cttttctctt    60
ctcaatgact gaatagaaaa gacgaacatt aacgcatgag aaagccccg gaagatcacc   120 ttccggggc ttttttattg cgctacaaat gaaagtacat agaaatta                168

<210> SEQ ID NO 179
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 179
cagataaaaa aaatccttag ctttcgctaa ggatgatttc ttccttggcc ctccatcctt    60
agatagctcg gtaccaaatt ccagaaaaga cacccgaaag ggtgtttttt cgttttggtc  120
ctcataggca atacgatcgc atgtcc                                        146

<210> SEQ ID NO 180
<211> LENGTH: 128
<212> TYPE: DNA
<213> ORGANISM: Artificial Sequence
<220> FEATURE:

<223> OTHER INFORMATION: Synthetic polynucleotide

<400> SEQUENCE: 180

```
ccaggcatca ataaaacga aaggctcagt cgaaagactg ggcctttcgt tttatctgtt      60
gtttgtcggt gaacgctctc ctagcataac cccttggggc tctaaacgg gtcttgaggg     120 gttttttg                                                             128
```

<210> SEQ ID NO 181
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 181

```
ctcggtacca aattccagaa aagagacgct ttcgagcgtc ttttttcgtt ttggtcctcc     60
ttggccctcc atccttagat agagttaacc aaaaggggg gatttatct cccctttaat     120 ttttccttca taggcaatac gatcgcatgt cc                                  152
```

<210> SEQ ID NO 182
<211> LENGTH: 144
<212> TYPE: DNA
<213> ORGANISM: Artificial Sequence
<220> FEATURE:
<223> OTHER INFORMATION: Synthetic polynucleotide

<400> SEQUENCE: 182

```
cgcagatagc aaaaaagcgc ctttagggcg ctttttttaca ttggtggtcc ttggccctcc    60
atccttagat agaggcgact gacgaaacct cgctccggcg gggttttttg ttatctgcat    120
cataggcaat acgatcgcat gtcc                                           144
```

<210> SEQ ID NO 183
<211> LENGTH: 82
<212> TYPE: DNA
<213> ORGANISM: Artificial Sequence
<220> FEATURE:
<223> OTHER INFORMATION: Synthetic polynucleotide

<400> SEQUENCE: 183

```
tcggtcagtt tcacctgatt tacgtaaaaa cccgcttcgg cgggttttg cttttggagg      60 ggcagaaaga tgaatgactg tc                                              82
```

<210> SEQ ID NO 184
<211> LENGTH: 103
<212> TYPE: DNA
<213> ORGANISM: Artificial Sequence
<220> FEATURE:
<223> OTHER INFORMATION: Synthetic polynucleotide

<400> SEQUENCE: 184

```
gcccccggaa gatcaccttc cgggggcttt tttattggcg gccggctgat tgatcaggcg      60
gccggctgat tggcgcgtta cctggtagcg cgccattttg ttt                       103
```

<210> SEQ ID NO 185
<211> LENGTH: 83
<212> TYPE: DNA
<213> ORGANISM: Artificial Sequence
<220> FEATURE:
<223> OTHER INFORMATION: Synthetic polynucleotide

<400> SEQUENCE: 185
gtaatcgtta atccgcaaat aacgtaaaaa cccgcttcgg cgggtttttt tatgggggga    60
gtttagggaa agagcatttg tca    83

<210> SEQ ID NO 186
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 186
aaaaaaaaac cccgcccctg acagggcggg gttttttttt t    41

<210> SEQ ID NO 187
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 187
tccggcaatt aaaaaagcgg ctaaccacgc cgcttttttt acgtctgcat gactgaatag    60
aaaagacgaa cattaacgca tgagaaagcc cccggaagat caccttccgg gggcttttt    120 attgcgctcc ttggccctcc atccttagat ag    152

<210> SEQ ID NO 188
<211> LENGTH: 167
<212> TYPE: DNA
<213> ORGANISM: Artificial Sequence
<220> FEATURE:
<223> OTHER INFORMATION: Synthetic polynucleotide

<400> SEQUENCE: 188
ggaagaccat actggaaaca cagaaaaaag cccgcacctg acagtgcggg ctttttttt    60 cgaccaaagg tgactgaata gaaaagacga acattcgcag atagcaaaaa agcgccttta    120
gggcgctttt ttacattggt ggtcataggc aatacgatcg catgtcc    167

<210> SEQ ID NO 189
<211> LENGTH: 160
<212> TYPE: DNA
<213> ORGANISM: Artificial Sequence
<220> FEATURE:
<223> OTHER INFORMATION: Synthetic polynucleotide

<400> SEQUENCE: 189
tccggcaatt aaaaaagcgg ctaaccacgc cgcttttttt acgtctgcat ccttggccct    60
ccatccttag atagctcggt accaaattcc agaaaagagg cctcccgaaa gggggccttt    120
ttttcgtttt ggtcctcata ggcaatacga tcgcatgtcc    160

<210> SEQ ID NO 190
<211> LENGTH: 199
<212> TYPE: DNA
<213> ORGANISM: Artificial Sequence
<220> FEATURE:
<223> OTHER INFORMATION: Synthetic polynucleotide

<400> SEQUENCE: 190
ttcagccaaa aaacttaaga ccgccggtct tgtccactac cttgcagtaa tgcggtggac    60
aggatcggcg gttttctttt ctcttctcaa tacatgaaag tacatagaaa ttactcggta    120

```
ccaaattcca gaaaagaggc ctcccgaaag gggggccttt tttcgttttg gtcctcatag    180
gcaatacgat cgcatgtcc                                                199

<210> SEQ ID NO 191
<211> LENGTH: 189
<212> TYPE: DNA
<213> ORGANISM: Artificial Sequence
<220> FEATURE:
<223> OTHER INFORMATION: Synthetic polynucleotide

<400> SEQUENCE: 191
ttcagccaaa aaacttaaga ccgccggtct tgtccactac cttgcagtaa tgcggtggac    60
aggatcggcg gttttctttt ctcttctcaa tccttggccc tccatcctta gatagtccgg   120
caattaaaaa agcggctaac cacgccgctt tttttacgtc tgcatcatag gcaatacgat   180
cgcatgtcc                                                          189

<210> SEQ ID NO 192
<211> LENGTH: 164
<212> TYPE: DNA
<213> ORGANISM: Artificial Sequence
<220> FEATURE:
<223> OTHER INFORMATION: Synthetic polynucleotide

<400> SEQUENCE: 192
ctcggtacca aattccagaa aagaggcctc ccgaaagggg ggccttttt cgttttggtc     60 ctgactgaat agaaaagacg aacattaacg catgagaaag ccccggaag atcaccttcc    120 gggggctttt ttattgcgct ccttggccct ccatccttag atag                    164

<210> SEQ ID NO 193
<211> LENGTH: 159
<212> TYPE: DNA
<213> ORGANISM: Artificial Sequence
<220> FEATURE:
<223> OTHER INFORMATION: Synthetic polynucleotide

<400> SEQUENCE: 193
ctcggtacca aattccagaa aagaggcctc ccgaaagggg ggccttttt cgttttggtc     60 ctccttggcc ctccatcctt agatgtccgg caattaaaaa agcggctaac cacgccgctt   120
tttttacgtc tgcatcatag gcaatacgat cgcatgtcc                          159

<210> SEQ ID NO 194
<211> LENGTH: 197
<212> TYPE: DNA
<213> ORGANISM: Artificial Sequence
<220> FEATURE:
<223> OTHER INFORMATION: Synthetic polynucleotide

<400> SEQUENCE: 194
ctcggtacca aagacgaaca ataagacgct gaaaagcgtc ttttttcgtt ttggtcctac    60
aaatgaaagt acatagaaat tattcagcca aaaaacttaa gaccgccggt cttgtccact   120
accttgcagt aatgcggtgg acaggatcgg cggttttctt ttctcttctc aatccttggc   180
cctccatcct tagatag                                                  197

<210> SEQ ID NO 195
<211> LENGTH: 121
<212> TYPE: DNA
<213> ORGANISM: Artificial Sequence
<220> FEATURE:
<223> OTHER INFORMATION: Synthetic polynucleotide
```

<400> SEQUENCE: 195
gggaactgcc agacatcaaa taaaacaaaa ggctcagtcg aagactggg ccttttgttt    60 tatctgttgt ttgtcggtga acactctccc gactagtagc ggccgctgca gaaagaggag   120
a                                                                  121

<210> SEQ ID NO 196
<211> LENGTH: 152
<212> TYPE: DNA
<213> ORGANISM: Artificial Sequence
<220> FEATURE:
<223> OTHER INFORMATION: Synthetic polynucleotide

<400> SEQUENCE: 196
aacgcatgag aaagcccccg gaagatcacc ttccgggggc ttttttattg cgctcatagg    60
caatacgatc gcatgtcctc cggcaattaa aaaagcggct aaccacgccg cttttttttac   120 gtctgcatcc ttggccctcc atccttagat ag                                 152

<210> SEQ ID NO 197
<211> LENGTH: 91
<212> TYPE: DNA
<213> ORGANISM: Artificial Sequence
<220> FEATURE:
<223> OTHER INFORMATION: Synthetic polynucleotide

<400> SEQUENCE: 197
gggaactgcc agacatcaaa taaaacaaaa ggctcagtcg aagactggg ccttttgttt    60 tatctgttgt ttgtcggtga acactctccc g                                  91

<210> SEQ ID NO 198
<211> LENGTH: 195
<212> TYPE: DNA
<213> ORGANISM: Artificial Sequence
<220> FEATURE:
<223> OTHER INFORMATION: Synthetic polynucleotide

<400> SEQUENCE: 198
aaagcaagct gataaaccga tacaattaaa ggctcctttt ggagcctttt tttttggaga    60
ttttcaacat gaaaaaatta ttatttgatg atcagatagc ggcggggaac tgccagacat   120
caaataaaac aaaaggctca gtcggaagac tgggcctttt gttttatctg ttgtttgtcg   180
gtgaacactc tcccg                                                    195

<210> SEQ ID NO 199
<211> LENGTH: 164
<212> TYPE: DNA
<213> ORGANISM: Artificial Sequence
<220> FEATURE:
<223> OTHER INFORMATION: Synthetic polynucleotide

<400> SEQUENCE: 199
aacgcatgag aaagcccccg gaagatcacc ttccgggggc ttttttattg cgctccttgg    60
ccctccatcc ttagatagct cggtaccaaa ttccagaaaa gaggcctccc gaaagggggg   120
ccttttttcg ttttggtcct cataggcaat acgatcgcat gtcc                    164

<210> SEQ ID NO 200
<211> LENGTH: 193
<212> TYPE: DNA
<213> ORGANISM: Artificial Sequence
<220> FEATURE:

<223> OTHER INFORMATION: Synthetic polynucleotide

<400> SEQUENCE: 200
aacgcatgag aaagcccccg aagatcacc ttccggggc ttttttattg cgctccttgg    60
ccctccatcc ttagatagtt cagccaaaaa acttaagacc gccggtcttg tccactacct  120
tgcagtaatg cggtggacag gatcggcggt tttcttttct cttctcaatc ataggcaata  180
cgatcgcatg tcc                                                     193

<210> SEQ ID NO 201
<211> LENGTH: 67
<212> TYPE: DNA
<213> ORGANISM: Artificial Sequence
<220> FEATURE:
<223> OTHER INFORMATION: Synthetic polynucleotide

<400> SEQUENCE: 201
cctaggacct gtaggatcgt acaggtttac gcaagaaaat ggtttgttac tttcgaataa   60
atctaga                                                             67

<210> SEQ ID NO 202
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 202
cggtggaatc cctatcagtg atagagattg acatccctat cagtgataga tataatgagc   60
actctaga                                                            68

<210> SEQ ID NO 203
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 203
aacaaacaga caatctggtc tgtttgtatt atggaaaatt tttctgtata atagattcaa   60
caaacagaca atctggtctg tttgtattat                                    90

<210> SEQ ID NO 204
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 204
aaaaagagtt tgacatgata cgaaacgtac cgtatcgtta aggttactag agtctaga     58

<210> SEQ ID NO 205
<211> LENGTH: 116
<212> TYPE: DNA
<213> ORGANISM: Artificial Sequence
<220> FEATURE:
<223> OTHER INFORMATION: Synthetic polynucleotide

<400> SEQUENCE: 205
ggggcctcgc ttgggttatt gctggtgccc ggccgggcgc aatattcatg ttgatgattt   60
attatatatc gagtggtgta tttatttata ttgtttgctc cgttaccgtt attaac      116

<210> SEQ ID NO 206
<211> LENGTH: 753
<212> TYPE: DNA
<213> ORGANISM: Artificial Sequence
<220> FEATURE:
<223> OTHER INFORMATION: Synthetic polynucleotide

<400> SEQUENCE: 206

| | |
|---|---|
| atgaaaaaca taaatgccga cgacacatac agaataatta ataaaattaa agcttgtaga | 60 |
| agcaataatg atattaatca atgcttatct gatatgacta aaatggtaca ttgtgaatat | 120 |
| tatttactcg cgatcattta tcctcattct atggttaaat ctgatatttc aatcctagat | 180 |
| aattaccccta aaaaatggag gcaatattat gatgacgcta atttaataaa atatgatcct | 240 |
| atagtagatt attctaactc caatcattca ccaattaatt ggaatatatt tgaaaacaat | 300 |
| gctgtaaata aaaaatctcc aaatgtaatt aaagaagcga aacatcagg tcttatcact | 360 |
| gggtttagtt tccctattca tacggctaac aatggcttcg gaatgcttag ttttgcacat | 420 |
| tcagaaaaag acaactatat agatagttta ttttttacatg cgtgtatgaa cataccatta | 480 |
| attgttcctt ctctagttga taattatcga aaaataaata tagcaaataa taaatcaaac | 540 |
| aacgatttaa ccaaaagaga aaaagaatgt ttagcgtggg catgcgaagg aaaaagctct | 600 |
| tgggatattt caaaaatatt aggttgcagt gagcgtactg tcactttcca tttaaccaat | 660 |
| gcgcaaatga aactcaatac aacaaaccgc tgccaaagta tttctaaagc aattttaaca | 720 |
| ggagcaattg attgcccata ctttaaaaat taa | 753 |

<210> SEQ ID NO 207
<211> LENGTH: 624
<212> TYPE: DNA
<213> ORGANISM: Artificial Sequence
<220> FEATURE:
<223> OTHER INFORMATION: Synthetic polynucleotide

<400> SEQUENCE: 207

| | |
|---|---|
| atgtccagat tagataaaag taaagtgatt aacagcgcat tagagctgct taatgaggtc | 60 |
| ggaatcgaag gtttaacaac ccgtaaactc gcccagaagc taggtgtaga gcagcctaca | 120 |
| ttgtattggc atgtaaaaaa taagcgggct ttgctcgacg ccttagccat tgagatgtta | 180 |
| gataggcacc atactcactt tgccctttta gaagggaaa gctggcaaga ttttttacgt | 240 |
| aataacgcta aaagttttag atgtgcttta ctaagtcatc gcgatggagc aaaagtacat | 300 |
| ttaggtacac ggcctacaga aaaacagtat gaaactctcg aaaatcaatt agcctttta | 360 |
| tgccaacaag gttttcact agagaatgca ttatatgcac tcagcgctgt ggggcatttt | 420 |
| actttaggtt gcgtattgga agatcaagag catcaagtcg ctaaagaaga agggaaaca | 480 |
| cctactactg atagtatgcc gccattatta cgacaagcta tcgaattatt tgatcaccaa | 540 |
| ggtgcagagc cagccttctt attcggcctt gaattgatca tatgcggatt agaaaaacaa | 600 |
| cttaaatgtg aaagtgggtc ctaa | 624 |

<210> SEQ ID NO 208
<211> LENGTH: 612
<212> TYPE: DNA
<213> ORGANISM: Artificial Sequence
<220> FEATURE:
<223> OTHER INFORMATION: Synthetic polynucleotide

<400> SEQUENCE: 208

| | |
|---|---|
| atgagcccga aacgtcgtac ccaggcagaa cgtgcaatgg aaacccaggg taaactgatt | 60 |
| gcagcagcac tgggtgttct gcgtgaaaaa ggttatgcag ttttcgtat tgcagatgtt | 120 |
| ccgggtgcag ccggtgttag ccgtggtgca cagagccatc attttccgac caaactggaa | 180 |
| ctgctgctgg caacctttga atggctgtat gagcagatta ccgaacgtag ccgtgcacgt | 240 |
| ctggcaaaac tgaaaccgga agatgatgtt attcagcaga tgctggatga tgcagcagaa | 300 |
| tttttctgg atgatgattt tagcatcagc ctggatctga ttgttgcagc agatcgtgat | 360 |
| ccggcactgc gtgaaggtat tcagcgtacc gttgaacgta atcgttttgt tgttgaagat | 420 |
| atgtggctgg gtgtgctggt gagccgtggt ctgagccgtg atgatgccga agatattctg | 480 |
| tggctgattt ttaacagcgt tcgtggtctg gcagttcgta gcctgtggca gaaagataaa | 540 |
| gaacgttttg aacgtgtgcg taatagcacc ctggaaattg cacgtgaacg ttatgcaaaa | 600 |
| ttcaaacgtt ga | 612 |

<210> SEQ ID NO 209
<211> LENGTH: 603
<212> TYPE: DNA
<213> ORGANISM: Artificial Sequence
<220> FEATURE:
<223> OTHER INFORMATION: Synthetic polynucleotide

<400> SEQUENCE: 209

| | |
|---|---|
| atggcacgta ccccgagccg tagcagcatt ggtagcctgc gtagtccgca tacccataaa | 60 |
| gcaattctga ccagcaccat tgaaatcctg aaagaatgtg gttatagcgg tctgagcatt | 120 |
| gaaagcgttg cacgtcgtgc cggtgcaagc aaaccgacca tttatcgttg gtggaccaat | 180 |
| aaagcagcac tgattgccga agtgtatgaa atgaaagcg aacaggtgcg taaatttccg | 240 |
| gatctgggta gctttaaagc cgatctggat tttctgctgc gtaatctgtg aaagtttgg | 300 |
| cgtgaaacca tttgtggtga agcatttcgt tgtgttattg cagaagcaca gctggaccct | 360 |
| gcaaccctga cccagctgaa agatcagttt atggaacgtc gtcgtgagat gccgaaaaaa | 420 |
| ctggttgaaa atgccattag caatggtgaa ctgccgaaag ataccaatcg tgaactgctg | 480 |
| ctggatatga ttttggttt tgttggtat cgcctgctga ccgaacagct gaccgttgaa | 540 |
| caggatattg aagaatttac cttcctgctg attaatggtg tttgtccggg tacacagcgt | 600 |
| taa | 603 |

<210> SEQ ID NO 210
<211> LENGTH: 906
<212> TYPE: DNA
<213> ORGANISM: Artificial Sequence
<220> FEATURE:
<223> OTHER INFORMATION: Synthetic polynucleotide

<400> SEQUENCE: 210

| | |
|---|---|
| atggaactgc gtgacctgga tttaaacctg ctggtggtgt tcaaccagtt gctggtcgac | 60 |
| agacgcgtct ctgtcactgc ggagaacctg ggcctgaccc agcctgccgt gagcaatgcg | 120 |
| ctgaaacgcc tgcgcaccct gctacaggac ccactcttcg tgcgcacaca tcagggaatg | 180 |
| gaacccacac cctatgccgc gcatctggcc gagcacgtca cttcggccat gcacgcactg | 240 |
| cgcaacgccc tacagcacca tgaaagcttc gatccgctga ccagcgagcg taccttcacc | 300 |
| ctggccatga ccgacattgg cgagatctac ttcatgccgc ggctgatgga tgcgctggct | 360 |
| caccaggccc ccaattgcgt gatcagtacg gtgcgcgaca gttcgatgag cctgatgcag | 420 |
| gcccttgcaga acggaaccgt ggacttggcc gtgggcctgc ttcccaatct gcaaactggc | 480 |

```
ttctttcagc gccggctgct ccagaatcac tacgtgtgcc tatgtcgcaa ggaccatcca      540
gtcacccgcg aacccctgac tctggagcgc ttctgttcct acggccacgt gcgtgtcatc      600
gccgctggca ccggccacgg cgaggtggac acgtacatga cacgggtcgg catccggcgc      660
gacatccgtc tggaagtgcc gcacttcgcc gccgttggcc acatcctcca gcgcaccgat      720
ctgctcgcca ctgtgccgat atgtttagcc gactgctgcg tagagcccct cggcctaagc      780
gccttgccgc acccagtcgt cttgcctgaa atagccatca acatgttctg gcatgcgaag      840
taccacaagg acctagccaa tatttggttg cggcaactga tgtttgacct gtttacggat      900
tgataa                                                                 906

<210> SEQ ID NO 211
<211> LENGTH: 90
<212> TYPE: DNA
<213> ORGANISM: Artificial Sequence
<220> FEATURE:
<223> OTHER INFORMATION: Synthetic polynucleotide

<400> SEQUENCE: 211
tcaatgtatt gatgccgtcc atatcatgaa tcaaaacaat ccatttgatc aatatcaagc       60
tcactcttaa gcttcactca tccgctgcat                                        90

<210> SEQ ID NO 212
<211> LENGTH: 930
<212> TYPE: DNA
<213> ORGANISM: Artificial Sequence
<220> FEATURE:
<223> OTHER INFORMATION: Synthetic polynucleotide

<400> SEQUENCE: 212
atgcgtttca acaagctcga cctcaatctt ctggtcgccc tggatgcact gctcacggag       60
atgagcatca gccgcgccgc cgaaaagatc catctgagcc agtcggccat gagcaatgcc      120
ctggcgcggc tgcgcgagta tttcgatgat gaattgctga tccaggtggg ccggcgcatg      180
gagcccacgc cgcgcgccga ggtgctcaag gatgcggtgc atgatgtgct gcggcgtatc      240
gatggctcca tcgcggcgct gccggccttc gtgccggccg agtccacgcg cgagtttcgc      300
atctcggttt cggactttac gctctccgtc ctcatccccc gggtgctggc gcgcgcgcac      360
gccgagggca agcacatccg ctttgccctg atgccgcagg tgcaagaccc gacccgctcg      420
ctggatcggg ccgaggtgga cctgctggtc ttgccgcagg aattctgcac gcccgatcat      480
cctgccgaag aggtcttccg cgaacggcat gtctgcgtgg tctggcgcga cagtgcgctg      540
gcgcaaggcg agctgacgct ggaacgctac atggcctcag gccatgtggt gatggtgccg      600
cctggggcca atgcgtcgtc ggtggaggcg tggatggcca ggaagctggg ctttgcgcgc      660
cgggtggaag tgaccagctt cagcttcgct tctgcgctgg cgctggtaca ggggacggac      720
cgcatcgcca cggtgcatgc ccggctgcgc agctgctgg ctccgcaatg gccggtggtg      780
atcaaggaga gtccgctgtc gctgggcgag atgcggcaga tgatgcagtg gcatcgctac      840
cgcagcaatg atcctggcat ccagtggctg cgtcgggtgt ttctggagag tgcgcaggag      900
atggatgcgg cgctgccagg catctgctga                                       930

<210> SEQ ID NO 213
<211> LENGTH: 286
<212> TYPE: DNA
<213> ORGANISM: Artificial Sequence
<220> FEATURE:
```

<223> OTHER INFORMATION: Synthetic polynucleotide

<400> SEQUENCE: 213

```
cagacattgc cgtcactgcg tcttttactg gctcttctcg ctaaccaaac cggtaacccc      60
gcttattaaa agcattctgt aacaaagcgg gaccaaagcc atgacaaaaa cgcgtaacaa     120
aagtgtctat aatcacggca gaaaagtcca cattgattat ttgcacggcg tcacactttg     180
ctatgccata gcattttat ccataagatt agcggatcct acctgacgct ttttatcgca     240
actctctata ttttctccat acccgttttt ttgggctagc gaattc                    286
```

<210> SEQ ID NO 214
<211> LENGTH: 930
<212> TYPE: DNA
<213> ORGANISM: Artificial Sequence
<220> FEATURE:
<223> OTHER INFORMATION: Synthetic polynucleotide

<400> SEQUENCE: 214

```
atgcaatatg gacaattggt ttcttctctg aatggcggga gtatgaaaag tatggctgaa      60
gcgcaaaatg atcccctgct gccgggatac tcgtttaatg cccatctggt ggcgggttta     120
acgccgattg aggccaacgg ttatctcgat tttttatcg accgaccgct gggaatgaaa     180
ggttatattc tcaatctcac cattcgcggt caggggtgg tgaaaaatca gggacgagaa     240
tttgtttgcc gaccgggtga tattttgctg ttcccgccag gagagattca tcactacggt     300
cgtcatccgg aggctcgcga atggtatcac cagtgggttt actttcgtcc gcgcgcctac     360
tggcatgaat ggcttaactg gccgtcaata tttgccaata cggggttctt tcgcccggat     420
gaagcgcacc agccgcattt cagcgacctg tttgggcaaa tcattaacgc cgggcaaggg     480
gaagggcgct attcggagct gctggcgata aatctgcttg agcaattgtt actgcggcgc     540
atggaagcga ttaacgagtc gctccatcca ccgatggata tcgggtacg cgaggcttgt     600
cagtacatca gcgatcacct ggcagacagc aattttgata tcgccagcgt cgcacagcat     660
gtttgcttgt cgccgtcgcg tctgtcacat cttttccgcc agcagttagg gattagcgtc     720
ttaagctggc gcgaggacca acgtatcagc caggcgaagc tgcttttgag caccacccgg     780
atgcctatcg ccaccgtcgg tcgcaatgtt ggttttgacg atcaactcta tttctcgcgg     840
gtatttaaaa aatgcaccgg ggccagcccg agcgagttcc gtgccggttg tgaagaaaaa     900
gtgaatgatg tagccgtcaa gttgtcataa                                     930
```

<210> SEQ ID NO 215
<211> LENGTH: 1419
<212> TYPE: DNA
<213> ORGANISM: Artificial Sequence
<220> FEATURE:
<223> OTHER INFORMATION: Synthetic polynucleotide

<400> SEQUENCE: 215

```
atggttacta tcaatacgga atctgcttta acgccacgtt ctttgcggga tacgcggcgt      60
atgaatatgt ttgtttcggt agctgctgcg gtcgcaggat tgttatttgg tcttgatatc     120
ggcgtaatcg ccggagcgtt gccgttcatt accgatcact ttgtgctgac cagtcgtttg     180
caggaatggg tggttagtag catgatgctc ggtgcagcaa ttggtgcgct gtttaatggt     240
tggctgtcgt tccgcctggg gcgtaaatac agcctgatgg cggggggccat cctgtttgta     300
ctcggttcta tagggtccgc ttttgcgacc agcgtagaga tgttaatcgc cgctcgtgtg     360
gtgctgggca ttgctgtcgg gatcgcgtct tacaccgctc ctctgtatct ttctgaaatg     420
```

```
gcaagtgaaa acgttcgcgg taagatgatc agtatgtacc agttgatggt cacactcggc    480
atcgtgctgg cgtttttatc cgatacagcg ttcagttata gcggtaactg gcgcgcaatg    540
ttgggggttc ttgctttacc agcagttctg ctgattattc tggtagtctt cctgccaaat    600
agcccgcgct ggctggcgga aaaggggcgt catattgagg cggaagaagt attgcgtatg    660
ctgcgcgata cgtcggaaaa agcgcgagaa gaactcaacg aaattcgtga aagcctgaag    720
ttaaaacagg gcggttgggc actgtttaag atcaaccgta acgtccgtcg tgctgtgttt    780
ctcggtatgt tgttgcaggc gatgcagcag tttaccggta tgaacatcat catgtactac    840
gcgccgcgta tcttcaaaat ggcgggcttt acgaccacag aacaacagat gattgcgact    900
ctggtcgtag gctgaccctt tatgttcgcc acctttattg cggtgtttac ggtagataaa    960
gcagggcgta aaccggctct gaaaattggt ttcagcgtga tggcgttagg cactctggtg   1020
ctgggctatt gcctgatgca gtttgataac ggtacggctt ccagtggctt gtcctggctc   1080
tctgttggca tgacgatgat gtgtattgcc ggttatgcga tgagcgccgc gccagtggtg   1140
tggatcctgt gctctgaaat tcagccgctg aaatgccgcg atttcggtat acctgttcg    1200 accaccacga actgggtgtc gaatatgatt atcggcgcga ccttcctgac actgcttgat   1260
agcattggcg ctgccggtac gttctggctc tacactgcgc tgaacattgc gtttgtgggc   1320
attactttct ggctcattcc ggaaaccaaa aatgtcacgc tggaacatat cgaacgcaaa   1380
ctgatggcag gcgagaagtt gagaaatatc ggcgtctga                          1419
```

<210> SEQ ID NO 216
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 216

```
ctcgagtgtt gacaattaat catcggctcg tataatgtgt ggaattgtga gcgctcacaa     60
tttcacacat ctaga                                                     75
```

<210> SEQ ID NO 217
<211> LENGTH: 221
<212> TYPE: DNA
<213> ORGANISM: Artificial Sequence
<220> FEATURE:
<223> OTHER INFORMATION: Synthetic polynucleotide

<400> SEQUENCE: 217

```
aacaaataca catgggcgca tgcctattac tgcccttgcg atatggaagg caagcttta     60 gtaacaatag aaaactgggt cctactctcg aagaatgcac tgcggcggtc acgtcaacac    120
gtgctgcacc gttgagaatg aatgctgggc agattgccag cggcgtcatt tcggctgtc    180 ccgtcctcac ggttttgcgc tgcatcgcaa gagattggga a                        221
```

<210> SEQ ID NO 218
<211> LENGTH: 849
<212> TYPE: DNA
<213> ORGANISM: Artificial Sequence
<220> FEATURE:
<223> OTHER INFORMATION: Synthetic polynucleotide

<400> SEQUENCE: 218

```
atgacgtcag cagcgaatct ggtgaggatc acgcagcccg cgatcagccg gctgatcagg     60
```

| | |
|---|---|
| gatctcgaag aggaaattgg gatcagcctc ttcgaaagaa cgggcaaccg gttacgtcct | 120 |
| acgcgggagg ccggtattct gttcaaggaa gtgtcgcgac atttcaacgg gattcagcac | 180 |
| atcgacaaag tcgcggctga actgaagaag tctcatatgg ggtccctaag ggtcgcctgt | 240 |
| tatacagcgc cagctctgag ttttatgtcc ggcgtcattc agacgttcat cgccgatcgg | 300 |
| cccgacgtgt cggtctacct cgacacagtt ccttcccaga cggtcctcga attggtctcg | 360 |
| ctccagcact acgatctcgg aatatcgata ttggctggcg actatcctgg tctcaccacc | 420 |
| gaacctgtcc cttcctttcg tgcggtctgc ctgctgccgc cggggcatcg tctcgaagac | 480 |
| aaggaaactg ttcatgcgac ggaccttgaa ggagagtcat tgatttgcct ctctccagtg | 540 |
| agccttctac ggatgcaaac ggacgccgca ctggacagct gcggcgtcca ctgtaatcgc | 600 |
| aggatagaaa gtagtctggc gctgaatctc tgcgatctgg taagcagggg aatgggggtt | 660 |
| ggtatcgtcg acccctccac tgccgactac tacagtgcaa atccggttat tcagcgctcc | 720 |
| tttgatccgg ttgtcccctc ccattttgct atagttcttc cgaccgacag cccaccgccg | 780 |
| cgcttggtta gcgagttccg ggcagcgttg cttgatgctt tgaaagcctt gccctatgaa | 840 |
| accatttga | 849 |

<210> SEQ ID NO 219
<211> LENGTH: 119
<212> TYPE: DNA
<213> ORGANISM: Artificial Sequence
<220> FEATURE:
<223> OTHER INFORMATION: Synthetic polynucleotide

<400> SEQUENCE: 219

| | |
|---|---|
| aaacgcacca taacatctgc ttattcttgc ccggtcatta tgaatttgac cgaatgcata | 60 |
| tcgaatgtaa agctcaccct ataaatcaca actcttccgg gccaaccggg atcagacgt | 119 |

<210> SEQ ID NO 220
<211> LENGTH: 897
<212> TYPE: DNA
<213> ORGANISM: Artificial Sequence
<220> FEATURE:
<223> OTHER INFORMATION: Synthetic polynucleotide

<400> SEQUENCE: 220

| | |
|---|---|
| atgaatctca ggcaggtcga ggcgttccgg gcagtcatgc tgacggggca aatgacggcg | 60 |
| gcggctgaac taatgctggt gactcagccg gccatcagtc gcctaatcaa ggactttgaa | 120 |
| caggcgacaa aactgcagct cttcgagagg cgtgggaacc atattatccc gacacaggag | 180 |
| gcaaagacgc tgtggaaaga ggtcgatcgg gcgttcgtcg ggcttaatca tataggcaac | 240 |
| ctggctgccg acatcggcag gcaggcagcg gggacgctcc gcattgctgc aatgcctgct | 300 |
| ctggcaaacg gcctcttgcc gcggtttctt gctcagttca tccgtgacag accaaatctc | 360 |
| caggtctccc taatgggact gccctcaagc atggtcatgg aagccgttgc gtccggcagg | 420 |
| gccgacatcg gttatgccga tggcccacag gagcgccaag gttttctaat cgaaacccgg | 480 |
| tcgcttcccg ctgttgtcgc tgtcccgatg ggacatcgac ttgctggcct tgaccgtgtc | 540 |
| acgccacagg accttgccgg tgagcgtatt ataaaacagg agactggcac tctcttcgcc | 600 |
| atgcgggtag aggtggcgat tggtggtatt caacgccggc cgtcaattga agtgagcctg | 660 |
| tcgcatactg cgctaagtct cgtccgcgaa ggcgccggga tcgcaattat cgatccagcc | 720 |
| gcggcgatcg agttcacgga caggatcgta ctgcgaccgt tctcgatctt cattgacgcc | 780 |
| ggattcctcg aagtccggtc agcaattggc gctccctcaa ccatcgtcga tcgtttcaca | 840 |

```
accgaattct ggaggtttca tgatgacttg atgaagcaga acggcctaat ggagtaa      897
```

<210> SEQ ID NO 221
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 221

```
agcgcgggtg agagggattc gttaccaata gacaattgat tggacgttca atataatgct    60
agc                                                                  63
```

<210> SEQ ID NO 222
<211> LENGTH: 226
<212> TYPE: DNA
<213> ORGANISM: Artificial Sequence
<220> FEATURE:
<223> OTHER INFORMATION: Synthetic polynucleotide

<400> SEQUENCE: 222

```
ccctttgtgc gtccaaacgg acgcacggcg ctctaaagcg ggtcgcgatc tttcagattc    60
gctcctcgcg ctttcagtct tgttttggc gcatgtcgtt atcgcaaaac cgctgcacac   120
ttttgcgcga catgctctga tcccctcat ctgggggggc ctatctgagg gaatttccga   180
tccggctcgc ctgaaccatt ctgctttcca cgaacttgaa aacgct                 226
```

<210> SEQ ID NO 223
<211> LENGTH: 93
<212> TYPE: DNA
<213> ORGANISM: Artificial Sequence
<220> FEATURE:
<223> OTHER INFORMATION: Synthetic polynucleotide

<400> SEQUENCE: 223

```
ttttgttcga ttatcgaaca aattattgaa atatcgaaca aaacctctaa actactgtgg    60
cactgaatca aaaaattata aaccctgatc aga                                 93
```

<210> SEQ ID NO 224
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 224

```
cacccagcag tatttacaaa caaccatgaa tgtaagtata ttccttagca a             51
```

<210> SEQ ID NO 225
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 225

```
attggatcca attgacagct agctcagtcc taggtaccat tggatccaat               50
```

<210> SEQ ID NO 226
<211> LENGTH: 54
<212> TYPE: DNA
<213> ORGANISM: Unknown
<220> FEATURE:

<223> OTHER INFORMATION: R. sp. IRBG74

<400> SEQUENCE: 226
atttcacaca tctagagcta atcatctcgt actaaagagg agaaattaac catg    54

<210> SEQ ID NO 227
<211> LENGTH: 49
<212> TYPE: DNA
<213> ORGANISM: Unknown
<220> FEATURE:
<223> OTHER INFORMATION: R. sp. IRBG74

<400> SEQUENCE: 227
atttcacaca tctagagcta atcatcgcgt actcaggagg caagtaatg    49

<210> SEQ ID NO 228
<211> LENGTH: 40
<212> TYPE: DNA
<213> ORGANISM: Unknown
<220> FEATURE:
<223> OTHER INFORMATION: R. sp. IRBG74

<400> SEQUENCE: 228
atttcacaca tctagaatta aagaggagaa attaaccatg    40

<210> SEQ ID NO 229
<211> LENGTH: 54
<212> TYPE: DNA
<213> ORGANISM: Unknown
<220> FEATURE:
<223> OTHER INFORMATION: R. sp. IRBG74

<400> SEQUENCE: 229
taacaatttc acacatctag agctaatcat ctcgtactaa agaggcaagt aatg    54

<210> SEQ ID NO 230
<211> LENGTH: 54
<212> TYPE: DNA
<213> ORGANISM: Unknown
<220> FEATURE:
<223> OTHER INFORMATION: R. sp. IRBG74

<400> SEQUENCE: 230
taacaatttc acacatctag agctaatcat cgcgtactaa ggaggcaagt aatg    54

<210> SEQ ID NO 231
<211> LENGTH: 54
<212> TYPE: DNA
<213> ORGANISM: Unknown
<220> FEATURE:
<223> OTHER INFORMATION: R. sp. IRBG74

<400> SEQUENCE: 231
taacaatttc acacatctag agctaatcat cgcgtactca agaggcaagt aatg    54

<210> SEQ ID NO 232
<211> LENGTH: 54
<212> TYPE: DNA
<213> ORGANISM: Unknown
<220> FEATURE:
<223> OTHER INFORMATION: R. sp. IRBG74

<400> SEQUENCE: 232
taacaatttc acacatctag agctaatctt cgcgtactaa agaggcaagt aatg    54

```
<210> SEQ ID NO 233
<211> LENGTH: 54
<212> TYPE: DNA
<213> ORGANISM: Unknown
<220> FEATURE:
<223> OTHER INFORMATION: R. sp. IRBG74

<400> SEQUENCE: 233
taacaatttc acacatctag agctaatcat ctcgtactca ggaggcaagt aatg       54

<210> SEQ ID NO 234
<211> LENGTH: 54
<212> TYPE: DNA
<213> ORGANISM: Unknown
<220> FEATURE:
<223> OTHER INFORMATION: R. sp. IRBG74

<400> SEQUENCE: 234
taacaatttc acacatctag agctaatcat ctcgtactaa tgaggcaagt aatg       54

<210> SEQ ID NO 235
<211> LENGTH: 54
<212> TYPE: DNA
<213> ORGANISM: Unknown
<220> FEATURE:
<223> OTHER INFORMATION: R. sp. IRBG74

<400> SEQUENCE: 235
taacaatttc acacatctag agctaatcat cgcgtactaa tgaggcaagt aatg       54

<210> SEQ ID NO 236
<211> LENGTH: 54
<212> TYPE: DNA
<213> ORGANISM: Unknown
<220> FEATURE:
<223> OTHER INFORMATION: R. sp. IRBG74

<400> SEQUENCE: 236
taacaatttc acacatctag agctaatcat cgcgtactca cgaggcaagt aatg       54

<210> SEQ ID NO 237
<211> LENGTH: 54
<212> TYPE: DNA
<213> ORGANISM: Unknown
<220> FEATURE:
<223> OTHER INFORMATION: R. sp. IRBG74

<400> SEQUENCE: 237
taacaatttc acacatctag agctaatcat cgcgtactaa aaaggcaagt aatg       54

<210> SEQ ID NO 238
<211> LENGTH: 54
<212> TYPE: DNA
<213> ORGANISM: Unknown
<220> FEATURE:
<223> OTHER INFORMATION: R. sp. IRBG74

<400> SEQUENCE: 238
taacaatttc acacatctag agctaatctt cgcgtactaa aaaggcaagt aatg       54

<210> SEQ ID NO 239
<211> LENGTH: 54
<212> TYPE: DNA
<213> ORGANISM: Unknown
<220> FEATURE:
<223> OTHER INFORMATION: R. sp. IRBG74
```

<400> SEQUENCE: 239
taacaatttc acacatctag agctaatctt cgcgtactaa gaaggcaagt aatg   54

<210> SEQ ID NO 240
<211> LENGTH: 54
<212> TYPE: DNA
<213> ORGANISM: Unknown
<220> FEATURE:
<223> OTHER INFORMATION: R. sp. IRBG74

<400> SEQUENCE: 240
taacaatttc acacatctag agctaatcat ctcgtactaa ataggcaagt aatg   54

<210> SEQ ID NO 241
<211> LENGTH: 54
<212> TYPE: DNA
<213> ORGANISM: Unknown
<220> FEATURE:
<223> OTHER INFORMATION: R. sp. IRBG74

<400> SEQUENCE: 241
taacaatttc acacatctag agctaatcat ctcgtactaa taaggcaagt aatg   54

<210> SEQ ID NO 242
<211> LENGTH: 54
<212> TYPE: DNA
<213> ORGANISM: Unknown
<220> FEATURE:
<223> OTHER INFORMATION: R. sp. IRBG74

<400> SEQUENCE: 242
taacaatttc acacatctag agctaatctt ctcgtactaa agaggcaagt aatg   54

<210> SEQ ID NO 243
<211> LENGTH: 54
<212> TYPE: DNA
<213> ORGANISM: Unknown
<220> FEATURE:
<223> OTHER INFORMATION: R. sp. IRBG74

<400> SEQUENCE: 243
taacaatttc acacatctag agctaatcat cgcgtactca ataggccagt aatg   54

<210> SEQ ID NO 244
<211> LENGTH: 54
<212> TYPE: DNA
<213> ORGANISM: Unknown
<220> FEATURE:
<223> OTHER INFORMATION: R. sp. IRBG74

<400> SEQUENCE: 244
taacaatttc acacatctag agctaatcat cgcgtactaa gtaggcaagt aatg   54

<210> SEQ ID NO 245
<211> LENGTH: 54
<212> TYPE: DNA
<213> ORGANISM: Unknown
<220> FEATURE:
<223> OTHER INFORMATION: R. sp. IRBG74

<400> SEQUENCE: 245
taacaatttc acacatctag agctaatcat ctcgtactaa cgaggcaagt aatg   54

<210> SEQ ID NO 246
<211> LENGTH: 54

-continued

<212> TYPE: DNA
<213> ORGANISM: Unknown
<220> FEATURE:
<223> OTHER INFORMATION: R. sp. IRBG74

<400> SEQUENCE: 246
taacaatttc acacatctag agctaatcat cgcgtactca gcaggcaagt aatg    54

<210> SEQ ID NO 247
<211> LENGTH: 54
<212> TYPE: DNA
<213> ORGANISM: Unknown
<220> FEATURE:
<223> OTHER INFORMATION: R. sp. IRBG74

<400> SEQUENCE: 247
taacaatttc acacatctag agctaatctt cgcgtactaa gtaggcaagt aatg    54

<210> SEQ ID NO 248
<211> LENGTH: 54
<212> TYPE: DNA
<213> ORGANISM: Unknown
<220> FEATURE:
<223> OTHER INFORMATION: R. sp. IRBG74

<400> SEQUENCE: 248
taacaatttc acacatctag agctaatctt cgcgtactaa ttaggcaagt aatg    54

<210> SEQ ID NO 249
<211> LENGTH: 54
<212> TYPE: DNA
<213> ORGANISM: Unknown
<220> FEATURE:
<223> OTHER INFORMATION: R. sp. IRBG74

<400> SEQUENCE: 249
taacaatttc acacatctag agctaatctt ctcgtactaa caaggcaagt aatg    54

<210> SEQ ID NO 250
<211> LENGTH: 54
<212> TYPE: DNA
<213> ORGANISM: Unknown
<220> FEATURE:
<223> OTHER INFORMATION: R. sp. IRBG74

<400> SEQUENCE: 250
taacaatttc acacatctag agctaatcat ctcgtactca ataggcaagt aatg    54

<210> SEQ ID NO 251
<211> LENGTH: 54
<212> TYPE: DNA
<213> ORGANISM: Unknown
<220> FEATURE:
<223> OTHER INFORMATION: R. sp. IRBG74

<400> SEQUENCE: 251
taacaatttc acacatctag agctaatcat ctcgtactaa gcacgcaagt aatg    54

<210> SEQ ID NO 252
<211> LENGTH: 54
<212> TYPE: DNA
<213> ORGANISM: Unknown
<220> FEATURE:
<223> OTHER INFORMATION: R. sp. IRBG74

<400> SEQUENCE: 252

-continued

```
taacaatttc acacatctag agctaatcat cgcgtactaa ctacgcaagt aatg        54
```

<210> SEQ ID NO 253
<211> LENGTH: 54
<212> TYPE: DNA
<213> ORGANISM: Unknown
<220> FEATURE:
<223> OTHER INFORMATION: R. sp. IRBG74

<400> SEQUENCE: 253

```
taacaatttc acacatctag agctaatctt cgcgtactaa gaacgcaagt aatg        54
```

<210> SEQ ID NO 254
<211> LENGTH: 54
<212> TYPE: DNA
<213> ORGANISM: Unknown
<220> FEATURE:
<223> OTHER INFORMATION: R. sp. IRBG74

<400> SEQUENCE: 254

```
taacaatttc acacatctag agctaatctt cgcgtactaa aaacgcaagt aatg        54
```

<210> SEQ ID NO 255
<211> LENGTH: 54
<212> TYPE: DNA
<213> ORGANISM: Unknown
<220> FEATURE:
<223> OTHER INFORMATION: R. sp. IRBG74

<400> SEQUENCE: 255

```
taacaatttc acacatctag agctaatctt cgcgtactaa caacgcaagt aatg        54
```

<210> SEQ ID NO 256
<211> LENGTH: 54
<212> TYPE: DNA
<213> ORGANISM: Unknown
<220> FEATURE:
<223> OTHER INFORMATION: R. sp. IRBG74

<400> SEQUENCE: 256

```
taacaatttc acacatctag agctaatctt ctcgtactca tgacgcaagt aatg        54
```

<210> SEQ ID NO 257
<211> LENGTH: 40
<212> TYPE: DNA
<213> ORGANISM: Unknown
<220> FEATURE:
<223> OTHER INFORMATION: R. sp. IRBG74

<400> SEQUENCE: 257

```
atttcacaca tctagaatta aagagaagaa attaaccatg                        40
```

<210> SEQ ID NO 258
<211> LENGTH: 29
<212> TYPE: DNA
<213> ORGANISM: Unknown
<220> FEATURE:
<223> OTHER INFORMATION: R. sp. IRBG74

<400> SEQUENCE: 258

```
ctagtgcgaa ctagctcata ccgcagatg                                    29
```

<210> SEQ ID NO 259
<211> LENGTH: 42
<212> TYPE: DNA
<213> ORGANISM: P. protegens

```
<400> SEQUENCE: 259
ctagcgcagg tccaacgttt ttctaagcaa ggaggtcata tg                      42

<210> SEQ ID NO 260
<211> LENGTH: 42
<212> TYPE: DNA
<213> ORGANISM: P. protegens

<400> SEQUENCE: 260
ctagcgaagg tccaacgttt ttctaagcaa ggaggtcata tg                      42

<210> SEQ ID NO 261
<211> LENGTH: 42
<212> TYPE: DNA
<213> ORGANISM: P. protegens

<400> SEQUENCE: 261
ctagcgaagg tccaacgttt ttctaagcca ggaggtcata tg                      42

<210> SEQ ID NO 262
<211> LENGTH: 42
<212> TYPE: DNA
<213> ORGANISM: P. protegens

<400> SEQUENCE: 262
ctagcgcagg tccaacgttt ttctaagcca ggaggtcata tg                      42

<210> SEQ ID NO 263
<211> LENGTH: 42
<212> TYPE: DNA
<213> ORGANISM: P. protegens

<400> SEQUENCE: 263
ctagcgaagc tccaacgttt ttctaagcaa ggaggtcata tg                      42

<210> SEQ ID NO 264
<211> LENGTH: 33
<212> TYPE: DNA
<213> ORGANISM: P. protegens

<400> SEQUENCE: 264
gaattctaca ctaacggaca ggagggtccg atg                                33

<210> SEQ ID NO 265
<211> LENGTH: 33
<212> TYPE: DNA
<213> ORGANISM: P. protegens

<400> SEQUENCE: 265
gaattctaaa ctaacggaca ggagggtccg atg                                33

<210> SEQ ID NO 266
<211> LENGTH: 33
<212> TYPE: DNA
<213> ORGANISM: P. protegens

<400> SEQUENCE: 266
gaattctaag ctaacggaca ggagggtccg atg                                33

<210> SEQ ID NO 267
<211> LENGTH: 33
<212> TYPE: DNA
```

<213> ORGANISM: P. protegens

<400> SEQUENCE: 267
gaattcttaa ctaacggaca ggagggtccg atg                                   33

<210> SEQ ID NO 268
<211> LENGTH: 33
<212> TYPE: DNA
<213> ORGANISM: P. protegens

<400> SEQUENCE: 268
gaattctaca ctaacggaca ggagggtcgg atg                                   33

<210> SEQ ID NO 269
<211> LENGTH: 33
<212> TYPE: DNA
<213> ORGANISM: P. protegens

<400> SEQUENCE: 269
gaattctacg ctaacggaca ggagggtccg atg                                   33

<210> SEQ ID NO 270
<211> LENGTH: 33
<212> TYPE: DNA
<213> ORGANISM: P. protegens

<400> SEQUENCE: 270
gaattctcaa ctaacggaca ggagggtccg atg                                   33

<210> SEQ ID NO 271
<211> LENGTH: 33
<212> TYPE: DNA
<213> ORGANISM: P. protegens

<400> SEQUENCE: 271
gaattctaag ctaacggaca ggagggtcgg atg                                   33

<210> SEQ ID NO 272
<211> LENGTH: 33
<212> TYPE: DNA
<213> ORGANISM: P. protegens

<400> SEQUENCE: 272
gaattctcag ctaacggaca ggagggtccg atg                                   33

<210> SEQ ID NO 273
<211> LENGTH: 33
<212> TYPE: DNA
<213> ORGANISM: P. protegens

<400> SEQUENCE: 273
gaattctcaa ctaacggaca ggagggtccg atg                                   33

<210> SEQ ID NO 274
<211> LENGTH: 33
<212> TYPE: DNA
<213> ORGANISM: P. protegens

<400> SEQUENCE: 274
gaattctacg ctaacggaca ggagggtcgg atg                                   33

<210> SEQ ID NO 275
<211> LENGTH: 35

```
<212> TYPE: DNA
<213> ORGANISM: P. protegens

<400> SEQUENCE: 275
gaattctcaa ctaacggaca ggagatatac atatg                    35

<210> SEQ ID NO 276
<211> LENGTH: 33
<212> TYPE: DNA
<213> ORGANISM: P. protegens

<400> SEQUENCE: 276
gaattctcag ctaacggaca ggagggtcgg atg                      33

<210> SEQ ID NO 277
<211> LENGTH: 33
<212> TYPE: DNA
<213> ORGANISM: P. protegens

<400> SEQUENCE: 277
gaattctaaa ctaacggaca ggagggtcgg atg                      33

<210> SEQ ID NO 278
<211> LENGTH: 33
<212> TYPE: DNA
<213> ORGANISM: P. protegens

<400> SEQUENCE: 278
gaattctcag ctcacggaca ggagggtcgg atg                      33

<210> SEQ ID NO 279
<211> LENGTH: 34
<212> TYPE: DNA
<213> ORGANISM: P. protegens

<400> SEQUENCE: 279
gaattctcaa ctaacggaca ggagggtcgg gatg                     34

<210> SEQ ID NO 280
<211> LENGTH: 33
<212> TYPE: DNA
<213> ORGANISM: P. protegens

<400> SEQUENCE: 280
gaattctaca ctcacggaca ggagggtcgg atg                      33

<210> SEQ ID NO 281
<211> LENGTH: 33
<212> TYPE: DNA
<213> ORGANISM: P. protegens

<400> SEQUENCE: 281
gaattctaag ctcacggaca ggagggtcgg atg                      33

<210> SEQ ID NO 282
<211> LENGTH: 33
<212> TYPE: DNA
<213> ORGANISM: P. protegens

<400> SEQUENCE: 282
gaattctcaa ctcacggaca ggagggtcgg atg                      33

<210> SEQ ID NO 283
```

```
<211> LENGTH: 33
<212> TYPE: DNA
<213> ORGANISM: P. protegens

<400> SEQUENCE: 283
gaattctaca ctaacggaca gcagggtcgg atg                                    33

<210> SEQ ID NO 284
<211> LENGTH: 42
<212> TYPE: DNA
<213> ORGANISM: P. protegens

<400> SEQUENCE: 284
ctagcgcagg tccaaccttt ttctaagcaa gtaggtcata tg                          42

<210> SEQ ID NO 285
<211> LENGTH: 33
<212> TYPE: DNA
<213> ORGANISM: P. protegens

<400> SEQUENCE: 285
gaattctcag ctaacggaca gcagggtcgg atg                                    33

<210> SEQ ID NO 286
<211> LENGTH: 42
<212> TYPE: DNA
<213> ORGANISM: P. protegens

<400> SEQUENCE: 286
ctagcgcagg tccaaccttt ttctaagcaa ctaggtcata tg                          42

<210> SEQ ID NO 287
<211> LENGTH: 42
<212> TYPE: DNA
<213> ORGANISM: P. protegens

<400> SEQUENCE: 287
ctagcgaagg tccaaccttt ttctaagcca gtaggtcata tg                          42

<210> SEQ ID NO 288
<211> LENGTH: 33
<212> TYPE: DNA
<213> ORGANISM: P. protegens

<400> SEQUENCE: 288
gaattctacg ctcacggaca gcagggtcgg atg                                    33

<210> SEQ ID NO 289
<211> LENGTH: 33
<212> TYPE: DNA
<213> ORGANISM: P. protegens

<400> SEQUENCE: 289
gaattctccg ctcacggaca ggagggtccg atg                                    33

<210> SEQ ID NO 290
<211> LENGTH: 33
<212> TYPE: DNA
<213> ORGANISM: P. protegens

<400> SEQUENCE: 290
cttctcggcc agctgacagg ggaagctcgc atg                                    33
```

<210> SEQ ID NO 291
<211> LENGTH: 34
<212> TYPE: DNA
<213> ORGANISM: P. protegens

<400> SEQUENCE: 291
cttctcggcc agctgacagg aggaagctcg catg    34

<210> SEQ ID NO 292
<211> LENGTH: 582
<212> TYPE: PRT
<213> ORGANISM: R. sphaeroides

<400> SEQUENCE: 292

```
Met Asp Thr Ser Ala Ala Arg Ser Gly Ala Val Ala Glu Arg Gly Glu
1               5                   10                  15

Glu Tyr Leu Thr Leu Asp Ala Leu Cys Glu Ile Ala Lys Leu Leu Thr
            20                  25                  30

Gly Ala Ser Asp Pro Ile Ala Cys Met Pro Ala Val Phe Gly Val Leu
        35                  40                  45

Gly Ala Phe Met Gly Leu Arg His Gly Ala Leu Ala Ile Leu Gln Glu
    50                  55                  60

Gly Ala Gln Ala Glu Thr Gln Arg Asn Ala Arg His Val Asn Pro Tyr
65                  70                  75                  80

Val Ile Ala Ala Thr Ala Ser Gly Val Pro Pro Ala Gly Ala Glu Ala
                85                  90                  95

Arg Ala Ile Pro Ala Gln Val Ala Arg His Val Phe Arg Asn Gly Val
            100                 105                 110

Ser Leu Val Ser Cys Asp Ile Leu Glu Glu Phe Gly Ala Glu Ala Leu
        115                 120                 125

Pro Pro Gly Leu Gly Asp Ser Arg Gln Ala Leu Ala Val Pro Ile
    130                 135                 140

Arg Asp Gln Ala Asn Ser Pro Phe Val Leu Gly Val Leu Cys Ala Tyr
145                 150                 155                 160

Arg Ser Leu Lys Asp Asn Gly Ala Arg Tyr Leu Asp Thr Asp Leu Arg
                165                 170                 175

Val Leu Asn Met Val Ala Val Leu Glu Gln Ser Ile Arg Phe Arg
            180                 185                 190

Arg Leu Val Ala Arg Asp Arg Asp Arg Ile Val Gln Glu Ala Arg Glu
        195                 200                 205

Ala Ile Arg Val Ala Ala Glu Ala Thr Ala Gly Pro Pro Val Glu Ala
    210                 215                 220

Pro Ala Glu Leu Ala Leu Glu Gly Val Ile Gly Ser Ser Pro Ala Ile
225                 230                 235                 240

Gln Arg Val Ile Gly Gln Ile Arg Lys Val Ala Gly Thr His Thr Pro
                245                 250                 255

Val Leu Leu Arg Gly Glu Ser Gly Thr Gly Lys Glu Val Phe Ala Arg
            260                 265                 270

Ala Leu His Ala Leu Ser Glu Arg Arg Asp Lys Ala Phe Ile Lys Val
        275                 280                 285

Asn Cys Ala Ala Leu Ser Gln Ser Leu Leu Glu Ser Glu Leu Phe Gly
    290                 295                 300

His Glu Lys Gly Ser Phe Thr Gly Ala Val Gln Gln Lys Lys Gly Arg
305                 310                 315                 320

Pro Glu Met Ala Glu Gly Gly Thr Leu Phe Leu Asp Glu Ile Gly Glu
                325                 330                 335
```

```
Ile Ser Leu Glu Phe Gln Ala Lys Leu Leu Arg Ile Leu Gln Glu Gly
            340                 345                 350

Glu Phe Glu Arg Val Gly Gly Thr Arg Thr Leu Arg Val Asp Val Arg
            355                 360                 365

Leu Val Thr Ala Thr Asn Lys Asp Leu Glu Arg Ala Val Ala Asn Gly
            370                 375                 380

Thr Phe Arg Ala Asp Leu Tyr Phe Arg Ile Cys Val Val Pro Ile Val
385                 390                 395                 400

Leu Pro Pro Leu Arg Asp Arg Lys Glu Asp Ile Gly Leu Leu Ala Gln
            405                 410                 415

Gly Leu Leu Glu Arg Phe Asn Lys Arg Asn Gly Met Lys Lys Lys Leu
            420                 425                 430

His Pro Ser Ala Val Ala Ala Leu Ala Gln Cys Asn Phe Pro Gly Asn
            435                 440                 445

Val Arg Glu Leu Glu Asn Cys Ile Ala Arg Val Ala Ala Leu Ser Pro
            450                 455                 460

Glu Thr Val Ile His Ala Asp Asp Leu Ala Cys His His Asp His Cys
465                 470                 475                 480

Leu Ser Ala Asp Leu Trp Arg Leu Gln Thr Gly Ser Ala Ser Pro Val
            485                 490                 495

Gly Gly Leu Ala Gln Gly Pro Leu Glu Leu Pro Val Leu Gly Ser Arg
            500                 505                 510

Pro Pro Ala Ala Ala Pro Ser Ala Pro Pro Pro Pro Pro Thr Val
            515                 520                 525

Pro Ser Ala Pro Leu Asp Gly Glu Ala Ala Glu Arg Glu Ala Leu Ile
            530                 535                 540

Glu Ala Met Glu Arg Ala Gly Trp Val Gln Ala Lys Ala Ala Arg Leu
545                 550                 555                 560

Arg Gly Met Thr Pro Arg Gln Ile Gly Tyr Ala Leu Lys Lys Tyr Asn
            565                 570                 575

Ile Arg Val Glu Lys Phe
            580

<210> SEQ ID NO 293
<211> LENGTH: 615
<212> TYPE: PRT
<213> ORGANISM: A. caulinodans

<400> SEQUENCE: 293

Met Pro Met Thr Asp Ala Phe Gln Val Arg Val Pro Arg Val Ser Ser
1               5                   10                  15

Ser Thr Ala Gly Asp Ile Ala Ala Ser Ser Ile Thr Thr Arg Gly Ala
            20                  25                  30

Leu Pro Arg Pro Gly Gly Met Pro Val Ser Met Ser Arg Gly Thr Ser
            35                  40                  45

Pro Glu Val Ala Leu Ile Gly Val Tyr Glu Ile Ser Lys Ile Leu Thr
            50                  55                  60

Ala Pro Arg Arg Leu Glu Val Thr Leu Ala Asn Val Val Asn Val Leu
65                  70                  75                  80

Ser Ser Met Leu Gln Met Arg His Gly Met Ile Cys Ile Leu Asp Ser
            85                  90                  95

Glu Gly Asp Pro Asp Met Val Ala Thr Thr Gly Trp Thr Pro Glu Met
            100                 105                 110

Ala Gly Gln Ile Arg Ala His Val Pro Gln Lys Ala Ile Asp Gln Ile
```

```
            115                 120                 125
Val Ala Thr Gln Met Pro Leu Val Gln Asp Val Thr Ala Asp Pro
    130                 135                 140

Leu Phe Ala Gly His Glu Asp Leu Phe Gly Pro Pro Glu Glu Ala Thr
145                 150                 155                 160

Val Ser Phe Ile Gly Val Pro Ile Lys Ala Asp His His Val Met Gly
                165                 170                 175

Thr Leu Ser Ile Asp Arg Ile Trp Asp Gly Thr Ala Arg Phe Arg Phe
                180                 185                 190

Asp Glu Asp Val Arg Phe Leu Thr Met Val Ala Asn Leu Val Gly Gln
                195                 200                 205

Thr Val Arg Leu His Lys Leu Val Ala Ser Arg Asp Arg Leu Ile
    210                 215                 220

Ala Gln Thr His Arg Leu Glu Lys Ala Leu Arg Glu Lys Ser Gly
225                 230                 235                 240

Ala Glu Pro Glu Val Ala Glu Ala Asn Gly Ser Ala Met Gly Ile
                245                 250                 255

Val Gly Asp Ser Pro Leu Val Lys Arg Leu Ile Ala Thr Ala Gln Val
                260                 265                 270

Val Ala Arg Ser Asn Ser Thr Val Leu Leu Arg Gly Glu Ser Gly Thr
                275                 280                 285

Gly Lys Glu Leu Phe Ala Arg Ala Ile His Glu Leu Ser Pro Arg Lys
                290                 295                 300

Gly Lys Pro Phe Val Lys Val Asn Cys Ala Ala Leu Pro Glu Ser Val
305                 310                 315                 320

Leu Glu Ser Glu Leu Phe Gly His Glu Lys Gly Ala Phe Thr Gly Ala
                325                 330                 335

Leu Asn Met Arg Gln Gly Arg Phe Glu Leu Ala His Gly Gly Thr Leu
                340                 345                 350

Phe Leu Asp Glu Ile Asp Glu Ile Thr Pro Ala Phe Gln Ala Lys Leu
                355                 360                 365

Leu Arg Val Leu Gln Glu Gly Glu Phe Glu Arg Val Gly Gly Asn Arg
                370                 375                 380

Thr Leu Lys Val Asp Val Arg Leu Val Cys Ala Thr Asn Lys Asn Leu
385                 390                 395                 400

Glu Glu Ala Val Ser Lys Gly Glu Phe Arg Ala Asp Leu Tyr Tyr Arg
                405                 410                 415

Ile His Val Val Pro Leu Ile Leu Pro Pro Leu Arg Glu Arg Pro Gly
                420                 425                 430

Asp Ile Pro Lys Leu Ala Lys Asn Phe Leu Asp Arg Phe Asn Lys Glu
                435                 440                 445

Asn Lys Leu His Met Met Leu Ser Ala Pro Ala Ile Asp Val Leu Arg
                450                 455                 460

Arg Cys Tyr Phe Pro Gly Asn Val Arg Glu Leu Glu Asn Cys Ile Arg
465                 470                 475                 480

Arg Thr Ala Thr Leu Ala His Asp Ala Val Ile Thr Pro His Asp Phe
                485                 490                 495

Ala Cys Asp Ser Gly Gln Cys Leu Ser Ala Met Leu Trp Lys Gly Ser
                500                 505                 510

Ala Pro Lys Pro Val Met Pro His Val Pro Ala Pro Thr Pro Leu
                515                 520                 525

Thr Pro Leu Ser Pro Ala Pro Leu Ala Thr Ala Ala Pro Ala Ala Ala
                530                 535                 540
```

```
Ser Pro Ala Pro Ala Ala Asp Ser Leu Pro Val Thr Cys Pro Gly Thr
545                 550                 555                 560

Glu Ala Cys Pro Ala Val Pro Pro Arg Gln Ser Glu Lys Glu Gln Leu
                565                 570                 575

Leu Gln Ala Met Glu Arg Ser Gly Trp Val Gln Ala Lys Ala Ala Arg
            580                 585                 590

Leu Leu Asn Leu Thr Pro Arg Gln Val Gly Tyr Ala Leu Arg Lys Tyr
        595                 600                 605

Asp Ile Asp Ile Lys Arg Phe
    610             615
```

CONTROL OF NITROGEN FIXATION IN RHIZOBIA THAT ASSOCIATE WITH CEREALS

RELATED APPLICATION

This application claims priority under 35 U.S.C. § 119(e) to U.S. Provisional Application Ser. No. 62/820,765, filed Mar. 19, 2019, the entire contents of which are incorporated by reference herein.

GOVERNMENT SUPPORT

This invention was made with government support under Grant No. IOS1331098, awarded by the National Science Foundation (NSF). The government has certain rights in this invention.

BACKGROUND OF THE INVENTION

In agriculture, nitrogen is a limiting nutrient that needs to be added as fertilizer to those crops that cannot produce it on their own, including the cereals rice, corn, and wheat. In contrast, legumes are able to obtain nitrogen from the atmosphere using nitrogen-fixing bacteria that reside in root nodules. However, the majority of the world's calories are from cereals; thus, it has been a longstanding problem in genetic engineering to transfer this ability to these crops. This would reduce the need for nitrogenous fertilizer and the economic, environmental, and energy burdens that it brings.

SUMMARY OF THE INVENTION

The present disclosure is based, at least in part, rhizobia and methods for making rhizobia that can fix nitrogen under aerobic free-living conditions. The present disclosure also provides refactored nif-clusters that confer the ability to fix nitrogen under aerobic free-living conditions.

Accordingly, one aspect of the present disclosure provides a rhizobium that can fix nitrogen under aerobic free-living conditions, comprising a symbiotic rhizobium having an exogenous nif cluster, wherein the exogenous nif cluster confers nitrogen fixation capability on the symbiotic rhizobium under aerobic free-living conditions, and wherein the rhizobium is not *Azorhizobium caulinodans*. In some embodiments, the exogenous nif cluster is from a free-living diazotroph. In some embodiments, the exogenous nif cluster is from a symbiotic diazotroph. In some embodiments, the exogenous nif cluster is from a photosynthetic Alphaproteobacteria. In some embodiments, the exogenous nif cluster is from a Gammaproteobacteria. In some embodiments, the exogenous nif cluster is from a cyanobacteria. In some embodiments, the exogenous nif cluster is from a firmicutes. In some embodiments, the exogenous nif cluster is from *Rhodobacter sphaeroides*. In some embodiments, the exogenous nif cluster is from *Rhodopseudomonas palustris*. In some embodiments, the exogenous nif cluster is an inducible refactored nif cluster. In some embodiments, the inducible refactored nif cluster is an inducible refactored *Klebsiella* nif cluster. In some embodiments, the rhizobium is IRBG74. In some embodiments, the exogenous nif cluster comprises 6 nif genes. In some embodiments, the 6 nif genes are nifHDK(T)Y, nifEN(X), nifJ, nifBQ, nifF, and nifUSVWZM. In some embodiments, each nif gene of the exogenous nif cluster is preceded by a T7 promoter. In some embodiments, the T7 promoter is a wild-type promoter. In some embodiments, the rhizobium further comprises an endogenous nif cluster. In some embodiments, the nif cluster has a nifV gene. In some embodiments, the nifV gene is endogenous. In some embodiments, the exogenous nif cluster further comprises a terminator. In some embodiments, the T7 promoter has a terminator and the terminator is downstream from the T7 promoter. In some embodiments, the exogenous nif cluster is a refactored v3.2 nif cluster as shown in FIG. 2H.

Another aspect of the present disclosure provides a plant growth promoting bacterium that can fix nitrogen under aerobic free-living conditions, comprising a bacterium having an exogenous nif cluster having at least one inducible promoter, wherein the exogenous nif cluster confers nitrogen fixation capability on the bacterium, under aerobic free-living conditions, and wherein the bacterium is not *Azorhizobium caulinodans*. In some embodiments, the bacterium is a symbiotic bacterium. In some embodiments, the bacterium is an endophyte. In some embodiments, the endophyte is rhizobium IRBG74. In some embodiments, the bacterium is an epiphyte. In some embodiments, the epiphyte is pseudomonas protogens PF-5. In some embodiments, the plant growth promoting bacterium is associated with a genetically modified cereal plant. In some embodiments, the genetically modified cereal plant includes an exogenous gene encoding a chemical signal. In some embodiments, the nitrogen fixation is under the control of the chemical signal. In some embodiments, the chemical signal is opine, phlorogluconol or rhizopene. In some embodiments, the exogenous nif cluster comprises 6 nif genes. In some embodiments, the 6 nif genes are nifHDK (T)Y, nifEN(X), nifJ, nifBQ, nifF, and nifUSVWZM. In some embodiments, the inducible promoter is a T7 promoter. In some embodiments, the inducible promoter is $P_{A1lacO1}$ promoter. In some embodiments, the inducible promoter is activated by an agent selected from a group that includes IPTG, sodium salicylate, octapine, nopaline, the quorum signal 3OC6HSL, aTc, cuminic acid, DAPG, and salicylic acid. In some embodiments, the exogenous nif cluster further comprises a terminator. In some embodiments, the inducible promoter has a terminator and the terminator is downstream from the inducible promoter.

Another aspect of the present disclosure provides an *Azorhizobium caulinodans* capable of inducible ammonium-independent nitrogen fixation in a cereal crop, comprising: (i) a modified nif cluster, wherein an endogenous nifA gene is deleted or altered; and (ii) at least one operon comprising nifA and RNA polymerase sigma factor (RpoN), wherein the operon comprises a regulatory element including an inducible promoter. In some embodiments, the inducible promoter is $P_{A1lacO1}$ promoter. In some embodiments, the inducible promoter is activated by an agent selected from the group consisting of IPTG, sodium salicylate, octapine, nopaline, the quorum signal 3OC6HSL, aTc, cuminic acid, DAPG, and salicylic acid. In some embodiments, the endogenous nifA gene is altered with at least one of the following substitutions: (i) L94Q, (ii) D95Q, and (iii) both L94Q and D95Q.

Another aspect of the present disclosure provides a method of engineering a rhizobium that can fix nitrogen under aerobic free-living conditions, comprising transferring an exogenous nif cluster to a symbiotic rhizobium, wherein the exogenous nif cluster confers nitrogen fixation capability on the symbiotic rhizobium, under aerobic free-living conditions, and wherein the rhizobium is not *Azorhizobium caulinodans*. In some embodiments, the exogenous nif cluster comprises 6 nif genes. In some embodiments, the 6 nif genes are nifHDK(T)Y, nifEN(X), nifJ, nifBQ, nifF and nifUSVWZM. In some embodiments, each of the nif genes is preceded by a wild-type T7 promoter. In some embodiments, the exogenous nif cluster is transferred to the rhizobium in a plasmid. In some embodiments, the exogenous nif cluster further comprises a terminator. In some embodiments, the wild-type T7 promoter has a terminator, and the terminator is downstream from the wild-type T7 promoter. In some embodiments, the endogenous NifL gene is deleted.

Another aspect of the present disclosure provides a method of producing nitrogen for consumption by a cereal plant, comprising providing a plant growth promoting bacterium that can fix nitrogen under aerobic free-living conditions in proximity of the cereal plant, wherein the plant growth promoting bacterium is a symbiotic bacterium having an exogenous nif cluster, wherein the exogenous nif cluster confers nitrogen fixation capability on the symbiotic bacterium, enabling nitrogen fixation under aerobic free-living conditions. In some embodiments, the plant growth promoting bacterium is a rhizobium. In some embodiments, the plant growth bacterium is a bacterium as described in the present disclosure. In some embodiments, the cereal plant is a genetically modified cereal plant. In some embodiments, the genetically modified cereal plant includes an exogenous gene encoding a chemical signal. In some embodiments, the nitrogen fixation is under the control of the chemical signal. In some embodiments, the chemical signal is opine, phlorogluconol or rhizopene. In some embodiments, the nitrogen fixation is under the control of a chemical signal. In some embodiments, the chemical signal is a root exudate, biocontrol agent or phytohormone. In some embodiments, the root exudate is selected from the group consisting of sugars, hormones, flavonoids, and antimicrobials. In some embodiments, the chemical signal is vanillate. In some embodiments, the chemical signal is IPTG, aTc, cuminic acid, DAPG, and salicylic acid, 3,4-dihydroxybenzoic acid, 3OC6HSL or 3OC14HSL.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. For purposes of clarity, not every component may be labeled in every drawing. It is to be understood that the data illustrated in the drawings in no way limit the scope of the disclosure. In the drawings:

(FIG. 1A) Eight nif clusters from free-living nitrogen fixing bacteria are aligned based on phylogenetic relationships of 16S rRNA sequences. The genes and operons are based on K. oxytoca M5al. Dots in the DNA line indicate where multiple regions were cloned from genomic DNA and combined to form one large plasmid-borne nif cluster. A complete list of strain genotypes is provided in Table 8. Nitrogenase activity from transfer of the native nif clusters was measured in three species. The activities of the R. palustris and R. sphaeroides nif clusters were also measured in 12 Rhizobia strains. Asterisks indicate ethylene production below the detection limit (<10 a.u.). Error bars represent s.d. from three independent experiments. (FIG. 1B) Transcriptomic profile of the native K. oxytoca nif cluster in K. oxytoca, compared with those obtained from its transfer to the indicated species. (FIG. 1C) Transcription levels (FPKM) of the native K. oxytoca nif cluster across species. Transcriptional units are underlined. (FIG. 1D) Transcription levels (FPKM) of the K. oxytoca nif genes in K. oxytoca (→Klebsiella) compared to that obtained when transferred to a new host. (FIG. 1E) Same as in (FIG. 1C), except the translational efficiency is compared, as calculated using ribosome profiling. (FIG. 1F) Same as in (FIG. 1D), except the ribosome densities (RD) are compared, as calculated using ribosome profiling. R2 in log-log plots was calculated from the line (y=x+b), where b is an expression variable between hosts.

(FIG. 2A) The genetic systems for the controller for E. coli MG1655 (left) and R. sp. IRBG74 (right) are shown. A variant of T7 RNAP (R6232S, N-terminal lon tag, GTG start codon) is used for the E. coli controller. Several genetic parts were substituted to build the R. sp. IRBG74 controller (red) (FIG. 16). The sequences for the genetic parts are provided in Table 10. (FIG. 2B) The response functions for the controllers with the reporter plasmid pMR-79 (Table 9 and Table 10). The IPTG concentrations used to induce nitrogenase were circled in red. (FIG. 2C) The genetic parts used to build the refactored v2.1 nif gene cluster are shown (Table 10). (FIG. 2D) The activity of the refactored nif gene cluster v2.1 in different hosts is shown. Asterisks indicate ethylene production below the detection limit (<10 a.u.). (FIG. 2E) The activities of the v2.1 promoters and terminators in E. coli MG1655 and R. sp. IRBG74 as calculated from RNA-seq data (see Materials and Methods). (FIG. 2F) The translation efficiency of the v2.1 nif genes in E. coli MG1655 and R. sp. IRBG74, as calculated using ribosome profiling and RNA-seq. Lines connect points that occur in the same operon. (FIG. 2G) The ribosome density (RD) is compared for the refactored v2.1 nif genes in a new host (E. coli MG155; R. sp. IRBG74) versus that measured for the nif genes from the native K. oxytoca cluster in K. oxytoca (Klebsiella). The points corresponding to nifH is marked H. (FIGS. 2H-2L) The same as (FIGS. 2C-2G) but with the refactored nif cluster v3.2. Genetic parts are provided in Table 10. (FIG. 2M) Nitrogenase activity is shown as a function of T7 promoter strength. The refactored nif cluster v3.2 was expressed from three controller strains with varying strengths (FIG. 16). Error bars represent s.d. from three independent experiments.

(FIG. 3A) The controller is shown, carried on a pBBR1 origin plasmid (genetic parts are provided in Table 10). NifA and RpoN co-induce the expression of three sites in the genome (identified by consensus NifA binding sequences). (FIG. 3B) Expression from the nifH promoter was evaluated using a fluorescent reporter (see Materials and Methods). NifA and RpoN were complemented (+) individually or in combination in the A. caulinodans ΔnifA strain where the genomic rpoN remains intact. (FIG. 3C) The response function for the induction of the nifH promoter by the controller is shown. (FIG. 3D) The nitrogenase activity is shown for wild-type A. caulinodans ORS571 compared to the ΔnifA complemented with the controller plasmid (+) and the addition of 1 mM IPTG (+). (FIG. 3E) The effect of the absence or presence of 10 mM ammonium chloride is shown. The WT NifA from A. caulinodans ORS571 is compared to different combinations of amino acid substitutions with additional RpoN expression. NifA/RpoN expression is induced by 1 mM IPTG (+) for the ΔnifA strain containing the controller plasmid pMR-121, 122, 123, and 124 (+). Asterisks indicate ethylene production below the detection limit (<10 au). (FIG. 3F) The nitrogenase activity is shown as a function of the oxygen concentration in the headspace (see Materials and Methods). The native nif cluster (wild-type *A. caulinodans* ORS571) is compared to the inducible version including the controller plasmid and 1 mM IPTG. Error bars represent s.d. from three independent experiments.

(FIG. 4A) The controllers, based on *P. stutzeri* NifA, were used for all three clusters. Plasmids and genetic parts are provided in Table 9 and Table 10. (FIG. 4B) The nif clusters from *K. oxytoca*, *P. stutzeri*, and *A. vinelandii* are shown. The deleted regions corresponding the NifLA regulators are marked. The dotted lines indicate that multiple regions from the genome were cloned and combined for form the nif cluster. The clusters were carried the plasmids pMR-4, 6, 8 (Table 9). (FIG. 4C) The induction of the nifH promoters from each species by the controller are shown (0.5 mM IPTG) (see Materials and Methods). (FIG. 4D) The nitrogenase activities of the native cluster (intact nifLA) is compared to the inducible clusters in the presence and absence of 0.5 mM IPTG. The dashed lines indicate the activity of the native clusters in the wild-type context (top to bottom, *K. oxytoca* M5al, *P. stutzeri* A1501 and *A. vinelandii* DJ). (FIG. 4E) The sensitivity of the native and inducible (+0.5 mM IPTG) nif clusters to 17.1 mM ammonium acetate are compared. Asterisks indicate ethylene production below the detection limit (<10 au). (FIG. 4F) The nitrogenase activity is shown as a function of the oxygen concentration in the headspace (see Materials and Methods). The native nif cluster is compared to the inducible version including the controller plasmid and 0.5 mM IPTG. Error bars represent s.d. from three independent experiments.

(FIG. 5A) Schematic showing the origins of the chemicals. "Introduced DNA" refers to the genetic modification of the plant to produce nopaline and octopine. (FIG. 5B) The genetic sensors built for *A. caulinodans* are shown. Sequences for the genetic parts are provided in Table 10. (FIG. 5C) The response functions for the sensors are shown. Either the sensor expresses T7 RNAP, which then activates PT7, or it expresses NifA (*P. protegens* Pf-5) or NifA/RpoN (*A. caulinodans*) and activates the nifH promoter (species origin in parentheses). (FIG. 5D) The nitrogenase activity is measured in the presence or absence of inducer (see Materials and Methods). The refactored *Klebsiella* nif clusters v2.1 and v3.2 were used in *E. coli* MG1655 and R. sp. IRBG74, respectively. The inducible *A. vinelandii* nif cluster was used in *P. protegens* Pf-5. The controller containing nifA/rpoN was used in *A. caulinodans* ΔnifA. The inducer concentrations are: 50 μM vanillic acid, 500 μM DHBA, 50 μM cuminic acid, 25 nM 3OC6HSL, 500 nM 3OC14HSL, 33 μM arabinose, 100 μM naringenin, 100 nM DAPG, 200 μM salicylic acid, 1 mM nopaline and 1 mM octopine. Error bars represent s.d. from three independent experiments.

(FIG. 7A) The same controller system based on *K. oxytoca* NifA was used for all three clusters. The controller plasmid pMR-99 and genetic parts are provided in Table 9 and Table 10. (FIG. 7B) The nif clusters from *K. oxytoca*, *P. stutzeri*, and *A. vinelandii* are shown. The deleted regions corresponding the NifLA regulators are marked. The dotted lines indicate that multiple regions from the genome were cloned and combined for form the nif cluster. The clusters were carried the plasmids pMR-3, 5, 7 (Table 9). (FIG. 7C) The induction of the nifH promoters from each species by the controller is shown (50 μM IPTG) (see Materials and Methods) (FIG. 7D) The nitrogenase activities of the native cluster (intact nifLA) is compared to the inducible clusters in the presence and absence of 50 μM IPTG. The dashed lines indicate the activity of the native clusters in the wild-type context (top to bottom, *K. oxytoca* M5al, *P. stutzeri* A1501 and *A. vinelandii* DJ).

(FIG. 7E) Regulation of nitrogenase activity by ammonia. Ammonium tolerance of nitrogenase from the native (black bar) and inducible (gray bar) systems was tested in the presence of 17.1 mM ammonium acetate. Asterisks indicate ethylene production below the detection limit (<10 au). (FIG. 7F) Regulation of nitrogenase activity by oxygen. The native nif cluster is compared to the inducible version including the controller plasmid and 50 μM IPTG. Nitrogenase activities were measured after 3 h of incubation at constant oxygen concentrations (0 to 3%) in the headspace (see Materials and Methods). Error bars represent s.d. from three independent experiments.

(FIG. 10A) The reporter construct used to measure nifH promoter activity is shown. The nifH promoter activity was analyzed in the R. sp. IRBG74 wild-type background using flow cytometry. Additional copies of NifA of R. sp. IRBG74 increased activity of the R. sp. IRBG74 nifH promoter but failed to complement or enhance activity of the other nifH promoters including *K. oxytoca*, *P. stutzeri* and *A. caulinodans*. Error bars represent s.d. from three independent experiments. (FIG. 10B) Plasmid maps used to assess the effect of NifA overexpression in R. sp. IRBG74. WT, wild-type; Rsp, R. sp. IRBG74; Kox, *K. oxytoca* M5al; Pst, *P. stutzeri* A1501; Aca, *A. caulinodans* ORS571

(FIG. 11A) Constitutive promoters are rank-ordered by their strength. Plasmids used to measure promoter activity are depicted on the top. (FIG. 11B) The strength of the T7 promoter wild-type and its variants was analyzed in the controller strains containing the IPTG-inducible T7 RNAP on the genome of R. sp. IRBG74 and P. protegens Pf-5 with 1 mM IPTG induction. A reporter plasmid used to measure T7 promoter activity is shown on the right. (FIG. 11C) Correlation of T7 promoter strength between species. Error bars represent s.d. from three independent experiments.

(FIG. 12A) The strengths of the synthetic RBSs in R. sp. IRBG74 were analyzed in the plasmid pMR-40 containing the IPTG-inducible system with 1 mM IPTG induction. 33 of the RBSs spanning a range of 5,684-fold expression were selected and their sequences are provided in Table 11. (FIG. 12B) The strengths of the synthetic RBSs in P. protegens Pf-5 was analyzed in the plasmid pMR-65 containing the arabinose-inducible system with 7 µM arabinose induction. 33 of the RBSs spanning a range of 1,075-fold expression were selected and their sequences are provided in Table 11.

(FIG. 13A) The strength of terminators was analyzed in the controller R. sp. IRBG74 strains MR16 containing the IPTG-inducible T7 RNAP on the genome with 1 mM IPTG induction. (FIG. 13B) Plasmids used to measure terminator strength are shown on right. Genetic parts are provided in Table 10. Error bars represent s.d. from three independent experiments.

(FIG. 15A) Inducible promoter characterization in P. protegens Pf-5. (FIG. 15B) Optimization of the arabinose-inducible systems. Constitutive expression of a plasmid-borne AraE transporter decreased a dissociation constant of arabinose (dark gray). A mutation in the −10 region (TACTGT to TATATT) of the $P_{BAD}$ promoter increased promoter strength (black). (FIG. 15C) Optimization of IPTG-inducible systems. The IPTG-inducible promoters were induced by 1 mM IPTG. The combination of the $P_{tac}$ promoter and the LaI (Q18M/A47V/F161Y) protein yielded an expression range of 110-fold. Plasmids and genetic parts are provided in Table 9 and Table 10. Error bars represent s.d. from three independent experiments.

(FIG. 20A) Controllers whose output is T7 RNAP from the genome of P. protegens Pf-5 are described. Substituted genetic parts including a new RBS and IPTG-inducible promoter for the controller optimization compared to the controller module pKT249 in E. coli MG1655 highlighted in red. The response functions for the controllers with the reporter plasmid pMR-80 was measured in the P. protegens Pf-5 controller strain MR7. Controllers driving the expression of GFP by the T7 promoter achieved large dynamic range and 96-fold activation by IPTG. Error bars represent s.d. from three independent experiments. (FIG. 20B) The genetic parts used to build the refactored v3.2 nif gene cluster are shown (Table 10). (FIG. 20C) The activity of the refactored nif cluster v3.2. Nitrogenase expression was induced by 1 mM IPTG. (FIG. 20D) Function of the transcriptional parts of the cluster v3.2 was analyzed by RNA-seq (FIG. 19). The performance of the promoters (left) and terminators (right) was calculated (see Materials and Methods). (FIG. 20E) The translation efficiency of the nif genes v3.2 as calculated using ribosome profiling and RNA-seq. Lines connect points that occur in the same operon. (FIG. 20F) The ribosome density (RD) is compared for the refactored v3.2 nif genes in P. protegens Pf-5 versus that measured for the nif genes from the native K. oxytoca cluster in K. oxytoca (→Klebsiella).

FIG. 22 includes a diagram showing the multiple sequence alignment of NifA of A. caulinodans ORS571 with R. spheroides 2.4.1 was generated using MUSCLE2. The corresponding residues for ammonium tolerance in R. sphaeroides are outlined in red. The A. caulinodans strand corresponds to SEQ ID NO: 293, and the R. sphaeroides strand corresponds to SEQ ID NO: 292.

(FIG. 23A) The ability of the various NifA to activate the nifH promoters was tested with pairwise combinations of the nifH promoters and the NifA in E. coli MG1655 and P. protegens Pf-5. Error bars represent s.d. from three independent experiments. (FIG. 23B) Plasmids used to measure nifH promoter activity by NifA overexpression are shown and provided in Table 9. Genetic parts are provided in Table 10. Pst, P. stutzeri A1501; Avi, A. vinelandii DJ; Kox, K. oxytoca M5al FIGS. 24A-24B include diagrams showing optimization of the controllers in P. protegens Pf-5 and E. coli MG1655 that induce the nifH promoters.

(FIG. 26A) Nitrogenase activity assay at constant oxygen levels in the headspace. Experimental setup used in this study to analyze oxygen tolerance of nitrogenase. Following the expression induction of nitrogenase with preincubation under low oxygen conditions, targeted oxygen concentrations in the headspace is maintained by oxygen spiking while monitoring with oxygen monitoring system (Methods). (FIG. 26B) Nitrogenase activity in *E. Coli* MG1655 and *P. protegens* Pf-5 over a cours of three hours.

(FIG. 28A) Controller plasmids used to drive expression of T7 promoters. (FIG. 28B) Inducibility of the T7 promoter by the controller plasmids encoding T7 RNAP under the regulation of the 12 sensors was tested with a reporter plasmid pMR121 (right). (FIG. 28C) Inducible control of nitrogenase activity in response to 12 inducers was with the plasmid pMR136 (right) carrying the refactored nif cluster v2.1 on pBBR1 origin. The choline-Cl inducible system was omitted for activity assay as the system was not inducible. For the DAPG-, DHBA-, and vanillic acid-inducible system, the refactored cluster was carried on a lower copy number plasmid pMR31 (right) as transformation of the plasmid pMR29 gave rise to no colony formation. The inducers concentrations are: 400 µM arabinose, 1 mM choline-Cl, 500 nM 3OC14HSL, 50 µM cuminic acid, 25 nM 3OC6HSL, 25 µM DAPG, 500 µM DHBA, 1 mM IPTG, 100 nM aTc, 250 µM naringenin, 50 µM vanillic acid, and 250 µM salicylic acid. Plasmid and genetic parts are provided in Table 9 and 10. Error bars represent s.d. from three independent experiments.

DETAILED DESCRIPTION OF THE INVENTION

Figure 1A:
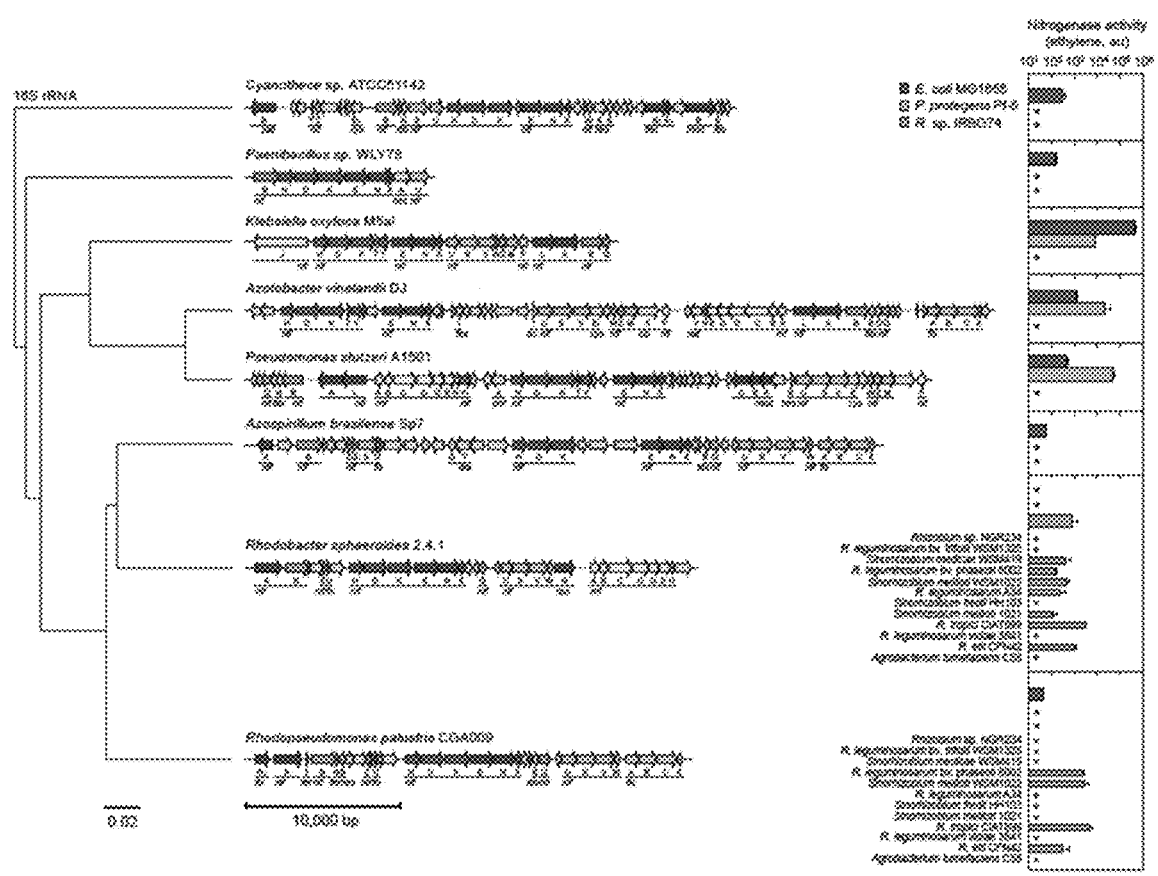
FIGS. 1A-1F include diagrams showing transfer of nif clusters across species.
Figure 1B:
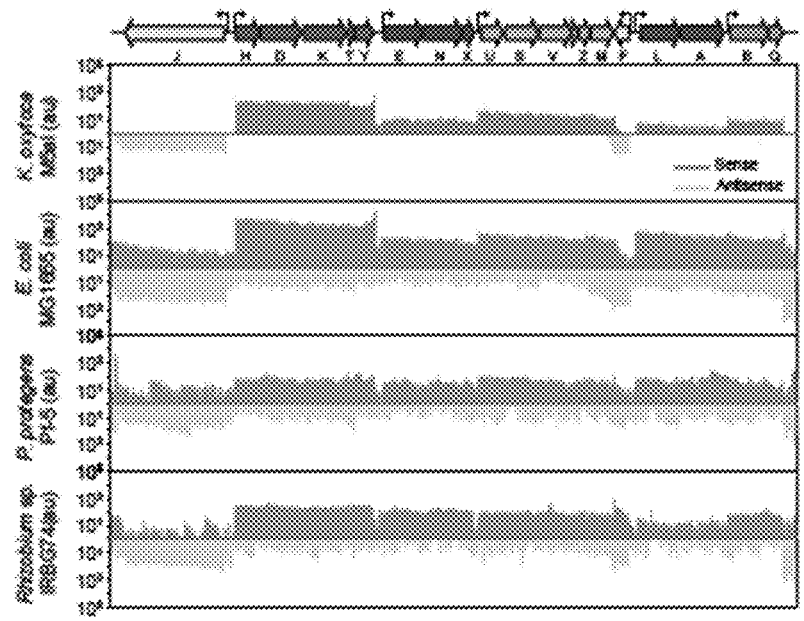
Figure 1C:
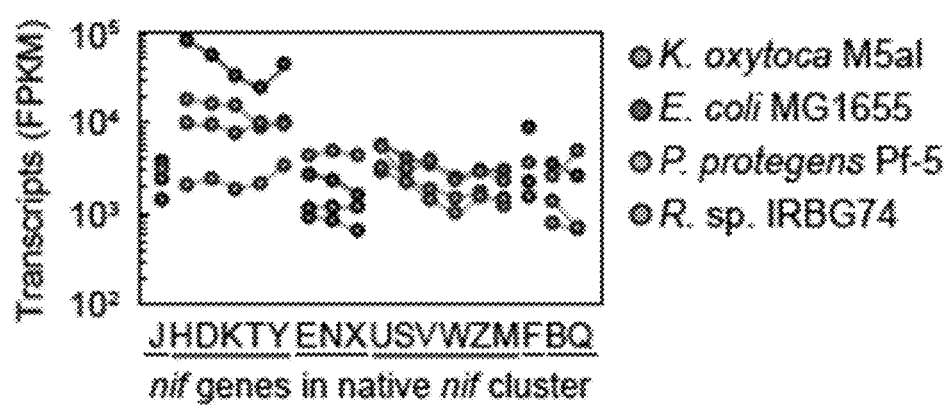

Nitrogen fixation in the root nodules of leguminous plants is a major contributor to world food production and therefore, the practical applications of this field are of major interest. Legumes obtain nitrogen from air through bacteria residing in root nodules, some species of which also associate with cereals but do not fix nitrogen under these conditions. Disabling native regulation can turn on expression, even in the presence of nitrogenous fertilizer and low $O_2$, but continuous nitrogenase production confers an energetic burden.

The present disclosure in some aspects describes the surprising discovery that bacteria can be genetically altered in a manner that will enable the bacteria to deliver fixed nitrogen to cereal crops. Several strategies to implement control over nitrogen fixation in bacteria that live on or inside the roots of cereals are described. At least two approaches can be taken. In one embodiment, the native regulation is replaced. In alternative embodiments, a nif cluster is transferred from another species and placed under inducible control. The Examples section below includes a description of the achievement of these two approaches in multiple species with multiple constructs. For example, *A. caulinodans*, ammonium-independent control was achieved using a sensor to drive the co-expression of a NifA mutant and RpoN in a ΔnifA strain. *Rhizobium* sp. IRBG74 can be engineered to express functional nitrogenase under free living conditions either by transferring a native nif cluster from *Rhodobacter* or a refactored cluster from *Klebsiella*. Multiple approaches enable *P. protegens* Pf-5 to express functional nitrogenase, of which the transfer of the nif cluster from *Azotobacter vinelandii* DJ yields the highest activity and $O_2$ tolerance.

To date, it has not been shown that a *Rhizobium* strain can be engineered to fix nitrogen under free-living conditions when it does not do so naturally. Some *Rhizobia* isolated from legume root nodules are also cereal endophytes, however most are unable tofix nitrogen under free-living conditions (outside of the nodule) (Ramachandran, V. K., East, A. K., Karunakaran, R., Downie, J. A. & Poole, P. S. Adaptation of *Rhizobium leguminosarum* to pea, alfalfa and sugar beet rhizospheres investigated by comparative transcriptomics. Genome biology 12, R106 (2011); Frans, J. et al. in Nitrogen Fixation 33-44 (Springer, 1990)). There have been reports of cereal yield improvements due to these bacteria, including a 20% increase for rice by *Rhizobium* sp. IRBG74, but this is likely due to other growth-promoting mechanisms, such as improved nutrient uptake or root formation (Ramachandran, V. K., East, A. K., Karunakaran, R., Downie, J. A. & Poole, P. S. Adaptation of *Rhizobium leguminosarum* to pea, alfalfa and sugar beet rhizospheres investigated by comparative transcriptomics. Genome biology 12, R106 (2011); Delmotte, N. et al. An integrated proteomics and transcriptomics reference data set provides new insights into the *Bradyrhizobium japonicum* bacteroid metabolism in soybean root nodules. Proteomics 10, 1391-1400 (2010); Hoover, T. R., Imperial, J., Ludden, P. W. &

Shah, V. K. Homocitrate is a component of the iron-molybdenum cofactor of nitrogenase. Biochemistry 28, 2768-2771 (1989)). *Azorhizobium caulinodans* ORS571 is exceptional because it is able to fix nitrogen in both aerobic free-living and symbiotic states, has been shown to be a rice and wheat endophyte, and does not rely on plant metabolites to produce functional nitrogenase. However, when *Rhizobia* or *Azorhizobium* are living in cereal roots, there is low nitrogenase expression and $^{15}N2$ transfer rates suggest any reported uptake is due to bacterial death.

Cereal Crops, Nitrogen Fixation, and Bacteria

Cereal crops are broadly defined as any grass cultivated for the edible components of its grain (also referred to as caryopsis), composed of the endosperm, germ, and bran. Cereal crops are considered staple crops in many parts of the world. They are grown in greater quantities and provide more food energy worldwide than any other type of crop. Non-limiting examples of cereal crops include maize, rye, barley, wheat, sorghum, oats, millet and rice. As used herein, the terms "cereal crop" and "cereal plant" are used interchangeably.

Nitrogen fixation is the process by which atmospheric nitrogen is assimilated into organic compounds as part of the nitrogen cycle. The fixation of atmospheric nitrogen associated with specific legumes is the result of a highly specific symbiotic relationship with rhizobial bacteria. These indigenous bacteria dwell in the soil and are responsible for the formation of nodules in the roots of leguminous plants as sites for the nitrogen fixation. Most *Rhizobium* symbioses are confined to leguminous plants. Furthermore, *Rhizobium* strains which fix nitrogen in association with the agriculturally-important temperate legumes are usually restricted in their host range to a single legume genus.

The nif genes are genes encoding enzymes involved in the fixation of atmospheric nitrogen into a form of nitrogen available to living organisms. The primary enzyme encoded by the nif genes is the nitrogenase complex which converts atmospheric nitrogen (N2) to other nitrogen forms (e.g. ammonia) which the organism can process. As used herein, the term "nif cluster" refers to a gene cluster comprising nif genes. As used herein, the term "refactored" refers to an engineered gene clusture, i.e. its genes have reordered, deleted or altered in some way.

Rhizobia are diazotrophic bacteria. In general, they are gram negative, motile, non-sporulating rods. In terms of taxonomy, they fall into two classes: alphaproteobacteria and betaproteobacteria. Non-limiting examples of rhizobia include include *Azorhizobium caulinodans, Rhizobium*(R.) sp. IRBG74, *R. radiobacter, R. rhizogenes, R. rubi, R. vitis,* Alfalfa *Rhizobia* (*R. meliloti*), Chickpea *Rhizobia* (*Rhizobium* sp.), Soybean *Rhizobia* (*Bradyrhizobium japonicum*), Leucaena *Rhizobia* (*Rhizobium* sp.), *R. leguminosarum* by *trifolii, R. leguminosarum* by *phaseoli*, and *Rhizobium leguminosarum* by *viciae* (see for example U.S. Pat. No. 7,888, 552, herein incorporated by reference). In some embodiments, the rhizobia of the present invention are *Azorhizobium caulinodans*. In some embodiments, the rhizobia of the present invention are not *Azorhizobium caulinodans*.

As used herein, the term "free-living conditions" refers to a bacterium (e.g. rhizobium) that is not within a leguminous root nodule. It generally refers to something that has not formed a parasitic (or dependent) relationship with another organism or is not on a substrate. As used herein, the term "symbiotic" refers to the interaction between two organisms living in close proximity. Close proximity can be about 0.2 μm, 0.4 μm, 0.6 μm, 0.8 μm, 1 μm, 5 μm, 10 μm, 20 μm, 50 μm, 100 μm, 500 μm, 1 mm, 1 cm, 5 cm, 10 cm. Close proximity can also be less than 0.2 μm. In many cases, a symbiotic relationship refers to a mutually beneficial interaction.

As used herein, "aerobic free-living conditions" refer to conditions under which a bacterium is not within a leguminous root nodule and the bacterium is in the presence of oxygen. Aerobic free-living conditions can also be referred to as nonsymbiotic or non-parasitic conditions in the presence of oxygen. The bacterium can be in close proximity to a crop, as defined above.

As used herein, the term "endophyte" refers to a group of organisms, often fungi and bacteria, that live within living plant cells for at least part of its life cycle without having an apparent detrimental effect on the plant cell. This is contrasting with an epiphyte, which is a plant that grows on another plant, without being parasitic.

As used herein, the term "diazotroph" refers to microorganisms that are able to grow without external sources of fixed nitrogen. The group includes some bacteria and some archae. There are free-living and symbiotic diazotrophs. An example of a free-living diazotroph is *Klebsiella pneumoniae*. *K. pneumoniae* is a facultative anaerobes—these species can grow either with or without oxygen, but they only fix nitrogen anaerobically.

As used herein, the term "Alphaproteobacteria" refers to a diverse class of bacteria falling under the phylum Proteobacteria. Non-limiting examples of Alphaproteobacteria include species *Rhodobacter sphaeroides* and *Rhodopseudomonas palustris*. As used herein, the term "Gammaproteobacteria" refers to another class of bacteria falling under the phylum of Proteobacteria. All proteobacteria are gram negative. As used herein, the term "Cyanobacteria" refers to a phylum of bacteria that obtain their energy through photosynthesis. They are also referred to as Cyanophyta. They have characteristic internal membranes and thylakoids, the latter being for photosynthetic purposes. As used herein, the term "Firmicutes" refer to a phylum of bacteria. This phylum includes the classes Bacilli, Clostridia, and Thermolithobacteria.

Nif Genes

Typically, the genes necessary for nitrogen fixation occur together in a gene cluster, including the nitrogenase subunits, the biosynthesis of metalloclusters cluster and, e-transport, and regulator proteins. Nif genes are genes that encode the enzyme involved in nitrogen fixation. In most cases nif genes occur as an operon. Some of these genes encode the subunits for the nitrogenase complex, which is the primary enzyme imparting the ability to convert atmospheric nitrogen ($N_2$) to forms of nitrogen accessible to living organisms. In most genes, the regulation of the nif gene transcription is conducted by NifA protein, which is responsive to nitrogen levels. When there are nitrogen deficits, NtrC activates NifA expression, which in turn leads to the activation of the remaining nif genes. When nitrogen levels are adequate or in excess, NifL protein, encoded by NifL. NifL inhibits NifA activity.

Nif gene pathways are generally sensitive to small changes in expression. The genes that form nitrogenase. Important genes include nifHDK, which form the subunits for nitrogenase. The chaperone NifY is required to achieve full activity and broadens the tolerance to changes in expression level. NifJ and nif regulate electron transport. The nifUSVWZM operon encodes proteins for early Fe—S cluster formation (NifUS) and proteins for component maturation (NifVWZ for Component I and NifM for Component II), whereas nifBQ encodes proteins for FeMo-co core synthesis (NifB) and molybdenum integration (NifQ). NifEN is tolerant to varied expression levels.

Exemplary sequences for various nif genes are provided in Table 10. Non-limiting examples of nif genes include nifH, nifD, nifK, nifE, nifN, nifU, nifS, nifV, nifW, nifX, nifB, nifQ, nifY, nifT, nifJ, nifF, nifX, nifU, and nifS Nitrogen Fixation and Regulatory Elements The nitrogen fixation (nif) genes are organized as genomic clusters, ranging from a 10.5 kb single operon in *Paenibacillus* to 64 kb divided amongst three genomic locations in *A. caulinodans*. Conserved genes include those encoding the nitrogenase enzyme (nlfHDK), FeMoCo biosynthesis, and chaperones. Species that can fix nitrogen under more conditions tend to have larger gene clusters that include environment-specific paralogues, alternative electron transport routes, and oxygen protective mechanisms. Often, the functions of many genes in the larger clusters are unknown.

There is evolutionary evidence for the lateral transfer of nif clusters between species (Pascuan, C., Fox, A. R., Soto, G. & Ayub, N. D. Exploring the ancestral mechanisms of regulation of horizontally acquired nitrogenases. Journal of molecular evolution 81, 84-89 (2015); Kechris, K. J., Lin, J. C., Bickel, P. J. & Glazer, A. N. Quantitative exploration of the occurrence of lateral gene transfer by using nitrogen fixation genes as a case study. Proceedings of the National Academy of Sciences 103, 9584-9589 (2006)). However, achieving such a transfer via genetic engineering poses a challenge as many things can go awry, including differences in regulation, missing genes, and the intracellular environment (Frans, J. et al. in Nitrogen Fixation 33-44 (Springer, 1990); Poudel, S. et al. Electron transfer to nitrogenase in different genomic and metabolic backgrounds. Journal of bacteriology 200, e00757-00717 (2018); Thöny, B., Anthamatten, D. & Hennecke, H. Dual control of the *Bradyrhizobium japonicum* symbiotic nitrogen fixation regulatory operon fixR nifA: analysis of cis- and trans-acting elements. Journal of bacteriology 171, 4162-4169 (1989); Han, Y. et al. Interspecies Transfer and Regulation of *Pseudomonas stutzeri* A1501 Nitrogen Fixation Island in *Escherichia coli*. Journal of microbiology and biotechnology 25, 1339-1348 (2015)). Nitrogenase is under stringent control because it is oxygen sensitive and energetically expensive: it can make up 20% of the cell mass and each $NH_3$ requires ~40 ATP. It is also irreversibly deactivated by oxygen. Across species, transcription of nif genes is strongly repressed by fixed nitrogen (ammonia) and oxygen with these signals converging on the NifA regulatory protein that works in concert with the sigma factor RpoN. Diverse, species-specific, and often poorly understood signals control these regulators, including plant-produced chemicals, ATP, reducing power, temperature, and carbon sources. Those bacteria that can fix nitrogen in a wider range of environmental conditions tend to be controlled by more complex regulatory networks.

When a nif cluster is transferred from one species to another, it either preserves its regulation by environmental stimuli or has an unregulated constitutive phenotype. Maintaining the native regulation, notably ammonium repression, limits their use in agriculture because such levels are likely to fluctuate according to soil types, irrigation, and fertilization. Nitrogen-fixing diazotrophs have been engineered to reduce ammonia sensitivity by disrupting NifL or mutating NifA and placing the entire cluster under the control of T7 RNA polymerase (RNAP). Constitutive expression of nitrogenase is also undesirable as it imparts a fitness burden on the cells. For example, when the nif cluster from *P. stutzeri* A1501 was transferred to *P. protegens* Pf-5, this was reported to result in sufficient ammonia production to support maize and wheat growth, but the bacteria quickly declined after a month when competing with other species in soil. Constitutive activity is detrimental even before the bacteria are introduced to the soil, impacting production, formulation, and long-term storage. Therefore, uncontrolled nitrogenase production could lead to more expensive production, shorter shelf life, and more in-field variability.

An important aspect of the nif clusters or nif genes the present disclosure is that they can each be under the control of a regulatory element. In some embodiments 2 or more genes are under the control of a regulatory element. In some embodiments, all the genes are under the control of a regulatory element. The regulatory elements may also be activation elements or inhibitory elements. An activation element is a nucleic acid sequence that when presented in context with a nucleic acid to be expressed will cause expression of the nucleic acid in the presence of an activation signal. An inhibitory signal is a nucleic acid sequence that when presented in context with a nucleic acid to be expressed will cause expression of the nucleic acid unless an inhibitory signal is present. Each of the activation and inhibitory elements may be a promoter, such as a bacteriophage T7 promoter, sigma 70 promoter, sigma 54 promoter, lac promoter, etc. As used herein, the term "promoter" is intended to refer to those regulatory sequences which are sufficient to enable the transcription of an operably linked DNA molecule. Promoters may be constitutive or inducible. As used herein, the term "constitutive promoter" refers to a promoter that is always on (i.e. causing transcription at a constant level). Examples of constitutive promoters include, without limitation, sigma 70 promoter, bla promoter, lacI. promoter, etc. Non-limiting examples of inducible promoters are shown in Table 6. The $P_{A1lacO1}$ promoter is another example of an inducible promoter that can be used in the present invention.

TABLE 6

Examples of regulatory elements (e.g. inducible promoters, repressors).

| Name | Chemical inducer and/or repressor | Essential regulatory gene(s) |
| --- | --- | --- |
| ParaBAD ("PBAD") | L-arabinose (ON) & glucose (OFF) | araC |
| PrhaBAD | L-rhamnose (ON) & glucose (OFF) | rhaR & rhaS |
| Plac | lactose or IPTG (ON) & glucose (OFF) | lacI |
| Ptac | lactose or IPTG (ON) | lacI |
| Plux | acyl-homoserine lactone (ON) | luxR |
| Ptet | tetracycline or aTc (ON) | tetR |
| Psal | salycilate (ON) | nahR |
| Ptrp | tryptophan (OFF) | (NONE) |
| Ppho | phosphate (OFF) | phoB & phoR |

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268:1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only.

As used herein, the term "terminator" (as referred to as a transcription terminator) is a section of nucleic acid sequence that marks the end of a gene or operon in genomic DNA during transcription. They stop transcription of a polymerase. Terminators can be classified into several groups. At the first group of termination signals the core enzyme can terminate in vitro at certain sites in the absence of any other factors (as tested in vitro). These sites of termination are called intrinsic terminators or also class I terminators. Intrinsic terminators usually share one common structural feature, the so called hairpin or stem-loop structure. On the one hand the hairpin comprises a stem structure, encoded by a dG-dC rich sequence of dyad symmetrical structure. On the other hand the terminator also exhibits a dA-dT rich region at the 3'-end directly following the stem structure. The uridine rich region at the 3' end is thought to facilitate transcript release when RNA polymerase pauses at hairpin structures. Two or more terminators can be operatively linked if they are positioned to each other to provide concerted termination of a preceding coding sequence. Particularly preferred, the terminator sequences are downstream of coding sequences, i.e. on the 3' position of the coding sequence. The terminator can e.g. be at least 1, at least 10, at least 30, at least 50, at least 100, at least 150, at least 200, at least 250, at least 300, at least 400, at least 500 nucleotides downstream of the coding sequence or directly adjacent. Examples of terminators include, but are not limited to, T7 terminator, rrnBT1, L3S2P21, tonB, rrnA, rrnB, rrnD, RNAI, crp, his, ilv lambda, M13, rpoC, and trp (see for example U.S. Pat. No. 9,745,588, incorporated herein by reference).

RpoN

As used herein "RpoN" refers to a gene that encodes the sigma factor sigma-54 (σ54, sigma N, or RpoN), a protein in *Escherichia coli* and other species of bacteria. Sigma factors are initiation factors that promote attachment of RNA polymerase to specific initiation sites and are then released. Bacteria normally only have one functional copy of the alternative sigma factor, σ54 or RpoN, which regulates a complex genetic network that extends into various facets of bacterial physiology, including metabolism, survival in strenuous environments, production of virulence factors, and formation of biofilms. RpoN is one of seven RNA polymerase sigma subunits in *E. coli* required for promoter-initiated transcription and RpoN plays a major role in the response of *E. coli* to nitrogen-limiting conditions. Under such conditions, RpoN directs the transcription of at least 14 *E. coli* operons/regulators in the nitrogen regulatory (Ntr) response. RpoN also plays an important role in stress resistance (e.g. resistance to osmotic stress) and virulence of bacteria. RpoN is structurally and functionally distinct from the other *E. coli* σ factors. It is able to bind promoter DNA in the absence of core RNA polymerase and it recognizes promoter sequences with conserved GG and GC elements located −24 to −12 nucleotides upstream of the transcription start site. Additionally, Regulatory proteins like NtrB and NtrC can activate σ54 holoenzyme.

Without being bound by theory or mechanism, it is believed that RpoN works in concert with NifA to turn on the transcription of nif clusters. An exemplary sequence for RpoN is provided in Table 10.

Gene Cluster Nucleic Acids

In some embodiments of the present disclosure a genetic cluster includes a nucleotide sequence that is at least about 85% or more homologous or identical to the entire length of a naturally occurring genetic cluster sequence, e.g., at least 5%, 10%, 15%, 20%, 25%, 30%, 35%, 40%, 50% or more of the full length naturally occurring genetic cluster sequence). In some embodiments, the nucleotide sequence is at least about 90%, 91%, 92%, 93%, 94%, 95%, 96%, 97%, 98%, 99% or 100% homologous or identical to a naturally occurring genetic cluster sequence. In some embodiments, the nucleotide sequence is at least about 85%, e.g., is at least about 90%, 91%, 92%, 93%, 94%, 95%, 96%, 97%, 98%, 99% or 100% homologous or identical to a genetic cluster sequence, in a fragment thereof or a region that is much more conserved, such as an essential, but has lower sequence identity outside that region.

Calculations of homology or sequence identity between sequences (the terms are used interchangeably herein) are performed as follows. To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

In some embodiments the gene clusters are native gene clusters. In some embodiments, the gene clusters are refactored gene clusters. In some instances, the nucleic acids may include non-naturally occurring nucleotides and/or substitutions, i.e. Sugar or base substitutions or modifications.

One or more substituted sugar moieties include, e.g., one of the following at the 2' position: OH, SH, SCH3, F, OCN, OCH3OCH3, OCH3O(CH2)n CH3, O(CH2)n NH2 or O(CH2)n CH3 where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; 0-, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of a nucleic acid; or a group for improving the pharmacodynamic properties of a nucleic acid and other substituents having similar properties.

Similar modifications may also be made at other positions on the nucleic acid, particularly the 3' position of the sugar on the 3' terminal nucleotide and the 5' position of 5' terminal nucleotide. Nucleic acids may also have sugar mimetics such as cyclobutyls in place of the pentofuranosyl group.

Nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-' 7' 7; and Gebeyehu, G., et al. Nucl. Acids Res., 15:4513 (1987)). A "universal" base known in the art, e.g., inosine, can also be included.

As used herein, the equivalent terms "expression" or "gene expression" are intended to refer to the transcription of a DNA molecule into RNA, and the translation of such RNA into a polypeptide.

As used herein, a "gene cluster" refers to a set of two or more genes that encode gene products. As used herein, a "nif gene cluster" refers to a set of two or more genes that encode nitrogen fixation genes.

"Exogenous" with respect to genes indicates that the nucleic acid or gene is not in its natural (native) environment. For example, an exogenous gene can refer to a gene that is from a different species. In contrast, "endogenous" with respect to genes indicates that the gene is in its native environment. As used herein, the terms "endogenous" and "native" are used interchangeably.

As used herein, the term "delete" or "deleted" refers to the removal of a gene (e.g. endogenous gene) from a sequence or cluster. As used herein, the term "alter" or "altered" refers to the modification of one or more nucleotides in a gene or the deletion of one or more base pairs in a gene. This alteration may render the gene dysfunctional. Herein, "ΔnifA" refers to a strain or cluster within which NO was deleted or altered. Method of deletion and alteration, in the context of genes, are known in the art.

As used herein, the term "chemical signals" refers to chemical compounds. Any substance consisting of two or more different types of atoms (chemical elements) in a fixed stoichiometric proportion can be termed a chemical compound. Chemical signals can be synthetic or natural chemical compounds. In some embodiments of the present invention, a bacterium of the present disclosure or a sensor of the present disclosure is under the control of a chemical signal. In some embodiments, the signal is a native biological signal (e.g. root exudate, biological control agent, etc.). In some embodiments, the chemical signal is a quorum sensing signal from the bacterium. Non-limiting examples of chemical signals include root exudates (as defined below), biocontrol agents (as defined below), phytohormones, vanillate, IPTG, aTc, cuminic acid, DAPG, and salicylic acid, 3,4-dihydroxybenzoic acid, 3OC6HSL and 3OC14HSL.

As used herein, the term "root exudate" refers to chemicals secreted or emitted by plant roots in response to their environment. These allow plant to manipulate or alter their immediate environment, specifically their rhizosphere. Root exudates are a complex mixture of soluble organic substances, which may contain sugars, amino acids, organic acids, enzymes, and other substances. Root exudates include, but are not limited to, ions, carbon-based compounds, amino acids, sterols, sugars, hormones (phytohormones), flavonoids, antimicrobials, and many other chemical compounds. The exudates can serve as either positive regulators or negative regulators.

As used herein, the term "phytohormone" refers plant hormones and they are any of various hormones produced by plants that influence process such as germination, growth, and metabolism in the plant.

As used herein, the term "vanillate" refers to a methoxybenzoate that is the conjugate base of vanillic acid. It is a plant metabolite.

Biological control or biocontrol is a method of controlling pests such as insects, mites, weeds and plant diseases using other organisms. Natural enemies of insect pests, also known as biological control agents, include predators, parasitoids, pathogens, and competitors. Biological control agents of plant diseases are most often referred to as antagonists. Biological control agents of weeds include seed predators, herbivores and plant pathogens. The inducible clusters or promoters of the present invention may be modulated by a secretion of (or chemical otherwise associated with) a biological control agent. Herein, that is referred to as a "biocontrol agent".

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Herein, inducible nitrogenase activity is engineered in two cereal endophytes (*Azorhizobium caulinodans* ORS571 and *Rhizobium* sp. IRBG74) and the epiphyte *Pseudomonas protegens* Pf-5, a maize seed inoculant. For each organism, different strategies are taken to eliminate ammonium repression and place nitrogenase expression under the control of agriculturally-relevant signals, including root exudates, biocontrol agents, and phytohormones. The present disclosure demonstrates that *Rhizobium* sp. (e.g., IRBG74) can be engineered to fix nitrogen under free living conditions, inter alia, by transferring either a nif cluster from *Rhodobacter* or *Klebsiella*. For *P. protegens* Pf-5, the transfer of an inducible cluster from *Azotobacter vinelandii* yields the highest ammonia and oxygen tolerance. Collectively, data from the transfer of 12 nif gene clusters between diverse species (including *E. coli* and 12 additional *Rhizobia*) help identify the barriers that must be overcome to engineer a bacterium to deliver a high nitrogen flux to a cereal crop and provide a solution such that *Rhizobium* can be engineered to fix nitrogen under free living conditions.

Materials and Methods

Bacterial strains and growth media. All bacterial strains and their derivatives used in this study are listed in Table 7. *E. coli* DH10-beta (New England Biolabs, MA, Cat # C3019) was used for cloning. *E. coli* K-12 MG1655 was used for the nitrogenase assay. *P. protegens* Pf-5 was obtained from the ATCC (BAA-477). Strains used in this study are listed in Table 8. For rich media, LB medium (10 g/L tryptone, 5 g/L yeast extract, 10 g/L NaCl), LB-Lennox medium (10 g/L tryptone, 5 g/L yeast extract, 5 g/L NaCl), and TY medium (5 g/L tryptone, 3 g/L yeast extract, 0.87 g/L CaCl2.2H2O) were used. For minimal media, BB medium (0.25 g/L MgSO4.7H$_2$O, 1 g/L NaCl, 0.1 g/L CaCl$_2$.2H$_2$O, 2.9 mg/L FeCl$_3$, 0.25 mg/L Na$_2$MoO$_4$.2H$_2$O, 1.32 g/L NH$_4$CH$_3$CO$_2$, 25 g/L Na$_2$HPO$_4$, 3 g/L KH$_2$PO$_4$ pH [7.4]), UMS medium (0.5 g/L MgSO$_4$.7H$_2$O, 0.2 g/L NaCl, 0.375 mg/L EDTA-Na$_2$, 0.16 ZnSO$_4$.7H$_2$O, 0.2 mg/L Na$_2$MoO$_4$.2H$_2$O, 0.25 mg/L H$_3$BO$_3$, 0.2 mg/L MnSO$_4$.H$_2$O, 0.02 mg/L CuSO$_4$.5H$_2$O, 1 mg/L CoCl$_2$.6H$_2$O, 75 mg/L CaCl$_2$.2H$_2$O, 12 mg/L FeSO$_4$.7H$_2$O, 1 mg/L thiamine hydrochloride 2 mg/L D-pantothenic acid hemicalcium salt, 0.1 mg/L biotin, 87.4 mg/L K$_2$HPO, 4.19 g/L MOPS pH [7.0]), and Burk medium (0.2 g/L MgSO$_4$.7H$_2$O, 73 mg/L CaCl$_2$.2H$_2$O, 5.4 mg/L FeCl$_3$.6H$_2$O, 4.2 mg/L Na$_2$MoO$_4$.2H$_2$O, 0.2 g/L KH$_2$PO$_4$, 0.8 g/L K$_2$HPO$_4$ pH [7.4]) were used. Antibiotics were used at the following concentrations (μm/mL): *E. coli* (kanamycin, 50; spectinomycin, 100; tetracycline, 15; gentamicin, 15). *P. protegens* Pf-5 (kanamycin, 30; tetracycline, 50; gentamicin, 15; carbenicillin, 50). R. sp. IRBG74 (neomycin, 150; gentamicin, 150; tetracycline, 10; nitrofurantoin, 10). *A. caulinodans* (kanamycin, 30; gentamicin, 15; tetracycline, 10; nitrofurantoin, 10). Chemicals including inducers used in this study are listed in Table 12.

Strain construction. In order to increase transformation efficiency in R. sp. IRBG74, a type-I restriction modification system was inactivated by deleting hsdR, which encodes a restriction enzyme for foreign DNA (this strain was the basis for all experiments) (Ferri, L., Gori, A., Biondi, E. G., Mengoni, A. & Bazzicalupo, M. J. P. Plasmid electroporation of *Sinorhizobium* strains: The role of the restriction gene hsdR in type strain Rm1021. 63, 128-135 (2010)). A sacB markerless insertion method was utilized to allow replacements of a native locus with synthetic parts by homologous recombination. Two homology arms of ~500 bp flanking the hsdR gene were amplified by PCR, cloned and yielded a suicide plasmid pMR-44. The suicide plasmid was mobilized into R. sp. IRBG74 by triparental mating. Single-crossover recombinants were selected for resistance to gentamicin and subsequently grown and plated on LB plates supplemented with 15% sucrose to induce deletion of the vector DNA part containing the counter selective marker sacB which converts sucrose into a toxic product (levan). Two native nif gene clusters encompassing nifHDKENX (genomic location 219.579-227,127) and nifSW-fixABCX-nifAB-fdxN-nifTZ (genomic location 234,635-234,802) of R. sp. IRBG74 were sequentially deleted using pMR45-46. To increase genetic stability recA gene was deleted using the plasmid pMR47. The R. sp. IRBG74 Δnif, hsdR, recA strain was the basis for all experiments unless indicated otherwise. Two homology arms of ~900 bp flanking the nifA gene were amplified by PCR, cloned and yielded a suicide plasmid pMR-47 to generate nifA deletion in *A. caulinodans* ORS571, The suicide plasmid pMR47 in *E. coli* was mobilized into *A. caulinodans* by triparental mating. Single-crossover recombinants were selected for resistance to gentamicin and subsequently grown and plated on plain TY plates supplemented with 15% sucrose to induce deletion of the vector DNA part. All markerless deletions were confirmed by gentamicin sensitivity and diagnostic PCR. A list of the mutant strains is provided in Table 8.

Plasmid system. Plasmids with the pBBR1 origin were derived from pMQ131 and pMQ132. Plasmids with the pRO1600 origin were derived from pMQ80. Plasmids with the RK2 origin were derived from pJP2. Plasmids with the RSF1010 origin were derived from pSEVA651. Plasmids with the IncW origin were derived from pKT249. Plasmids used in this study are provided in Table 9.

Phylogenetic analysis of nif clusters. Phylogenetic analysis was performed based on the full-length 16S rRNA gene sequences (*K. oxytoca*, BWI76_05380; *A. vinelandii*, Avin_55000; *R. sphaeroides*, DQL45_00005; *Cyanothece* ATCC51142, cce_RNA045; *A. brasilense*, AMK58_25190; *R. palustris*, RNA_55; *P. protegens*, PST_0759; *Paenibacillus* sp. WLY78, JQ003557). A multiple sequence alignment was generated using MUSCLE (Edgar, R. C. J. N. a. r. MUSCLE: multiple sequence alignment with high accuracy and high throughput. 32, 1792-1797 (2004)). A phylogenetic tree was constructed using the Geneious software (R9.0.5) with the Jukes-Cantor distance model and UPGMA as a tree build method, with bootstrap values from 1,000 replicates.

nif cluster construction. To obtain large nif clusters on mobilizable plasmids that carry origin of transfer (oriT) for conjugative transfer of the plasmids, the genomic DNAs from *K. oxytoca, P. stutzeri, A. vinelandii, A. caulinodans* and *R. sphaeroides* were purified using Wizard genomic DNA purification kit, following the isolation protocol for gram negative bacteria (Promega, Cat # A1120). The genomic DNAs of *Cyanothece* ATCC51142, *A. brasilense* ATCC29729, *R. palustris* ATCC BAA-98, and *G. diazotrophicus* ATCC49037 were obtained from ATCC. Each nif cluster was amplified into several fragments (4-10 kb) with upstream and downstream 45 bp linkers at the 5' and 3' most end of the cluster by PCR with primer sets (Table 7) and assembled onto linearized *E. coli*-yeast shuttle vectors pMR-1 for *E. coli* and *Rhizobia*, and pMR-2 for *P. protegens* Pf-5 using yeast recombineering. For the nif cluster of *Paenibacillus* sp. WLY78, the DNA sequence information were gleaned from contig ALJV01 and the DNA of the nif cluster was synthesized by GeneArt gene synthesis (Thermo Fisher Scientific, MA) into four fragments that were used as templates for PCR amplification and assembly. Amplified fragments from two to eight (Table 7) were assembled with a linearized vector into a single large plasmid by one-pot yeast assembly procedure (Shanks, R. M. et al. *Saccharomyces cerevisiae*-based molecular tool kit for manipulation of genes from gram-negative bacteria. 72, 5027-5036 (2006)). Once assembled, the nif cluster-plasmids were isolated from yeast using Zymoprep Yeast Miniprep kit (Zymo Research Cat # D2004) and transformed into *E. coli*. The purified plasmid was isolated from *E. coli* and sequenced to verify the correct assembly and sequence (MGH CCIB DNA Core facility, Cambridge, Mass.). *E. coli* containing a mutation-free plasmid were stored for further experiments. Plasmids containing nif clusters are provided in Table 9.

Construction of refactored nif v3.2. The six transcriptional units (nifHDKTY, nifENX, nifJ, nifBQ, nifF, nifUSVWZM) were amplified from the plasmid pMR-3 that harbors the native *Klebsiella* nif cluster. Each unit was divided onto six level-1 module plasmids where the nif genes are preceded by a terminator. T7 promoter wild-type or T7 promoter variant PT7.P2 was placed between a terminator and the first gene of the transcriptional unit.

Assembly linkers (~45 bp) were placed at both ends of the units. The level-1 plasmids (pMR32-37) were provided in Table 9 and 10. Each of the six plasmids was linearized by digestion with restriction enzymes and assembled with a linearized pMR-1 or pMR-2 vector into a single large plasmid by one-pot yeast assembly procedure, yielding pMR38 and pMR39.

Transformation. Electroporation was used to transfer plasmids into P. protegens Pf-5. A single colony was inoculated in 4 mL of LB and grown for 16 h at 30° C. with shaking at 250 rpm. The cell pellets were washed twice with 2 mL of 300 mM sucrose and dissolved in 100 µl of 300 mM sucrose at RT. A total of 50-100 ng DNA was electroporated and recovered in 1 mL of LB media for 1 h before plating on selective LB plates. Triparental mating was used to transfer DNA from E. coli to Rhizobia. An aliquot of 40 µl of late-log phase ($OD_{600}$~0.6) donor cells and 40 µl of late-log phage helper cells containing pRK7013 were mixed with 200 µl of late-log phase ($OD_{600}$~0.8) recipient Rhizobia cells and washed in 200 µl of TY medium. Mating was initiated by spotting 20 µl of the mixed cells on TY plates and incubated at 30° C. for 6 h. The mating mixtures were plated on TY medium supplemented with nitrofurantoin to isolate Rhizobia transconjugants.

Figure 11A:
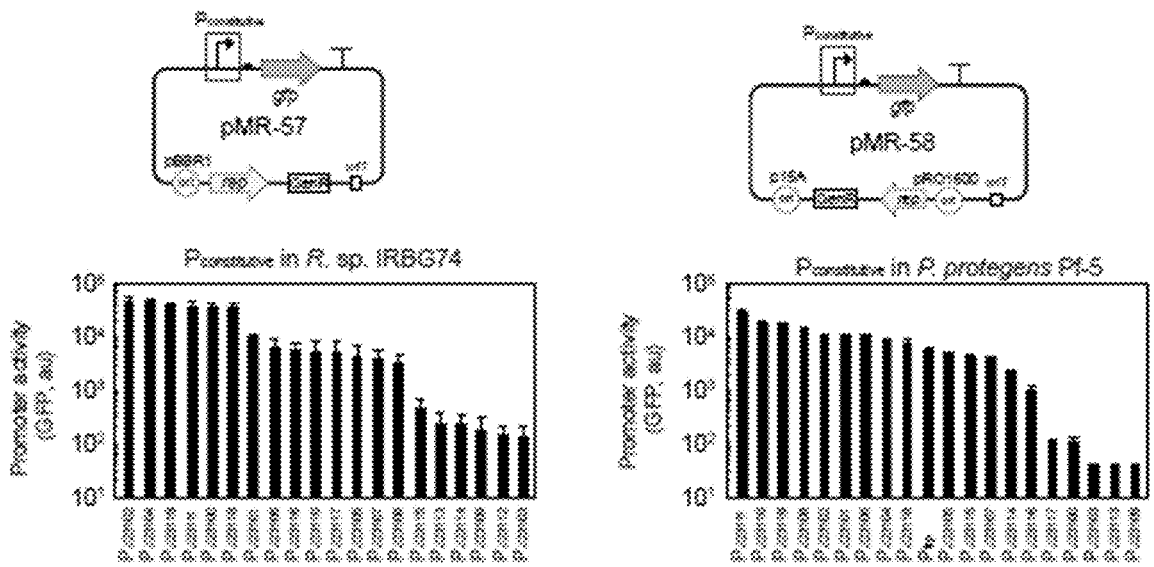
FIGS. 11A-11C include diagrams showing Promoter characterization in R. sp. IRBG74 and *P. protegens* Pf-5.
Figure 11B:
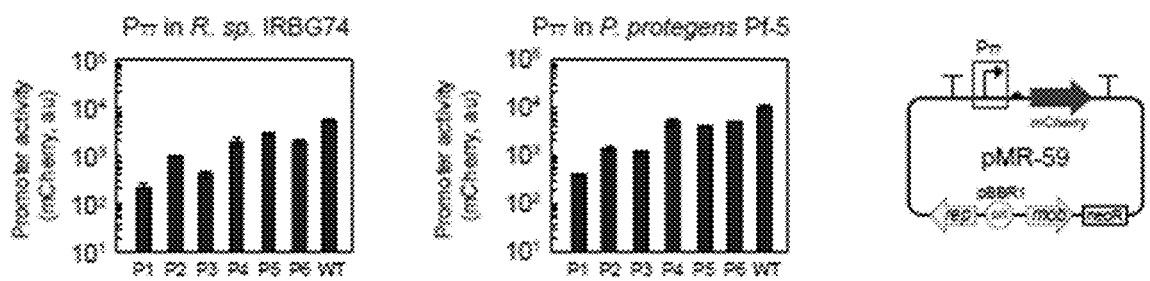
Figure 11C:
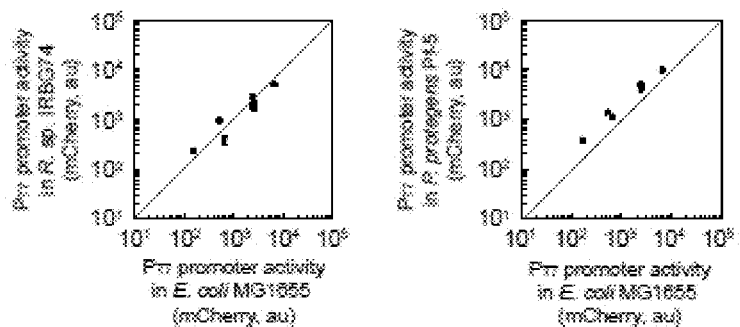
Figure 12A:
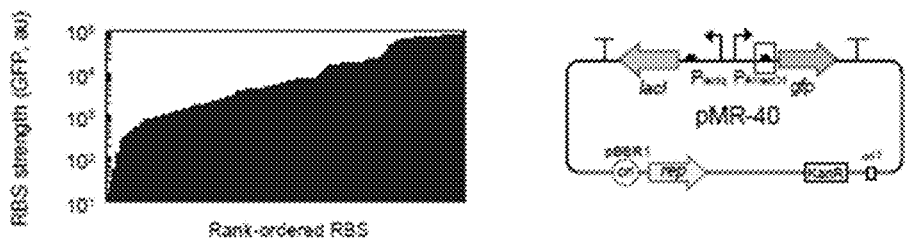
FIGS. 12A-12B include diagrams showing RBS characterization in R. sp. IRBG74 and P. protegens Pf-5. RBS library for GFP was designed using the RBS library calculator at the highest-resolution mode.
Figure 12B:
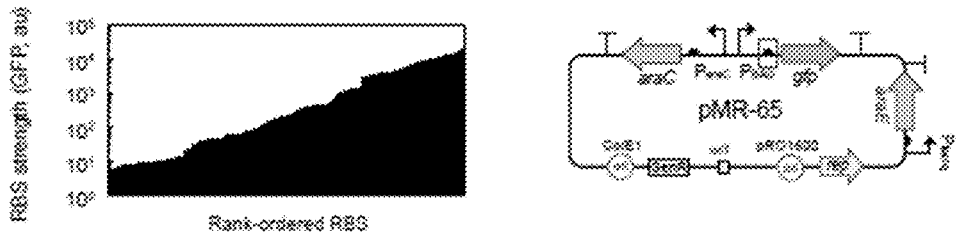
Figure 13A:
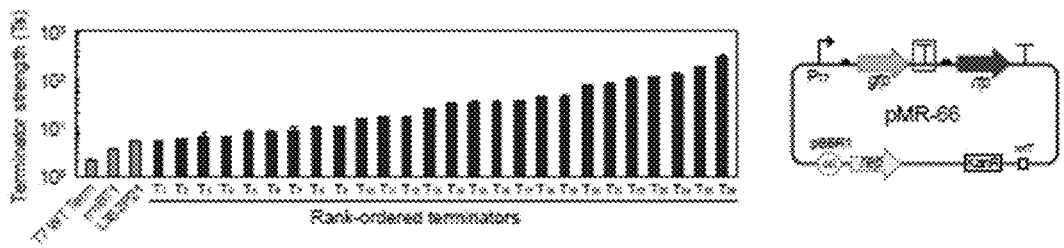
FIGS. 13A-13B include diagrams showing the characterization of terminators for T7 RNAP in R. sp. IRBG74 (FIG. 13A) and P. protegens Pf-5 (FIG. 13B).
Figure 13B:
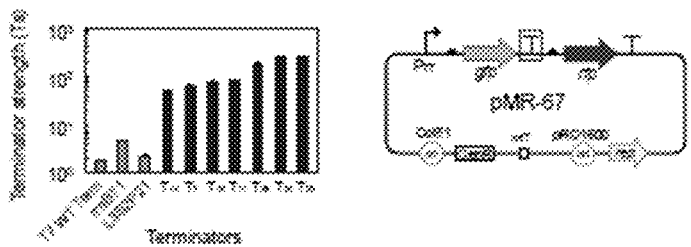
Figure 14:
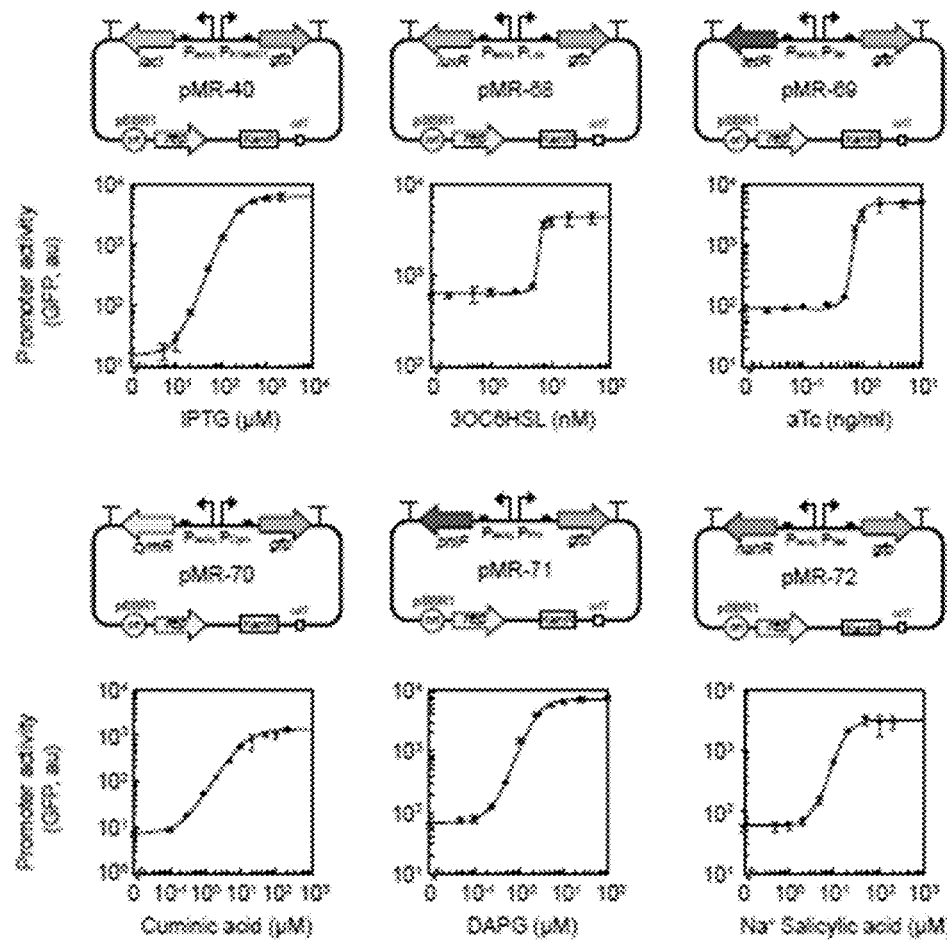
FIG. 14 includes diagrams showing the response functions for the sensors in R. sp. IRBG74. Plasmids used to characterize the sensors are shown on top of each panel and provided in Table 9. Genetic parts are provided in Table 10. Error bars represent s.d. from three independent experiments. Experimental details are provided in Methods.

Construction and characterization genetic parts for Rhizobia. Genetic part libraries were built on a pBBR1-ori plasmid pMR-1 using Gibson assembly (New England Biolabs, Cat # E2611). The fluorescence proteins, GFPmut3b and mRFP1 were used as reporters. The Anderson promoter library (Anderson, J. et al. BglBricks: A flexible standard for biological part assembly. 4, 1 (2010)) on the BioBricks Registry were utilized for the characterization of constitutive promoters (FIGS. 11A-11C). To characterize inducible promoters, a regulator protein is constitutively expressed by the PlacIq promoter, and GFP expression is driven by a cognate inducible promoter from the opposite direction, facilitating replacement of the reporter with gene of interest (e.g., T7 RNAP and nifA) and transfer of the controller unit across different plasmid backbones for diverse microbes. The following combinations of cognate regulators and inducible promoters were characterized. IPTG inducible LacI-A1lacO1, DAPG inducible PhlF-PPhl, aTc inducible TetR-PTet, 3OC6HSL inducible LuxR-PLux, salicylic acid inducible NahR-$P_{Sal}$, and cuminic acid inducible CymR-$P_{Cym}$ systems were optimized for R. sp. IRBG74 (FIG. 14). Opine inducible OccR-$P_{occ}$, and nopaline inducible NocR-Pnoc systems were optimized for A. caulinodans (FIGS. 20A-20F and Tables 9 and 10). For RBS characterization, an IPTG-inducible GFP expression plasmid pMR-40 was used and GFP was expressed to the highest levels with 1 mM IPTG (FIGS. 12A-12B). RBS library for GFP was designed using the RBS library calculator at the highest-resolution mode, and the 3' end of the 16S rRNA sequences were adjusted according to the species (3'-ACCTCCTTC-5' for R. sp. IRBG74). Terminators for T7 RNAP were characterized by placing a terminator between two fluorescence reporters expressed from a single T7 wild-type promoter located upstream of the first fluorescence protein GFP. The expression of the two fluorescence proteins is enabled by the controller strain MR18 encoding the IPTG-inducible T7 RNAP system by 1 mM IPTG (FIGS. 13A-13B). The terminator strength (Ts) was determined by normalizing fluorescence levels of a terminator construct by a reference construct pMR-66 where a 40 bp spacer was placed between the reporters. All genetic parts for Rhizobia were characterized as follows. Single colonies were inoculated into 0.5 ml TY supplemented with antibiotics in 96-deepwell plates (USA Scientific, Cat #18962110) and grown overnight at 30° C., 900 rpm in a Multitron incubator (INFORS HT, MD). 1.5 µl of overnight cultures was diluted into 200 µl of TY with antibiotics and appropriate inducers in 96-well plates (Thermo Scientific, Cat #12565215) and incubated for 7 h at 30° C., 1,000 rpm in an ELMI DTS-4 shaker (ELMI, CA). After growth, 8 µl of culture sample was diluted into 150 µl PBS with 2 mg/mL kanamycin for flow cytometry analysis. Plasmids and genetic parts are listed in Table 9 and 10.

Figure 15A:
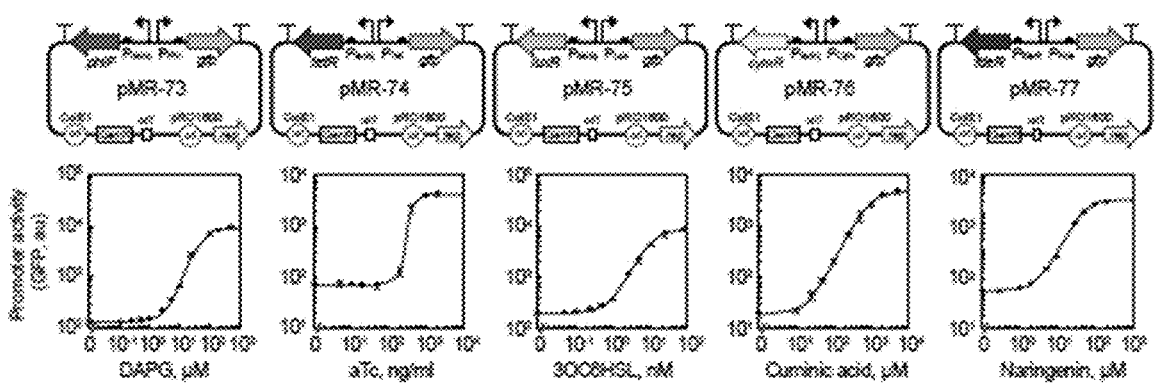
FIGS. 15A-15C include diagrams showing the response functions for the sensors in P. protegens Pf-5. The output changes as a function of input inducer concentrations. Plasmids used to characterize the sensors are shown on top of each panel.
Figure 15B:
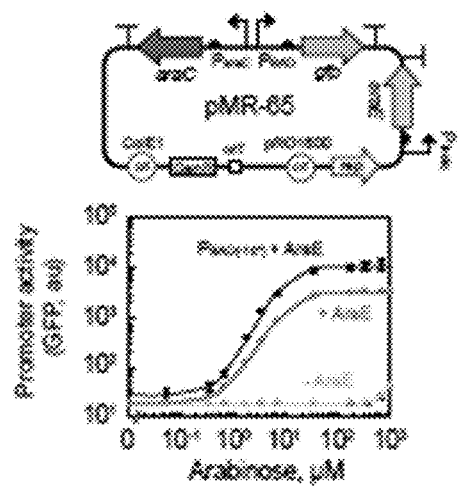
Figure 15C:
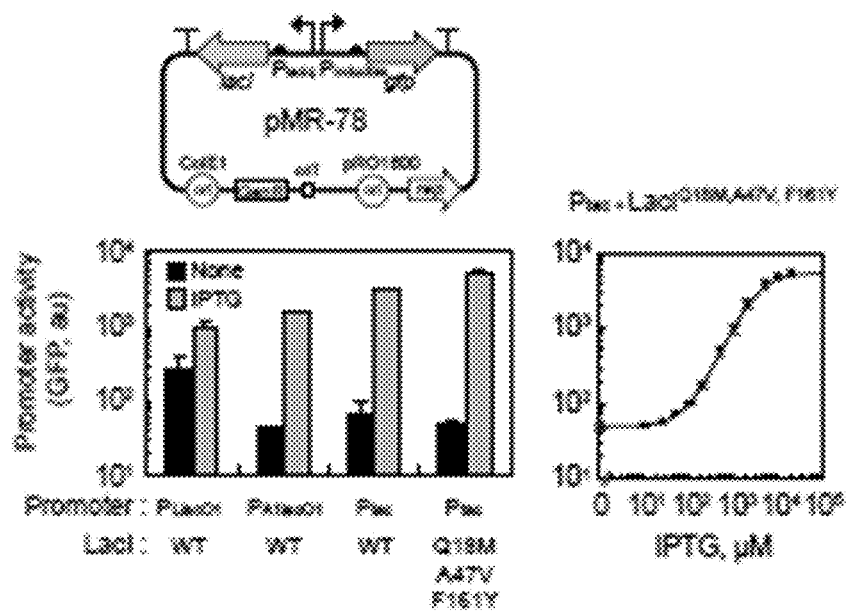

Construction and characterization genetic parts for P. protegens. Genetic part libraries were built on a pRO1600-ori plasmid pMR-2 using Gibson assembly (New England Biolabs, Cat # E2611). The fluorescence proteins, GFPmut3b and mRFP1 were used as reporters. The Anderson promoter library on the BioBricks Registry were utilized for the characterization of constitutive promoters (FIGS. 11A-11C). The following combinations of cognate regulators and inducible promoters were characterized. IPTG inducible LacI-$P_{tac}$, DAPG inducible PhlF-$P_{Phl}$, aTc inducible TetR-$P_{Tet}$, 3OC6HSL inducible LuxR-$P_{Lux}$, arabinose inducible AraC-$P_{BAD}$, cuminic acid inducible CymR-$P_{Cym}$, and naringenin inducible FdeR-$P_{Fde}$ were optimized (FIGS. 15A-15C). For RBS characterization, an arabinose-inducible GFP expression plasmid pMR-65 was used and GFP was expressed with 1 mM IPTG (FIGS. 12A-12B). RBS library for GFP was designed using the RBS library calculator at the highest-resolution mode, and the 3' end of the 16S rRNA sequences were adjusted according to the species (3'-ACCTCCTTA-5' for P. protegens Pf-5). Terminators for T7 RNAP were characterized by placing a terminator between two fluorescence reporters expressed from a single T7 wild-type promoter located upstream of the first fluorescence protein GFP. The expression of the two fluorescence proteins is enabled by an IPTG-inducible T7 RNAP expression system of the controller strain MR7 (FIGS. 13A-13B). All genetic parts for P. protegens Pf-5 were characterized as follows. Single colonies were inoculated into 1 ml LB supplemented with antibiotics in 96-deepwell plates (USA Scientific, Cat #18962110) and grown overnight at 30° C., 900 rpm in a Multitron incubator (INFORS HT, MD). 0.5 µl of overnight cultures was diluted into 200 µl of LB with antibiotics and appropriate inducers in 96-well plates (Thermo Scientific, Cat #12565215) and incubated for 7 h at 30° C., 1,000 rpm in an ELMI DTS-4 shaker (ELMI, CA). After growth, 10 µl of culture sample was diluted into 150 µl PBS with 2 mg/mL kanamycin for flow cytometry analysis. Plasmids and genetic parts are listed in Tables 9 and 10.

Genomic integration and characterization of controllers. The mini-Tn7 insertion system was used to introduce a controller into the genome of P. protegens Pf-5. The IPTG-inducible T7 RNAP expression system and a tetracycline resistant marker tetA was placed between two Tn7 ends (Tn7L and Tn7R). The controller plasmid pMR-85 was introduced into P. protegens Pf-5 by double transformation with pTNS3 encoding the TnsABCD transposase. A genomically-integrated controller located 25 bp downstream of the stop codon of glmS was confirmed by PCR and sequencing. A markerless insertion method using homologous recombination was employed in R. sp. IRBG74. A controller encoding inducible T7 RNAP system flanked by two homology fragments that enables the replacement of recA was cloned into a suicide plasmid. These controller plasmids (IPTG-inducible, pMR82-84; DAPG-inducible, pMR85) in E. coli was mobilized into R. sp. IRBG74 MR18 (AhsdR. Anif) by triparental mating, generating the controller strains (MR19, 20, 21 and 22, respectively). The controller integration in the genome was confirmed by gentamicin sensitivity and diagnostic PCR. All controllers were characterized in a manner identical to that described in genetic part characterization.

Figure 28A:
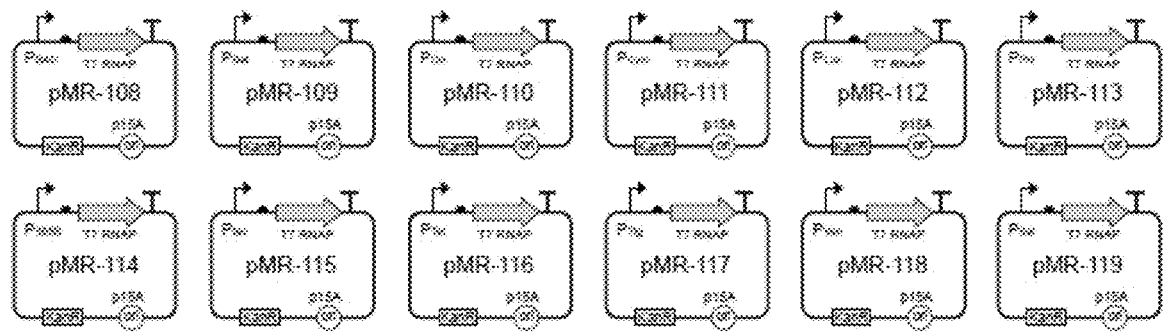
FIGS. 28A-28C include diagrams showing regulation of nitrogenase activity in *E. coli* MG1655 "Marionette" strain5.
Figure 28B:
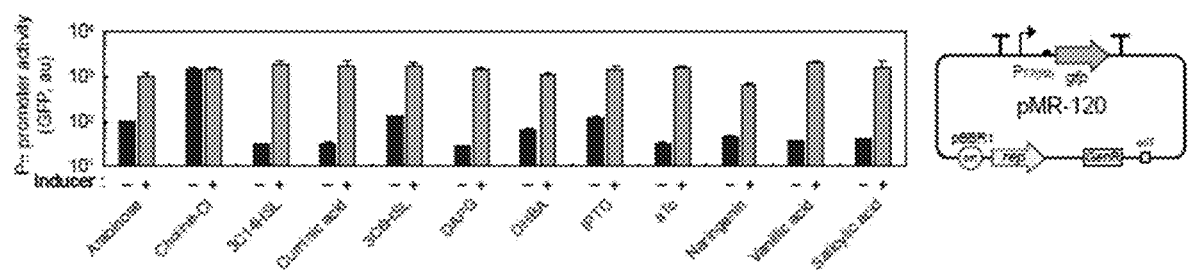
Figure 28C:
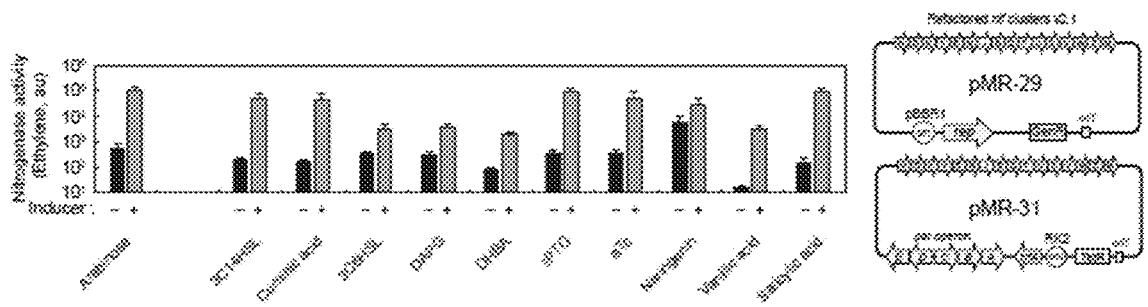

Construction and characterization of Marionette-based controllers. To regulate nitrogenase expression in the *E. coli* Marionette MG1655, the yfp in the 12 reporter plasmids was replaced with T7 RNAP while keeping other genetic parts (e.g., promoters and RBSs) unchanged (FIGS. 28A-28C). The reporter plasmid pMR-120 in which gfpmut3b is fused to the PT7(P2) promoter (FIGS. 28A-28C) was co-transformed to analyze the response functions of each of the 12 T7 RNAP controller plasmids. To characterize controllers, single colonies were inoculated into 1 ml LB supplemented with antibiotics in 96-deepwell plates (USA Scientific, Cat #18962110) and grown overnight at 30° C., 900 rpm in a Multitron incubator (INFORS HT, MD). 0.5 µl of overnight cultures was diluted into 200 µl of LB with antibiotics and appropriate inducers in 96-well plates (Thermo Scientific, Cat #12565215) and incubated for 6 h at 30° C., 1,000 rpm in an ELMI DTS-4 shaker (ELMI, CA). After growth, 4 µl of culture sample was diluted into 150 µl PBS with 2 mg/mL kanamycin for flow cytometry analysis.

Flow cytometry. Cultures with fluorescence proteins were analyzed by flow cytometry using a BD Biosciences LSRII Forterssa analyzer with a 488 nm laser and 510/20-nm band pass filter for GFP and a 561 nm laser and 610/20 nm band pass filter for mCherry and mRFP1. Cells were diluted into 96-well plates containing phosphate buffered saline solution (PBS) supplemented with 2 mg/mL kanamycin after incubation. Cells were collected over 20,000 events which were gated using forward and side scatter to remove background events using FlowJo (TreeStar Inc., Ashland, Oreg.). The median fluorescence from cytometry histograms was calculated for all samples. The median autofluorescence was subtracted from the median fluorescence and reported as the fluorescence value in arbitrary unit (au).

Nitrogenase assay (*E. coli* and *K. oxytoca*). Cultures were initiated by inoculating a single colony into 1 mL of LB supplemented with appropriate antibiotics in 96-deepwell plates (USA Scientific, Cat #18962110) and grown overnight at 30° C., 900 rpm in a Multitron incubator. 5 µl of overnight cultures was diluted into 500 µl of BB medium with 17.1 mM $NH_4CH_3CO_2$ and appropriate antibiotics in 96-deepwell and incubated for 24 h at 30° C., 900 rpm in a Multitron incubator. Cultures were diluted to an $OD_{600}$ of 0.4 into 2 mL of BB medium supplemented with appropriate antibiotics, 1.43 mM serine to facilitate nitrogenase depression, and an inducer (if necessary) in 10 mL glass vials with PTFE-silicone septa screw caps (Supelco Analytical, Cat # SU860103). Headspace in the vials was replaced with 100% argon gas using a vacuum manifold. Acetylene freshly generated from $CaC_2$ in a Burris bottle was injected to 10% (vol/vol) into each culture vial to begin the reaction. The acetylene reduction was carried out for 20 h at 30° C. with shaking at 250 rpm in an Innova 44 shaking incubator (New Brunswick) to prevent cell aggregations, followed by quenching via the addition of 0.5 mL of 4 M NaOH to each vial.

Nitrogenase assay (*P. protegens* Pf-5). Cultures were initiated by inoculating a single colony into 1 mL of LB supplemented with appropriate antibiotics in 96-deepwell plates (USA Scientific, Cat #18962110) and grown overnight at 30° C., 900 rpm in a Multitron incubator. 5 µl of overnight cultures was diluted into 500 µl of BB medium with 17.1 mM $NH_4CH_3CO_2$ and appropriate antibiotics in 96-deepwell and incubated for 24 h at 30° C., 900 rpm in a Multitron incubator. Cultures were diluted to an $OD_{600}$ of 0.4 into 2 mL of BB medium supplemented with appropriate antibiotics, 1.43 mM serine and an inducer (if necessary) in 10 mL glass vials with PTFE-silicone septa screw caps. Headspace in the vials was replaced with 99% argon and 1% oxygen gas (Airgas, MA USA) using a vacuum manifold. Acetylene was injected to 10% (vol/vol) into each culture vial to begin the reaction. The acetylene reduction was carried out for 20 h at 30° C. with shaking at 250 rpm, followed by quenching via the addition of 0.5 mL of 4 M NaOH to each vial.

Nitrogenase assays (*Rhizobia* strains). Cultures were initiated by inoculating a single colony into 0.5 mL of TY medium supplemented with appropriate antibiotics in 96-deepwell plates (USA Scientific, Cat #18962110) and grown overnight at 30° C., 900 rpm in a Multitron incubator. 5 µl of overnight cultures was diluted into 500 µl of UMS medium with 30 mM succinate, 10 mM sucrose, and 10 mM $NH_4Cl$ and appropriate antibiotics in 96-deepwell and incubated for 24 h at 30° C., 900 rpm in a Multitron incubator. Cultures were diluted to an $OD_{600}$ of 0.4 into 2 mL of UMS medium plus 30 mM succinate and 10 mM sucrose supplemented with appropriate antibiotics, 1.43 mM serine and an inducer (if necessary) in 10 mL glass vials with PTFE-silicone septa screw caps. Headspace in the vials was replaced with 99% argon and 1% oxygen gas using a vacuum manifold. Acetylene was injected to 10% (vol/vol) into each culture vial to begin the reaction. The acetylene reduction was carried out for 20 h at 30° C. with shaking at 250 rpm, followed by quenching via the addition of 0.5 mL of 4 M NaOH to each vial.

Nitrogenase assays (*A. caulinodans* and *P. stutzeri*). Cultures were initiated by inoculating a single colony into 0.2 mL of TY medium supplemented with appropriate antibiotics in 96-deepwell plates and grown overnight at 37° C. and 30° C. for *A. caulinodans* and *P. stutzeri*, respectively, 900 rpm in a Multitron incubator. 5 µl of overnight cultures was diluted into 500 µl of UMS medium with 30 mM lactate and 10 mM $NH_4Cl$ and appropriate antibiotics in 96-deepwell and incubated for 24 h at 37° C. and 30° C. for *A. caulinodans* and *P. stutzeri*, respectively, 900 rpm in a Multitron incubator. Cultures were diluted to an $OD_{600}$ of 0.4 into 2 mL of UMS medium plus 30 mM lactate supplemented with appropriate antibiotics and an inducer (if necessary) in 10 mL glass vials with PTFE-silicone septa screw caps. Headspace in the vials was replaced with 99% argon plus 1% oxygen gas using a vacuum manifold. Acetylene was injected to 10% (vol/vol) into each culture vial to begin the reaction. The acetylene reduction was carried out for 20 h at 30° C. with shaking at 250 rpm, followed by quenching via the addition of 0.5 mL of 4 M NaOH to each vial.

Nitrogenase assays (*A. vinelandii*). Cultures were initiated by inoculating a single colony into 0.5 mL of Burk medium supplemented with appropriate antibiotics in 96-deepwell plates (USA Scientific, Cat #18962110) and grown overnight at 30° C., 900 rpm in a Multitron incubator. 5 µl of overnight cultures was diluted into 500 µl of Burk medium with 17.1 mM $NH_4CH_3CO_2$ and appropriate antibiotics in 96-deepwell and incubated for 24 h at 30° C., 900 rpm in a Multitron incubator. Headspace in the vials was replaced with 97% argon and 3% oxygen gas (Airgas, MA USA) using a vacuum manifold. Acetylene was injected to 10% (vol/vol) into each culture vial to begin the reaction. The acetylene reduction was carried out for 20 h at 30° C. with shaking at 250 rpm, followed by quenching via the addition of 0.5 mL of 4 M NaOH to each vial.

Nitrogenase activity assay in the presence of ammonium. Following overnight incubation in minimal medium with a nitrogen source (described above), cultures were diluted to an $OD_{c600}$ of 0.4 in 2 mL of nitrogen-free minimal medium, 1.43 mM serine (for *E. coli* and *P. protegens* Pf-5) and an inducer (for inducible systems) in 10 mL glass vials with PTFE-silicone septa screw caps. Ammonium (17.1 mM $NH_4CH_3CO_2$ for *E. coli* and *P. protegens* Pf-5 and 10 mM NH4Cl for *Rhizobia*) was added to a nitrogen-free minimal medium when testing ammonium tolerance of nitrogenase activity. Headspace in the vials was replaced with either 100% argon gas for *E. coli*, 99% argon plus 1% oxygen for *Pseudomonas* and *Rhizobia* using a vacuum manifold. Acetylene was injected to 10% (vol/vol) into each culture vial to begin the reaction. The acetylene reduction was carried out for 20 h at 30° C. with shaking at 250 rpm followed by quenching via the addition of 0.5 mL of 4 M NaOH to each vial.

Figure 26A:
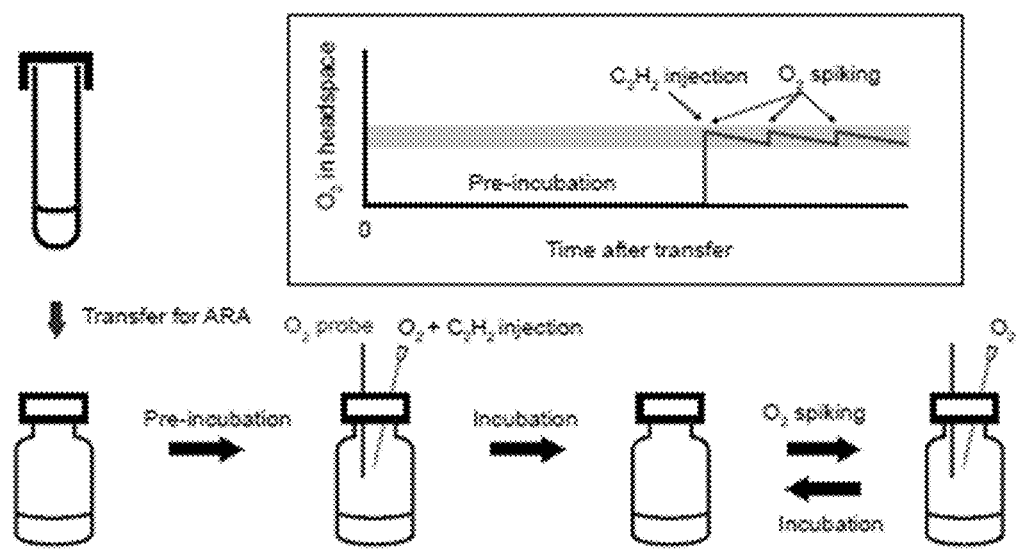
FIGS. 26A-26B include diagrams describing the nitrogenase activity assay.
Figure 26B:
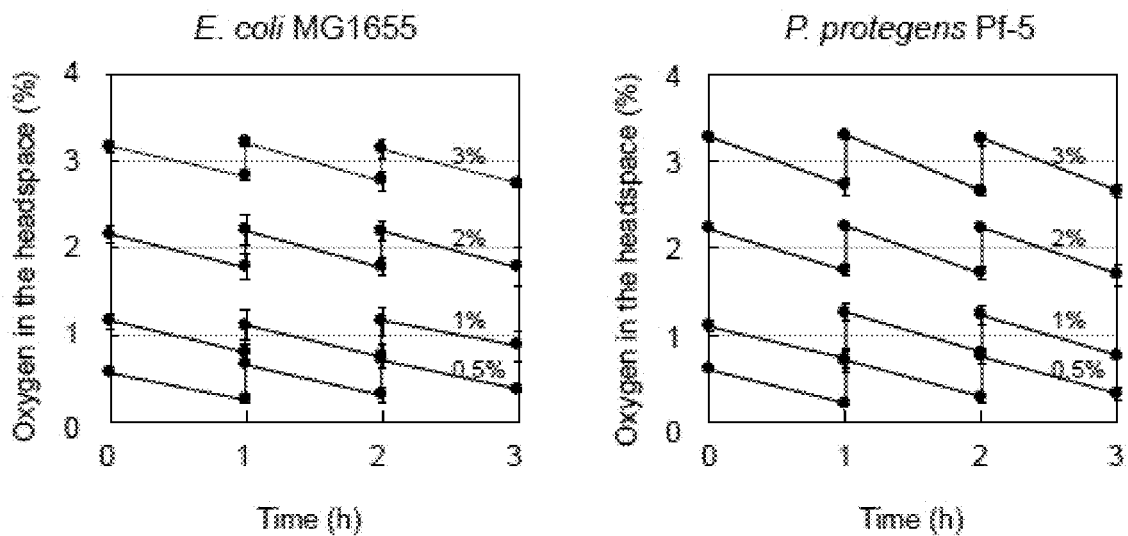

Nitrogenase activity assay at varying oxygen levels. Following overnight incubation in minimal medium with a nitrogen source (described above), cultures were diluted to an $OD_{600}$ of 0.4 in 2 mL of minimal medium, 1.43 mM serine (for *E. coli* and *P. protegens* Pf-5), and an inducer (for inducible systems) in 10 mL glass vials with PTFE-silicone septa screw caps. The vial headspace was replaced with either 100% nitrogen gas for *E. coli* or 99% nitrogen plus 1% oxygen for *P. protegens* Pf-5 and *A. caulinodans* using a vacuum manifold. Cultures were incubated with shaking at 250 rpm at 30° C. for 6 h and 9 h for *P. protegens* Pf-5 and *A. caulinodans*, respectively, after which oxygen concentrations in the headspace were recorded with the optical oxygen meter FireStingO2 equipped with a needle-type sensor OXF500PT (Pyro Science, Germany). After the induction period, no oxygen remained in the headspace for all species as confirmed by the oxygen meter. The initial oxygen levels in the headspace were adjusted by injecting pure oxygen via syringe into the headspace of the vials and stabilized with shaking at 250 rpm at 30° C. for 15 m followed by the injection of acetylene to 10% (vol/vol) into each culture vial to begin the reaction and initial oxygen concentrations in the headspace were recorded concomitantly. The oxygen levels in the headspace were maintained around the setting points (<±0.25% O2) while incubating at 250 rpm and 30° C. by injecting oxygen every hour for 3 h with oxygen monitoring before and after oxygen spiking (FIGS. 26A-26B). The reactions were quenched after 3 h of incubation by the injection of 0.5 mL of 4 M NaOH to each vial using a syringe.

Ethylene quantification. Ethylene production was analyzed by gas chromatography using an Agilent 7890A GC system (Agilent Technologies, Inc., CA USA) equipped with a PAL headspace autosampler and flame ionization detector as follows. An aliquot of 0.5 mL headspace preincubated to 35° C. for 30 s was injected and separated for 4 min on a GS-CarbonPLOT column (0.32 mm×30 m, 3 microns; Agilent) at 60° C. and a He flow rate of 1.8 mL/min. Detection occurred in a FID heated to 300° C. with a gas flow of 35 mL/min H2 and 400 mL/min air. Acetylene and ethylene were detected at 3.0 min and 3.7 min after injection, respectively. Ethylene production was quantified by integrating the 3.7 min peak using Agilent GC/MSD ChemStation Software.

Sample preparation for RNA-seq and Ribosome profiling. Cultures of *K. oxytoca, E. coli, P. protegens* Pf-5 or *R.* sp. IRBG74 were grown following the same protocol as used for nitrogenase activity assay (described above) with a few changes. Following overnight incubation in minimal medium with a nitrogen source, cultures were diluted to an $OD_{600}=0.4$ in 25 mL of minimal medium (with an inducer, if needed) and antibiotics in 125 mL Wheaton serum vials (DWK Life Sciences, Cat #223748) with septum stoppers (Fisher Scientific, Cat # FB57873). The vial headspace was replaced with either 100% nitrogen gas for *E. coli* and *K. oxytoca* or 99% nitrogen plus 1% oxygen for *P. protegens* Pf-5 and *R.* sp. IRBG74 using a vacuum manifold. Cultures grown 6 h at 30° C., 250 rpm were filtered onto a nitrocellulose filter 0.45 µM pore size (Fisher Scientific, Cat # GVS1215305). Cell pellets were combined from three vials using a stainless-steel scoopula, followed by flash-frozen in liquid nitrogen. The frozen pellets were added to 650 µl of frozen droplets of lysis buffer (20 mM Tris (pH 8.0), 100 mM NH4Cl, 10 mM MgCl2, 0.4% Triton X-100, 0.1% NP-40, 1 mM chloramphenicol and 100 U/mL DNase I) in prechilled 25 mL canister (Retsch, Germany, Cat #014620213) in liquid nitrogen and pulverized using TissueLyser II (Qiagen USA) with a setting at 15 Hz for 3 min for 5 times with intermittent cooling between cycles. The pellet was removed by centrifugation at 20,000 rcf at 4° C. for 10 min and the lysate was recovered in the supernatant.

RNA-seq experiments. RNA-seq and Ribosome-footprint profiling was carried out according to the method described earlier with a few modifications(Li, G.-W., Oh, E. & Weissman, J. S. J. N. The anti-Shine-Dalgarno sequence drives translational pausing and codon choice in bacteria. 484, 538 (2012); Li, G.-W., Burkhardt, D., Gross, C. & Weissman, J. S. Quantifying absolute protein synthesis rates reveals principles underlying allocation of cellular resources. Cell 157, 624-635 (2014)). The total RNA was isolated using the hot phenol-SDS extraction method. The rRNA fractions were determined and subtracted from the total using the MICROBExpress kit (Thermo Fisher Scientific, Cat # AM1905). The remaining mRNAs and tRNAs were fragmented by RNA fragmentation reagents (Thermo Fisher Scientific, Cat # AM8740) at 95° C. for 1 m 45 s. RNA fragments (10-45 bp) were isolated from a 15% TBE-Urea polyacrylamide gel (Thermo Fisher Scientific, Cat # EC6885). The 3' ends of the RNA fragments were dephosphorylated using T4 polynucleotide kinase (1U/µl, New England Biolabs, Cat # M0201S) in a 20 µl reaction volume supplemented with 1 µl of 20 U SUPERase•In at 37° C. for 1 h, after which the denatured fragments (5 pmoles) were incubated at 80° C. for 2 min and ligated to 1 µg of the oligo (/5rApp/CTGTAGGCACCATCAAT/3ddc/, Integrated DNA technologies) (SEQ ID NO: 1) in a 20 µl reaction volume supplemented with 8 µl of 50% PEG 8000, 2 µl of 10×T4 RNA ligase 2 buffer, 1 µl of 200 U/µl truncated K277Q T4 ligase 2 (New England Biolabs, Cat # M0351) and 1 µl of 20 U/µl of SUPERase•In at 25° C. for 3 h. The ligated fragments (35-65 bp) were isolated from a 10% TBE-Urea polyacrylamide gel (Invitrogen, Cat # EC6875). cDNA libraries from the purified mRNA products were reverse-transcribed using Superscript III (Thermo Fisher Scientific, Cat #18080044) with oCJ485 primer (/5Phos/AGATCGGAAGAGCGTCGTGTAGG-GAAAGAGTGT/iSp18/CAAGCAGAAGA CGGCAT-ACGAGATATTGATGGTGCCTACAG (SEQ ID NO: 2, SEQ ID NO: 3)) at 50° C. for 30 min and RNA products subsequently were hydrolyzed by the addition of NaOH at a final concentration of 0.1 M, followed by incubation at 95° C. for 15 min. The cDNA libraries (125-150 bp) were isolated from on a 10% TBE-Urea polyacrylamide gel (Invitrogen, Cat # EC6875). The cDNA products were circularized in a 20 µl reaction volume supplemented with 2 µl of 10×CircLigase buffer, 1 µl of 1 mM ATP, 1 µl of 50 mM MnC12 and 1 µl of CircLigase (Epicenter, Cat # CL4115K) at 60° C. for 2 h and heat-inactivated at 80° C. for 10 min.

5 µl of circularized DNA was amplified using Phusion HF DNA polymerase (New England Biolabs, Cat # M0530) with o231 primer (CAAGCAGAAGACGGCATACGA (SEQ ID NO: 4)) and indexing primers (AATGATACGGCGACCACCGAGATCTACACGATCG-GAAGAGCACACGTCTGAACT CCAGTCACNNNNN-NACACTCTTTCCCTACAC (SEQ ID NO: 5)) for 7 to 10 cycles. The amplified products (125-150 bp) were recovered from an 8% TBE-Urea polyacrylamide gel (Invitrogen, Cat # EC62152). The purified products were analyzed by Bio-Analyzer (Agilent, CA USA) and sequenced with a sequencing primer (CGACAGGTTCAGAGTTCTA-CAGTCCGACGATC (SEQ ID NO: 6)) using an Illumina HiSeq 2500 with a rapid run mode. To generate the RNA-seq read profile for each nif cluster, the raw trace profiles are multiplied by $10^7$ and normalized by respective total reads from coding sequences of each species (K. oxytoca M5al, CP020657.1; E. coli MG1655, NC_000913.3; P. protegens Pf-5, CP000076; R. sp. IRBG74 HG518322, HG518323, HG518324 and an appropriate plasmid carrying a nif cluster). The mRNA expression level of each gene was estimated using total sequencing reads mapped onto the gene, representing fragments per kilobase of transcript per million fragments mapped units (FPKM).

Ribo-seq experiments. 0.5 mg of RNA was diluted into 195 µl of the lysis buffer including 0.5 U RNase inhibitor SUPERase•In (Invitrogen, Cat # AM2694), 5 mM CaCl2 and were treated with 5 µl of 750 U of micrococcal nuclease (Sigma Aldrich, Cat #10107921001) at 25° C. for 1 h to obtain ribosome-protected monosomes. The digestions were quenched by the addition of EGTA to a final concentration of 6 mM and then kept on ice before the isolation of monosomes. Subsequently, the monosome fraction was collected by sucrose density gradient (10-55% w/v) ultracentrifugation at 35,000 rpm for 3 h, followed by a hot phenol-SDS extraction to isolate ribosome-protected mRNA fragments. The mRNA fragments (15-45 bp) were isolated from a 15% TBE-Urea polyacrylamide gel. The 3' ends of the purified fragments were dephosphorylated and ligated to the modified oligo. cDNA libraries generated by Superscript III were circularized by CircLigase as described above. rRNA products were depleted by a respective biotinylated oligo mix for E. coli and P. protegens Pf-5. 5 µl of circularized DNA was amplified using Phusion HF DNA polymerase with o231 primer and indexing primers for 7 to 10 cycles. The amplified products (125-150 bp) were recovered from an 8% TBE-Urea polyacrylamide gel. The purified products were analyzed by BioAnalyzer and sequenced with a sequencing primer (CGACAGGTTCAGAGTTCTA-CAGTCCGACGATC (SEQ ID NO: 7)) using an Illumina HiSeq 2500 with a rapid run mode. Sequences were aligned to reference sequences using Bowtie 1.1.2 with the parameters-k1-m2-v1. A center-weighting approach was used to map the aligned footprint reads ranging from 22 to 42 nucleotides in length. To map P-site of ribosome from footprint reads, 11 nucleotides from the both ends were trimmed, and the remaining nucleotide were given the same score, normalized by the length of the center region. Aligned reads (10-45 nucleotides) were mapped to the reference with equal weight of each nucleotide. A Python 3.4 script was used to perform the mapping. To generate the Ribo-seq read profile for each nif cluster, the raw trace profiles are multiplied by $10^8$ and normalized by respective total reads from coding sequences of each species. To calculate the ribosome density of each gene, read densities were first normalized in the following ways: (i) The first and last 5 codons of the gene are excluded for the calculation to remove the effects of translation initiation and termination. (ii) A genome-wide read density profile was fitted to an exponential function and the density at each nucleotide on a given gene was corrected using this function. (iii) If the average read density on a gene is higher than 1, a 90% winsorization was applied to reduce the effect of outliers. The sum of normalized reads on a gene was normalized by the gene length and the total read densities on coding sequences to yield the ribosome density.

Figure 29:
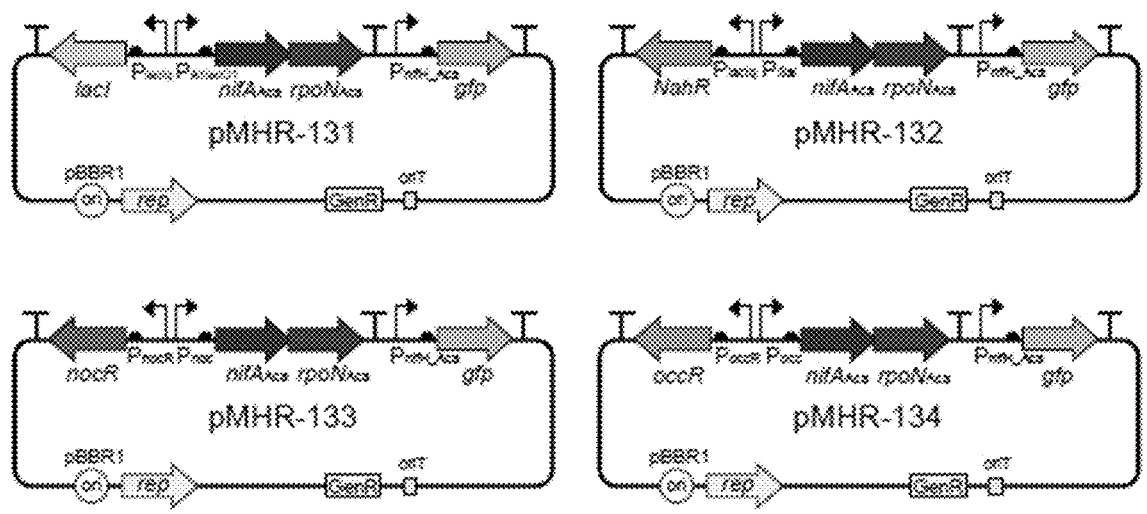
FIG. 29 includes schematic plasmid maps used to assess the effect of inducible expression of NifA/RpoN on the activity of the nifH promoter in *A. caulinodans* ORS571.

Calculation of genetic part strengths based on—seq data. The activity of a promoter is defined as the change in RNAP flux $\delta J$ around a transcription start site $x_{tss}$ (Gorochowski, T. E. et al. Genetic circuit characterization and debugging using RNA-seq. 13, 952 (2017)). The promoter strength is calculated by $$\delta j = \frac{\gamma}{n}\left[\sum_{i=x_{tss}+1}^{x_{tss}+1+n} m(i) - \sum_{i=x_{tss}-1}^{x_0-1-n} m(i)\right] \quad (1)$$

where m(i) is the number of transcripts at each position I from FPKM-normalized transcriptomic profiles, $\gamma=0.0067$ s$^{-1}$ is the degradation rate of mRNA, n is the window length before and after $x_{tss}$. The window length is set to 10. The terminator strength $T_s$ is defined as the fold-decrease in transcription before and after a terminator, which can be quantified from FPKM-normalized transcriptomic profiles as $$T_s = \frac{\sum_{i=x_1+1}^{x_1+n} m(i)}{\sum_{i=x_0-1}^{x_0-n} m(i)} \quad (2)$$

where $x_0$ and $x_1$ are the beginning and end positions of the terminator part, respectively. Translation efficiency was calculated by dividing the ribosome density by the FPKM.

nifH expression analysis. Complementation of NifA was tested using plasmid pMR-128 to 130 that contains the sfgfp fused to the nifH promoter in the A. caulinodans ΔnifA mutant. The inducible NifA/RpoN expression was provided by the plasmid pMR-121 into which sfgfp driven by the nifH promoter was added to analyze MN promoter activity, yielding pMR-131 (FIG. 29). The IPTG-inducible system in the plasmid pMR-124 was substituted with other inducible systems including the salicylic acid-inducible, nopaline-inducible and octopine-inducible systems, yielding pMR-125, 126, and 127, respectively. Each of the plasmids was mobilized into the A. caulinodans ΔnifA mutant, which was grown following the same protocol as used for nitrogenase activity (described herein). Following overnight incubation in minimal medium with a nitrogen source, cultures were diluted to an $OD_{600}$=0.4 in 2 mL of UMS medium plus 30 mM lactate, antibiotics and an inducer (for inducible systems) in 10 mL glass vials with PTFE-silicone septa screw caps. Headspace in the vials was replaced with 99% argon plus 1% oxygen using a vacuum manifold. The vials were incubated with shaking at 250 rpm at 30° C. for 9 h, after which 10 µl of cultures was diluted into 150 µl PBS with 2 mg/mL kanamycin for flow cytometry analysis. To test activation of the nifH promoters by diverse NifA proteins, the plasmids pMR-51, 53, 88, 89 and 90 were introduced into E. coli MG1655 and the plasmids pMR-91, 92, 93, 94 and 95 to P. protegens Pf-5. The plasmid pMR-101 was used to provide inducible NifA expression by IPTG in *E. coli*. The controller encoding the IPTG-inducible NifAwas inserted into the genome of *P. protegens* Pf-5 using the plasmids pMR-96, 97 and 98. The IPTG-inducible system of the NifA controller plasmid pMR-96 was replaced with the arabinose-inducible and the naringenin-inducible system, yielding pMR-99 and 100, respectively. The inducibility of nifH expression was assessed by the reporter plasmids pMR-105 to 107 and pMR102 to 104 for *E. coli* and *P. protegens* Pf-5, respectively. The controller plasmids were transformed into *E. coli* or *P. protegens* Pf-5 with the reporter plasmids. Following overnight incubation in minimal medium with a nitrogen source, cultures were diluted to an $OD_{600=0.4}$ in 2 mL of BB medium, antibiotics and an inducer (for inducible systems) in 10 mL glass vials with PTFE-silicone septa screw caps. Headspace in the vials was replaced with either 100% argon for *E. coli* or 99% argon plus 1% oxygen for *P. protegens* Pf-5 using a vacuum manifold. The vials were incubated with shaking at 250 rpm at 30° C. for 9 h, after which 10 µl of cultures was diluted into 150 µl PBS with 2 mg/mL kanamycin for flow cytometry analysis.

Figure 22:
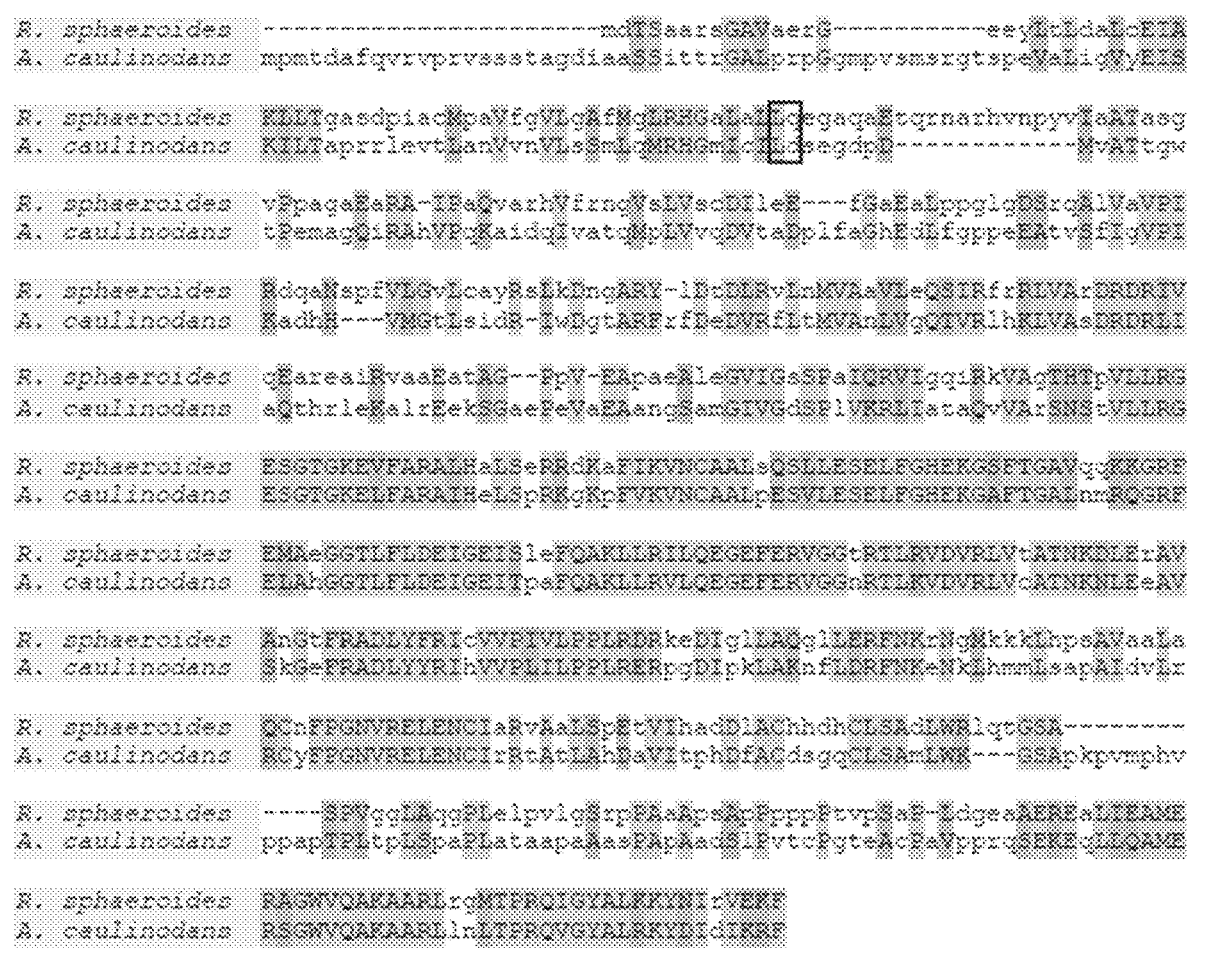

Sequence alignment. NifA sequences of *R. sphaeroides* 2.4.1 (RSP_0547) and *A. caulinodans* ORS571 (AZC_1049) were obtained from NCBI. NifA protein sequences were aligned with MUSCLE (ebi.ac.uk/Tools/msa/muscle/) with a default settings (FIG. 22).

Results

Performance of Native Nif Clusters in *E. coli*, *P. Protegens* Pf-5, and Symbiotic *Rhizobia*

A set of diverse native nif clusters were cloned in order to determine their relative performance in different strains and the associated species barriers (FIG. 1A). Previously-defined boundaries for the well-studied nif cluster from *K. oxytoca* (Arnold, W., Rump, A., Klipp, W., Priefer, U. B. & Püler, A. J. J. o. m. b. Nucleotide sequence of a 24,206-base-pair DNA fragment carrying the entire nitrogen fixation gene cluster of *Klebsiella pneumoniae*. 203, 715-738 (1988)) and the small (10 kb) cluster from *Paenibacillus polymyxa* WLY7870 were used. Similarly, the published boundaries (43.7 kb) of the *P. stutzeri* A1501(Yan, Y. et al. Nitrogen fixation island and rhizosphere competence traits in the genome of root-associated *Pseudomonas stutzeri* A1501. *Proceedings of the National Academy of Sciences* (2008).) and *A. vinelandii* DJ clusters were used(Hamilton, T. L. et al. Transcriptional profiling of nitrogen fixation in *Azotobacter vinelandii*. J Bacteriol 193, 4477-4486, doi: 10.1128/JB.05099-11 (2011)). A region of the *P. stutzeri* A1501 nif cluster (Pst1307-Pst1312) was excluded as these genes are predicted to have no effect on nitrogenase. *A. vinelandii* DJ contains three putative electron transport systems (the Rnfl and Rnf2 complexes and the Fix complex) located in other regions of the genome. RNA-seq data shows that Rnf2 is not co-expressed with the nif genes, so only the Rnfl and Fix complexes were included by fusing their DNA to create a single 46.9 kb construct. The nif cluster (40.1 kb) from *Azospirillum brasilense* Sp7 was selected because this species is a cereal endophyte and fixes nitrogen in free-living conditions. Several less-studied gene clusters were also cloned in order to probe species barriers. As a representative of cyanobacteria, the gene cluster from *Cyanothece* sp. ATCC51142 was cloned following published boundaries. Its transcriptional activator PatB occurs outside of the nif cluster, which was cloned along with its native promoter and fused to nif cluster to form a single construct (31.7 kb). Several gene clusters were selected from photosynthetic purple bacteria (*Rhodopseudomonas palustris* CGA009 (Oda, Y. et al. Functional genomic analysis of three nitrogenase isozymes in the photosynthetic bacterium *Rhodopseudomonas palustris*. 187, 7784-7794 (2005)) and *Rhodobacter sphaeroides* 2.4.1(Haselkorn, R. & Kapatral, V. in Genomes and genomics of nitrogen-fixing organisms, 71-82 (Springer, 2005))) as these are members of the same alphaproteobacteria class as *Rhizobia*. The rnf cluster, encoded on a separate chromosome of *R. sphaeroides* 2.4.1, was added to the nif cluster to provide electrons to nitrogenase. Finally, the gene clusters from the sugarcane and rice endosymbiant *Gluconacetobacter diazotrophicus* PA1 5 (28.9 kb) as well as the three nif clusters from *A. caulinodans* ORS571 (64 kb)[37] were cloned together with an upstream regulator fixLJK, but these were found to be inactive in all species tested, so they are not shown in FIGS. 1A-1F. The precise genomic locations for all the nif clusters are provided in Table 7 and the plasmids containing nif clusters are provided in Table 8.

Each cluster was amplified from genomic DNA as multiple fragments by PCR and assembled with the plasmid backbone using yeast assembly (see Methods and Materials Section). The *P. polymyxa* WLY78 cluster was de novo synthesized based on the DNA sequence on contig ALJV01 (Shanks, R. M. et al. *Saccharomyces cerevisiae*-based molecular tool kit for manipulation of genes from gram-negative bacteria. 72, 5027-5036 (2006)). The clusters were cloned into different plasmid systems to facilitate transfer. For transfer to *E. coli* and R. sp. IRBG74, the broad-host range plasmid based on a pBBR1 origin was used (a second compatible RK2-origin plasmid was used for the nif cluster from *A. caulinodans* ORS571). These plasmids contain the RK2 oriT to enable the conjugative transfer of large DNA (see Materials and Methods). For transfer to *P. protegens* Pf-5, this plasmid system was found to be unstable and produce a mixed population. To transfer into this strain, the *Pseudomonas*-specific plasmid pRO1600 with the oriT was used. After construction, all of the plasmids were verified using next-generation sequencing (see Methods and Materials Section).

The set of 10 nif clusters were transferred into *E. coli* MG1655, the cereal epiphyte *P. protegens* Pf-5, and the cereal endophyte R. sp. IRBG74 to create 30 strains (FIG. 1A). *E. coli* was selected as a control as most of the published successful transfers have been to this recipient. Native *P. protegens* Pf-5 does not fix nitrogen. R. sp. IRBG74 contains two nif clusters in different genomic locations, which were left intact, but does not have nitrogenase activity under free living conditions. The genomic cluster does not have the required NifV enzyme as it obtains homocitrate from the plant. All of the clusters in the set have nijV, except the one from *P. polymyxa* WLY78. A test was run to determine whether the expression of recombinant nijV from *A. caulinodans* ORS571 in R. sp. IRBG74 would result in active nitrogenase, but no activity was detected.

Figure 6:
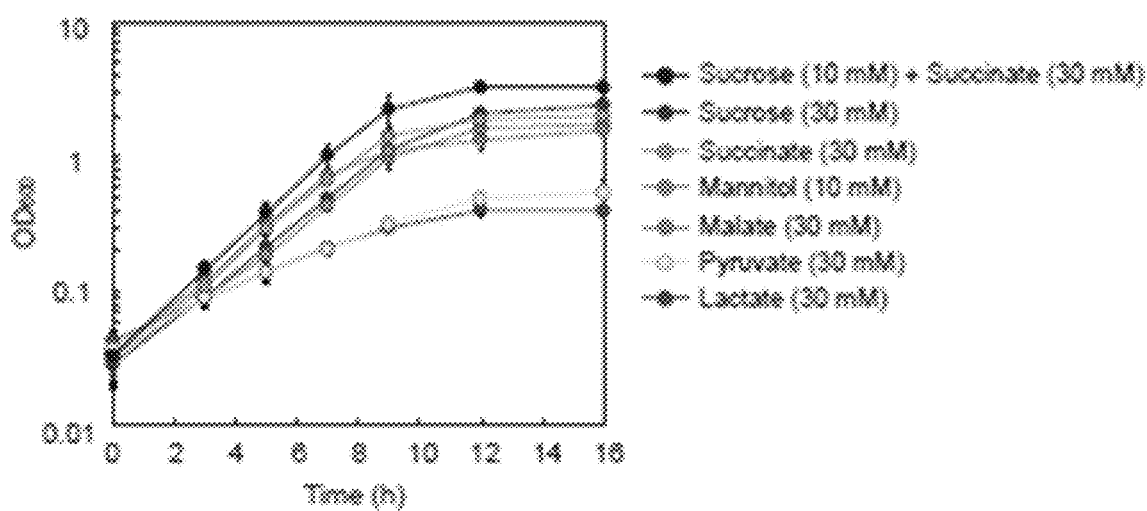
FIG. 6 includes a plot of the growth curve of R. sp. IRBG74 in UMS minimal medium with varying carbon sources. Cultures grown overnight in 2 mL TY medium in 15 mL culture tubes at 30° C. and 250 rpm were diluted to an $OD_{600}$ of 0.02 into 1 mL of UMS minimal medium plus varying carbon sources in 96-deepwell plates and incubated for 16 hours at 30° C. and 900 rpm. Bacterial growth was spectrophotometrically monitored at $OD_{600}$ nm. Error bars represent s.d. from three independent experiments.
Figure 7A:
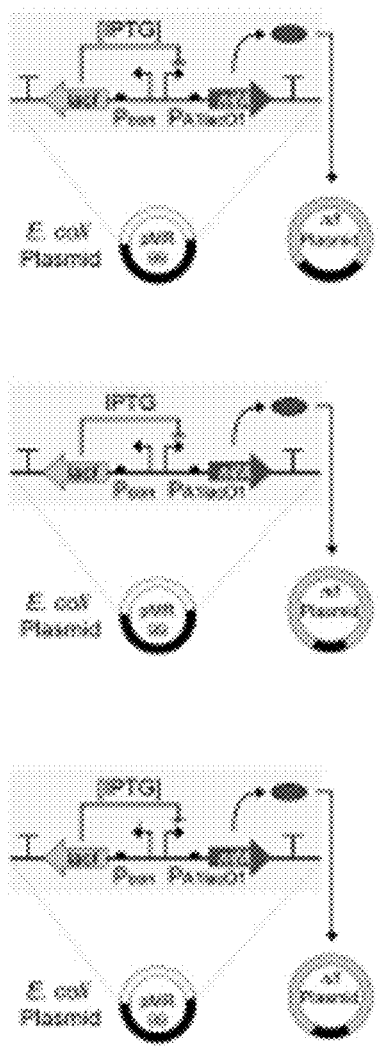
FIGS. 7A-7F include diagrams showing the nitrogenase activity when different inducible nif clusters are transferred to *E. coli* MG1655.
Figure 7B:
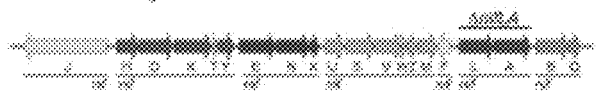
Figure 7B:
Figure 7B:
Figure 7C:
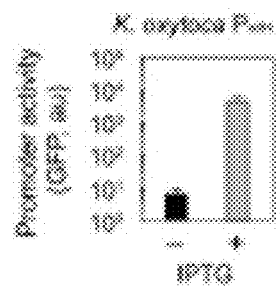
Figure 7C:
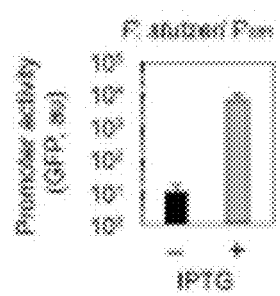
Figure 7C:
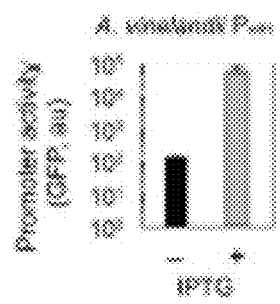
Figure 7D:
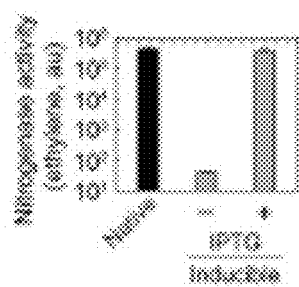
Figure 7D:
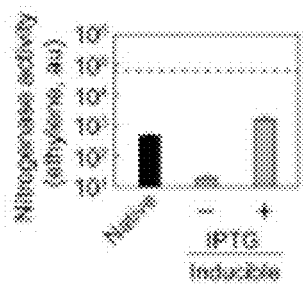
Figure 7D:
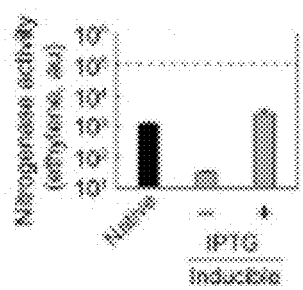
Figure 7E:
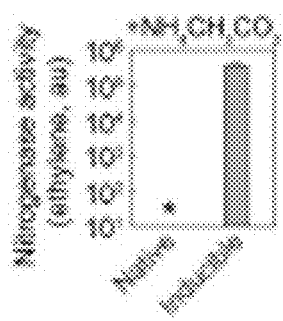
Figure 7E:
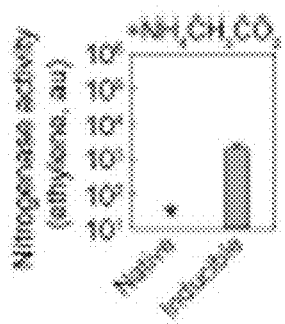
Figure 7E:
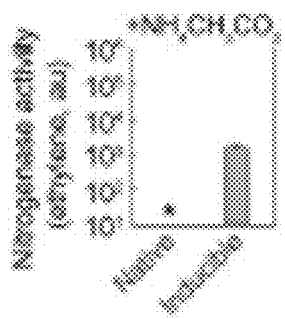
Figure 7F:
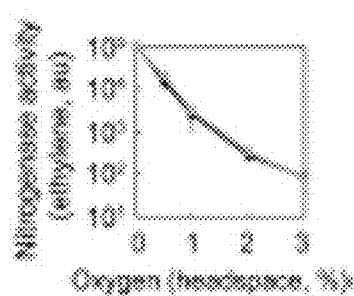
Figure 7F:
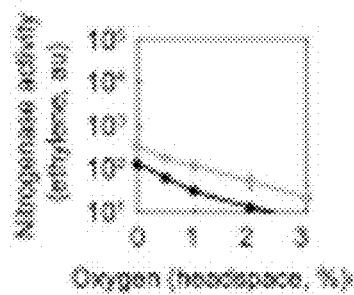
Figure 7F:
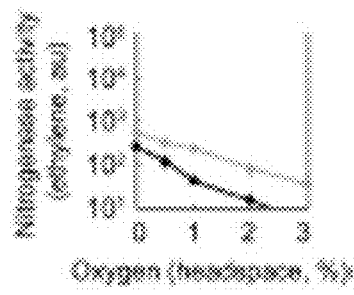

The bacteria were grown in appropriate media, including antibiotics, and then evaluated for nitrogenase activity using an acetylene reduction assay (see Methods and Materials Section). *E. coli* and *Pseudomonas* were grown at 30° C. in BB minimal media, as described previously[71]. However, no growth was observed for R. sp. IRBG74 under these conditions. Different media and carbon sources were tested and it was found that UMS media with dicarboxylic acids (malate or succinate), the major carbon source from plants[147], with 10 mM sucrose yielded the highest growth rates (FIG. 6). After overnight growth, cells were transferred to stoppered test tubes in ammonium-free minimal media to a final $OD_{600}$ of 0.4. For *E. coli*, the headspace air is completely replaced with argon gas. For *P. protegens* Pf-5 and R. sp. IRBG74, the initial headspace concentration of oxygen was maintained at 1% because these bacteria require oxygen for their metabolism. The cells are incubated at 30° for 20 hours in the presence of excess acetylene and the conversion to ethylene was quantified by GC-MS (see Methods and Materials Section). There was no significant growth for any of the strains under these conditions, so the nitrogenase activities reported correspond to the same cell densities.

A surprising 6 out of 10 clusters were functional in *E. coli* MG1655, with the *K. oxytoca* cluster producing the highest activity (FIG. 1A). The *K. oxytoca* cluster is also functional in *P. protegens* Pf-5, albeit with 60-fold less activity as compared to that in *E. coli* MG1655. Interestingly, the clusters from *P. stutzeri* and *A. vinelandii*—both obligate aerobes—are able to achieve high activities in *P. protegens* Pf-5. The resulting nitrogenase activities are 3- to 7-fold higher than that achieved from *K. oxytoca*, which only fixes nitrogen under strict anaerobic conditions. These clusters have common organizational features and similar electron transport chains, such as the Rnf complex.

A single gene cluster, from *R. sphaeroides*, yielded nitrogenase activity in R. sp. IRBG74 (FIG. 1A). Notably, both *Rhizobium* and *Rhodobacter* are alphaproteobacter and their nif clusters may contain interchangeable genes. When the native nif clusters are knocked out of R. sp. IRBG74, introducing the *R. sphaeroides* cluster alone does not yield active nitrogenase. These data point to a complex complementation between the endogenous and introduced gene clusters. To determine whether this approach could be generalized to other symbiotic *Rhizobia*, the *Rhodobacter* and *Rhodopseudomonas* gene clusters were transferred to a panel of 12 species isolated from diverse legumes (FIG. 1A). Remarkably, the transfer of these clusters was able to produce detectable nitrogenase activity in 7 of the strains.

Hereafter, studies were conducted to better characterize the extent to which changes in transcription and translation impacted the differences in activity observed when a native cluster is transferred between species. Differences in promoter activity, ribosome binding sites, and codon usage could change the expression levels of nif genes in detrimental ways. To quantify this effect, RNA-seq and ribosome profiling experiments were performed to evaluate the expression *K. oxytoca* nif cluster in *K. oxytoca* as well as *E. coli* MG1655, *P. protegens* Pf-5, and R. sp. IRBG74. RNA-seq experiments provide mRNA levels of genes (calculated as FPKM) and can be used to measure the performance of promoters and terminators. Ribosome profiling can be used to quantify protein synthesis rates, ribosome binding site (RBS) strength and ribosome pausing internal to genes. The ribosome density (RD) has been shown to correlate with protein expression rates. The translation efficiency is calculated by normalizing the RD by the number of transcripts (FPKM from Ribo-seq). Ribosome profiling has been applied to determine the relative levels of proteins expressed in multi-subunit complexes.

Figure 1D:
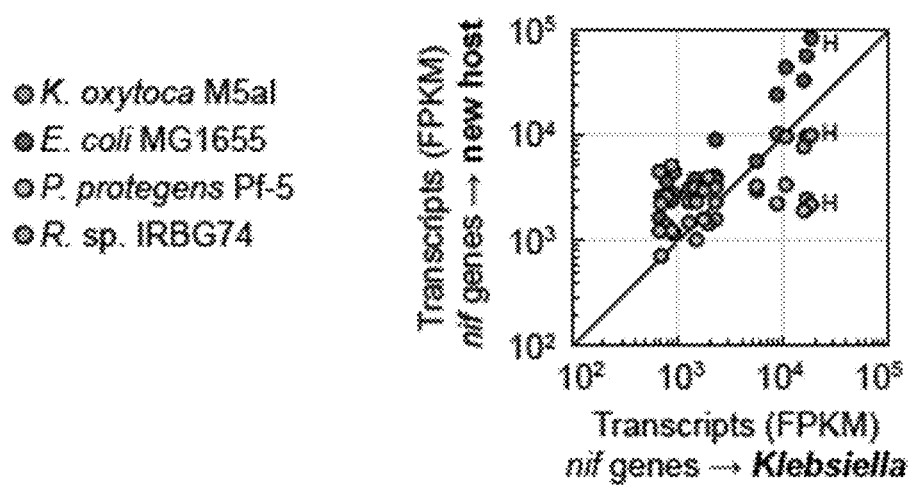

The RNA-seq profiles in both the sense and antisense direction are very close when compared between *K. oxytoca* and *E. coli* (FIGS. 1B-1C) and the ratios between mRNAs is preserved ($R^2=0.89$) (FIG. 1D). This is consistent with the observation that this cluster yields a similar activity in both hosts. In contrast, the RNA-seq profiles differ more significantly for *P. protegens* Pf-5 and R. sp. IRBG74 (FIGS. 1B-1C), and there was no correlation between mRNA transcripts (FIG. 1D).

Figure 1E:
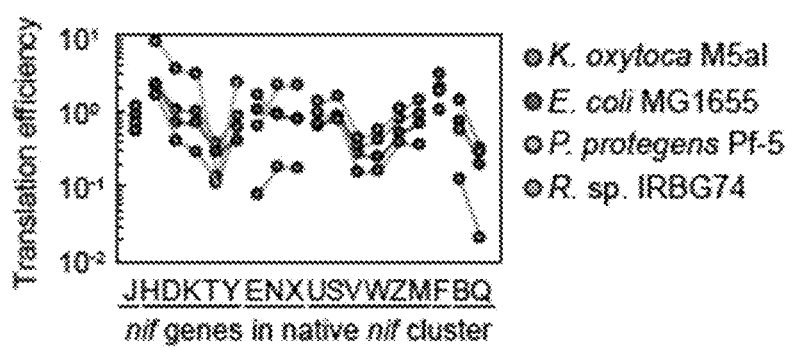
Figure 1F:
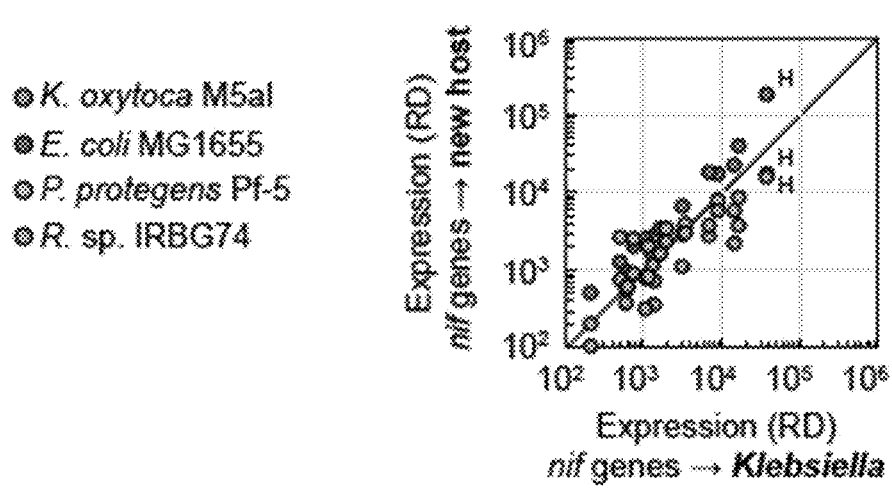
Figure 9:
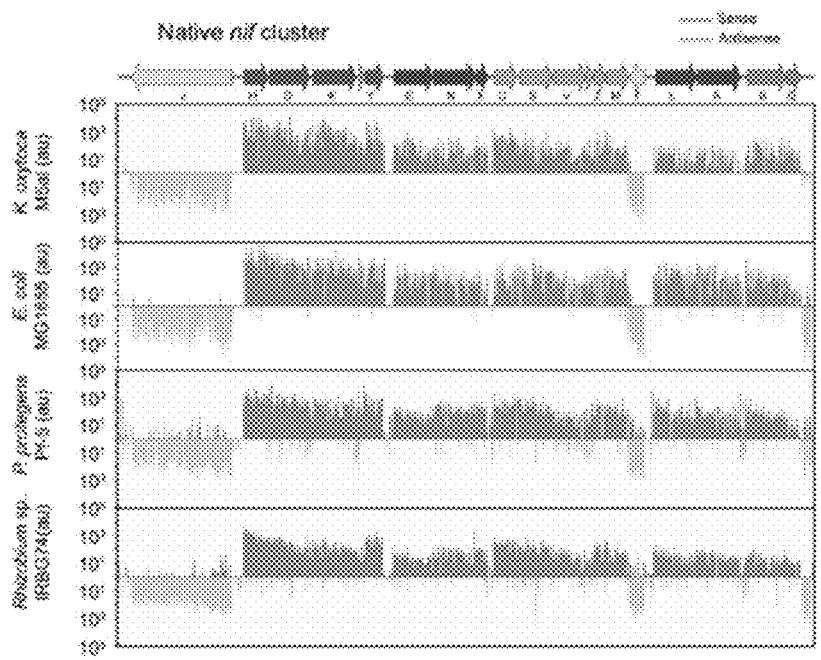
FIG. 9 includes a diagram showing the ribosome profiling data for the *K. oxytoca* native nif cluster in *K. oxytoca* M5al, *E. coli* MG1655, *P. protegens* Pf-5 and R. sp. IRBG74 (see Materials and Methods).
Figure 10A:
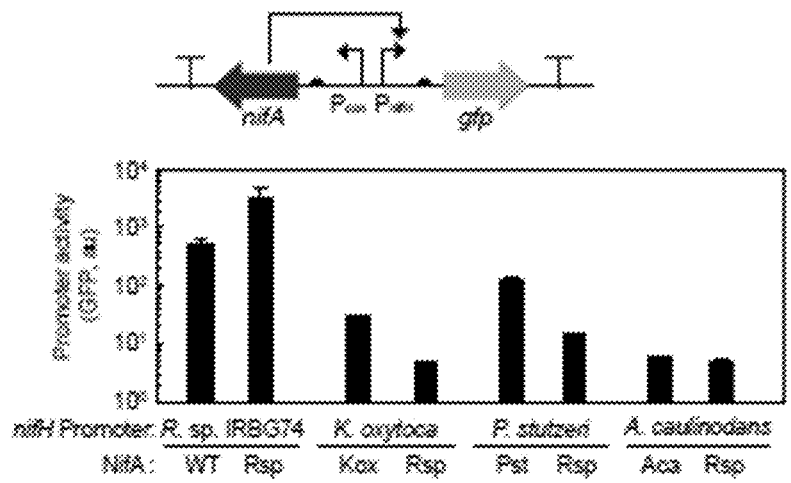
FIGS. 10A-10B include diagrams showing the effect of NifA overexpression on the nifH promoter activity in R. sp. IRBG74.
Figure 10B:
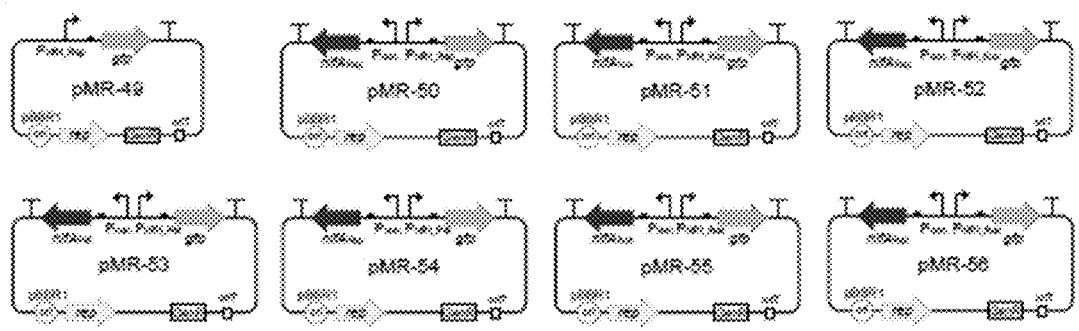

The ratios between protein expression rates were measured using ribosome profiling (FIG. 1E and FIG. 9). It is noteworthy that the ratios measured in *K. oxytoca* almost perfectly correlate with immunoblotting assays of *A. vinelandii* and the stoichiometry of H:D:K reflects the known 2:1:1 ratio. Interestingly, unlike mRNA levels, the ratios in expression rates are strongly correlated when the cluster is transferred between species: *E. coli* ($R^2=0.94$), *P. protegens* Pf-5 ($R^2=0.61$), and R. sp. IRBG74 ($R^2=0.71$) (FIGS. 1E-1F). The production of NifH is significantly lower in R. sp. IRBG as compared to other strains. In an attempt to increase the induction of the cluster in this host, NifA was overexpressed, but this proved unsuccessful in producing high levels of active nitrogenase (FIGS. 10A-10B).

The following summarizes the results of the transfer of native nif clusters to new species. The most successful recipient is *E. coli*. However, this is not a viable agricultural strain and activity is eliminated in the presence of 17.1 mM ammonium, consistent with previous results (FIGS. 7A-7E, and FIGS. 8A-8B). Moderately high activity can be obtained in *P. protegens* Pf-5, but this yields a constitutively-on response (the *K. oxytoca* cluster) or is strongly repressed by ammonium (the *A. vinelandii* cluster). It was also found that the *P. stutzeri* cluster in *P. protegens* Pf-5 is inactive in the presence of ammonium, in disagreement with previously published results (Setten, L. et al. Engineering *Pseudomonas protegens* Pf-5 for nitrogen fixation and its application to improve plant growth under nitrogen-deficient conditions. PLoS One 8, e63666 (2013)). In previous studies, the published strain is not made available by the authors nor is its sequence, thus it is impossible to replicate the strain perfectly and differences in the cluster boundary or mutations to the regulation during construction could explain the discrepancy in results. Only low levels of activity could be obtained by transferring clusters to *Rhizobia*. To address these issues, different approaches were applied to engineer the clusters to generate higher activity, exhibit less repression by ammonium, and be inducible.

Transfer of Refactored *Klebsiella* Nif Clusters to R. Sp. IRBG74

The process of refactoring a gene cluster involves the complete reconstruction of the genetic system from the bottom-up, using only well-characterized genetic parts. An exhaustive approach is to recode the genes (to eliminate internal regulation), reorganize into operons, control expression with synthetic ribosome binding sites (RBSs), and use T7 RNAP promoters and terminators. A separate "controller," carried in a genetically distinct location, links synthetic sensors and circuits to the expression of T7 RNAP. For various applications, this approach has proven useful for transferring multi-gene systems between species, simplifies optimization through part replacement and enzyme mining, and enables the replacement of environmental signals that naturally control the cluster with the stimuli that induce the synthetic sensors(Smanski, M. J. et al. Synthetic biology to access and expand nature's chemical diversity. Nature Reviews Microbiology 14, 135 (2016); Song, M. et al. Control of type III protein secretion using a minimal genetic system. 8, 14737 (2017); Guo, C.-J. et al. Discovery of reactive microbiota-derived metabolites that inhibit host proteases. 168, 517-526. e518 (2017); Ren, H., Hu, P., Zhao, H. J. B. & bioengineering. A plug-and-play pathway refactoring workflow for natural product research in *Escherichia coli* and *Saccharomyces cerevisiae*. 114, 1847-1854 (2017)). In previous studies, the *Klebsiella* nif cluster was refactored, which was subsequently used as a platform to optimize activity by changing the genetic organization and the parts controlling expression. The top variant (v2.1) fully recovered activity in a *K. oxytoca* nif knockout and is functional in *E. coli*. An interesting observation during optimization is that the genetic organization of the native cluster, including the existence of operons, was not correlated with activity.

Figure 2A:
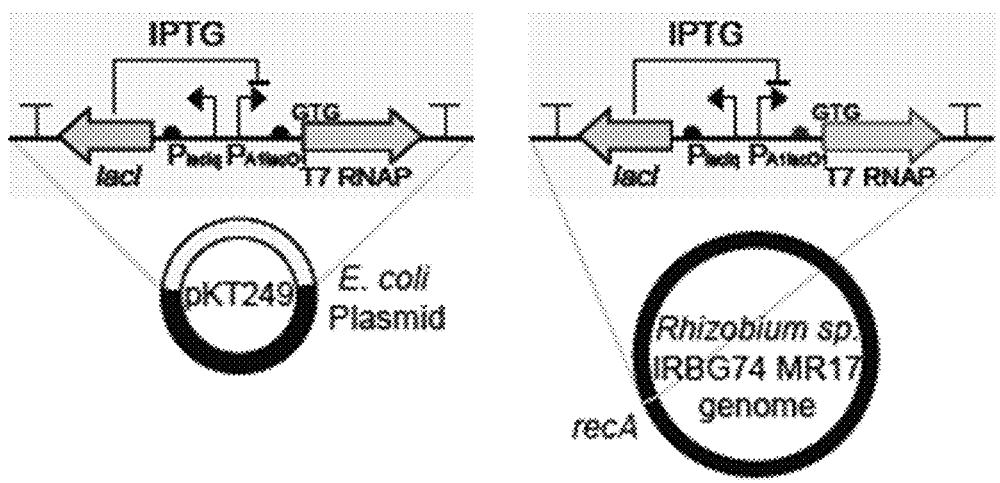
FIGS. 2A-2M include diagrams showing the transfer of the refactored K. oxytoca nif clusters to R. sp. IRBG74.

The present disclosure sought to study the performance of the refactored v2.1 cluster in R. sp. IRBG74. An advantage of using T7 RNAP is that it is functional in essentially all prokaryotes, so the refactored cluster can be transferred as-is and transcription induced by expressing T7 RNAP in the new host. However, a new controller needs to be built for each host based on regulation and regulatory parts that work in that species. Previously, a controller for *E. coli* was designed based on the IPTG-inducible T7 RNAP carried on a plasmid (pKT249) (FIG. 2A). To transfer the refactored cluster to R. sp. IRBG74, first a controller was constructed that functions in this species and produces an equivalent range of T7 RNAP expression.

While a handful of inducible systems and sets of genetic parts have been previously described for *Rhizobia*, a new part collection needed to be built and characterized in order to have those needed to create a controller with sufficient dynamic range. First, a set of 20 constitutive promoters (Anderson, J. et al. BglBricks: A flexible standard for biological part assembly. 4, 1 (2010)) and seven T7 RNAP-dependent promoters (emme, K., Zhao, D. & Voigt, C. A. Refactoring the nitrogen fixation gene cluster from *Klebsiella oxytoca*. *Proceedings of the National Academy of Sciences* 109, 7085-7090 (2012)) that were found to span a range of 382-fold and 23-fold expression, respectively, were characterized (FIGS. 11A-11C). Second, a library of 285 ribosome binding sites (RBSs) were screened using the RBS Library Calculator, representing an expression range of 5,600-fold (FIGS. 12A-12B). Finally, a set of 29 terminators was characterized, of which 17 were found to have a terminator strength>10 (FIGS. 13A-13B). Using these part libraries, six inducible systems for R. sp. IRBG74 were then constructed that respond to IPTG, the quorum signal 3OC6HSL, aTc, cuminic acid, DAPG, and salicylic acid (FIG. 14). After optimization, these systems generate between 7- to 400-fold induction.

Figure 2B:
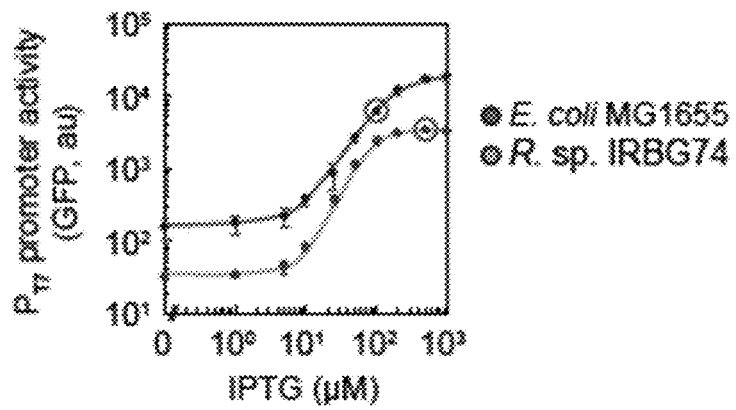
Figure 16:
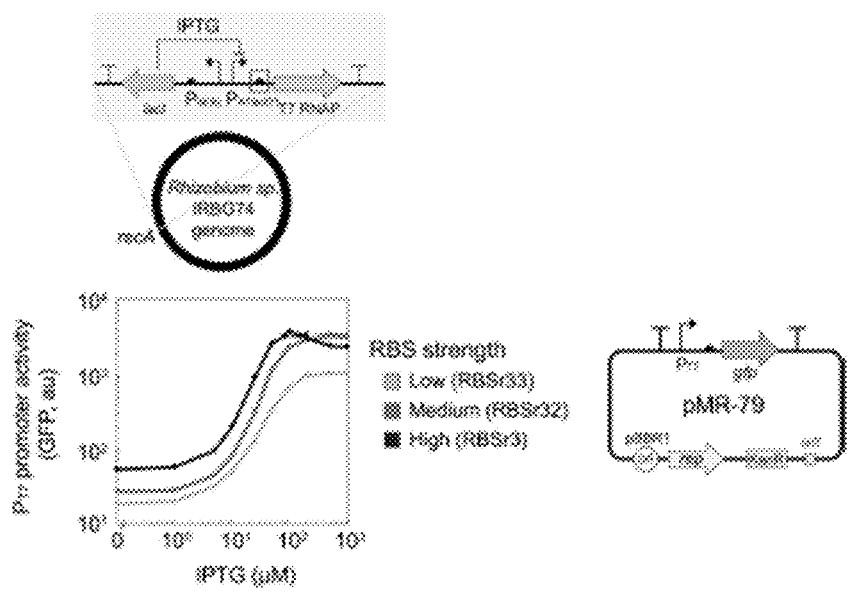
FIG. 16 includes diagrams showing the tuning controller strength in R. sp. IRBG74. The controller containing the IPTG-inducible T7 RNAP is integrated into the genome of R. sp. IRBG74 (top). Controller strengths were adjusted by modulating the RBS of T7 RNAP in the plasmids pMR-81, 82, and 83. Response functions of the T7 promoter were measured with the reporter plasmid pMR-79 (right) in the R. sp. IRBG74 controller strains MR16, MR17, and MR18. Genetic parts and RBS sequences are provided in Table 10 and Table 5. Error bars represent s.d. from three independent experiments.

A controller was then constructed by using the optimized IPTG-inducible system to drive the expression of a variant of T7 RNAP (R6232S, N-terminal lon tag, GTG start codon) (FIG. 2A). RBS variants controlling T7 RNAP expression were tested and an intermediate strength was selected to maximize induction while limiting toxicity (FIG. 16). The controller was carried on the genome by replacing recA (see Methods and Materials). The response function of the final controller is compared to that obtained for pKT249 in *E. coli*, showing that they sweep through the same range of expression at intermediate levels of induction (FIG. 2B). To achieve the same level of induction in the two species, 0.1 mM IPTG is selected for *E. coli* and 0.5 mM for R. sp. IRBG74 (circled points in FIG. 2B).

Figure 2C:
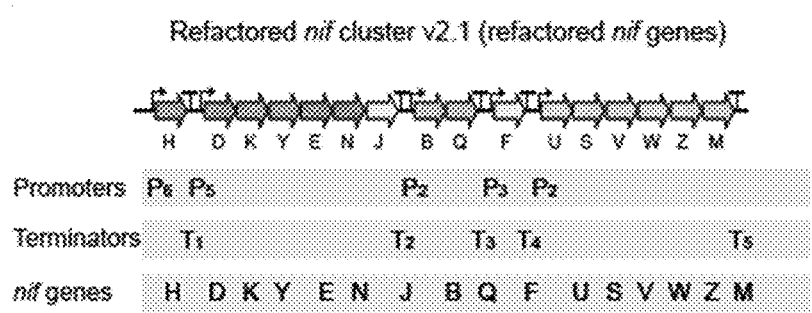
Figure 2D:
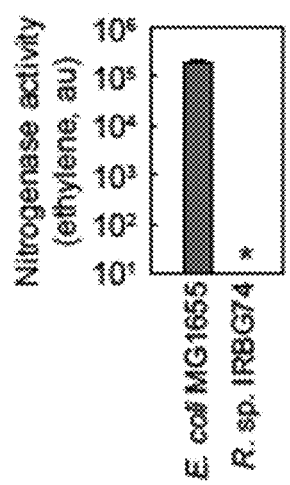
Figure 2E:
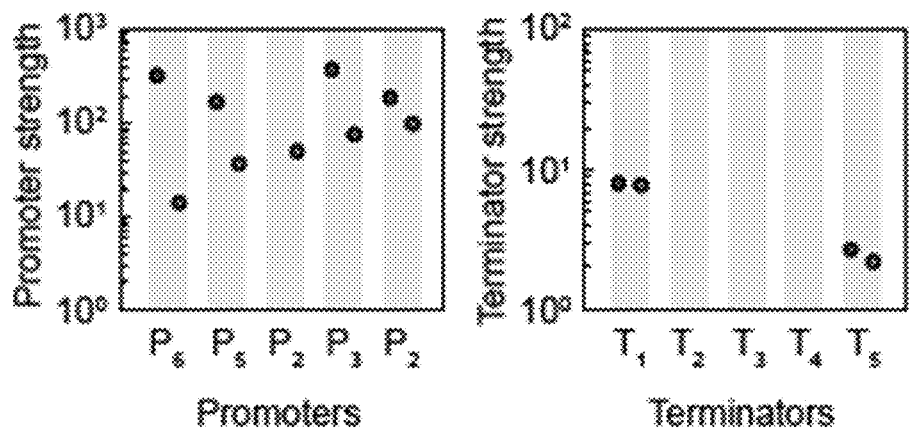
Figure 2F:
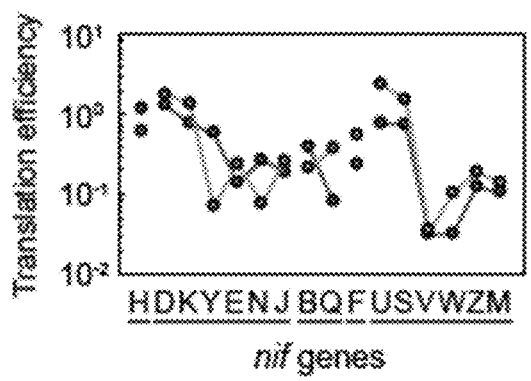
Figure 17:
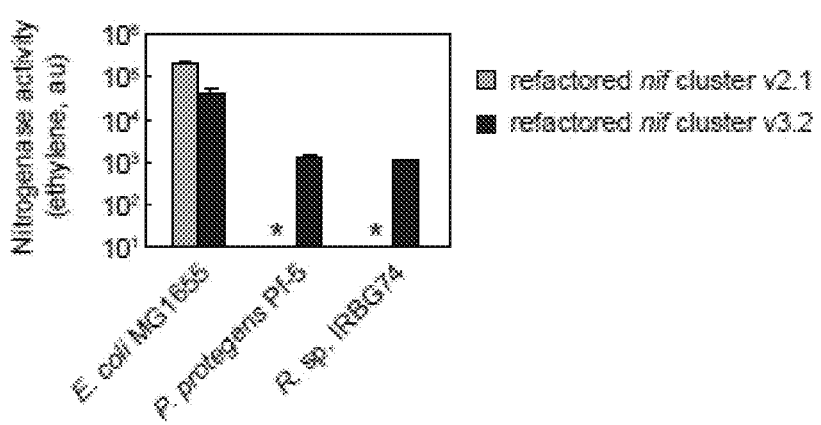
FIG. 17 includes a plot showing the nitrogenase activity of the refactored nif clusters across species. Error bars represent s.d. from three independent experiments.
Figure 18:
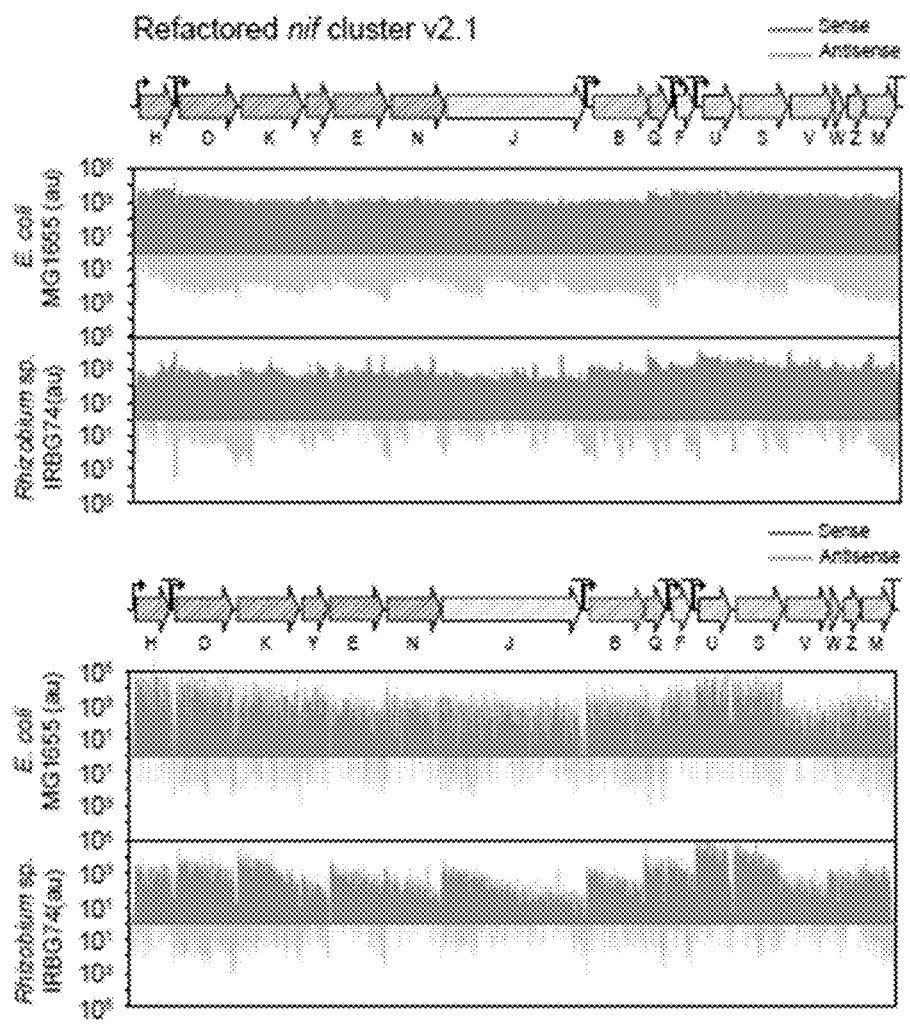
FIG. 18 includes diagrams showing RNA-seq (top) and Ribosome profiling (bottom) data, respectively in E. coli MG1655 and R. sp. IRBG74. The nif genes were induced by 1 mM IPTG for 6 hours (see Materials and Methods).
Figure 19:
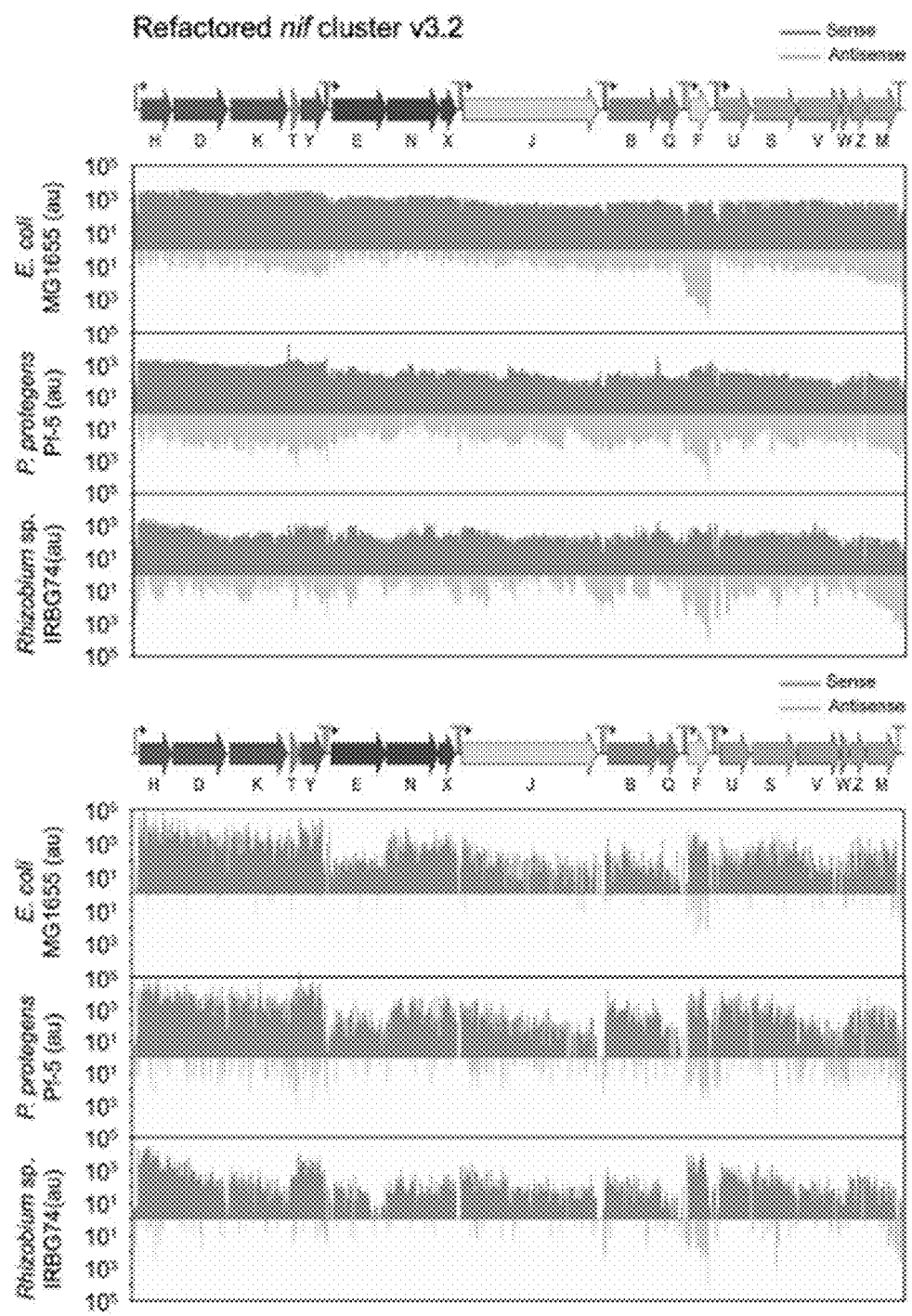
FIG. 19 includes diagrams showing RNA-seq (top) and ribosome profiling (bottom) data, respectively, in E. coli MG1655 and P. protegens Pf-5 and R. sp. IRBG74. The nif genes were induceb by 1 mM, 0.1 mM, and 0.5 mM IPTG for 6 h in E. coli MG1655, P. protegens Pf-5 and R. sp. IRBG74, respectively (see Materials and Methods).
Figure 20A:
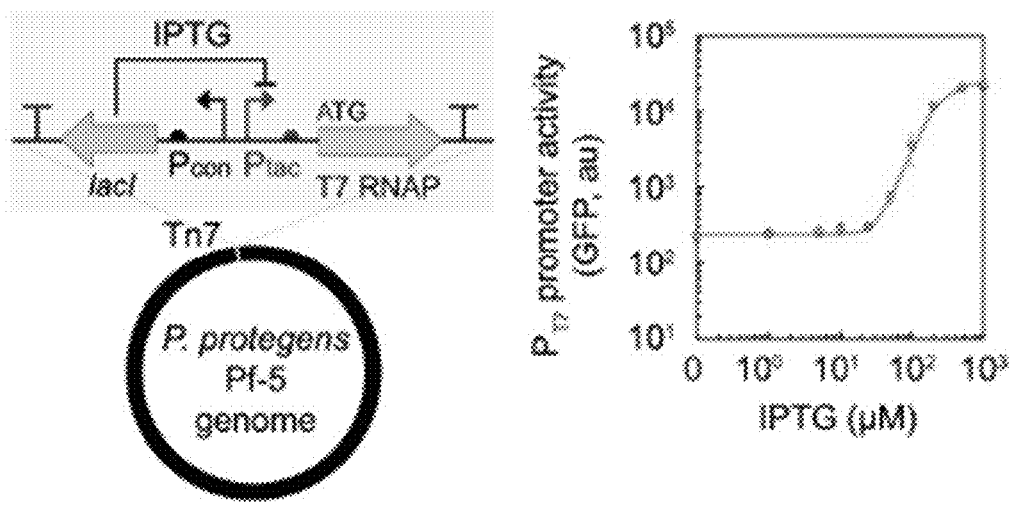
FIGS. 20A-20F include diagrams showing the transfer of the refactored nif cluster v3.2 in P. protegens Pf-5.
Figure 20B:
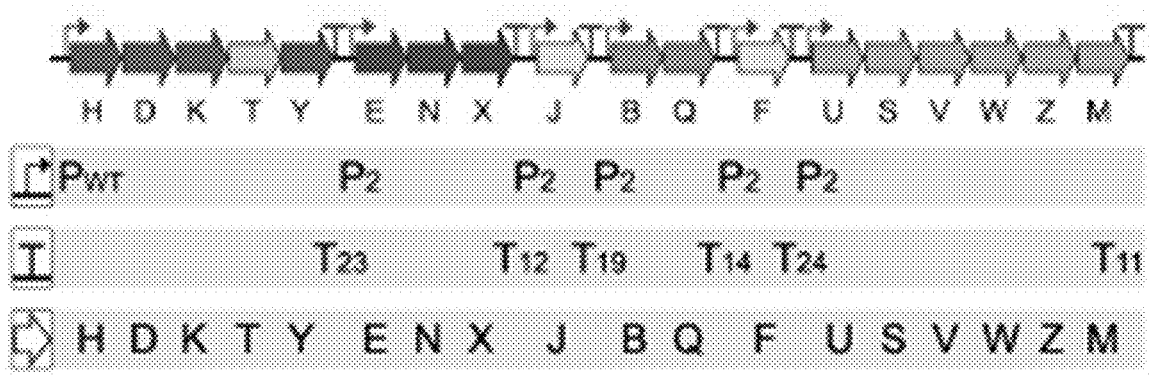
Figure 20C:
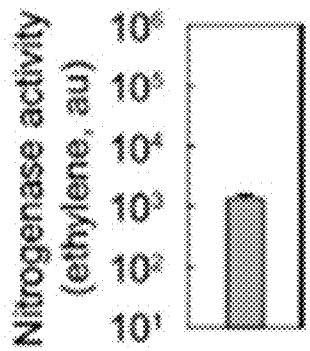
Figure 20D:
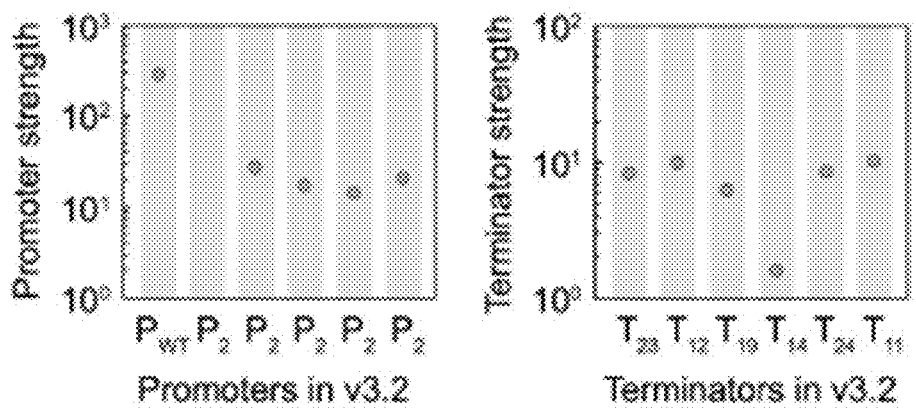
Figure 20E:
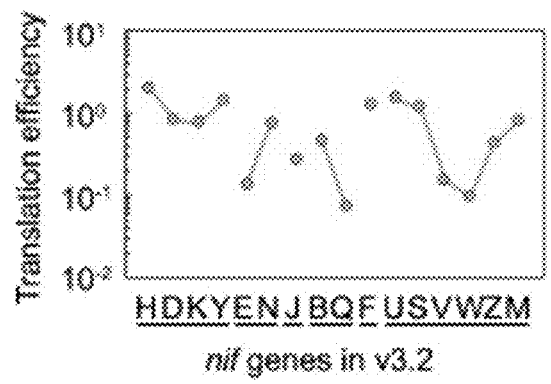
Figure 20F:
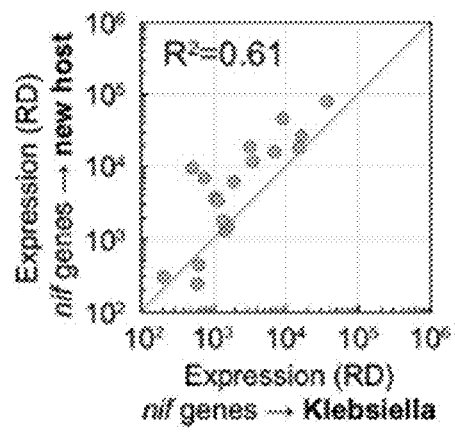

The refactored v2.1 cluster was then transferred to R. sp. IRBG74, but no activity was observed (FIGS. 2C-2D). Activity was also not observed when the v2.1 cluster was transferred to *P. protegens* Pf-5 (FIG. 17). To determine if the genetic parts that make up the refactored cluster were functioning as designed, RNA-seq and ribosome profiling experiments were performed (FIG. 18). From these data, the strengths of promoters/terminators and the transcription level and translation rates of genes could be calculated (see Methods and Materials). The performance of the promoters in R. sp. IRBG74 was systematically lower than *E. coli*, particularly the first promoter controlling nifH (FIG. 2E). The terminators were functioning the same in the two species, albeit weakly, and no termination could be detected from the three terminators in the center of the cluster (FIG. 2E). The translation of the genes differed significantly between organisms (FIG. 2F). When the expression rates of the nif genes from the refactored cluster are compared with their levels in their native context in *K. oxytoca*, there is almost no correlation (FIG. 2F). Importantly, there is 9-fold less NifH expressed from the refactored cluster in R. sp. IRBG74 as compared to the same cluster in *E. coli*. Thus, the refactored cluster produces wildly different expression levels of the component genes when transferred between organisms, even when transcription is matched between them using different controllers.

Figure 2G:
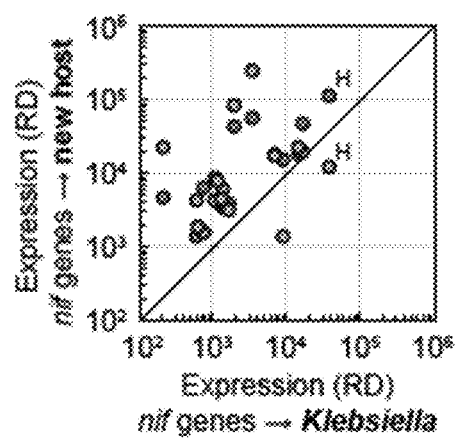

Based on these results, a new refactored cluster (v3.2) (FIG. 2G) was designed. A very strong promoter was chosen for nifH. The transcription was broken up by adding promoters to divide nifENX and nifJ and selecting stronger terminators. Noting that the expression ratios between nif genes are better preserved when the native cluster is transferred to a new host (FIG. 1D) but not the refactored cluster (FIG. 2F), it was hypothesized that this could be due to the disruption of the operon structures and the associated translational coupling between genes. The *K. oxytoca* operons were cloned intact, including native RBSs and replaced these regions of the refactored cluster (FIG. 2G). Note that this also preserves nifT and na, which were not included in first versions because they were either inessential(Simon, H. M., Homer, M. J. & Roberts, G. P. J. J. o. b. Perturbation of nifT expression in *Klebsiella pneumoniae* has limited effect on nitrogen fixation. 178, 2975-2977 (1996)) or inhibitory (Gosink, M. M., Franklin, N. M. & Roberts, G. P. J. J. o. b. The product of the *Klebsiella pneumoniae* nifX gene is a negative regulator of the nitrogen fixation (nif) regulon. 172, 1441-1447 (1990)).

Figure 2H:
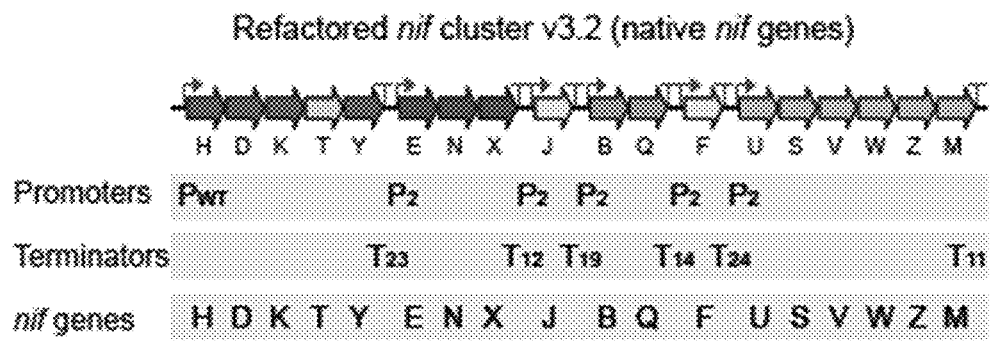
Figure 2I:
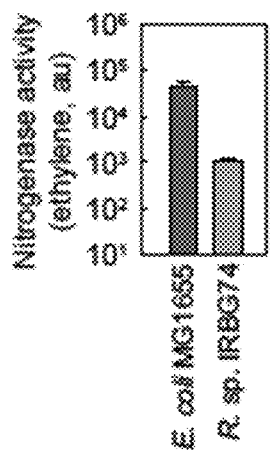
Figure 2J:
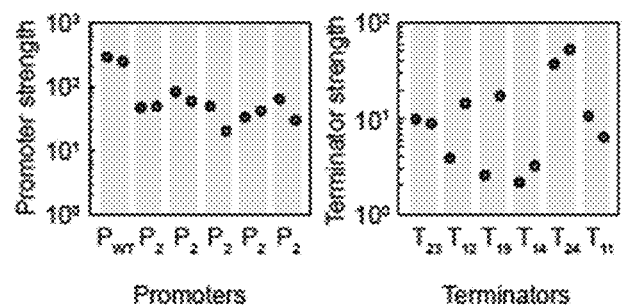
Figure 2K:
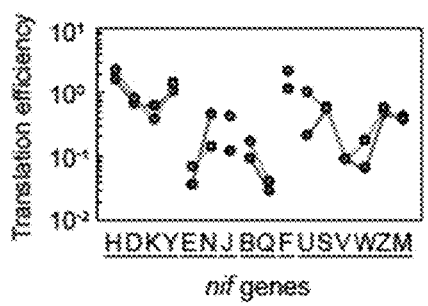
Figure 2L:
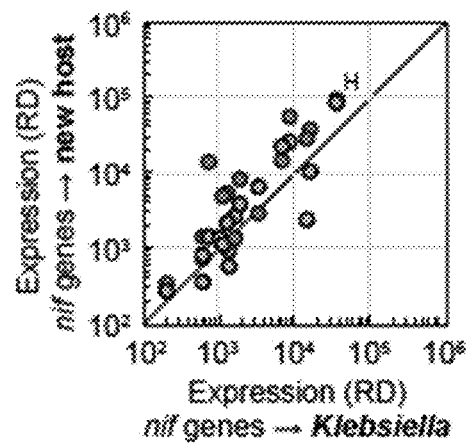
Figure 2M:
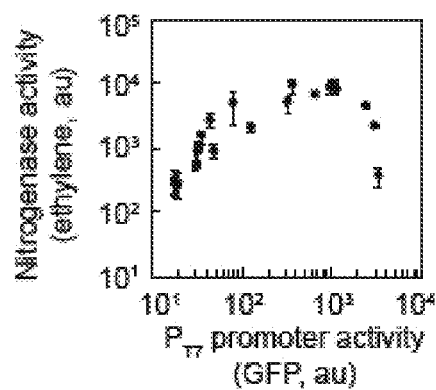

Compared to v2.1, the v3.2 cluster is less active in *E. coli* but is active in R. sp. IRBG74 (FIG. 2H) and *P. protegens* Pf-5 (FIG. 17). This experiment was performed in the double nif knockout strain in R. sp. IRBG74, thus indicating that the refactored cluster is self-contained in producing nitrogenase activity. RNA-seq and ribosome profiling was applied to evaluate the performance of v3.2 in all three species (FIG. 2I, FIG. 19, and FIGS. 20A-20F). The promoters perform similarly in the different hosts, but there was significant diversity in terminator function. Despite this, the translation rates (RD) of the genes were remarkably consistent and NifH expression is nearly identical (FIG. 2J). The higher expression of NifH and the preserved ratios between proteins is the likely reason that the refactored cluster is functional in R. sp. IRBG74. The next attempt was to increase expression level of the nif genes in R. sp. IRBG74 by increasing the concentration of inducer used, but a clear optimum beyond which increased expression caused a rapid decline in activity was found (FIG. 2M). This indicates a potential upper limit in obtaining activity in R. sp. IRB G74 under free living conditions using only the genes from *K. oxytoca*.

Replacement of *A. caulinodans* Nif Regulation with Synthetic Control

The *A. caulinodans* nif genes are distributed across three clusters in different genomic locations. The regulatory signals converge on the NifA activator that, in concert with the RpoN sigma factor, turns on transcription of the genomic nif clusters. Numerous and not fully characterized environmental signals are integrated upstream of this node, including NtrBC(Kaminski, P. A. & Elmerich, C. J. M. m. The control of *Azorhizobium caulinodans* nifA expression by oxygen, ammonia and by the HF-I-like protein, NrfA. 28, 603-613

(1998)), NtrXY(Pawlowski, K., Klosse, U., De Bruijn, F. J. M. & MGG, G. G. Characterization of a novel *Azorhizobium caulinodans* ORS571 two-component regulatory system, NtrY/NtrX, involved in nitrogen fixation and metabolism. 231, 124-138 (1991)), FixLJK(Kaminski, P. & Elmerich, C. J. M. m. Involvement of fixLJ in the regulation of nitrogen fixation in *Azorhizobium caulinodans*. 5, 665-673 (1991); Kaminski, P., Mandon, K., Arigoni, F., Desnoues, N. & Elmerich, C. J. M. m. Regulation of nitrogen fixation in *Azorhizobium caulinodans*: identification of a fixK-like gene, a positive regulator of nifA. 5, 1983-1991 (1991)), NrfA (Kaminski, P. A. & Elmerich, C. J. M. m. The control of *Azorhizobium caulinodans* nifA expression by oxygen, ammonia and by the HF-I-like protein, NrfA. 28, 603-613 (1998)), and PII proteins (e.g., GlnB and GlnK(Michel-Reydellet, N. & Kaminski, P. A. J. J. o. b. *Azorhizobium caulinodans* PIIand GlnK proteins control nitrogen fixation and ammonia assimilation. 181, 2655-2658 (1999))). Tthe clusters (64 kb total, containing 76 genes) were cloned into the plasmid systems described above and transferred into R. sp. IRBG74 and *P. protegens* Pf-5, but no activity was found in either strain. Overexpression of *A. caulinodans* NifA and RpoN did not lead to activity and, upon further investigation, these regulators were found to be inactive in these strains. The size of the clusters and the lack of genetic and gene function information would complicate fully refactoring the system. For these reasons, it was decided to modify the regulation controlling mf such that it can be placed under the control of synthetic sensors.

Figure 3A:
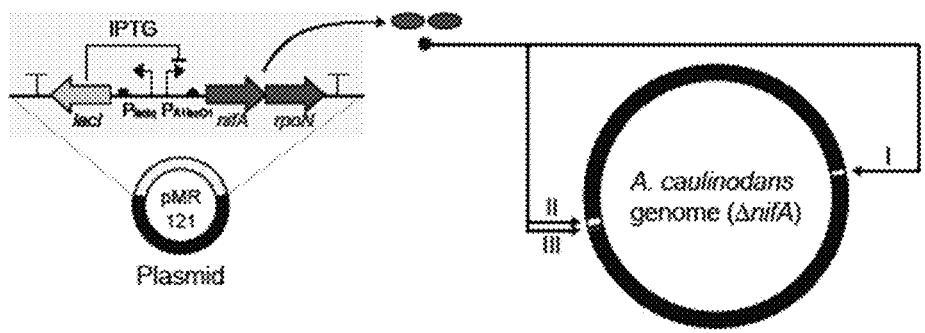
FIGS. 3A-3F include diagrams showing the control of nitrogen fixation in A. caulinodans ORS571.
Figure 3A:
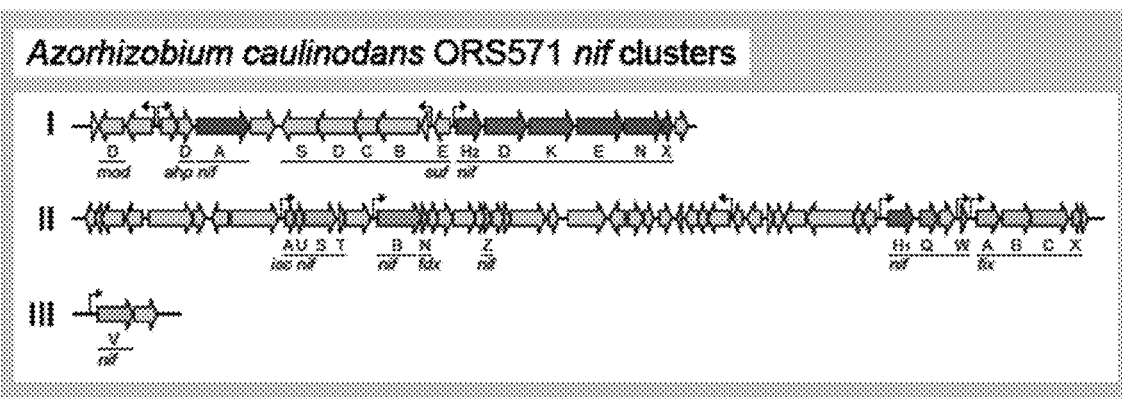
Figure 3B:
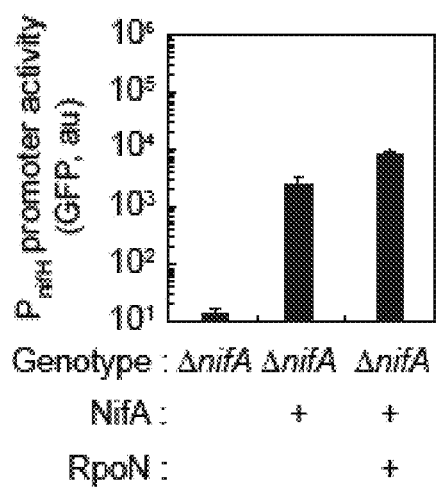
Figure 3C:
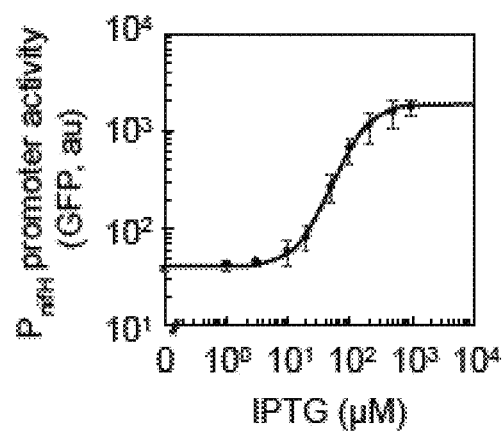
Figure 21:
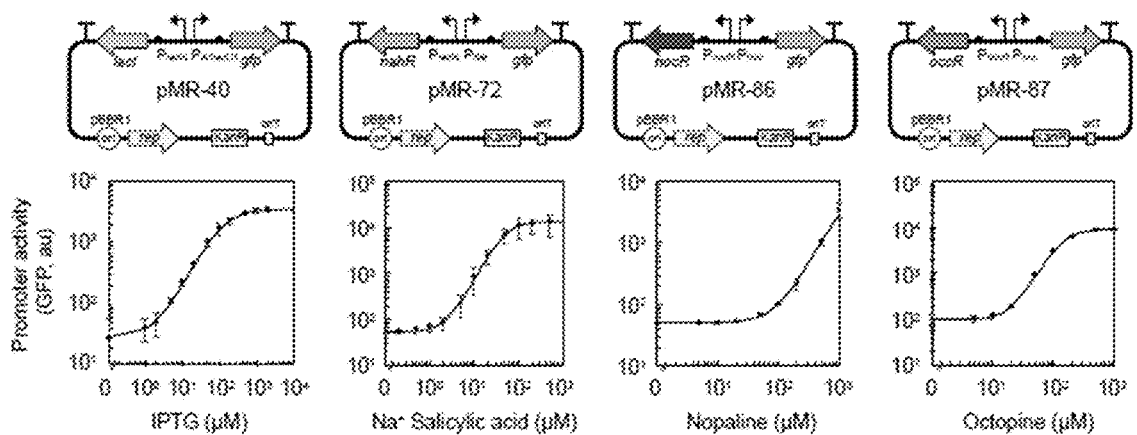
FIG. 21 includes diagrams showing the response function of inducible promoters in A. caulinodans ORS571. Plasmids used to characterize inducible promoters are shown on top of each panel and provided in Table 10. Error bars represent s.d. from three independent experiments.

The primary goal herein was to eliminate ammonium repression of nitrogenase activity, which converges on the regulation of NifA. The native nifA gene was knocked out of the genome using the sacB markerless deletion method (see Methods and Materials), with the intent of placing NifA under inducible control (FIG. 3A). There is only basal activity from the nifH promoter in the ΔnifA strain (FIG. 3B). When NifA is overexpressed, the promoter turns on and its activity is further enhanced by the co-expression of RpoN in an operon (note that the genomic rpoN gene is left intact for these experiments). The IPTG-inducible system designed for *Rhizobium* (previous section) was tested in *A. caulinodans* carried on a pBBR1-ori plasmid. Using GFP, this was found to induce expression over several orders of magnitude (FIG. 21). Then, the *A. caulinodans* nifA and rpoN gene was placed under IPTG control and the fluorescent reporter fused to the *A. caulinodans* MN promoter (encompassing 281 nt upstream of the ATG), carried on the same plasmid (see Materials and Methods). The response function from the nifH promoter was analyzed at the condition used for nitrogen fixation, exhibiting a wide dynamic range to 45-fold (FIG. 3C).

Figure 3D:
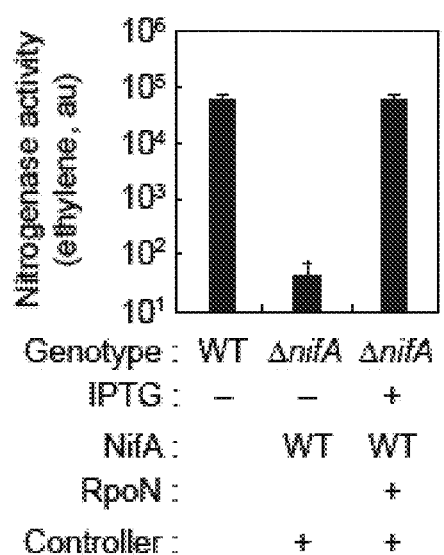
Figure 3E:
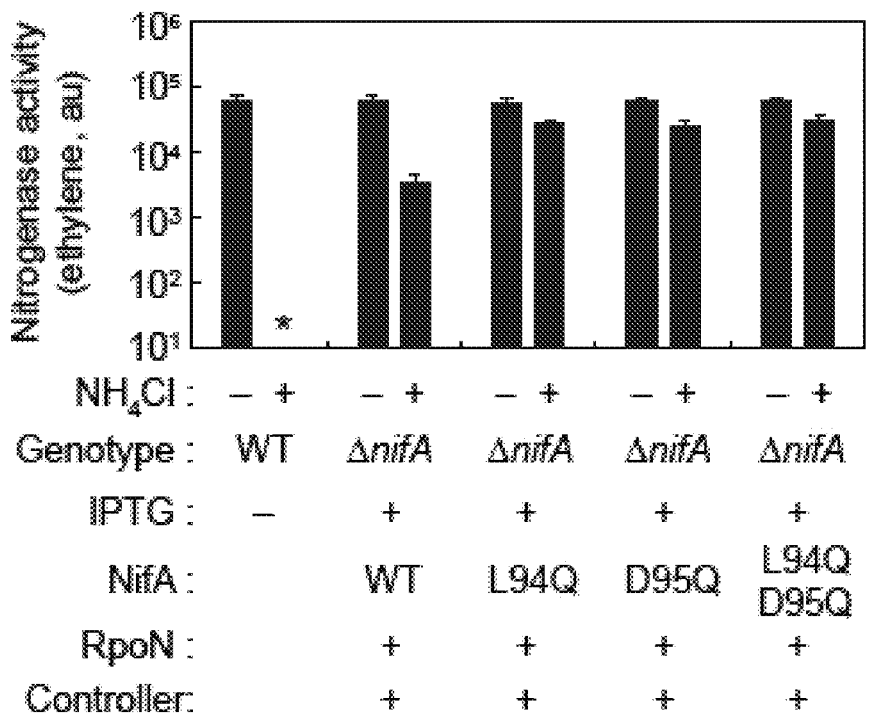

The controller was designed to co-express NifA and RpoN and tested for its ability to induce nitrogenase (FIG. 3D). When fully induced, there is a complete recovery of activity as compared to the wild-type strain. The repression of nitrogenase activity by ammonium was then evaluated. The presence of 10 mM ammonium chloride leads to no detectable activity by the wild-type strain (FIG. 3E). Even when both NifA and RpoN are under inducible control, there is strong repression with only 5% of the nitrogenase activity of the wild-type. This suggests that the post-transcriptional control of NifA activity by ammonium remains intact.

In related alphaproteobacteria, mutations have been identified in NifA that abrogate ammonium repression(Paschen, A., Drepper, T., Masepohl, B. & Klipp, W. *Rhodobacter capsulatus* nifA mutants mediating nif gene expression in the presence of ammonium. FEMS microbiology letters 200, 207-213 (2001); Rey, F. E., Heiniger, E. K. & Harwood, C. S. Redirection of metabolism for biological hydrogen production. *Applied and environmental microbiology* 73, 1665-1671 (2007)). These mutations occur in the N-terminal GAF domain. Using a multiple sequence alignment, two equivalent residues were identified to mutate in *A. caulinodans* (L94Q and D95Q) (FIG. 22). These mutations were made and then tested individually and in combination (FIG. 3D). When the double mutant of NifA is co-expressed with RpoN, the presence of ammonium only results in a slight decrease in activity.

Figure 3F:
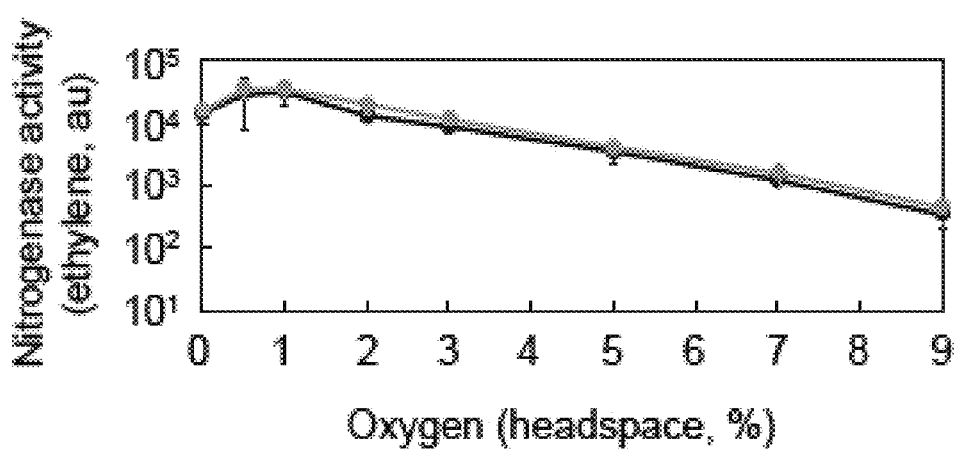

Oxygen irreversibly inhibits nitrogenase and represses nif clusters. The inducible nif clusters were tested for oxygen sensitivity, noting that *A. caulinodans* is an obligate aerobe and fixes nitrogen under micro-aerobic conditions. The tolerance of nitrogenase to oxygen was then assessed as a function of the concentration of oxygen in the headspace, held constant by injecting oxygen while monitoring its level (Methods and FIG. 26A). The native and inducible gene clusters responded nearly identically to oxygen (FIG. 3F). The optimum activity occurs between 0.5% to 1% with a wide tolerance (30% activity at 3% oxygen).

Introduction of Controllable Nif Activity in *P. protegens* Pf-5

Figure 4A:
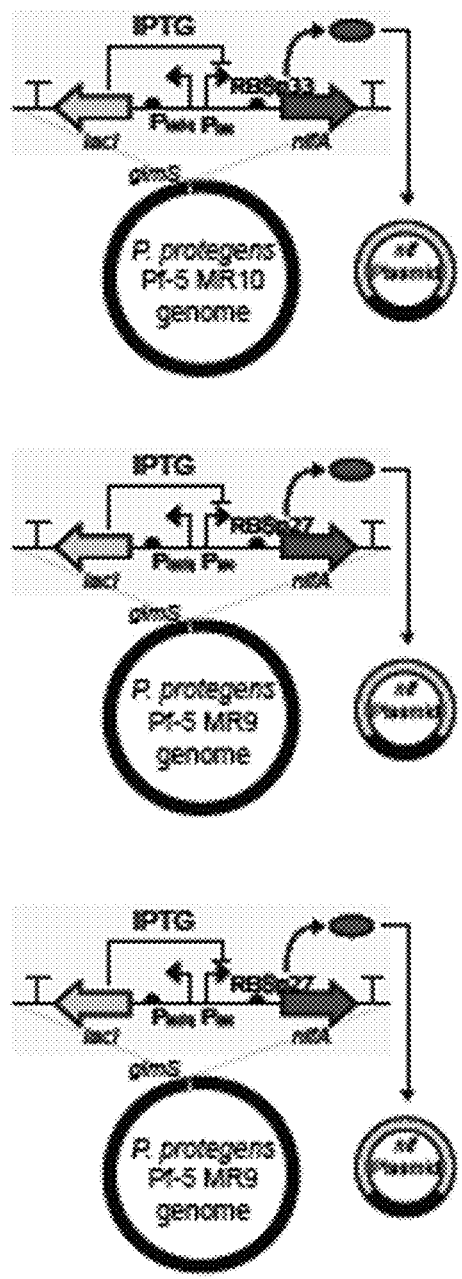
FIGS. 4A-4F include diagrams showing Nitrogenase activity of the inducible nif clusters in *Pseudomonas protegens* Pf-5.
Figure 4B:
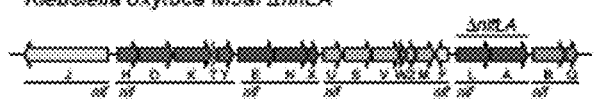
Figure 4B:
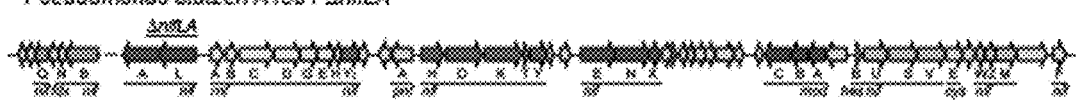
Figure 4B:
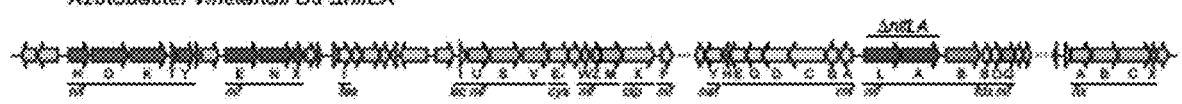
Figure 4C:
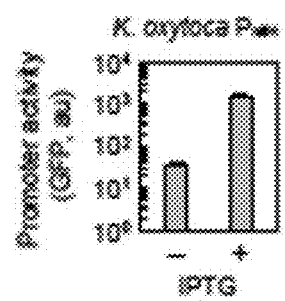
Figure 4C:
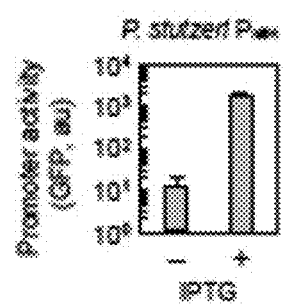
Figure 4C:
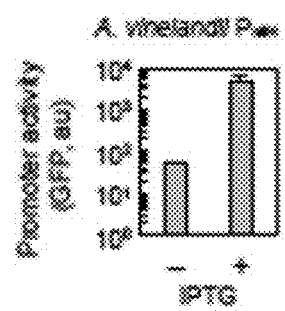

The native *K. oxytoca*, *P. stutzeri*, and *A. vinelandii* nif clusters are all functional in *P. protegens* Pf-5 (FIG. 1A). However, when the native *P. stutzeri* and *A. vinelandii* clusters are transferred, nitrogenase is strongly repressed. In contrast, transferring the native *K. oxytoca* cluster produces uncontrolled (constitutively on) nitrogenase activity (FIG. 4E). For these three clusters in *P. protegens* Pf-5, it was sought to gain regulatory control by removing the nifA master regulators from the clusters and expressing them from a controller (FIG.A).

As with *Rhizobia*, it was found that first, part libraries for *P. protegens* Pf-5 had to be built before building controllers with sufficient dynamic range. A range of 20 constitutive promoters and seven T7 promoters that span a range of 778-fold and 24-fold expression, respectively, was characterized (FIGS. 11A-11C). A library of 192 RBSs was screened, representing an expression range of 4,079-fold (FIGS. 12A-12B). A set of seven terminators that share no sequence homology between each other and have a terminator strength>10 in R. sp. IRBG74 was selected and characterized together with the three well-used terminators (e.g., T7 terminator, rrnBT1, and L3S2P21). These seven terminators showed a terminator strength>50 (FIGS. 13A-13B).

The inducible systems designed for *Rhizobium* were transferred as-is to a Pseudomas-specific pRO1600 plasmid (see Methods and Materials). The 3OC6HSL-, aTc-, cuminic acid-, and DAPG-inducible systems were all found to be functional (FIG. 15A). In addition, a naringenin-inducible system based on the $P_{fde}$ promoter was constructed and found to be functional. The strength of arabinose inducible system was increased by substituting the −10 box in $P_{BAD}$ promoter and arabinose import was improved by constitutive expression of the arabinose transporter AraE (FIG. 15B). Finally, the IPTG-inducible system was optimized for *P. protegens* Pf-5 by replacing the $P_{A1lacO1}$ promoter with the $P_{tac}$ promoter and making three amino acid substitutions to LacI (Meyer, A. J., Segall-Shapiro, T. H., Glassey, E., Zhang, J. & Voigt, C. A. J. N. c. b. *Escherichia coli* "Marionette" strains with 12 highly optimized small-molecule sensors. 1 (2018).). This effort resulted in seven new inducible systems that produce 41- to 554-fold induction in *P. protegens* Pf-5 (FIG. 15C).

Figure 23A:
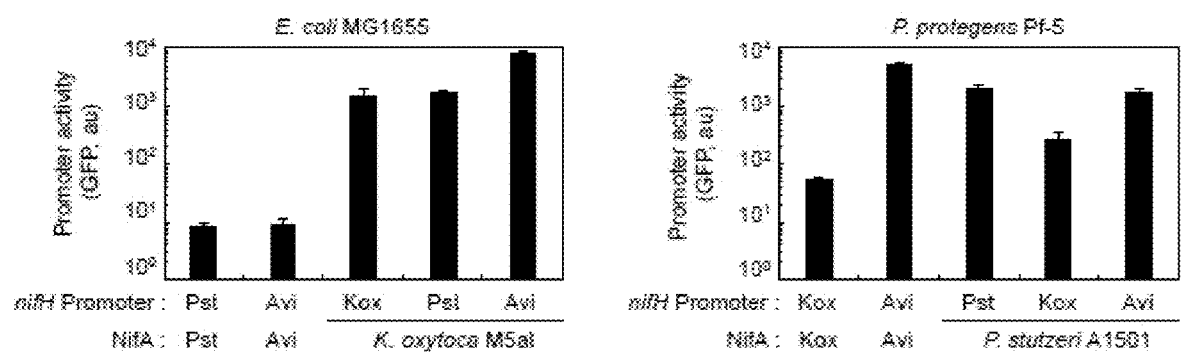
FIGS. 23A-23B include diagrams showing functional testing of the NifA homologues that activate the nifH promoters.
Figure 23B:
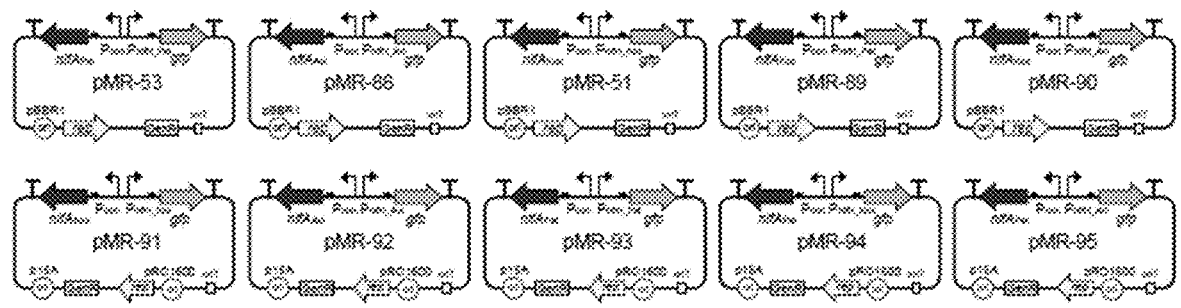
Figure 24A:
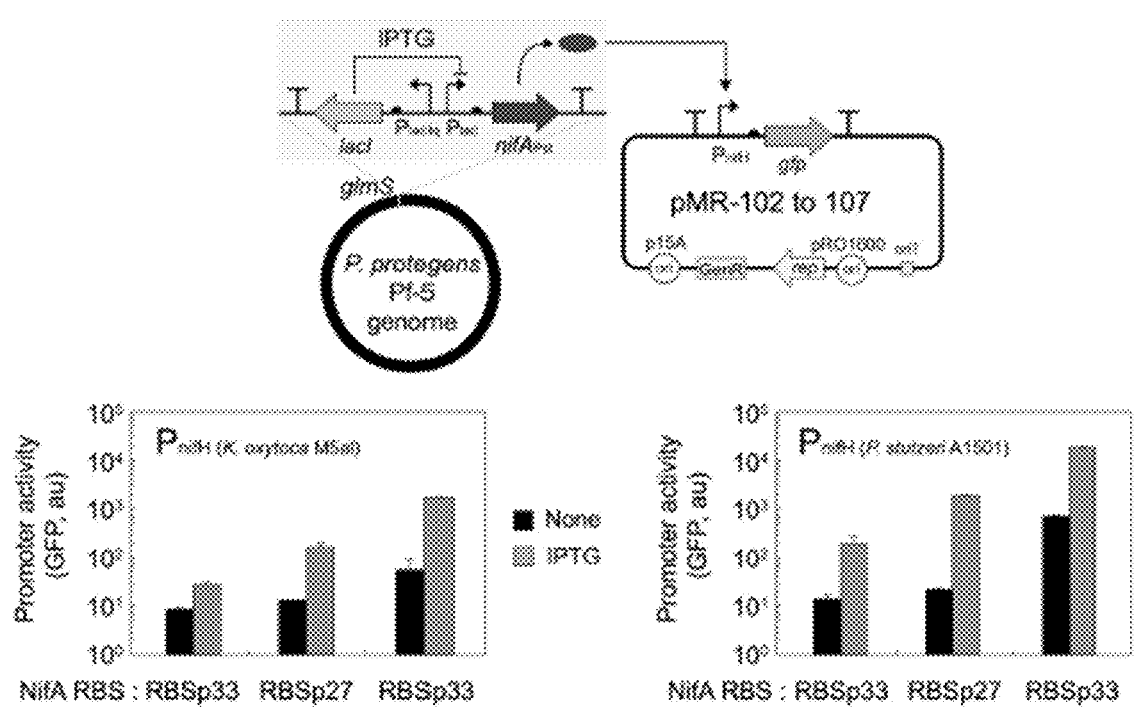
(FIG. 24A) The controllers with different strengths were designed by RBS replacement and tested with the reporter plasmids (pMR103-105) in which each of the three nifH promoter is fused to sfgfp (Methods). The nifH promoters were induced with 0.5 mM IPTG. Genetic parts and RBS sequences are provided in Table 10 and 11, respectively.
Figure 24B:
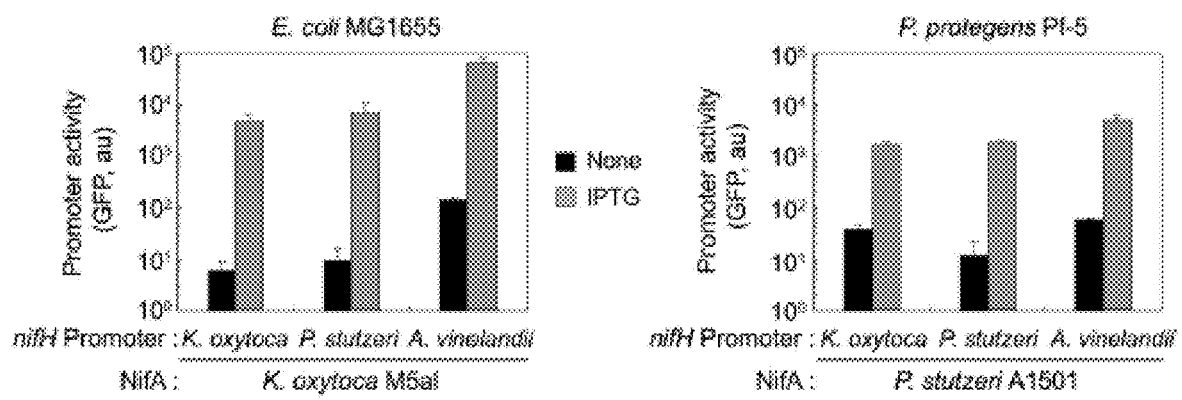
(FIG. 24B) Activation of the nifH promoters in the *E. coli* MG1655 containing the controller plasmid pMR102 was tested with the reporter plasmids pMR106-108. The *P. protegens* Pf-5 controller strain MR10 was used to drive expression of the nifH promoter of *K. oxytoca* and the controller strain MR9 was used to drive expression of the nifH promoters of *P. stutzeri* and *A. vinelandii*. The nifH promoters were induced with 0.05 mM IPTG and 0.5 mM IPTG in *E. coli* MG1655 and *P. protegens* Pf-5, respectively. Error bars represent s.d. from three independent experiments.
Figure 25:
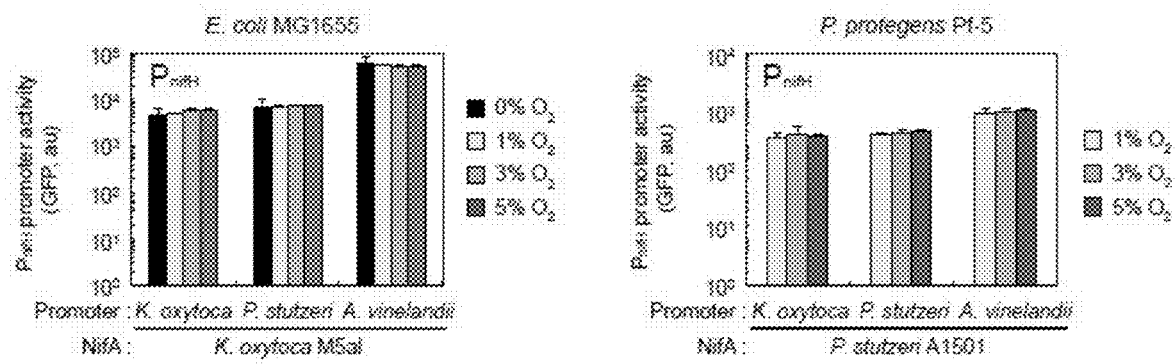
FIG. 25 includes diagrams showing the effect of oxygen on the activity of the nifH promoters. Expression from the nifH promoters was analyzed in *E. coli* MG1655 containing the controller plasmid pMR102, *P. protegens* Pf-5 MR10 (for *K. oxytoca*) and MR9 (for *P. stutzeri* and *A. vinelandii*) at varying initial oxygen levels in the headspace. The three nifH promoters were induced with 0.05 mM IPTG and 0.5 mM IPTG in *E. coli* MG1655 and *P. protegens* Pf-5, respectively, and incubated at varying initial oxygen concentrations. Oxygen has no effects on nifH expression in both strains. Error bars represent s.d. from three independent experiments.

To simplify the comparison between clusters, it was sought to build a single, universal controller that could induce all three. Each has a different NifA sequence, so the ability to cross induce the gene clusters was tested. To do this, the nifH promoters from each nif cluster were cloned and fused to gfp to build plasmid-based reporters (see Methods and Materials). The ability of the various NifA homologues to activate the nifH promoters was evaluated in *E. coli* and *P. protegens* Pf-5 (FIG. 23A-23B). The results suggest that it is more important to express a NifA variant from a similar species as the host, as opposed to expressing the NifA variant that is cognate to the transferred cluster. This may be due to the need for NifA to recruit host transcriptional machinery, whereas the NifA binding sites in the promoters are well conserved across species. Based on these data, the controller was constructed using the *P. stutzeri* NifA, placed under the control of the optimized IPTG-inducible system, described above. The RBSs of NifA were synthetically designed to span a wide range of expression of nif genes (FIG. 24A). The controller was inserted into the genome 25 bp downstream of the stop codon of glmS using the mini-Tn7 system. The ability for this controller to induce the nifH promoter from each cluster using a fluorescent reporter is shown in FIG. 4C and FIG. 24B.

Figure 4D:
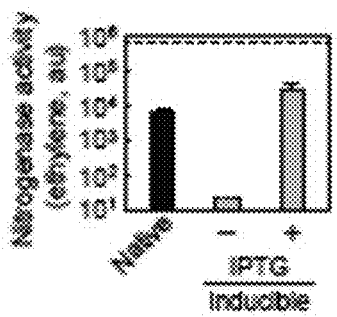
Figure 4D:
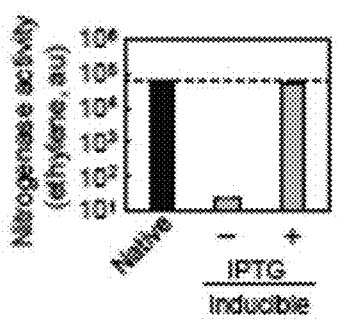
Figure 4D:
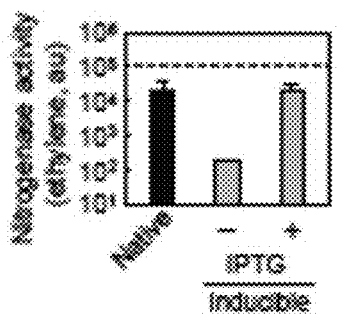
Figure 4E:
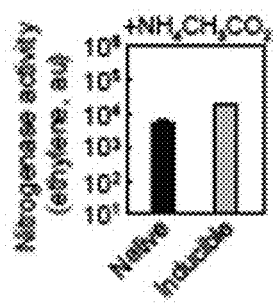
Figure 4E:
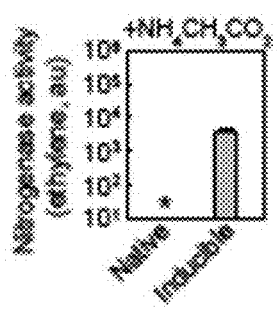
Figure 4E:
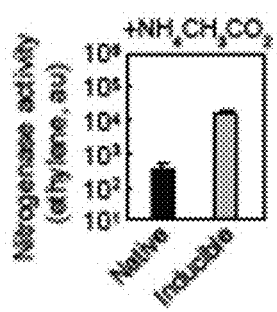

The nitrogenase activity for each of the gene clusters in *P. protegens* Pf-5 was then assessed (FIG. 4D). The three *P. protegens* Pf-5 strains containing the transferred clusters were modified to insert the controller and delete the native nifLA genes from each cluster (FIG. 4B). All three are inducible, with nitrogenase activity showing dynamic ranges of 1,200-fold, 2,300-fold, and 130-fold for the *K. oxytoca*, *P. stutzeri*, and *A. vinelandii* nif clusters, respectively. When induced, these systems all produce similar or even higher nitrogenase activities than can be achieved by the transfer of the unmodified native clusters (FIG. 4D). For reference, the nitrogenase activities produced by *K. oxytoca*, *P. stutzeri*, and *A. vinelandii* are shown as dashed lines in FIG. 4D (top to bottom) (see Methods and Materials). All three inducible clusters produce similar levels of activity that approach those measured from wild-type *P. stutzeri* and *A. vinelandii*.

Figure 8A:
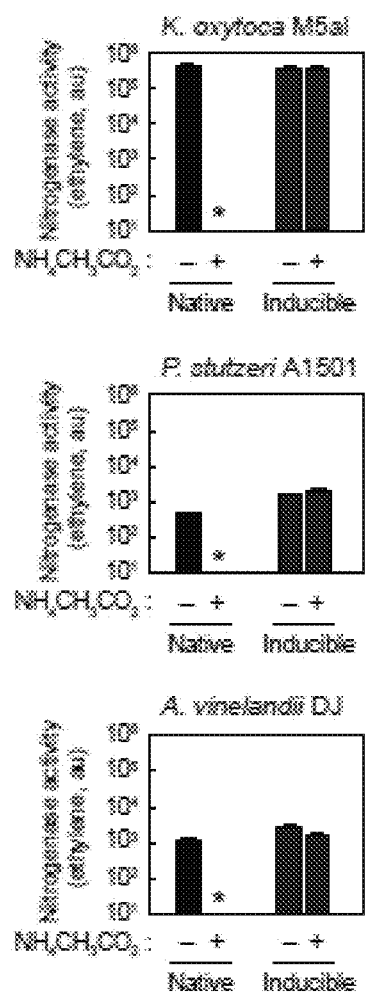
FIGS. 8A-8B include plots showing ammonium repression of the transferred nif clusters. Nitrogenase sensitivity to ammonium was measured by nitrogenase assay in the absence (−) or presence (+) of 17.1 mM ammonium acetate. The sensitivity of the native and inducible nif clusters in *E. coli* MG1655 (FIG. 8A) and *P. protegens* Pf-5 (FIG. 8B). Note that the data are from FIGS. 4A-4F and FIGS. 7A-7F. The nif clusters were induced by 50 μM and 0.5 mM IPTG in *E. coli* MG1655 and *P. protegens* Pf-5, respectively. Asterisks indicate ethylene production below the detection limit (<10 au). Error bars represent s.d. from three independent experiments.
Figure 8B:
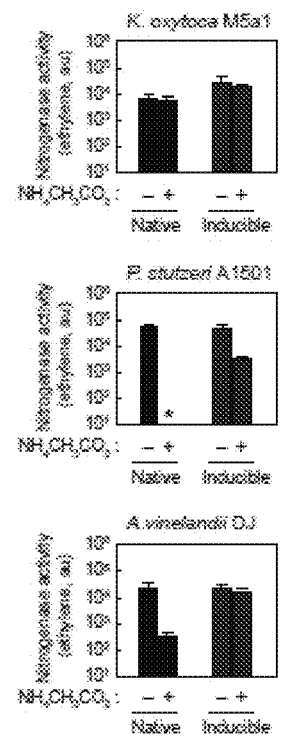

The native *P. stutzeri* and *A. vinelandii* clusters are strongly repressed by ammonium: the presence of 17.1 mM eliminates activity or reduces it 7-fold, respectively (FIG. 4E and FIGS. 8A-8B). The inducible clusters show little reduction in activity and the inducible *A. vinelandii* cluster exhibits almost no ammonia repression. While the native *K. oxytoca* cluster in *P. protegens* Pf-5 generates a constitutive response, there is still some repression, which is reduced by the inducible version.

Figure 4F:
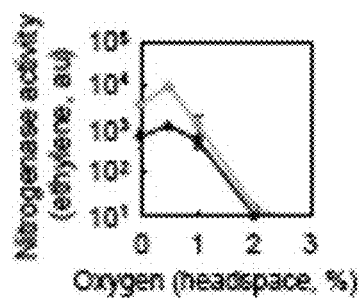
Figure 4F:
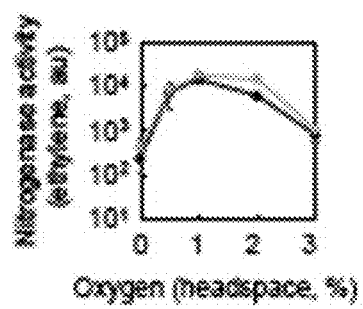
Figure 4F:
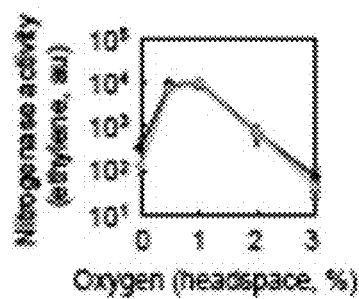

The inducible nif clusters were tested for oxygen sensitivity. Note that wild-type *A. vinelandii* is able to fix nitrogen under ambient conditions due to genetic factors internal and external to the cluster. First, it was established that the controller in *P. protegens* Pf-5 could induce transcription from the three nifH promoters in the presence of oxygen (FIGS. 26A-26B). The tolerance of nitrogenase to oxygen was then assessed as a function of the concentration of oxygen in the headspace, as described for *A. caulinodans* (previous section). The native and inducible clusters exhibited the same oxygen response (FIG. 4F). The nif cluster from *K. oxytoca* was the most sensitive, generating the highest activity under anaerobic conditions, but this is quickly abolished in the presence of 02. In contrast, the nif clusters from *P. stutzeri* and *A. vinelandii* showed wider tolerance with optima at 1% and 0.5%, respectively. However, both clusters lose activity at lower oxygen concentrations than *A. caulinodans*.

Figure 27:
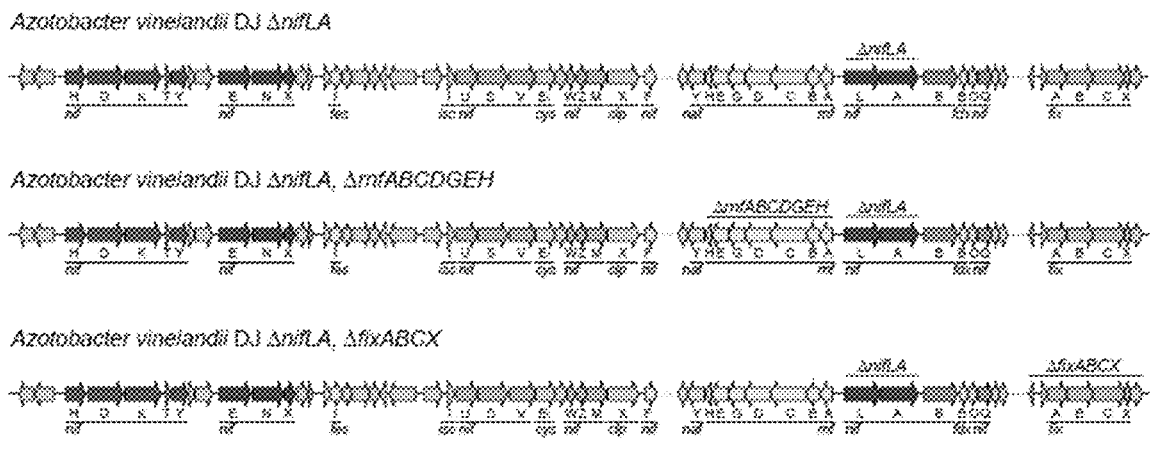
FIG. 27 includes diagrams showing the effect of the rnf and fix complex on nitrogenase activity. The modified nif clusters of *A. vinelandii* on the plasmids pMR25-28 were analyzed in the controller strain *P. protegens* Pf-5 MR9. The deleted regions from the clusters were provided in Table 9. Nitrogenase was induced with 0.5 mM IPTG. Removing the rnf complex from the cluster abrogated activity. The cluster without the fixABCX complex showed identical oxygen tolerance to the cluster with the complex. Error bars represent s.d. from three independent experiments.
Figure 27:
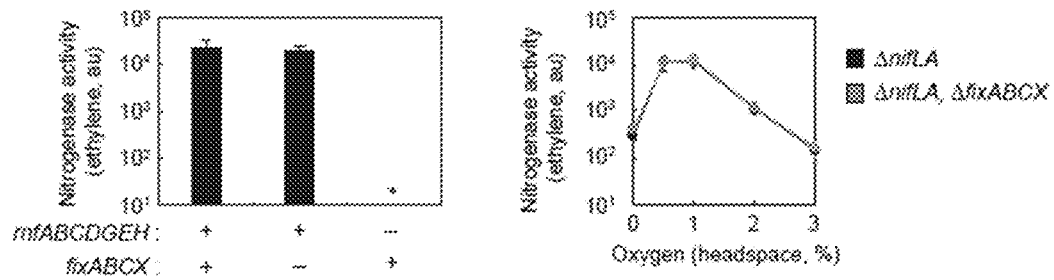

To explore the impact of the electron transport chains, several mutants to the *A. vinelandii* cluster were made (FIG. 27). The *A. vinelandii* cluster contains two potential electron transport systems to nitrogenase and the redundant system may help maintain redox status for nitrogenase at various oxygen levels. The dependence of nitrogenase activity on the oxygen concentration in various mutant backgrounds was re-measured. No effect was seen by adding the rnf2 operon or deleting the fix operon, however deleting rnf1 eliminated activity. This suggests that the rnf1 operon is the sole source of electrons in *P. protegens* Pf-5 under these conditions and the Fix complex cannot compensate the Rnf complex unlike the case of *A. vinelandii*.

Control of Nitrogen Fixation with Agriculturally-Relevant Sensors

The careful design and characterization of the controller has the benefit of simplifying the process by which different synthetic sensors are used to induce nitrogenase expression. By knowing the dynamic range required to go from inactive to active nitrogenase, one can quantitatively select sensors that have the produce a compatible response. This allows different environmental signals—or combinations of signals using genetic logic circuits—to be used to control expression. To demonstrate this, 11 synthetic sensors were selected that respond to a variety of chemical signals of relevance to the rhizosphere and demonstrate that these can be used to create inducible nitrogenase in our engineered strains of *E. coli* (carrying the refactored v2.1 nif), R. sp. IRBG74 (carrying the refactored v3.2 nif), *P. protegens* Pf-5 (carrying the inducible *A. vinelandii* nif), and *A. caulinodans* (inducible nifA/rpoN) (FIGS. 5A-5D).

Figure 5A:
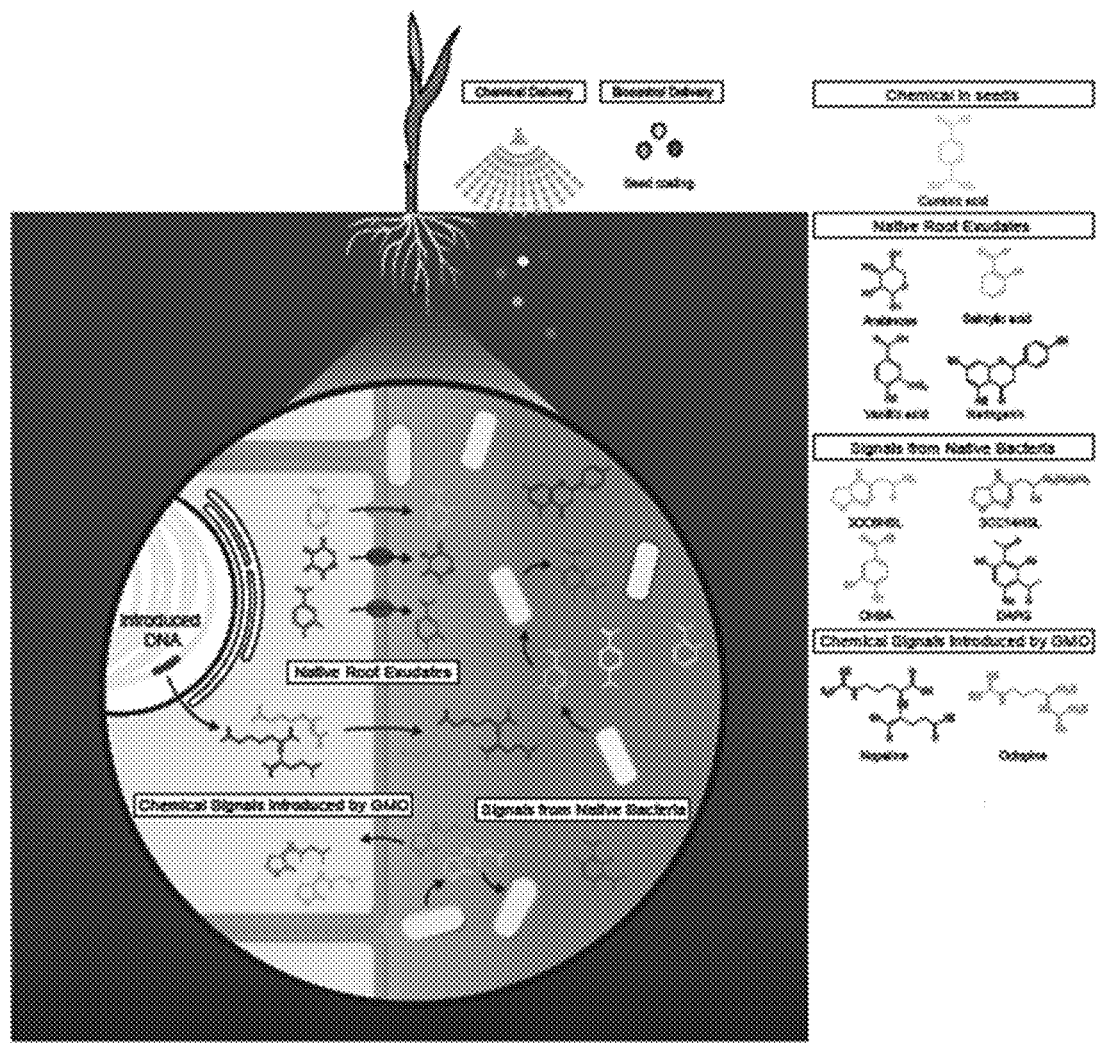
FIGS. 5A-5D include diagrams showing the control of nitrogenase activity with sensors that respond to diverse chemicals in the rhizosphere.

The roles of the chemical signals in the rhizosphere are shown in FIG. 5A. Cuminic acid is present in plant seeds and functions as a fungicide. Natural root exudates may include sugars, amino acids, organic acids, phenolic compounds, phytohormones, and flavonoids. These represent potential signals to control nitrogenase production close to the root surface. Cereals have been shown to release arabinose, vanillic acid, and salicylic acid. In addition, salicylic acid regulates the plant innate immune response and the impact of its exogenous addition to cereals has been studied. Naringenin is a common precursor for many flavonoids and improves endophytic root colonization when applied to rice and wheat. Genistein, a product from naringenin catalyzed by the isoflavone synthase, is released from maize roots. A quorum sensing mimic released by rice can regulate the 3OC6HSL receptor protein LuxR, which has been visualized using *E. coli* biosensor strains.

Bacteria either native to the rhizome or added as biocontrol agents introduced as a spray inoculant or seed coating produce chemical signatures. Inoculation of cereals with root colonizing *Pseudomonas* strains that produce DAPG elicits protection against fungal pathogens. Many bacteria produce quorum molecules, such as N-acyl homoserine lactones, as a means of communication and plants can respond to these signals[2]. The bacterium *Sinorhizobium meliloti* produces 3OC14HSL, which enhances Medicago nodulation and has been shown to induce systemic resistance in cereals. DHBA can be produced by root colonizing bacteria to increase iron solubility and play a role as a chemoattractant for *Agrobacterium* and *Rhizobium*.

Sensors for these chemicals were constructed based on the controllers for each species. For *E. coli* MG1655, a strain that contains 12 optimized sensors, carried in the genome, that respond to various small molecules ("Marionette") had been previously constructed (Meyer, A. J., Segall-Shapiro, T. H., Glassey, E., Zhang, J. & Voigt, C. A. J. N. c. b.

Figure 5B:
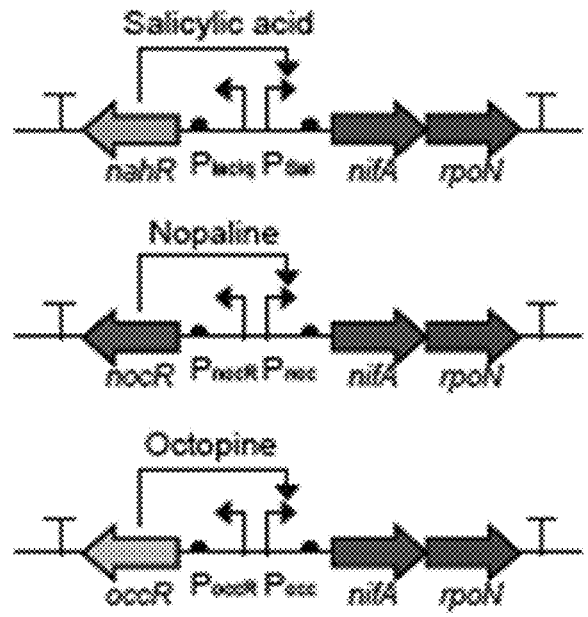
Figure 5C:
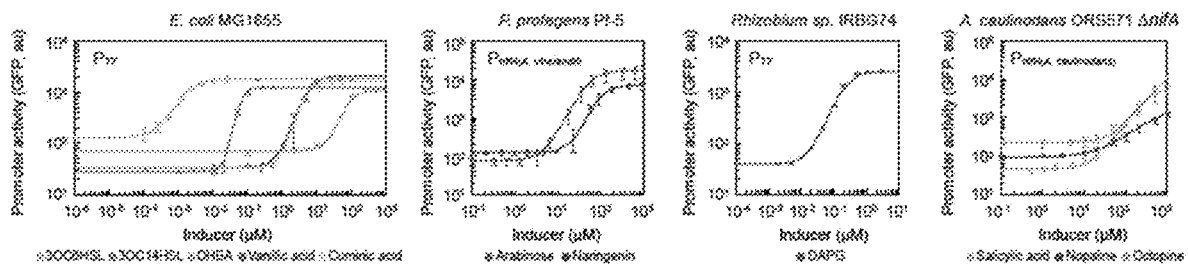

*Escherichia coli* "Marionette" strains with 12 highly optimized small-molecule sensors. 1 (2018).). The response functions of these sensors were characterized in standard units, making it simple to identify those that can be connected to nitrogenase expression without further tuning. Marionette contains sensors for vanillic acid, DHBA, cuminic acid, 3OC6HSL, and 3OC14HSL. For each sensor, the output promoter was transcriptionally fused to T7 RNAP and the response of the responsive promoter (PT7) was measured as a function of inducer concentration (FIG. 5B and FIG. 28B). Then, the v2.1 refactored nif cluster was introduced and nitrogenase activity was measured in the presence and absence of inducer (FIG. 5C and FIG. 28C). The inducible systems constructed for *P. protegens* Pf-5 that respond to arabinose and naringenin were used to drive NifA expression for the control of the *A. vinelandii* nif cluster (FIG. 4A). The induction of the nifH promoter by these sensors was first confirmed using a reporter (FIG. 5B). When this is replaced with the nif gene cluster, it results in an inducible response of nitrogenase activity (FIG. 5C). The best nitrogenase activity in R. sp. IRBG74 is low; however, herein it was demonstrated that it could be placed under inducible control. The DAPG-inducible system developed for R. sp. IRBG74 was connected to the control of T7 RNAP and this produces a strong response from PT7 (FIG. 5B). However, when used to drive the expression of the v3.2 refactored pathway, only a 9-fold induction is observed, consistent with the low nitrogenase activity observed in this strain (FIG. 5C). Finally, the salicylic acid sensor designed for *Rhizobium* was used to control NifA (L94Q/D95Q)/RpoN expression in *A. caulinodans* (FIG. 3A and FIG. 5B). This yielded a 1000-fold dynamic range of nitrogenase activity (FIG. 5C).

Figure 5D:
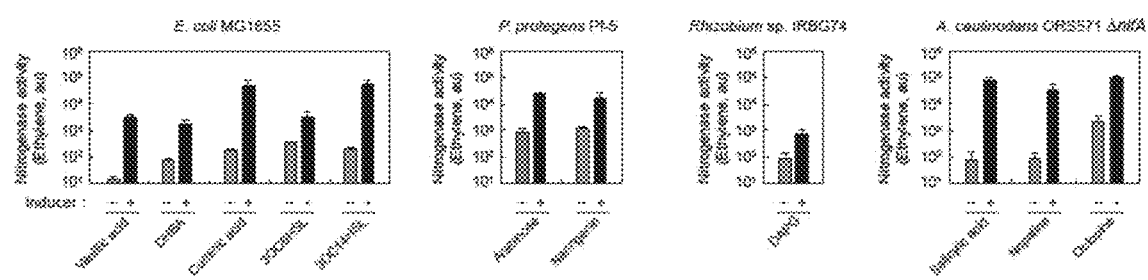

Plants could be engineered to release an orthogonal chemical signal that could then be sensed by a corresponding engineered bacterium. This would have the benefit of only inducing nitrogenase in the presence of the engineered crop. Further, if the molecule is metabolizable by the engineered bacterium, it could serve as a mechanism around which a synthetic symbiosis could be designed, where the plant provides the carbon and the bacterium fixed nitrogen in an engineered relationship. To this end, legumes and *Arabidopsis* have been engineered to produce opines, including nopaline and octopine. Sensors were constructed for these two opines for *A. caulinodans* based on the LysR-type transcriptional activators OccR (octopine) and NocR (nopaline) and their corresponding $P_{occ}$ and $P_{noc}$ promoters (FIG. 5D and FIG. 21). These sensors were connected to the expression of NifA(L94Q/D95Q)/RpoN and the response from $P_{nifH}$ was measured using a fluorescent reporter. Both response functions had a large dynamic range (FIG. 5B) and produced highly-inducible nitrogenase activity (FIG. 5C). The nopaline sensor yielded a 412-fold dynamic range and the octopine sensor led to 40% higher nitrogenase activity than the wild-type.

Discussion

Towards designing a bacterium that can deliver fixed nitrogen to a cereal crop, this work provides a side-by-side comparison of diverse species, natural nif clusters, and engineering strategies. The goal was to obtain inducible nitrogenase activity in a strain that can associate with cereals as an endophyte or epiphyte. To this end, ~100 strains involving the transfer of 10 natural nif clusters ranging in size from 10 kb to 64 kb to 16 diverse species of *Rhizobia*, *Azorhizobium*, Pseudomas, and *E. coli* were constructed. Different approaches were taken to make these nif clusters inducible, from bioinformatics and protein engineering to complete genetic reconstruction from the ground-up (refactoring). In addition to the highest activity, it is important that nitrogen fixation be robust to the addition of nitrogenous fertilizer (ammonia) and microaerobic environments. Two lead candidates have emerged from this effort. The most promising endophyte is a variant of *Azorhizobium* where nifA is knocked out of the genome and a nifA mutant and rpoN are complemented on a plasmid. For the epiphyte *P. protegens* Pf-5, the most versatile strain is based on the transfer of the *A. vinelandii* nif cluster and placement of nifA of *P. stutzeri* under inducible control. In both cases, nitrogenase activities were obtained that are nearly identical to wild-type *A. caulinodans* and *P. stutzeri*, respectively. Neither showed significant repression by ammonia and optimal activity was obtained in 1% oxygen. Based on these strains, it was demonstrated that nitrogenase can be placed under inducible control in response to cereal root exudates (arabinose, salicylic acid), phytohormones (naringenin) and putitive signaling molecules that could be released by genetically modified plants (nopaline and octopine).

Because R. sp. IRBG74 can fix nitrogen in a legume nodule and also associates with rice, significant effort was directed to engineering this strain to fix nitrogen when cereal-associated. The first attempt was simply complementing nifV, as this is absent in R. sp. IRBG74 and produces a metabolite provided by the plant, but this attempt was unsuccessful. Then, it was found that all of the initial nif clusters transferred, some of which have high activity in *P. protegens* Pf-5 and *E. coli*, are non-functional in R. sp. IRBG74, which led to trying clusters from alphaproteobacteria, one of which produced a very low level of activity that was dependent on the nif genes native to R. sp. IRBG74. The previously-published refactored gene clusters based on *Klebsiella* nif were attempted in R. sp. IRBG74 but these showed no activity. It was only after the construction of a new refactored cluster (v3.2) that activity was obtained under free-living conditions that was not dependent on the native nif genes. This allowed an increase in the expression levels, and an optimum was discovered beyond which activity was lost. This is the first time that nif activity has been engineered in a *Rhizobium* under free-living conditions that could otherwise not perform this function. This sets the foundation for further development and optimization of this strain.

The present disclosure encompasses different degrees of nif pathway re-engineering to promote heterologous transfer. The most ambitious is the complete refactoring of all the nif genes and regulation, where all regulatory genetic parts are replaced, genes are recoded, operons are reorganized, and transcription is performed by the orthogonal T7 RNAP. When this project was initiated, DNA synthesis was a novelty and a lack of DNA assembly methods made it difficult to make alternative designs. Further, the evaluation of performance relied on the overall nitrogenase activity, rather than an understanding of the underlying parts. As such, the first refactored pathway performed poorly. In subsequent studies, better part libraries and DNA assembly and automation platforms enabled the synthesis of many variants. Further, as the cost of RNA-seq declined, it was used to evaluate the performance of internal parts, such as promoters and terminators. This revealed that the first designs were effectively large single operons with little differential control over the transcription levels of individual genes. With these techniques allowed the optimization of the function of the refactored nif pathway and the discovery that many of the underlying genetic structure were not needed to achieve high activities.

In the present disclosure, ribosome profiling, a new technique that enables the measurement of translational parts (e.g., ribosome binding sites), was applied and expression levels were inferred. Further, nitrogenase activity and the function of underlying parts were assessed as the clusters were moved between species. Interestingly, the native *Klebsiella* nif cluster could be transferred and it performed similarly but the refactored cluster yielded widely varying expression levels in the different hosts, sometimes leading to a total loss in activity. This could be recovered by maintaining the native operon structure in the refactored cluster, implying that it was not due to the synthetic sensors, T7 RNAP, or promoters/terminators. This is one of the hypothesized functions of operons. Achieving this required maintenance of the codon usage and translational coupling of the native cluster. However, this does not mean that it will not be possible to also encode this function synthetically. There have been computational advances that enable the calculation of RBSs internal to upstream genes when encoded on an operon. If coupled with codon optimization algorithms, this would allow the design of de novo genetic parts that achieve a desired degree of translational coupling and expression level.

This work herein is the first step of a larger effort to build strains that can efficiently deliver fixed nitrogen to cereals. The present disclosure demonstrates the deregulation of nif clusters in *A. caulinodans* and *P. protegens* Pf-5, enabling them to be placed under the control of cereal root exudates. This derepresses the pathway in the presence of exogenous nitrogenous fertilizer—critical for the use of the bacterium as part of an integrated agricultural solution. Further, these organisms retain the ability to fix nitrogen in microaerobic environments, thus avoiding the need for a root nodule that enforces strict anaerobiosis. The complete deregulation of the nif pathway makes the bacterium non-competitive in the soil and lost quickly, thus limiting its impact to particular phases of the growth cycle. Thus, it is demonstrated that nitrogenase can be placed under the control of chemical root exudates. Fully realizing the goal of engineering microbial delivery to a cereal will require significant additional genetic engineering to maximize their ability to catabolize carbon sources from the plant and increase the flux of fixed nitrogen delivery by redirecting metabolism, introducing transporters, and the optimization of electron transfer. An intriguing possibility is to also genetically engineer the plant to produce orthogonal carbon sources, such as opines or less common sugars, and then placing the corresponding catabolism pathways into the bacterium.

EMBODIMENTS

1. A rhizobium that can fix nitrogen under aerobic free-living conditions, comprising a symbiotic rhizobium having an exogenous nif cluster, wherein the exogenous nif cluster confers nitrogen fixation capability on the symbiotic rhizobium under aerobic free-living conditions, and wherein the rhizobium is not *Azorhizobium caulinodans*.

2. The rhizobium of paragraph 1, wherein the exogenous nif cluster is from a free-living diazotroph.

3. The rhizobium of paragraph 1, wherein the exogenous nif cluster is from a symbiotic diazotroph.

4. The rhizobium of paragraph 1, wherein the exogenous nif cluster is from a photosynthetic Alphaproteobacteria.

5. The rhizobium of paragraph 1, wherein the exogenous nif cluster is from a Gammaproteobacteria.

6. The rhizobium of paragraph 1, wherein the exogenous nif cluster is from a cyanobacteria.

7. The rhizobium of paragraph 1, wherein the exogenous nif cluster is from a firmicutes.

8. The rhizobium of paragraph 1, wherein the exogenous nif cluster is from *Rhodobacter sphaeroides*.

9. The rhizobium of paragraph 1, wherein the exogenous nif cluster is from *Rhodopseudomonas palustris*.

10. The rhizobium of paragraph 1, wherein the exogenous nif cluster is an inducible refactored nif cluster.

11. The rhizobium of paragraph 10, wherein the inducible refactored nif cluster is an inducible refactored *Klebsiella* nif cluster.

12. The rhizobium of any one of the preceding paragraphs, wherein the rhizobium is IRBG74.

13. The rhizobium of any one of the preceding paragraphs, wherein the exogenous nif cluster comprises 6 nif genes.

14. The rhizobium of paragraph 13, wherein the 6 nif genes are nifHDK(T)Y, nifEN(X), nifJ, nifBQ, nifF, and nifUSVWZM.

15. The rhizobium of paragraphs 13 or 14, wherein each nif gene of the exogenous nif cluster is preceded by a T7 promoter.

16. The rhizobium of paragraph 15, wherein the T7 promoter is a wild-type promoter.

17. The rhizobium of any one of the preceding paragraphs, further comprising an endogenous nif cluster.

18. The rhizobium of any one of the preceding paragraphs, wherein the nif cluster has a nifV gene.

19. The rhizobium of paragraph 18, wherein the nifV gene is endogenous. 20. The rhizobium of any one of the preceding paragraphs, wherein the exogenous nif cluster further comprises a terminator.

21. The rhizobium of any one of paragraphs 15-20, wherein the T7 promoter has a terminator and wherein the terminator is downstream from the T7 promoter.

22. The rhizobium of paragraph 12, wherein the exogenous nif cluster is a refactored rhizobium IRBG74 nif cluster.

23. A plant growth promoting bacterium that can fix nitrogen under aerobic free-living conditions, comprising a bacterium having an exogenous nif cluster having at least one inducible promoter, wherein the exogenous nif cluster confers nitrogen fixation capability on the bacterium, under aerobic free-living conditions, and wherein the bacterium is not *Azorhizobium caulinodans*.

24. The plant growth promoting bacterium of paragraph 23, wherein the bacterium is a symbiotic bacterium.

25. The plant growth promoting bacterium of paragraph 23, wherein the bacterium is an endophyte.

26. The plant growth promoting bacterium of paragraph 25, wherein the endophyte is rhizobium IRBG74.

27. The plant growth promoting bacterium of paragraph 23, wherein the bacterium is an epiphyte.

28. The plant growth promoting bacterium of paragraph 27, wherein the epiphyte is pseudomonas protogens PF-5.

29. The plant growth promoting bacterium of any one of paragraphs 23-28, wherein the plant growth promoting bacterium is associated with a genetically modified cereal plant.

30. The plant growth promoting bacterium of paragraph 29, wherein the genetically modified cereal plant includes an exogenous gene encoding a chemical signal.

31. The plant growth promoting bacterium of paragraph 29, wherein the nitrogen fixation is under the control of the chemical signal.

32. The plant growth promoting bacterium of paragraphs 30 or 31, wherein the chemical signal is opine, phlorogluconol or rhizopene.

33. The rhizobium of any one of paragraphs 23-32, wherein the exogenous nif cluster comprises 6 nif genes.

34. The rhizobium of paragraph 33, wherein the 6 nif genes are nifHDK(T)Y, nifEN(X), nifJ, nifBQ, nifF, and nifUSVWZM.

35. The rhizobium of any one of paragraphs 23-34, wherein the inducible promoter is a T7 promoter.

36. The rhizobium of any one of paragraphs 23-34, wherein the inducible promoter is $P_{A1lacO1}$ promoter.

37. The rhizobium of any one of paragraphs 23-36, wherein the inducible promoter is activated by an agent selected from a group that includes IPTG, sodium salicylate, octapine, nopaline, the quorum signal 3OC6HSL, aTc, cuminic acid, DAPG, and salicylic acid.

38. The rhizobium of any one of paragraphs 23-37, wherein the exogenous nif cluster further comprises a terminator.

39. The rhizobium of any one of paragraphs 23-37, wherein the inducible promoter has a terminator and wherein the terminator is downstream from the inducible promoter.

40. An *Azorhizobium caulinodans* capable of inducible ammonium-independent nitrogen fixation in a cereal crop, comprising:

(i) a modified nif cluster, wherein an endogenous nifA gene is deleted or altered; and (ii) at least one operon comprising nifA and RNA polymerase sigma factor (RpoN), wherein the operon comprises a regulatory element including an inducible promoter.

41. The *Azorhizobium caulinodans* of claim 40, wherein the inducible promoter is $P_{A1lacO1}$ promoter.

42. The *Azorhizobium caulinodans* of paragraphs 40 or 41, wherein the inducible promoter is activated by an agent selected from IPTG, sodium salicylate, octapine, nopaline, the quorum signal 3OC6HSL, aTc, cuminic acid, DAPG, and salicylic acid.

43. The *Azorhizobium caulinodans* of any one of paragraphs 40-42, wherein the endogenous nifA gene is altered with at least one of the following substitutions:

(i) L94Q;

(ii) D95Q; and (iii) both L94Q and D95Q.

44. A method of engineering a rhizobium that can fix nitrogen under aerobic free-living conditions, comprising transferring an exogenous nif cluster to a symbiotic rhizobium, wherein the exogenous nif cluster confers nitrogen fixation capability on the symbiotic rhizobium, under aerobic free-living conditions, and wherein the rhizobium is not *Azorhizobium caulinodans*.

45. The method of paragraph 44, wherein the exogenous nif cluster comprises 6 nif genes.

46. The method of paragraph 45, wherein the 6 nif genes are nifHDK(T)Y, nifEN(X), nifJ, nifBQ, nifF and nifUSVWZM.

47. The method of paragraph 45 or 46, wherein each of the nif genes is preceded by a wild-type T7 promoter.

48. The method of any one of paragraphs 44-47, wherein the exogenous nif cluster is transferred to the rhizobium in a plasmid.

49. The method of any one of paragraphs 44-48, wherein the exogenous nif cluster further comprises a terminator.

50. The method of any one of paragraphs 47-49, wherein the wild-type T7 promoter has a terminator, and wherein the terminator is downstream from the wild-type T7 promoter.

51. The method of any one of paragraphs 44-50, wherein the endogenous NifL gene is deleted.

52. A method of producing nitrogen for consumption by a cereal plant, comprising providing a plant growth promoting bacterium that can fix nitrogen under aerobic free-living conditions in proximity of the cereal plant, wherein the plant growth promoting bacterium is a symbiotic bacterium having an exogenous nif cluster, wherein the exogenous nif cluster confers nitrogen fixation capability on the symbiotic bacterium, enabling nitrogen fixation under aerobic free-living conditions.

53. The method of paragraph 52, wherein the plant growth promoting bacterium is a rhizobium.

54. The method of paragraph 52, wherein the plant growth bacterium is the bacterium of any one of paragraphs 1-22 and 23-39.

55. The method of any one of paragraphs 52-54, wherein the cereal plant is a genetically modified cereal plant.

56. The method of paragraph 55, wherein the genetically modified cereal plant includes an exogenous gene encoding a chemical signal.

57. The method of paragraph 56, wherein the nitrogen fixation is under the control of the chemical signal.

58. The method of paragraph 56 or 57, wherein the chemical signal is opine, phlorogluconol or rhizopene.

59. The method of any one of paragraphs 52-55, wherein the nitrogen fixation is under the control of a chemical signal.

60. The method of paragraph 57 or 59, wherein the chemical signal is a root exudate, biocontrol agent or phytohormone.

61. The method of paragraph 60, wherein the root exudate is selected from the group consisting of sugars, hormones, flavonoids, and antimicrobials.

62. The method of paragraph 57 or 59, wherein the chemical signal is vanillate.

63. The method of paragraph 57 or 59, wherein the chemical signal is IPTG, aTc, cuminic acid, DAPG, and salicylic acid, 3,4-dihydroxybenzoic acid, 3OC6HSL or 3OC14HSL.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

ADDITIONAL TABLES

TABLE 7

Primers used for nif cluster cloning.

| Nif cluster | Forward primer (SEQ ID NOs: 8-64) | Reverse Primer (SEQ ID NOs: 65-121) | Genomic location | GenBank accession No. |
|---|---|---|---|---|
| Klebsiella oxytoca M5al | CGTAGGGCGCATTAATGCAGCTGGCACGACAGGTGAAT | GTGACGCTCGCGTATCAGGTTTG | 3,897,443-3,909,294 | CP020657.1 |
| | TCTAGACTGCTGGATACGCTGCTTAAG | ATCAGGCGCATATTTGAATGTAT | 3,909,255-3,920,878 | CP020657.1 |
| | GTCTACGCTGTTTGAGCTGCAAACCT | TTACTGCAGCGGCCGCTTCTAG<br>AGTGACCAAAAGCTTCCGCAACCC | | |
| Pseudomonas stutzeri A501 | GCCCGGAGAGCAAGCCCGTAGGGCGCCATTAATGCAGCTGG | ACTACCGCATCACTAGCAGGGCACG | 1,410,207-1,414,229 | NC_009434 |
| | CACGCAGGTGTTAGGTTGCCTGAATTCGGTGT | CACCGCGGACGAAATCGAAGTGAG | 1,419,757-1,424,637 | NC_009434 |
| | GGCTCACTTCGATTTCGTCCGCGGTGCGTCCCCTGCTAGT | TTGTCGACTCCCGGGGTCGAC | 1,424,588-1,429,971 | NC_009434 |
| | GATGCGTA | GGCTTTAACGGCATGTTCCGGGT | 1,429,922-1,434,417 | NC_009434 |
| | CGCCTGATTTCGCCTGATGAACAGG | GTAGTCCTCGTTGTGGCCGAACTC | 1,434,370-1,438,503 | NC_009434 |
| | TGACGCTGTTGACCACCGCC | AAAGCATCATCTCGGGTCGGGC | 1,438,454-1,442,613 | NC_009434 |
| | ATGGAAGTGCTGGCACCGGCTA | CGTCAGCGACAACGCCTCGA | 1,442,565-1,448,340 | NC_009434 |
| | CGCAACGGTTGGGGTAGGTTGG | CTATGAGCTGACTGAACCGCAGG | 1,448,291-1,459,252 | NC_009434 |
| | GACGTCCATCGCTTCGGCTTCGA | GAAAATACCGCATCAGGCGCATATTG | | |
| | CTGCGATCGACGCTGTCGAGCATCATCGCGGTTCA | TGAATGTATTTACTCGAGC | | |
| | | GCCGCTGGCGAATCTCCTTCCTCGGTTCG | | |
| Azotobacter vinelandii DJ | ATCCATTCTCAGGCTGTCTGTCTCGTCTCTACGTACGCG | GCCTTCGAACATGTGTCCCAG | 134,732-144,115 | NC_012560 |
| | GATCCCAGGCAACGTCTTCGTACTGCGGTACCGGGTTGCG | TCGAGTTCGAGCAGTTTCTCCAGC | 144,076-148,534 | NC_012560 |
| | GGGGCAGCCAGTGGAAAAGG | AGCGAACAATACCTGTGGCC | 148,500-152,895 | NC_012560 |
| | CTACGGCACGCCCTGGTTCGA | TGGCGCTTGCCCTTGTTCAA | 152,861-157,152 | NC_012560 |
| | GCTCGGAAAGTGCTGGAGAAAC | GCGCGGTGTAGAGTTCCGGGAGT | 157,101-162,181 | NC_012560 |
| | AAATCAGAACATTCATGGCCACAGG | TTAAACGGACAGAAGACGAGT | | |
| | TCTACCATGCGTGACTCTCGG | TTGCTCAGGGTCGGGTTGGC | 5,161,399-5,168,611 | NC_012560 |
| | CGTGCGGGC | | | |
| | ACTCGTCTTCTGTCCGTTTAAACTCCCGGAACTCTACCAC<br>CGC | | | |
| | CTTGGATAGACGAGGCACAGC | CATCATCCTCGGCCCCTTCA<br>GGTTGCAGGAGCCGGCTTG | 5,168,561-5,175,635 | NC_012560 |
| | GCCGGCTCCTGCAACCTGAAGGGGCCGAGGATGATG | GCAAGCCACTCCACTGACGAA | 995,860-1,000,698 | NC_012560 |
| Paenibacillus polymyxa WLY78 | GAATTGAGGATAAATGTCAGGGATTTCATG | ACAGGTTCCGCAGTTCACAAGC | 23,686-26,413 | AUV01.1 contig00089 |
| | CCAAGCATTTTGAGATCGCGGATG | GCTGATTTGTGATCGACAATATTCGG | 26,364-27,763 | AUV01.1 contig00089 |
| | CGGAGGTGCCGGTATGAGCGA | GAAAGCTACACGAAGCAAAGG | 27,714-29,113 | AUV01.1 contig00089 |
| | GAAGTTTGCAGCGAAAGAGGCG | CTTGAGAATCTGCCGGGGCGCCT | 29,064-30,463 | AUV01.1 contig00089 |
| | GGGATGATGCAGAATACATCCCG | ATCCACAAATCAACACCCTGCG | 30,414-31,813 | AUV01.1 contig00089 |
| | GGTGACCTGATGATGCAGAGGAGAG | AAAGCGTTCCAGTGCACGGTCAC | 31,764-34,402 | AUV01.1 contig00089 |

TABLE 7-continued

Primers used for nif cluster cloning.

| Nif cluster | Forward primer (SEQ ID NOs: 8-64) | Reverse Primer (SEQ ID NOs: 65-121) | Genomic location | GenBank accession No. |
|---|---|---|---|---|
| Cyanothece ATCC51142 | GGCCCGCGTTAGGTTGGCCTGAATTCGGTGTATCCCCC GGAGATACGTACCCGCCCTGTCAGGGGCG | GAGACTTTCCCCACCTTATTAT GCATGCAGATGTTATGGGAATTAACG | 1,931,343-1,929,132 | NC_010546.1 |
|  | GGGTTTTTTTGATAAGTCAAGCTATCAGAACCGATC | ACCTTGACAATCATTACACAGCG | 555,364-562,941 | NC_010546.1 |
|  | TAATTCCCATAACATCTGCATGCATAATAAGGTGGGGAAA GTCTCAGC | CAAATATAATGATCGACATTTTCACCAC CGTTAACTTTGTCGCAAAACTTCG | 562,897-570,603 | NC_010546.1 |
|  | AATGTATTTCTGATCGATGCGACG | ACCAAGGCGAATCTCCTCCTCCGTTCG | 570,558-577,494 | NC_010546.1 |
|  | GTTATCTGGCTGATGTTTGTGGTG GTCAAACTGTCTTGTTTAAAGCCG | CGATCACGCTACTCCGC CAATAAAAAAGCCCCGGAATGATCTTC CGGGGCCAGATTCAGTAACTGCTCAAG | 577,449-584,687 | NC_010546.1 |
| Azospirillum brasilense Sp7 | TTAAGGTCATGCAGCAGGAGAACTAAAGGCCCGCGTTAGG TTGGTAATAAAAAAGCCCCGGAATGATCTTCCGGGGCC | TGCGTCTTCTTCGGCATCGTCA TGAAATTGATTGCGGACGACG | 1,043,795-1,035,568 1,035,614-1,027,483 | CP012914 CP012914 |
|  | CTGCGCAAATACAACATCGAGATC | TTCAATAGTTAAGCAGATCGGCCTCG | 1,027,533-1,019,166 | CP012914 |
|  | GACGACTGAATAAGGATCGCGGAATG | CGGTGTTTACGAATAAATAATATTTCTACGAATAGAC | 1,019,211-1,010,628 | CP012914 |
|  | TATGTCACAGGCCCGACAAAGCG GATTGCTGGGTATCGCACACGAG CGAAGGAGTTCGCCCCAGTCTATTC | GCTCCAAAAGGAGCCTTTAATTGTATCGGTTTA TCAGCTTGCTTT GTTCCGCGGGTCTCGATACAACG | 1,010,677-1,003,838 | CP012914 |
| Rhodopseudomonas palustris CGA009 | AATACGATCGCATGTCCTAGGTAATACGACTCACTATAG GAGAGGTAATCAGTGGTGATTTGATGT | TCACTATAGGGGTCTTGCGGATCATCACTTTC GACGGTTCAGGTGGTCCGAAC | 5,215,514-5,207,699 5,207,743-5,201,639 |NC_005296.1 NC_005296.1 |
|  | CCAAGCAAAGGACCACCCTC AGCTTCGATATCATCCGCTGAT TTGTTCATGTCGGACCTAACCGA | GGTGAGAAATGATCATGATCGGCC CTCCAAAAGGAGCCTTTAATTGTATCGGTTTA TCAGCTTGCTTG ACGACAAGTGGAGAAGGATAG | 5,201,687-5,196,113 5,196,162-5,187,847 | NC_005296.1 NC_005296.1 |
| Rhodobacter shaeroides 2,4,1. | CAATACGATCGCATTCCTAGGTAATACGACTCACTATAG GGAGATGCATTTCACGCTTCGCATTC | TCCCATGGTCATGTCCTTTGCG GTGCGCTTTTCCACGAGAGC | 2,285,634-2,279,216 2,279,260-2,271,404 | NC_007493 NC_007493 |
|  | CCGCCTTCACCAGAGACACC ATCGAGAAGTTCTACGATGCCGT GCAAAAAAACCCCCTGA CAGGGCGGGTTTTTT TTTCAATTGGACCTGATGGCAGCAAG | AATTGCCCCGGCCCTGTCAGGGGCGGGGTTTTTTT TGCAGCGCCATTCCGTCTTC GCTCCAAAAGGAGCCTTTAATTGTATCGGTTTATC AGCTTGCTT GGAGAAAGCCTTGCGCGGCTAG | 2,271,450-2,264,419 245,956-252,936 | NC_007493 NC007494 |
| Azorhizobium caulinodans ORS571 | CTCGCATCCATTCTCAGGCTGTCTCGTCTCGTCTCTAG AGTCGGAGCTCTTGGGCCCTCTAAACGGGTCTTGAGGGGT | GCCCCCGAAGGTGATCTTCCGGGGGCTTTCTCAT GCGTTGA | 5,290,244-5,293,483 | NC_009937 |
|  | TTTTTGTTCTTGTTCTTGCACGCGAAGCTC ATAGGCAATACGATCGCATGTCCGTTTAAACTGATAAGGA CGGCACTGGCTGG CGATGCCGTCCAGCACCTC | CAGCCTTGAGATAGATCAAGTGC CTGATCCAGGCCTTCATCGG GACATGTTGTCTCTCTTGGAAC TTCTGGAATTGGTACCGAGTCAGTAACGTGCCACA GCCTCG | 1,183,854-1,175,614 1,175,653-1,170,712 1,179,751-1,162,529 | NC_009937 NC_009937 NC_009937 |
|  | CTGCCACGGTTCCAAGGTTC TAAAAAGCGGCTAACCACGC CGTTTTTTTACGTCTGCA | ATCAGGCGCATATTTGAATGTATTACTGCAG CGGCCCTACCTACTTGTGGGGT | 3,922,323-3,919,341 | NC_009937 |
|  | GTGTTGTCGAAGCTTGATGCGC CGCTGCTTAAGGTCATGCAGCAGGAGAACTAAAGGCCCGC TCTGCAAGGAATAGCGTC | CAGTTCCGGCTGGGGTTCAGCAGCCACC TGCAGTTAATTAAGGCGCTCCTTTCCTGATTCG GTCGTGTGTGAGATTGATCATGGCC | 3,930,607-3,934,260 3,934,220-3,937,923 | NC_009937 NC_009937 |
|  | CTATCGCCCACCTGACC CGTCAGAACGGCTCTGAGCCATCAGGAGGA | TGCATGTCCGTTCCTGCTG | 3,937,871-3,941,205 | NC_009937 |

TABLE 7-continued

Primers used for nif cluster cloning.

| Nif cluster | Forward primer (SEQ ID NOs: 8-64) | Reverse Primer (SEQ ID NOs: 65-121) | Genomic location | GenBank accession No. |
|---|---|---|---|---|
| | AGTAATATTGCGGATCGGCCAGCAGCGAGGAA | ACATGTCTTGAATTCCTTCGAACC | 3,941,164-3,959,444 | NC_009937 |
| | GGTGTCATTGGCAACGGTTCGAAG | TGCAATTGCGTTCGCTCCC | 3,959,405-3,962,598 | NC_009937 |
| | TCCCAAGAGCCCAACCGTTCCGGGAGCGAA | TGTCAGGGCAGGCAGGGCC | 3,962,559-3,966,562 | NC_009937 |
| Gluconacetobacter diazotrophicus PA1 | TTAAGGTCATGCAGCAGGAGAACTAAAGGCCCGCTTAGG | TCACCAGCCGTATCCGGAATATGTCAGGATCAT GACATCCC | 1,759,465-1,754,718 | CP001189 |
| | 5TTGGTAATAAAAAGCCCCCGGAATGATCTTCCGGGGGCC GATCGAGGAAATCGACGTG | ACGATTTCCATGCCCAGGTC | 1,754,739-1,746,565 | CP001189 |
| | ATATTCCGGATACGGCTGGTGAGGTGGA | CCTCCAGCACCTCTTCGATG | 1,746,608-1,738,322 | CP001189 |
| | CGCCACGTCGTCAATGCCTATAAC | GCTCCAAAAGGAGCCTTTAATTGTATCGGTTT ATCAGCTTGC | 1,738,366-1,730,601 | CP001189 |
| | TGACCACCGTGCAGAAGATCC | TTTGGGCAATACCTGAGACGTTTCA | | |

TABLE 8

Strains used in this study

| Name | Strain | Source | Description |
|---|---|---|---|
| MR1 | E. coli DH10-beta | NEB | Cat# C3019 |
| MR2 | E. coli K-12 MG1655 | Voigt lab | |
| MR3 | Klebsiella oxytoca M5al | Voigt lab | |
| MR4 | Pseudomonas stutzeri A1501 | Poole lab | |
| MR5 | Azotobacter vinelandii DJ | Peters lab | |
| MR6 | Pseudomonas protegens Pf-5 | ATCC | BAA-477 |
| MR7 | P. protegens Pf-5 controller ($P_{tac}$-T7RNAP) | This study | generated by pMR86 |
| MR8 | P. protegens Pf-5 controller v1 ($P_{tac}$-nifA) | This study | generated by pMR97 |
| MR9 | P. protegens Pf-5 controller v2 ($P_{tac}$-nifA v2) | This study | generated by pMR98 |
| MR10 | P. protegens Pf-5 controller v3 ($P_{tac}$-nifA v3) | This study | generated by pMR99 |
| MR11 | P. protegens Pf-5 controller v4 ($P_{BAD.10}$-nifA) | This study | generated by pMR100 |
| MR12 | P. protegens Pf-5 controller v5 ($P_{Fde}$-nifA) | This study | generated by pMR101 |
| MR13 | Rhizobium sp. IRBG74 | Áne lab | |
| MR14 | R. sp. IRBG74 ΔhsdR | This study | generated by pMR44 |
| MR15 | R. sp. IRBG74 ΔrecA | This study | generated by pMR47 |
| MR16 | R. sp. IRBG74 Δnif | This study | generated by pMR45-46. Two nif clusters (227,127-219,579 and 234,635-234,802) were removed. |
| MR17 | R. sp. IRBG74 ΔhsdR, recA | This study | |
| MR18 | R. sp. IRBG74 ΔhsdR, Δnif | This study | |
| MR19 | R. sp. IRBG74 ΔhsdR, recA Δnif | This study | |
| MR20 | R. sp. IRBG74 ΔhsdR Δnif ΔrecA::$P_{A1lacO1}$-T7RNAP v1 | This study | generated by pMR82 |
| MR21 | R. sp. IRBG74 ΔhsdR Δnif ΔrecA::$P_{A1lacO1}$-T7RNAP v2 | This study | generated by pMR83 |
| MR22 | R. sp. IRBG74 ΔhsdR Δnif ΔrecA::$P_{A1lacO1}$-T7RNAP v3 | This study | generated by pMR84 |
| MR23 | R. sp. IRBG74 ΔhsdR Δnif ΔrecA::$P_{Phl}$-T7RNAP | This study | generated by pMR85 |
| MR24 | Azorhizobium caulinodans ORS571 | Poole lab | |
| MR25 | Azorhizobium caulinodans ORS571 ΔnifA | This study | generated by pMR48 |
| MR26 | R. spp NGR234 | Poole lab | |
| MR27 | R. leguminosarum bv. Trifolii WSM1325 | Poole lab | |
| MR28 | Sinorhizobium medicae WSM419 | Poole lab | |
| MR29 | R. leguminosarum 8002 | Poole lab | |
| MR30 | Sinorhizobium meliloti WSM1022 | Poole lab | |
| MR31 | R. leguminosarum A34 | Poole lab | |
| MR32 | Sinorhizobium fredii HH103 | Poole lab | |
| MR33 | Sinorhizobium meliloti 1021 | Poole lab | |
| MR34 | R. tropici CIAT899 | Poole lab | |
| MR35 | R. leguminosarum viciae 3841 | Poole lab | |
| MR36 | R. etli CFN42 | Poole lab | |
| MR37 | Agrobacterium tumefaciens C58 | Poole lab | |

TABLE 9

Plasmids used in this study

| Name | Origin of replication | Marker | Description |
|---|---|---|---|
| pMR1 | pBBR1 | Kanamycin | Plasmid for nif cluster cloning |
| pMR2 | pRO1600, p15A | Gentamicin | Plasmid for nif cluster cloning |
| pMR3 | pBBR1 | Kanamycin | Native nif cluster of K. oxytoca M5al |
| pMR4 | pRO1600, p15A | Gentamicin | Native nif cluster of K. oxytoca M5al |
| pMR5 | pBBR1 | Kanamycin | Native nif cluster of P. stutzeri A1501 |
| pMR6 | pRO1600, p15A | Gentamicin | Native nif cluster of P. stutzeri A1501 |
| pMR7 | pBBR1 | Kanamycin | Native nif cluster of A. vinelandii DJ |
| pMR8 | pRO1600, p15A | Gentamicin | Native nif cluster of A. vinelandii DJ |
| pMR9 | pBBR1 | Gentamicin | Native nif cluster of Cyanothece ATCC51142 |
| pMR10 | pRO1600, p15A | Gentamicin | Native nif cluster of Cyanothece ATCC51142 |
| pMR11 | pBBR1 | Kanamycin | Native nif cluster of P. polymyxa WLY78 |
| pMR12 | pRO1600, ColE1 | Gentamicin | Native nif cluster of P. polymyxa WLY78 |
| pMR13 | pBBR1 | Kanamycin | Native nif cluster of A. brasilense Sp7 |
| pMR14 | pRO1600, ColE1 | Gentamicin | Native nif cluster of A. brasilense Sp7 |
| pMR15 | pBBR1 | Kanamycin | Native nif cluster of R. sphaeroides 2.4.1 |
| pMR16 | pRO1600, ColE1 | Gentamicin | Native nif cluster of R. sphaeroides 2.4.1 |
| pMR17 | pBBR1 | Kanamycin | Native nif cluster of R. palustris CGA009 |
| pMR18 | pRO1600, ColE1 | Gentamicin | Native nif cluster of R. palustris CGA009 |

TABLE 9-continued

Plasmids used in this study

| Name | Origin of replication | Marker | Description |
| --- | --- | --- | --- |
| pMR19 | pBBR1 | Kanamycin | Native nif cluster of *A. caulinodans* ORS571 (Part1 of 2) |
| pMR20 | RK2 | Tetracycline | Native nif cluster of *A. caulinodans* ORS571 (Part2 of 2) |
| pMR21 | pBBR1 | Kanamycin | Native nif cluster of *G. diazotrophicus* PA1 5 |
| pMR22 | pRO1600, ColE1 | Gentamicin | Native nif cluster of *G. diazotrophicus* PA1 5 |
| pMR23 | pRO1600, p15A | Gentamicin | nifLA (3,915,521-3,918,529) deletion in the nif cluster of *K. oxytoca* M5al |
| pMR24 | pRO1600, p15A | Gentamicin | nifLA (1,420,874-1,423,084) deletion in the nif cluster of *P. stutzeri* A1501 |
| pMR25 | pRO1600, p15A | Gentamicin | nifLA (5,168,709-5,171,731) deletion in the nif cluster of *A. vinelandii* DJ |
| pMR26 | pRO1600, p15A | Gentamicin | Native nif cluster of *A. vinelandii* DJ with the rnf2 operon |
| pMR27 | pRO1600, p15A | Gentamicin | rnf1 (5,168,156-5,162,716) operon deletion in the nif cluster of *A. vinelandii* DJ |
| pMR28 | pRO1600, p15A | Gentamicin | fix operon (995,860-1,000,698) deletion in the nif cluster of *A. vinelandii* DJ |
| pMR29 | pBBR1 | Kanamycin | Refactored nif cluster v2.1 |
| pMR30 | pRO1600, p15A | Gentamicin | Refactored nif cluster v2.1 |
| pMR31 | RK2 | Tetracycline | Refactored nif cluster v2.1 |
| pMR32 | ColE1 | Gentamicin | $P_{WT}$-nifHDKTY |
| pMR33 | ColE1 | Gentamicin | P2-nifENX |
| pMR34 | ColE1 | Gentamicin | P2-nifJ |
| pMR35 | ColE1 | Gentamicin | P2-nifBQ |
| pMR36 | ColE1 | Gentamicin | P2-nifF |
| pMR37 | ColE1 | Gentamicin | P2-nifUSVWZM |
| pMR38 | pBBR1 | Kanamycin | Refactored nif cluster v3.2 |
| pMR39 | pRO1600, p15A | Gentamicin | Refactored nif cluster v3.2 |
| pMR40 | pBBR1 | Kanamycin | LacI, $P_{A1lacO1}$-gfpmut3b |
| pMR41 | RSF1010 | Gentamicin | LacI, $P_{A1lacO1}$-gfpmut3b |
| pMR42 | RK2 | Tetracycline | LacI, $P_{tac}$-gfpmut3b |
| pMR43 | pRO1600, ColE1 | Gentamicin | LacI, $P_{A1lacO1}$-gfpmut3b |
| pMR44 | p15A | Gentamicin | Suicide plasmid for hsdR deletion in R. sp. IRBG74 |
| pMR45 | p15A | Gentamicin | Suicide plasmid for the nif cluster I (219,579-227,127) deletion in R. sp. IRBG74 |
| pMR46 | p15A | Gentamicin | Suicide plasmid for the nif cluster II (234,635-234,802) deletion in R. sp. IRBG74 |
| pMR47 | p15A | Gentamicin | Suicide plasmid for recA deletion in R. sp. IRBG74 |
| pMR48 | p15A | Gentamicin | Suicide plasmid for nifA deletion in *A. caulinodans* ORS571 |
| pMR49 | pBBR1 | Gentamicin | LacI, $P_{A1lacO1}$-nifV (*A. caulinodans* ORS571) |
| pMR50 | pBBR1 | Gentamicin | $P_{nifH}$(R. sp. IRBG7A)-sfgfp |
| pMR51 | pBBR1 | Gentamicin | NifA(R. sp. IRBG74), $P_{nifH}$(R. sp. IRBG74)-sfgfp |
| pMR52 | pBBR1 | Gentamicin | NifA(*K. oxytoca*), $P_{nifH}$(*K. oxytoca*)-sfgfp |
| pMR53 | pBBR1 | Gentamicin | NifA(R. sp. IRBG74), $P_{nifH}$(*K. oxytoca*)-sfgfp |
| pMR54 | pBBR1 | Gentamicin | NifA(*P. stutzeri*), $P_{nifH}$(*P. stutzeri*)-sfgfp |
| pMR55 | pBBR1 | Gentamicin | NifA(R. sp. IRBG74), $P_{nifH}$(*P. stutzeri*)-sfgfp |
| pMR56 | pBBR1 | Gentamicin | NifA(*A. caulinodans*), $P_{nifH}$(*A. caulinodans*)-sfgfp |
| pMR57 | pBBR1 | Gentamicin | NifA(R. sp. IRBG74), $P_{nifH}$(*A. caulinodans*)-sfgfp |
| pMR58 | pBBR1 | Kanamycin | Plasmid for consitutive promoter characterization. $P_{constitutive}$-gfpmut3b |
| pMR59 | pRO1600, p15A | Gentamicin | Plasmid for consitutive promoter characterization. $P_{constitutive}$-gfpmut3b |
| pMR60 | pBBR1 | Kanamycin | PT7(WT)-mCherry |
| pMR61 | pBBR1 | Kanamycin | PT7(P1)-mCherry |
| pMR62 | pBBR1 | Kanamycin | PT7(P2)-mCherry |
| pMR63 | pBBR1 | Kanamycin | PT7(P3)-mCherry |
| pMR64 | pBBR1 | Kanamycin | PT7(P4)-mCherry |
| pMR65 | pBBR1 | Kanamycin | PT7(P5)-mCherry |
| pMR66 | pRO1600, ColE1 | Gentamicin | AraE, AraC, $P_{BAD.10}$-gfpmut3b |
| pMR67 | pBBR1 | Kanamycin | Plasmid for terminator characterization. $P_{TT}$-gfpmut3b-mrfp1 |
| pMR68 | pRO1600, ColE1 | Gentamicin | Plasmid for terminator characterization. $P_{TT}$-gfpmut3b-mrfp1 |
| pMR69 | pBBR1 | Kanamycin | LuxR, $P_{Lux}$-gfpmut3b |
| pMR70 | pBBR1 | Kanamycin | TetR, $P_{Tet}$-gfpmut3b |
| pMR71 | pBBR1 | Kanamycin | CymR, $P_{Cym}$-gfpmut3b |
| pMR72 | pBBR1 | Kanamycin | PhlF, $P_{Phf}$-gfpmut3b |
| pMR73 | pBBR1 | Kanamycin | NahR, $P_{Sal}$-gfpmut3b |
| pMR74 | pRO1600, ColE1 | Gentamicin | PhlF, $P_{Phf}$-gfpmut3b |
| pMR75 | pRO1600, ColE1 | Gentamicin | TetR, $P_{Tet}$-gfpmut3b |
| pMR76 | pRO1600, ColE1 | Gentamicin | LuxR, $P_{Lux}$-gfpmut3b |

TABLE 9-continued

Plasmids used in this study

| Name | Origin of replication | Marker | Description |
|---|---|---|---|
| pMR77 | pRO1600, ColE1 | Gentamicin | CymR, $P_{Cym}$-gfpmut3b |
| pMR78 | pRO1600, ColE1 | Gentamicin | FdeR, $P_{Fde}$-gfpmut3b |
| pMR79 | pRO1600, ColE1 | Gentamicin | LacI(Q18M/A47V/F161Y), $P_{tac}$-gfpmut3b |
| pMR80 | pBBR1 | Kanamycin | $P_{T7}$-gfpmut3b |
| pMR81 | pRO1600, p15A | Gentamicin | $P_{T7}$-gfpmut3b |
| pMR82 | p15A | Gentamicin | Controller for R. sp. IRBG74, LacI, $P_{A1lacO1}$-T7RNAP (RBSr33 for T7RNAP) |
| pMR83 | p15A | Gentamicin | Controller for R. sp. IRBG74, LacI, $P_{A1lacO1}$-T7RNAP (RBSr32 for T7RNAP) |
| pMR84 | p15A | Gentamicin | Controller for R. sp. IRBG74, LacI, $P_{A1lacO1}$-T7RNAP (RBSr3 forT7RNAP) |
| pMR85 | p15A | Gentamicin | Controller for R. sp. IRBG74, PhlF, $P_{PhlF}$-T7RNAP (RBSr33 for T7RNAP) |
| pMR86 | ColE1 | Tetracycline | Controller for P. protegens Pf-5, LacI(Q18M/A47V/F161Y), $P_{tac}$-T7RNAP |
| pMR87 | pBBR1 | Kanamycin | NocR, $P_{noc}$-gfpmut3b |
| pMR88 | pBBR1 | Kanamycin | OccR, $P_{occ}$-gfpmut3b |
| pMR89 | pBBR1 | Gentamicin | NifA(A. vinelandii), $P_{nifH}$(A. vinelandii)-sfgfp |
| pMR90 | pBBR1 | Gentamicin | NifA(K. oxytoca), $P_{nifH}$(P. stutzeri)-sfgfp |
| pMR91 | pBBR1 | Gentamicin | NifA(K. oxytoca), $P_{nifH}$(A. vinelandii)-sfgfp |
| pMR92 | pRO1600, p15A | Gentamicin | NifA(K. oxytoca), $P_{nifH}$(K. oxytoca)-sfgfp |
| pMR93 | pRO1600, p15A | Gentamicin | NifA(A. vinelandii), $P_{nifH}$(A. vinelandii)-sfgfp |
| pMR94 | pRO1600, p15A | Gentamicin | NifA(P. stutzeri), $P_{nifH}$(P. stutzeri)-sfgfp |
| pMR95 | pRO1600, p15A | Gentamicin | NifA(P. stutzeri), $P_{nifH}$(K. oxytoca)-sfgfp |
| pMR96 | pRO1600, p15A | Gentamicin | NifA(P. stutzeri), $P_{nifH}$(A. vinelandii)-sfgfp |
| pMR97 | ColE1 | Tetracycline | NifA controller for P. protegens Pf-5, LacI(Q18M/A47V/F161Y), $P_{tac}$-nifA(P. stutzeri) (RBSp32 for NifA) |
| pMR98 | ColE1 | Tetracycline | NifA controller for P. protegens Pf-5, LacI(Q18M/A47V/F161Y), $P_{tac}$-nifA(P. stutzeri) (RBSp27 RBS for NifA) |
| pMR99 | ColE1 | Tetracycline | NifA controller for P. protegens Pf-5, LacI(Q18M/A47V/F161Y), $P_{tac}$-nifA(P. stutzeri) (RBSp33 for NifA) |
| pMR100 | ColE1 | Tetracycline | NifA controller for P. protegens Pf-5, AraE, AraC, $P_{BAD.10}$-nifA |
| pMR101 | ColE1 | Tetracycline | NifA controller for P. protegens Pf-5, FdeR, $P_{Fde}$-nifA |
| pMR102 | IncW | Spectinomycin | NifA controller plasmid for E. coli, LacI, $P_{A1lacO1}$-nifA(K. oxytoca) |
| pMR103 | pRO1600, p15A | Gentamicin | $P_{nifH}$(K. oxytoca)-sfgfp |
| pMR104 | pRO1600, p15A | Gentamicin | $P_{nifH}$(P. stutzeri)-sfgfp |
| pMR105 | pRO1600, p15A | Gentamicin | $P_{nifH}$(A. vinelandii)-sfgfp |
| pMR106 | pBBR1 | Gentamicin | $P_{nifH}$(K. oxytoca)-sfgfp |
| pMR107 | pBBR1 | Gentamicin | $P_{nifH}$(P. stutzeri)-sfgfp |
| pMR108 | pBBR1 | Gentamicin | $P_{nifH}$(A. vinelandii)-sfgfp |
| pMR109 | p15A | Kanamycin | $P_{BAD}$-T7RNAP |
| pMR110 | p15A | Kanamycin | $P_{Bet}$-T7RNAP |
| pMR111 | p15A | Kanamycin | $P_{Cin}$-T7RNAP |
| pMR112 | p15A | Kanamycin | $P_{Cym}$-T7RNAP |
| pMR113 | p15A | Kanamycin | $P_{Lux}$-T7RNAP |
| pMR114 | p15A | Kanamycin | $P_{Phl}$-T7RNAP |
| pMR115 | p15A | Kanamycin | $P_{3B5B}$-T7RNAP |
| pMR116 | p15A | Kanamycin | $P_{tac}$-T7RNAP |
| pMR117 | p15A | Kanamycin | $P_{Tet}$-T7RNAP |
| pMR118 | p15A | Kanamycin | $P_{Ttg}$-T7RNAP |
| pMR119 | p15A | Kanamycin | $P_{Van}$-T7RNAP |
| pMR120 | p15A | Kanamycin | $P_{Sal}$-T7RNAP |
| pMR121 | pBBR1 | Gentamicin | $P_{T7}$(P2)-gfpmut3b |
| pMR122 | pBBR1 | Gentamicin | NifA controller for A. caulinodans, LacI, $P_{A1lacO1}$-nifA-rpoN |
| pMR123 | pBBR1 | Gentamicin | NifA controller for A. caulinodans, LacI, $P_{A1lacO1}$-nifA(L94Q)-rpoN |
| pMR124 | pBBR1 | Gentamicin | NifA controller for A. caulinodans, LacI, $P_{A1lacO1}$-nifA(D95Q)-rpoN(A. caulinodans) |
| pMR125 | pBBR1 | Gentamicin | NifA controller for A. caulinodans, LacI, $P_{A1lacO1}$-nifA(L94Q/D95Q)-rpoN |
| pMR126 | pBBR1 | Gentamicin | NifA controller for A. caulinodans, NahR, $P_{Sal}$-nifA(L94Q/D95Q)-rpoN |
| pMR127 | pBBR1 | Gentamicin | NifA controller for A. caulinodans, NocR, $P_{noc}$-nifA(L94Q/D95Q)-rpoN |
| pMR128 | pBBR1 | Gentamicin | NifA controller for A. caulinodans, OccR, $P_{occ}$-nifA(L94Q/D95Q)-rpoN |
| pMR129 | pBBR1 | Gentamicin | $P_{nifH}$(A. caulinodans)-sfgfp |
| pMR130 | pBBR1 | Gentamicin | NifA, $P_{nifH}$(A. caulinodans)-sfgfp |
| pMR131 | pBBR1 | Gentamicin | NifA, RpoN, $P_{nifH}$(A. caulinodans)-sfgfp |
| pMR132 | pBBR1 | Gentamicin | LacI, $P_{A1lacO1}$-nifA(L94Q/D95Q)-rpoN, $P_{nifH}$-sfgfp |
| pMR133 | pBBR1 | Gentamicin | NahR, PSal-nifA(L94Q/D95Q)-rpoN, $P_{nifH}$-sfgfp |

TABLE 9-continued

Plasmids used in this study

| Name | Origin of replication | Marker | Description |
| --- | --- | --- | --- |
| pMR134 | pBBR1 | Gentamicin | NocR, Pnoc-nifA(L94Q/D95Q)-rpoN, $P_{nifH}$-sfgfp |
| pMR135 | pBBR1 | Gentamicin | OccR, Pocc-nifA(L94Q/D95Q)-rpoN, $P_{nifH}$-sfgfp |
| pMR136 | pBBR1 | Gentamicin | Refactored nif cluster v2.1 |

TABLE 10

Genetic part sequences used in this study

| Name | Genetic part | DNA sequence (SEQ ID Nos: 122-225) |
|---|---|---|
| P_AllacO1 | Promoter[6] | AGAGTGTTGACTTGTGAGCGGATAACAATGATACTTAGATTCAATTGTGAGCGGATAACAATTTCACACA |
| T7 RNAP | Gene | ATGAACACGATTAACATCGCTAAGAACGACTTCTCTGACATCGAACTGGCTGCTATCCCGTTCAACACTCTGGCTGACCATTACGTGAGCG<br>TTTAGCTCGGAACAGTTGGCCCTTGAGCATGAGTCTTACGAGCATGATGTTACGAGATGGGTGAAGCACCTTCCGCAAGATGTTTGAGCGTCAACTTAAAGCTG<br>GTCAGGTTGCGGATAACCGTGCCGCCAAGCCTCTCAGTTCCTCCTAAGATGATTGCACGCATCAACGACTGGTTTGAGGAAGTG<br>AAAGCTAAGCGCGGCAAGCGCCCGACAGCCTTCCAGTTCCTCCAGAAGAAATCAAGCCGGAAGATCTAGCGTACTACCATTAAGACCACTCT<br>GGCTTGCCTAACCAGTGCTGACAATACAACCGTTCAGGCTGTAGCAACGACTCAACAAGCGCTAGGGCACGCCAATGCCCATTGAGGACGAGCTCGCTTCGTCGTA<br>TCCGTGACCCTTGAAGCTAAGCACTTCAAGAAACACTTGTGAGGAACACTTGTGAGACAGCGCGTAGGGCACGCTACACAAGGAAGACTCTATTCATGTAGGATACG<br>GTTGTCGAGGCTGACATGCTCATTGAGTCAGCCGAAATGGTTAGCTTACCACCCGGAAGCCGTGGCTTCCAGCATATGGCGGTAGTAGGCTCAGACTATCGAAC<br>TCGCATCGAGATGTCCATTAGTGAGCGTGTCCACCGTGCAACCCGTGCAGGTGCGCTGCGTCTCCTTGCGCTGGCATCTCTGCGCGTCCAACCTTGCCGTAGTTCTCCAAG<br>CCGTGGACTGGCATTACTGGTGTGGCTATTGGGCTTAACAAAGACGATTAACATTGCGCAAAACACCGCATGGAAAATCAACAAGAAAGTCTAGCGGTCG<br>CCAAGTAATCACCAAGTGAAGACATTGTCCGCTGGAAGGCAATGGCTGAGCGTGAAGAACATCGCCGATGAAGCGAAGAACATCGAC<br>ATGAATCCTGAGCGCTCCACCGCTGGAAGTTTGCTAACCATAAGGACGCTTACCGTGCGGCGGAAAGGCTCGGCGTGTTTACGCTGCTG<br>GTTCATGCTTGAGCAAGCCAATAAGTTGCTAACCATAAGGACTGCTTACCGTCGGCGAAAGGTAAACCAATCGGTAAGGAAGGTTACTACTGGCTG<br>AAAATCCACGGGTCCAAACTGTGCGGTGCACAGTTCCGACAAGTTCGCTTCCCTGACCCAAGTTCATTGAGGAAAACCACGAGACATCATGGC<br>TTGCGCTAAGTCTCCACTGGAGAACACTTGGTGGGCTGAGCAAGATTCCGTTCTGCTTCCTGGCATCCAGCACTTCTCCGCATGCTCCGAGAT<br>AGCACCACGGCCTGAGCTATAACTGCTCCCTTCCGTGGCGTTTGACGGGTCTTGCTCGGACATCTTCAGGGATTGTCTAAGAAAGTCAACGAGATTCTACA<br>GAGTAGGTGGTCGCGCGGTTAACTTGCTTCTGTAGGAAACCGTTCAGGACATCTACGGGATTGTTGCTAAGAAAGTCAACGAGATTCTACA<br>AGCAGACCCAATCAATGGACCGATAACGAAGTAGTTACCGTCGACCGATGAGAACATCTGTGACTGGCTTGACATGAACAAGCAGCCACTA<br>AGGCACTGCCTGGCTGCAATGGCTGGTTATGCGCCTTACGGCTTACTGCAGTGACTAAGCGTTACGCTGATCATGAACCGTTCAGGGTCCAAAGATTC<br>GGCTTCCGTCAACAAGTGCTGAAGACATCCACAGCCAGCTATTGATTCCGCAGGGTCTGATGTTCACTGCCAAGCCGGATCCAGGCTGCTGG<br>ATACATGGCTAAGCTGATTGGAATCTGAGCGTGACGGTGGTACTGCTCCCAAGCGTTGCGTTGAAGCAATGAACTGGCTTAAGTCTGCTTCCTGGTGG<br>TGGCTGTCGAGGTCAAAGATAAGAAGACTGGAAGAGATTCTGTCGAACCTCAGATGTTCCTGTCAGTTCCGTTACAGCCTCATTACACCAACAAAGATAG<br>CAGGAATACAAGAGCCTATTCAGACGCCTTACGCCTAAGACATCCGGTATCCTCCTAACTTGTACAGACCGTAGCCACCTTCGTAAGACTGTAGTGTGGG<br>CGAGATTGATGCACAAACAGGAGTCGGATATCGCTCCACTGATCAGCTCGATTCACGACTCCTTCGGATGCATCGATCACTCCTTCGGTATGCGCTGCGAACCCTGTTCAAAGCAGTG<br>CACCAGAGGATGCGGAATCGAATCTTTGCACTGATCGAGTCTTGTGATGATACTTACGACCAGTTCTACGACCAGTTGCACGAGTTCAATTGGA<br>CAAAATGCCAGCACTTCCGGCTAAAGGTAACTTGAACCTCCGACATCTTAGAGTCGGACTTCGCGTTCGCGTAA |
| P_lacIq | Promoter[7] | CGAATGGTGCAAAACCTTTCGCGGTATGGCATGATAGCGCCCGGAAGAGAG |
| rpoN of A. caulinodans | Gene | ATGGCGATGAGCCCAAAGATGAGTTCCGCCAGAGCCAGTTCTCGGTGATGACGCCCAGTCTGATGCAGGCCATCAAGCTGCTCAGCTCTC<br>CAATCTCGAACTGGTCGCCTATGTGGAGGCCGAGCTCGAACCGCAATCCGCTGCTGGAGGCGCAGCCCAGACGCACGATC<br>CGCCGAACCCGCAGGAAGAGGCACCGAACCGGACTCTCGGCAACGCAATCCGCGCCGGTGTCCGGCGACTGATGGAAAGCGACATGGGCGTGAGCGC<br>GAGCCATCGAGATCCCGAGATCCTGAGCGGACCGAGATCTCTTCCGCGATGATGCGCGAGCGCATCGGCGCGGGCAGCGGCAGCGG<br>CTCGTCCATCGAATGGGCACGCCTGCGCCGACCCGGGCGACCGGCCGACCCGGCGAGGACTACAATCCGGCAGAAGCCTTCGCTGCCGAGAACGACGCTGGCCGACCATC<br>TGGAAGCCCAGCTCTCCGTGGCCGTGCTCGGAGCCGATCGGCGCGAGCAACTGGGCGCCCACCCAGCTGCCGCGACGCTGCGATCTCAGAGAGCTTCGACCGGT<br>TCCGGCGACCTCGGCATGCCGCGCGTCAGCGAATCGCTTGGCCTGCAGCTGCGAATCGGTGCTCGTGCCGCGACGTGCGCGATCCCGATGCAGGGCCGTCGACA<br>GGGCCTCGGCGCACGGGTCCTGCAGCGAATCCGCTCGGCGGACGCCGTCAATGCCGACGAAGGATCGCGGAAGACCTCGCGGACATGATCGCCGAGATC<br>ATCTGGAACTCCTCCGCCCGCTCGATCGAAGCCGGCTCCGCCTATGCGGCGGCCGATCGTGCCCCACGCGCTCCGCCGAGAACCTGCGGGTCGCGGAGGCTCCACGG<br>CAGCTCGGATCGCGGAACTGAATTCCGAGCGCGGCCCTTGCTGTGTGAACCAGATCGCTGTCGCAAGCACGCGGGGCCTGGCCAAGGGCGGCGCCGCTCCG<br>CCGAGGAAAAGACCTTCTCCGCGACTGCCTCGCAGGACGCGCTTCCGTGCCACCGGGCTGCGGGCTCGACCGGTCGACCTGCGACCAGCGCCGGCTCCACCATCCTCAAGGTG<br>GCGAGCGAGATCGTGCGCCAGCCAGGACGCCTTCCTGTGCACCGGATCCGGCACCTGCGCCCCCGAACCTGCCACGGTGCGCGGATGCCAT |

TABLE 10-continued

Genetic part sequences used in this study

| Name | Genetic part | DNA sequence (SEQ ID Nos: 122-225) |
|---|---|---|
| | | CGGCATGCACGAATCCACCGTTCTCGCGGTGACCTGCAGTTCGAACAAGTACATCTCCACCCCGCGCGGGTGCTGGAGATGAAGTTCTTCTCTCCT<br>CCTCCATCGCTTCCTCGGGTGGTGGCGGAGGCCCATGCGAGGCCTGTGGCAGGCCGCGCCACCGCATCGGAGGCCGCATGCGAGAGTGCGGAC<br>GACGTGCTGTCCGACGACACGCTGGTGCGAGAAGCTGAAGGACAGGACGATATCCCCGCAGCGATGATATCCGCGAAATATCGCGAGAGCAT<br>GAACATCCCGCTCCGTCCAGCGCCGCCGCGAAAAGCAGGCCCTGCGCAGCGACGCCCTGCAGCCGCGACGCCGGCCGCCCGGCTGA |
| laci | Gene | GTGAAACCAGTAACGTTATACGATGTCGCAGAGTATGCCGGTGTCTCTTATCAGACCGTTTCCCGCGTGGTGAACCAGGCCAGCCACGTTTC<br>TGCGAAAACTGCGGGAAAAAGTGGAAGCGGCAGTGGCGGATGTTGAATTACATTCCCGACTGGCGCGCAAAACAGTCGT<br>TGCTGATTGGCGTTGCCACCTCCAGTCTGGCCCTCACGCGCGGCGAGCCTGGCGCAACCGAACCCTCCGCCAACCGCGTCAGTGGGCTGAT<br>AGCCTGGTGTCGATGGTAGAACGAAGCGGCGTCATTGCTGTGAAGCTGCTGCACTAATGTTCCGGCGTTATTTCTTGATGTCTCTGACCAGA<br>CATTAACTATCCGCTGGATGACCAGGATGCCATTGCTGTGGAAGTGCCCCTGCCATTGCCCCTCTGGAGCACAATGTCAGCAAACCGCTG<br>CACCCATCAACAGTATTATTTTCTCCCATGAAGACGGTACGCGACTGGGCGTGGAGCATCTGGTCGCATTGGGTCACCAGCAAATCGCGCTG<br>TTAGCGGCGCATTAAGTTCTGTCTCGGCGCGTCTGGCTGGCTGGCATAAATATCTCACTCGCAATCAAATTCAGCCGATAGCGGA<br>ACGGAAGGCGACTGGAGTGCCATGTCCGGTTTTCAACAAACCATGCAAATGCTGAATGAGGGCATCGTTCCCACTGCGATGCTGGTTGCCA<br>ACGATCAGATGCCGTCATGTTATCCCGGCGCAATGCCGGCATTATCCGAGTCCGGGCTGGTGCCAATATCTCGGTAGTGGATACGACGATACC<br>GAAGACAGCTCATGTTATATCCCGTTGTCCGTCCGGATTTTCGCTCGCGAAACAGCGATTTTCGCGCTGGACGGCTTGCTGCAACT<br>CTTCAGGGCTGCTCTCGGCGTTGCCGAAGGCGTAACCTCTCATTAATGCCAGTCAGCTGGACGACGGGCATCCGGGTGCCCCAATACGCAAACCGCCT<br>CTCCCCGCGGGTTGGCCGATTCATTAATGCAGCTGGCACGACAGGTTTCCCGACTGGAAAGCGGGCAGTGA |
| gfpmut3b | Gene | ATGAGTAAAGGAGAAGAACTTTTCACTGGAGTTGTCCCAATTCTTGTTGAATTAGATGGTGATGTTAATGGGCACAAATTTTCTGTCAGTGG<br>AGAGGGTGAAGGTGATGCAACATACGGAAAACTTACCCTTAAATTTATTTGCACTACTGGAAAACTACCTGTTCCATGGCCAACACTTGTCA<br>CTACTTTCGGTTATGGTGTTCAATGCTTTGCGAGATACCCAGATCATATGAAACAGCATGACTTTTTCAAGAGTGCCATGCCCGAAGGTTAT<br>GTACAGGAAAGAACTATATTTTTCAAAGATGACGGGAACTACAAGACGTGCTGAAGTCAAGTTTGAAGGTGATACCCTTGTTAATAGAAT<br>CGAGTTAAAAGGTATTGATTTTAAAGAAGATGGAAACATTCTTGGACACAAATTGGAATACAACTATAACTCACACAATGTATACATCATGG<br>CAGACAAACAAAAGAATGGAATCAAAGTTAACTTCAAATTAGACACAACATTGAAGATGGAAGCGTTCAACTAGCAGACCATTATCAACAA<br>AATACTCCAATTGGCGATGGCCCTGTCCTTTTACCAGACAACCATTACCTGTCCACACAATCTGCCCTTTCGAAAGATCCCAACGAAAAGAG<br>AGACCACATGGTCCTTCTTGAGTTTGTAACAGCTGCTGGGATTACACATGGCATGATGAACTATACAAATAG |
| sfgfp | Gene | ATGCGTAAAGGCGAAGAGCTGTTCACTGGTGTCGTCCCTATTCTGGTGGAACTGGATGGTGATGTAAACGGTCATAAGTTTTCCGTCGTGG<br>CGAGGGTGAAGGTGACGCAACTAATGGTAAACTGACGCTGAAGTTCATCTGTACTACTGGTAAACTGCCTGTGCCATGGCCAACACTTGTCA<br>CTACTCTGACTTACGGTGTTCAATGCTTTTCCCGTTATCCGGACCATATGAAGCAGCATGACTTCTTCAAGTCCGCCATGCCGGAAGGCTATGTGCAGGGAGCGCACCACTGAAGGCTAAACCGCAT<br>GTGCAGGAACGCACGATTTCCTTTAAGGATGACGGCACGTACAAGACGGCGAAATTGAAGGTAATACATTTTTACACCGACATGACACCG<br>TGAGCTGAAGAACGGCATTAAGCTGGAATATAACTAATACTACGGACGCCAATATCCTCGGCCATAAGCTGGAATACAATTTTAACAGCAGCA<br>CCGATAAACAAAAAATCGGTGATGGTCCTGTTCTGCTGCCAGACAATCACTACCTGTCCACACAATCTGCCCTGTCTAAAGATCCGAACGAGAAACG<br>CGATCATATGGTTCTGCTGGAGTTTGTAACCGCTGCTGGGATTACACATGGCATGGATGAACTGTACAAATGA |
| mrfp1 | Gene | ATGGCTTCCTCCGAAGACGTTATCAAAGAGTTCATGCGTTTCAAAGTTCGTATGGAAGGTTCCGTTAACGGTCACGAGTTCGAAATCGAAGG<br>TGAAGGTGAAGGTCGTCCGTACGAAGGGCACAACACCGTAAACTGAAAGTTACCAAAGGTGGTCCGCTGCCGTTCGCTTGGGACATCCTGT<br>CCCCGCAGTTCCAGTACGGTTCCAAAGCTTATGTTAAACACCCGGCTGACATCCCTGACTACCTGAAACTGTCCTTCCCGGAAGGTTTCAA<br>ATGGGAACGTGTTATGAACTTCGAAGACGGTGGTGTTGTTACCGTTACCCAGGACTCCTCCCTGCAAGACGGTGAGTTCATCTACAAAGTTAA<br>ATTGCGTGGTACTAACTTCCCGTCCGACGGTCCGGTAATGCAGAAGAAAACCATGGGTTGGGAAGCTTCCACCGAACGTATGTACCCGGAAG<br>ACGGTGCTCTGAAAGGTGAAATCAAAATGCGTCTGAAACTGAAAGACGGTGGTCACTACGACGCTGAAGTTAAAACCACCTACATGGCTAAA<br>AAACCGGTTCAGCTGCCGGGTGCCTACAAGACCGACATCAAGCTGGACATCACCTCCCACAACGAAGACTACACCATCGTTGAACAGTATGAGA<br>ACGTGCTGAAGGTCGTTCACTCCACCGGTGCTTAA |
| mCherry | Gene | ATGGTTTCGAAGGGCGAGGAGGATAACATGGCCATCATCAAGGAGTTCATGCGCTTCAAGGTGCACATGGAGGGCTCCGTGAACGGCCACGA<br>GTTCGAGATCGAGGGCGAGGGCGAGGCGCCTACGAGGGCACCCAGACCGCCAAGCTGAAGGTGACCAAGGGTGGCCCCCTGCCCTTCG<br>CCTGGGACATCCTGTCCCCTCAGTTCATGTACGGCTCCAAGGCTACGTGAAGCACCCCGCCGACATCCCCGACTACTTGAAGCTGTCCTTC<br>CCCGAGGGCTTCAAGTGGGAGCGCGTGATGAACTTCGAGGACGGCGGCGTGGTGACCGTGACCCAGGACTCCTCCCTGCAGGACGGCGAGTT |

TABLE 10-continued

Genetic part sequences used in this study

| Name | Genetic part | DNA sequence (SEQ ID Nos: 122-225) |
|---|---|---|
| | | CATCTACAAGGTGAAGCTGCGCGGCACCAACTTCCCCTCCGACGGCCCCGTAATGCAGAAGAGACCATGGGCTGGGAGGCCTCCTCCGAGC |
| | | GGATGTACCCCGAGGACGGCGCCTGAAGGCGCAGATCAAGCAGAGAGCGTGAAGCTGAAGCTGAAGGACGGCGGCCACTACGACGCTGAGGTCAAGACC |
| | | ACCTACAAGGCCAAGAAGCCCGTGCAGCTGCCCGGCTACTACTACGTGGACATCAAGTTGGACATCACCTCCCACAACGAGGACTACACCAT |
| | | CGTGGAACAGTACGAACGCGCCGAGGGCCGCCACTCCACCGGCGGCATGGACGAGCTGTACAAGTAA |
| $P_{WT}$ | Promoter[8] | TAATACGACTCACTATAGGGAGA |
| $P_1$ | Promoter[8] | TAATACGACTCACTACAGGCAGA |
| $P_2$ | Promoter[8] | TAATACGACTCACTAGAGAGAGA |
| $P_3$ | Promoter[8] | TAATACGACTCACTAATGGGAGA |
| $P_4$ | Promoter[8] | TAATACGACTCACTAAAGGGAGA |
| $P_5$ | Promoter[8] | TAATACGACTCACTATAGGTAGA |
| $P_6$ | Promoter[8] | TAATACGACTCACTATAGGTAGA |
| nifV of A. caulinodans | Gene | GTGTTCCGTGGGAGGCCTGCCATGCTCGCCAAGACACCCGCGCTTCAGCGACGGCGTTCCTGAACGACACCACGCTGCG |
| | | CGACGGCGGAGCAGGCGGCGGTGTCGCTTCACCCGCAAGGAGAGATCGAGATCGCGCCCCTTGCCGCCGGTGTCCGGAGATCG |
| | | AGGCGGGAACGCGCCGCCATGGCGACGAAGAGTGGAAACATCCGCTTCATGTCTCGTGAACCTCTCGCGACGCGCGTCATGGCCTGGTGC |
| | | CGCATGCGGAGGACGACCTGATGCGGCCGTCCGCCGGCGTCGGCGACTGGCCTGTGACATGGTGGCGGCGGTGACATGGTGGCGGCTTTGAGGTGCGGTAGGG |
| | | CAAGCTCGGCAAGGATCGCGCTGGGCGGTCCGATTTCTCGCCGTGTCTGCGGAGGTGGTGACATCGGCGAAGGCGGCGCACCACGAGCTGAGTTCACGCCATGA |
| | | GCGAGGATTCCTCGCGGCCGATCCCGATTTCTCGGCACCTATGCATTGGTGCGCGGCTGGGCGGCCACCACAGATCGAGTTGAGTTCACGCCATGA |
| | | CGATCTCGGCCTTGCCACCGCCAATACGCTGAGGAAGTGGCCATCGCCCTCCGCCAGACGGCGGGCGGCCATCGCTCCGCCGCTGAAGCCCTG |
| | | CGGGCAATGCCCGCTGAGGAAGTGGCCATCGCCCTCCGCCAGACGGCGGGCGGCCATCGCTCCGCCGCTGAAGCCCTG |
| | | GCCGAACTAGTGTCGCGCCCTGCTCAAGGACCGGGCACCTATGCAGCTCTGAATCGGACTGTTCGGCGTGCCACACGGTGCTCGGAAAGCATT |
| | | CCGGTCTTGCGGCGGTGAGAAGGCGCTGGCGCAAGGAGGCCATCACCGGATGCGGTGCCCCATTCTCGACCGGGTGCGGGCT |
| | | TTTGCTGTCGCCACCAAGGAGAATGTTTCCCGGACGACACGCTTCCGGCCTTCTACCGACTAGAGACAGCTCGATCAGTGCTCCGCTGCTCCGCGG |
| | | GGCCGCCGTGGAAGGCGCAATCTGA |
| $P_{nifH}$ of K. oxytoca | Promoter | TGTTGCCTTCAAGCACACGCCTGTGCCAGCTCGCCGATGACAGAAGAGTTAGCGCCGAATTCAACGCGTTATGAAGAGAGTCGCCGCCAGCGCG |
| | | CCAAGAGATTGCTGGAATAAGACACAGGGGGCAACAAGCTGTTGAACAGGCGACCAAGTGTTCACCGTGCACCTGGCCGCGCCAATTGTTCT |
| | | GTTTCCACCATTTGGTCTGCCTTATTGCGCGTTTTGTTTTACCTCCTCGCGCGACAAATAACTTCATAAAAATCATAAGAATACAT |
| | | AAACAGGCCACGCTGGTATGTTCCCTATTCTCGCTGCAACA |
| $P_{nifH}$ of P. stutzeri | Promoter | TGTCATGTTCGCAACAGTTGCCGAAAGTGTGGAAAACCGGCTGGCCCGGCGATCTTTTTGTCGCCATTGCAACAGTCAGGCCTGTCGG |
| | | TTGTTAACTATCGAACCGCCGAAGGGATGTTGCTTAGTAATTTAATAATATTCTAATTAAAACAAGTGCTTAGATTATTTTTAGAAAACGCTGCACA |
| | | AAGGCTGCTATTGCCCTGTTGCGCAGGCTTGTCGCAGGCTTGTCGCCTATAGCCCAC |
| $P_{nifH}$ of A. vinelandii | Promoter | TGTCATGTTTAAACAGGGGCCGGACCAGGATGTGACGCTCGATGGGATGCTCGGGCCATTGTTCGGTTGAGCAATTACAACAGTCGG |
| | | AGTAGGGGGATTGTAGGGGATTGTGTATCAGACACCCCTCGCAGCTCCGTCGATGGATTAATTCATTTAAAATCAAATCTTTATTT |
| | | ATGTGTTGCGGGTGCTGGCACAGAGCTGCATTACCTTTGGTGCGCGAGTTGTTCGGGCTTACGGCCGAAC |

TABLE 10-continued

Genetic part sequences used in this study

| Name | Genetic part | DNA sequence (SEQ ID Nos: 122-225) |
|---|---|---|
| P*nifH* of *R.* sp. TRBG74 | Promoter | TTGACAAAGCCTCCGAGAGAGGCCCCCTAACCCTCCAGCCCTGATCGGCAGTATCATCTTGCGAATCTTGTCGATAGGCAAC GCTATACGACAAACGCTGGTTACAATTGCGGTCCGCGACAAGAATTGCTTGTCGGGTGCTCTATTTGAGCTAGTAGCTAGA AATCAGGAAGACAAAACTCTATTCGGTCTACCCGACGAGTTGGCACGGGTTCTTGTAACCATCCTTGCCAGGCGCGAAAGCCACCGGCAAT AATTCATGTTGCGGCAAC |
| P*nifH* Of *A. caulinodans* | Promoter | TGTCGCGTTTGAAACACGGGCTTTTGAAACCCTGCTTTCGATTCTGCAATGCACTGATTTTACTTGATTAATTCGACCACGACCACTGCACA CCCGTTGCAAAAACCCCTTGGTGCAGGCGACGAGGGTTGCCGGTCTCGGTTCGCGGATCTCCTGCGGATCCCCGGCTACCGACCCGCTCTCCGAAAAGT CCGGTCCCGATCCAGTTCGGCGGGGCCACAC |
| nifA of *K. oxytoca* | Gene | ATGATCCATAAATCGATTCGGACACCACCGTCAGACGTTTCGATCTCTCCAGCAGTTCGATCTCTGAG TCGCGCCACCGAAGCGAGCAAAACCCTGCAGGAGGTTCTGAGCGTGCTACATAACGATGCCTTTATGCAGCACGGATGATTTGCCTGTACG ACAGCCAGCAGGAGATCCTGACGGAGAGACCTGCGAAGCGCTGCAGAACGGAGATCAGACGTCGCCGGCAGTACGCAAATTCGCTACGGCCGGGG GAAGGATTAGTCGGTCGGTCTGGCGGCAGGGCCAGTCGCTGCCGCCGACCAGCGTTTCTTCGATCGTCTGAGCCT GTACGACTATGACCTGCCGTTTATGCCGCGTTCGGTGCAGGGGCCCCACTCCGGCCCCATCGGCGCTACGGCGGCAGCCGATGGCGTC AGGAAGAGCGGCTGCCCCGACTCTTCTGAAACCGTCTGAAATCGATCCCGAGACGATTCGCCTGATGATCTCCCAACTCC GCGCGGCAGGCCCGATGCGGCAGCAGAGCCCAGAATAGAGCGCCGTACCCCTTCGGCGCGGTTTCGGCCTGGGCAGAAATATGGTCGGTAA AGCCCGGCATGCGGCAGATTATGGATATTATTCGTCAGGGTTTCCCGGTGCTGTGTACGGCGGGAGAGCGGCACGGGA AAGAGCTCATCGCCAACGCCATCCAGAACTAATCTCCGCGCGCGCCTTGTCAAATTTAACTGCGCGGCGCTGCCGGACAACCTG CTGGAGAGCGAGCTGTTTGGTCATGAGAAAGGCGCGTTTACCGGCCGTAAGGCCCCTTTGAGCTTGGCGACGGCCGTCGGCG CTTATTCCTCGATGAGATCGGCGAAACCCTGCGGTCAACGTGCCATTATCGCGGCGACCAACCGCCATCTGGAAGAGGGTGCGGTGGGTCATTTCCGGAGGAT CTATACTACCGCCTGAACGTAATGCCTATCGCCGCCGCCGGCAGCTGCCGGCGAGCGATATCGCCGAGCTGGCGCACTTTCTGGTGCG AAAAATCGCCACCAGGGGGCGAACCTGCCCATCAGCAGCGATGGGGCGCCTGATAACAGCCTCGACGACGGTGATTTCTGTTCAACCATCGATAACCG AACTGGAAACTGTCTCCAGCAGCTTCGGCGGGTCGGCGGCCGAGGACGCGCCGCCCTGGTCGATAGAGCCAGCGAGCGCTGATCGCCCGCGCTGAAAA CCGAAAGCGCTCCGGCGCAGCGCGACGGGGCGCCTGCCGCATGACCGCCAAGGTTGCCGTATCGCATTCAGATTATGATATCACCATGC AGCGGGCTGGGTGCAGGCCAAAGCGGGCGGCTGCCAAAGCGCCCGCTGGAACACACCTC CGCGACTGTGA |
| nifA of *P. stutzeri* | Gene | ATGAACGCCACATTCGCCGAACGCCCAGCGCCCAGCGCGCCAACCCGCAACGAACTGTTGGATGCCGCGCTGGCGCTGGGGCAGGCGCTGGGGGCAGATCGCCCGAT CCTTAACCGCGGGCCGGGCCCATCCAGCATGCTTGGCCGGAGATCCTCCGCCGTGCCGAGATCGTGCCGATCTCCA TCTGCAACCGACAGGAACGCAGCCTGCAGGTGGCGCCGGTGCAGCGACTCCGAAACCGTGATCGACTCTGGCGAAAGCACCGTACCGC ATCGGCGAAGGCGTGTTCGGCAATGGACCTGTTCGGCCTCATCGCCGTGCCGATCAACGGCGGCGCGTATCATCCAGCCGTTCTCTTCGACCGACT GGCGCTGTACGACGAGCATGAGCGCGACGAGCTGATGCCGACACACCCGGTTTGATGGAAATCGCGGCGACGAGTCGCCCGATCTGCGTCCCACCGACC GAGGACGACGAAGTGCTCGCAGCAGCGTCGCAGCGCCAGAAGTCTTTCGACAAGCATGGTGTGGCGCAAGGTGTGGGCCACAC CGCCTCCATGCGGCCCAGGCCCATCCACTACAACTTCGACGGGTTCGACGGTTCGCGCTCACCGACGTCGGACGCGGTTGCCCACCGAGGG AGCTGATCGCCAGGCCATGAGCGCTGTTCGGTCACGAGAAAGGCCGCTTTCAGGAGAAAGGCAGCGCAAGGACGTTTCGAACAGGCCAAGCGCGCCCT GTTCCTGCACAGTCGGCGAGATCTGCGAGATGTCCCGGATGTTCCGCCAAGCCTGATGTTGCCGGTGTCGCCAAGCCTGCTGTCGGCGCA GCCAGACGCGTGAAGGTCAACGTGCGCATCGTCCGCCGACCACCAGCCGCCCAGATGCCCTACCGAGACGCAGAGGGTGGAGCAGAAGCAAGTTCCCGCAAGACCTC TATATAATTATATATAATTATTTTAAA GATCGCCCCGCCAGCAGGGTCGCAAACTCAAGCCGATGGTTGACCGAGCTGAATGAGCCACGCTGTTGGCCAACAGTGCCGCGAAC TGAAAAACTGCCTGGAACGCTCCTGGACGGTCCCATGGATGGCATCCATTCAGACCGCCAATTCCTCCTCACCGGCACCACCGCGCC ACGCGCTGGCGCGCGGTTCCCGAAGTCGACCTCCGAAGTCGACCTCCTGGAGGGCATTCGCGCGTCATCGCCAGACCGCGGCTG GGTTCCAAGGCCAAGGCCCGGTCCCCGCCCCCTGCTCGGCATGGACTGCCGGCAGATGCCTTACCGAGTGCAGAGACGCTGAACATTCATATGCCAAGATCT GA |

TABLE 10-continued

Genetic part sequences used in this study

| Name | Genetic part | DNA sequence (SEQ ID Nos: 122-225) |
|---|---|---|
| nifA of A. vinelandii | Gene | ATGAATGCAACCATCCCTCAGCCTCGGCCAAACAGAACCCGTCGAACTCTATGACCTGCAATTGCAGGCCCTGGGCGAGCATCGCCCGCAC GCTCAGCCGCGAACAACAGATCGACGAACTGCTCGAAGACTGCTCGGCCGTACTGCAATGACCTCGGCCTCTGCCGATGGCCTGGTGACCA TTTCCGACCCGGAACACGCCCTGCAGATCGGCCAACTCCATCACCACCGAACTGCTGGCCCAGGCCTGCGAAGGCGTGCGCTACAGA AGCGGCGAAGGCCTGATCGGCAACGTCGTTCATCGCCGTCAGGGAACCCATCGCAACGCATGGTGCTCGGCGGGGACTCCAGCCGGACT GCCGCCGACGAGCACATGCCCGCGACGAGCGCGACGAACTGCGTTCATGCGCTCAGATCGTCGCCAACCTGCTGCGTGGTGAACATC GAGGACGGCCGCGAGGCCGGGTGTTCGATCAGATCCGCGGGCTCGGCGCGGTCATCCACGTGGAAGCAGCAGGCGTACTACGGCCACAC CCCACCATGGCCCAGCCGCATCCACTACAACTCGCGGCCGGCGCGATCAGGCCTGCCCGGTGCCGCGCGCACCGCGGCTCGAACTGCTC GAGTCCGAACTCTTCGGCCACCAGGGCGCCGCTTCACCGACGTCAAGGGCGGAACGGCCAAGGGCCACCAGCCCACGCGCGCGACCCT GTTCCTCGACGAGATCGGCGGAGATCTCCGCGATGTCTCCGCAGCCTGGAAGGCTGCCGTCTGCAGGAAGGCGAGTTCCGCGAGGACCTC ACCAGACGGTGCGGTCAACGTGCGGCTCATCCGATCCGAAACATCCGGAGAAAAGGCGAGTGAGAAGGCAAGTTCCGCGAGGACCTC TACTACCCGTGAACGTCCATGGCCTGAACCCGCTGCCCGAACCCGGCACCCGCGCTCTGATGGCCCATCCGCCGTCTCCCTGACGTGCGGCAAC GATCGGGCCGCAGCAGGCCGCCCGGCTCAACCTGCGCGCCATCAGCGGCCATCCCTGATGGAGCCAACGTGCGCGGAAC TGGAGAACTGCCTGGAGCCCTGGAGCGCCGCTGCCCGAGTCATGAGCGGCCATCATGGGCCTGCTGGGCCATGACGCCCTCAACATCCACAGAGAGC CCGCCGTCGCCGGCGCGCCTGCCCGAGTCAACCTGGGCATCAACGAGAGACCCTGACGACCCGAATCGCCTGCCGCCTCGAACAGGCCGG CTGGGTGCAGGCCGAAGGCCCGGCAGGCCTGCAAGGCCGCATGCTGTCCAGATCGCTCCAAGGCCACCACCATGGCCAAGA TCTGA |
| nifA of R. sp. TRBG74 | Gene | ATGCTGCACAATGGGCTCAATGAGGGTATGACTGAACGATCCGCTCAAAACATCCACAAACCGGATTTCTGGGCAGCGTATCTATCGGAT ATCGAAATTTTGATTGGTCCAGACAGTTCGACACGAAGCTTGCCAATGTCATTAACGCCCCTCTCAGTAATTCTCCAATGCGGCGGCG CAATCGTCTTCTAAATGTTAAAGGAGAGCCCCCAAAGGCGCGGCCTAGAGCAAGCATCTCAAGGCGCCCGCTCCATTCCGGCG GAGCGTGCGATAGCGCACAGGCCGGAAGGCCTGTCGCCAAAGGGGCAGCTGATGCTGGTGCAAGGACGTTCGACTCATATGCGCCACAGAACGACCTAGAA CAACTCGAACGCCACAGGCCCCACTAGGATCCAATTTGAGGAACAGGTGCTGCCACTCGTTGCAAGTCGAAAAAGAACGCTTGGAACACTATGGAGATCGC AAGATGGCAGCACTAGGATCCAATTTGAGGAAGAGGTGCGCTTCCTCCATGGCTCCAAGCCTTCGGCCAGCAGTAGTTCAGGCGACACTGCCGAATCTGCCGACA CACCAGACCGGCGATGGTCATCGATTGGATTGTCGGGAAAGCCCTGCCTGCCAAGCAGGTTCAGGAAGCGTTGAAACGTCAAAGTTGTTGCAACAACCAATTCTG CGGTGCTTCTCAGGGGCGGAAAGCGGCCGTGTGTCGACGCGGCGGCCCGCAAGCATGAGAAAGGCCCGGCAACGGTTTGGGAAAGGGAACTGTGTCCATCCTCAG AAGTTGAACTGCGCCCGCGAACTGCAGACGGCGGACGCCGAACTGCTGCACCCTCGGACTGATCCAAGAAGTTTTGAAATCGGATGAGATCGGCGACGTTGACCTATATGCCGCCACGAACAAAGACCTAGAA TCTTGCAGGAAGGTGAACTTGACGAGTTCAGGGCGATGGGAGTTCAGGGCCGACTCGAGAGTTTCCTCGGCCGATGTCCGAGAGTTGAGCTCGCGTTCGCCGCTCGCCGGCTCGACGCATCGTTCCA TGTCAAAATGCAACTTCCCTGAAGATAGGAACCAGTGCTTTTCTTCAATCGCCTCGGTTACTCCAATGACCCGGCTGCACCCATTCTAACCGACC TCAGATTCTCCGTAAGAGTTTGTCGTCGAATGGAGAAGGCCGGTTGGGTTGTCAGCAGCAAGGCAGCTCGGATCCTCGGCGCCTCACCACCGCCGAGGCCAATCTCAACGGATACGCTCAATGGGTGCC CATGCGTAAGAGTTGTCGTCGAATCGCAATGGAGAAGGCCGGTTGGGTTGTCAGGCAGCAAGGCAGCTCGGATCCTCGGCCGTCACCACCGCGAGGTCGGCTAT GCAGAGCTGCTAATCAGTGCGATGGAGAAGGCCGGTTGGGTTGTCAGGCAGCAAGGCAGCTCGGATCCTCGGCCGTCACCACCGCGAGGTCGGCTAT GCTTTACGTAGGCATCGTATACAGGTGAAGAAAATCTAA |
| nifA of A. caulinodans | Gene | ATGCCAATGACCGACGCCTTCAGGTCCGCAGTACCTCGGTTTCGTCGAGCACCACCGCCGCGTCATCCATCACCACCGCGGG CGCGCTGCCGCGCCCGGAGGATGCCTGTGCCAAGTGACCGTCATGTCCCATGTCGCCAAGTCACGTCTGCTTCCTCCATGGCGAGATATCGAAGA TCCTGACGAGGCGCGCATCCGAAGTCGCCACGACGGCCATCTGGCCTGCTCGACGTGCTTGCTCTCCATGGCCAGATCGGCCATGGCATGATCGC AGGCCATCGACCAGCCGTCTGCCACGAGCCGATCGGGCTCGGCCTGGTGGTCAGGACGTGCAGGACGTGCGCGGATCCGTCTTCGCGGAGATCGTTTCG GCCCGCCTGAGGAGGCCACCGTCCGCCTTCCTCCGCGATCAAGTGTCGCCGATCAAGGCGCCACCATGTGGGCGAACATCTGCCCGAGATCTGCCATCTGG GATGGCGAGCACCGCCCGTTCGCTTCGACGAGGACCGGACCGGCAAGGAAAATCGCCACGCCCAGAGCCCCTGACATCTCGCCTGCACAAGCT GGTGGCGGAGCGCGACGCGGCCTGATCGCCAGACGACCAGCCCGCACACCGCGTCGAGGAAGAAAATCCGGCGCCGAGGTGG CCGAGGGCCCCAACGATCGCCATGGGCATCGGGCATCGGGCATCGGGGCTGAAACCGCCTGATCGCCACCGCCAAGCCCGAAGCGCGGCCGGAGGTGG CCGAGGCCCCAACGATCGCCATGGGCATCGGGCATCGGGCATCGGGGCTGAAACCGCCTGATCGCCACCGCCAAGCCCGAAGCGCGGCCGGAGGTGG |

TABLE 10-continued

Genetic part sequences used in this study

| Name | Genetic part | DNA sequence (SEQ ID Nos: 122-225) |
|---|---|---|
| | | AACTCCACCGTGCTGCTGCGCGGAGAGCGGCACCGGCAAGGAGTGTTCGCCCGTGCCATCCACGAACTGTCGCCCCGCAAGGGCAAGCC |
| | | CTTCGTGAAGGTGAACTGCGCCGCCCTCCCCGAATCGGTCGGCCCATGAGAAGGCGCCTTCACCGGTGCGCTGA |
| | | ACATGCGCCAGGGCCGCTTCGAGCTGTGGCCACGCGGAATCGGCGACGCTCTTCCTTGACGAGATCGGCGAGATCGGCCAAGCTG |
| | | CTGCGCGTGCTGCAGGAAGGCGAGTTCGAGCGGTCGGCGGCAATCGACGTCGAAGGTGATGCGGCTCGTGCGCCACCAACAAGAA |
| | | TCTGGAAGAGGCCGGTCTCCAAGGCTGCTCCCAAGCGCGAAGAACTTCCTCGACCGTTCAACAAGGAAAACAAGCTCCACATGGTGCCCTGATCCGCCGTCTGCCGCGAAC |
| | | GCCCGGGCGACAATTCCCAAGCTCGCGAAGAACTTCCTCGACCGTTCAACAAGGAAAACAAGCTCCACATGATGCTTCGGGCGTCGCCATC |
| | | GACGTGCTGCGCGTCTGCTATTTCCGGGACAACGTGCGGCCGAGAACTGTATCCGCAGCGCCAACGCTCGCCCACGATGCCGTCAT |
| | | CACCCCCATGACTTCGCTGCCTGCCGACAGCGGCCAGTGCCTCTCCGCCATGCTCTGGAAGGGCTCGGCCATGTGATGCCGCACGTGC |
| | | CGCCGGCGCCCACGCCGTGACTCGTCGCTTCCCCTGCCGTCCCCCGTGACCCGCCAGCGCCTGCGGCGAGCCCGGACCTGGCCGACAGC |
| | | CTGCCGGTCACTTGCCCCGGCACCGAGCCTGTCCCCGGAGCGAAAAGGAGCAGTTGCTCCAGGCCATGGAGCGCTC |
| | | CGGCTGGGTGCAGGCGAAGGCCGCGCCGCTCCTCCAACCTCACGCGCGCCAGTGGGTTATGCGCTGCGCAATATGACATCGACATCAAGC |
| | | GCTTCTGA |
| P$_{J23100}$ | Promoter[9] | TAGGTGTTGACGGCTAGCTCAGTCCTAGGTACAGTGCTAGCTCTAGA |
| P$_{J23101}$ | Promoter[9] | TAGGTGTTTACAGCTAGCTCAGTCCTAGGTATTATGCTAGCTCTAGA |
| P$_{J23102}$ | Promoter[9] | TAGGTGTTGACAGCTAGCTCAGTCCTAGGTACTGTGCTAGCTCTAGA |
| P$_{J23103}$ | Promoter[9] | TAGGTGCTGATAGCTAGCTCAGTCCTAGGGATTATGCTAGCTCTAGA |
| P$_{J23104}$ | Promoter[9] | TAGGTGTTGACAGCTAGCTCAGTCCTAGGTATTGTGCTAGCTCTAGA |
| P$_{J23105}$ | Promoter[9] | TAGGTGCTGCTGCTAGCTAGCTCAGTCCTAGGTACTATGCTAGCTCTAGA |
| P$_{J23106}$ | Promoter[9] | TAGGTGTTTACGGCTAGCTCAGTCCTAGGTATAGTGCTAGCTCTAGA |
| P$_{J23107}$ | Promoter[9] | TAGGTGTTTACGGCTAGCTCAGCCCTAGGTATTATGCTAGCTCTAGA |
| P$_{J23108}$ | Promoter[9] | TAGGTGCTGACAGCTAGCTCAGTCCTAGGTATAATGCTAGCTCTAGA |
| P$_{J23109}$ | Promoter[9] | TAGGTGTTTACAGCTAGCTCAGTCCTAGGGACTGTGCTAGCTCTAGA |
| P$_{J23110}$ | Promoter[9] | TAGGTGTTTACGGCTAGCTCAGTCCTAGGTACAATGCTAGGTCTAGA |
| P$_{J23111}$ | Promoter[9] | TAGGTGTTGACGGCTAGCTCAGTCCTAGGTATAGTGCTAGGTCTAGA |
| P$_{J23112}$ | Promoter[9] | TAGGTGCTGATAGCTAGCTCAGTCCTAGGGATTATGCTAGGTCTAGA |
| P$_{J23113}$ | Promoter[9] | TAGGTGCTGATGGCTAGCTCAGTCCTAGGGATTATGCTAGGTCTAGA |
| P$_{J23114}$ | Promoter[9] | TAGGTGTTTATGGCTAGCTCAGTCCTAGGTACAATGCTAGGTCTAGA |
| P$_{J23115}$ | Promoter[9] | TAGGTGTTTATAGCTAGCTCAGCCCTTGGTACAATGCTAGCTCTAGA |
| P$_{J23116}$ | Promoter[9] | TAGGTGTTGACAGCTAGCTCAGTCCTAGGGACTATGCTAGGTCTAGA |
| P$_{J23117}$ | Promoter[9] | TAGGTGTTGACGACAGCTAGCTCAGTCCTAGGGATTGTGCTAGGTCTAGA |

TABLE 10-continued

Genetic part sequences used in this study

| Name | Genetic part | DNA sequence (SEQ ID Nos: 122-225) |
|---|---|---|
| P$_{J23118}$ | Promoter[9] | TAGTGTTGACGGCTAGTCAGTCCTAGTATTGTGCTAGCTCTAGA |
| P$_{J23119}$ | Promoter[9] | TAGTGTTGACAGCTAGCTCAGTCCTAGTATAATGCTAGCTCTAGA |
| P$_{trp}$ | Promoter[10] | TAGTGTTGACATTATTCCATCGAACTAGTTAACTAGTACGAAGTT |
| T$_{T7}$ | Terminator[11] | TAGCATAACCCCTTGGGGCCTCTAAACGGGTCTTGAGGGGTTTTTTGT |
| T$_{T7.2}$ | Terminator[11] | TACTCGAACCCCTAGCCCGCTCTTATCGGGCGGCTAGGGGTTTTTGT |
| T$_{F7.3}$ | Terminator[11] | TACATATCGGGGGGTAGGGGTTTTTTGT |
| T$_{rrnBT1}$ | Terminator[12] | CCAGGCATCAAATAAAACGAAAGGCTCAGTCGAAAGACTGGGCCTTTCGTTTTATCTGTTGTTTGTCGGTGAACGCTCTC |
| T$_{L3S2P21}$ | Terminator[13] | CTCGGTACCAAATTCCAGAAAAGAGGCCTCCCGAAAGGGGGGCCTTTTTTCGTTTTGGTCC |
| T$_{1}$ | Terminator[13] | CTCGGTACCAAATTCCAGAAAAGACACCCGAAAGGGTGTTTTTTCGTTTTGGTCCTCCTTGGCCCTCCATCCTTAGATAGACAGATAAAAAAA ATCCTTAGCTTTCGCTAAGGATGATTTCTTCATAGGCAATACGATCGCATGTCC |
| T$_{2}$ | Terminator[14] | CCAGGCATCAAATAAAACGAAAGGCTCAGTCGAAAGACTGGGCCTTTCGTTTTATCTGTTGTTTGTCGGTGAACGCTCTCTACTAGAGTCAC ACTGGCTCACCTTCGGGTGGGCCTTTCTGCGTTTATA |
| T$_{3}$ | Terminator[13] | CCAGGCATCAAATAAAACGAAAGGCTCAGTCGAAAGACTGGGCCTTTCGTTTTATCTGTTGTTTGTCGGTGAACGCTCTCTACTAGAGTCAC ACTGGCTCACCTTCGGGTGGGCCTTTCTGCGTTTATA |
| T$_{4}$ | Terminator[13] | GGTCTTGTCCATTACCTTGCAGTCAGTGGGGGACAGGATCGGTGGACAGGATCGGACAGATCGAATGACTGAATAGAAAAGACGAACATTAA CGCATGAGAAAGCCCCCGGAAGATCACCTTCCGGGGCCTTTTTATTGCGCTACAAATGAAAGTACATAGAAATTA |
| T$_{5}$ | Terminator[13] | CAGATAAAAAAAATCCTTAGCTTTCGCTAAGGATGATTTCTTCATAGGCAATACGATCGCATGTCC CCCGAAAGGTGTTTTTTCGTTTTCAGTCCCTATAAATACGAAAGGGTCTTGAGGGGTTTTTTG |
| T$_{6}$ | Terminator[13] | CCAGGCATCAAATAAAACGAAAGGCTCAGTCGAAAGACTGGGCCTTTCGTTTTATCTGTTGTTTGTCGGTGAACGCTCTCTAGCATAACCC CTTGGGGCCTCTAAACGGGTCTTGAGGGGTTTTTTG |
| T$_{7}$ | Terminator[13] | CTCGGTACCAAATTCCAGAAAAGAGACCGCTTTCGAGCCTCTTTTTCGTTTTGGTCCTCCATTTTCGTTTTGGTCCTCCTTGGCCCTCCATCCTTAGATAGAGTTAACCAA AAAGGGGGATTTTATCTCCCCCTTAATTTTCCTTCATAGGCAATACGATCGCATGTCC |
| T$_{8}$ | Terminator[13] | CGCAGATAGCAAAAAGCGCCTTTAGGGCGCTTTTTTACATTGGTGCCCTCCATCCTTAGATAGAGGCGACTGACGAAACCTCG CTCCGGCCGGGGTTTTTGTTATCTGCATCATAGGCAATACGATCGCATGTCC |
| T$_{9}$ | Terminator[14] | TCGGTCAGTTTCACCTGATTTACGTAAAACCCGCTTCGGGCGGGTTTTTGCTTTGGAGGGGCAGAAAGATGAATGACTGTC |
| T$_{10}$ | Terminator[14] | GCCCCCGAAGATCACCTTCCGGGGGCTTTTTTTATTGGCGGCCGGCTGATTGATCAGGCGGCCGGCTGATTGGCGCGTTACCTGGTAGCGCG CCATTTGTTT |
| T$_{11}$ | Terminator[14] | GTAATCGTTAATCCGCAAATAACGTAAAAACCCGCTTCGGCGGGTTTTTTTATGGGGGAGTTTAGGGAAAGAGCATTTGTCA |
| T$_{12}$ | Terminator[14] | AAAAAAAACCCCGCCCCTGACAGGGCGGGGTTTTTTTT |

TABLE 10-continued

Genetic part sequences used in this study

| Name | Genetic part | DNA sequence (SEQ ID Nos: 122-225) |
|---|---|---|
| T13 | Terminator[13] | TCCGGCAATTAAAAAAGCGCTAACCACGCCGCTTTTTTACGTCTGCATGACTGAATAGAAAAGACGAACATTAACGCATGAGAAAGCCCCCGGAAGATCACCTTCCGGGGCCTTTTTTATTGCGCTCCTTGGCCCTCCATCCTTAGATAG |
| T14 | Terminator[13] | GGAAGACCATACTGGAAACACAGAAAAAGCCCGACCACCTGACAGTGCGGGCCTTTTTTTTCGACCAAAGGTGACTGAATAGAAAAGACGAACAATTCGCAGATAGCAAAAAAGCGCCTTTAGGGGCCTTTTTTCGTTCCTCATAGGCAATGCATCGCATGTCC |
| T15 | Terminator[13] | TCCGGCAATTAAAAAAGCGGTCTAACCACGCCGCTTTTTTTACGTCTGCATCCTTGGCCCTCCATCCTTAGATAGTCGGTACCAAATTCCAGAAAGAGGCCTCCGAAAGGGGGCCTTTTTCGTTTCGTCCATAGGCAATGATCGCATGTCC |
| T16 | Terminator[13] | TTCAGCCAAAAACTTAAGACCGCCGGTCTTGTCCACTACCTTGCAGTCAGGCGTGACAGGATCGGCGGTTTCTTTTCTTCTCAATACATGAAAGTACATAGAGAATTACTCGGTACCAAATTCCAGAAAATAACAGCCTCCCGAAAAGAGGCCTAACCACCGCGCTTTTTTACGTCTGCATCATAGGCAATAGATCGCATACGATCGCCATGTCC |
| T17 | Terminator[13] | TTCAGCCAAAAACTTAAGACCGCCGGTCTTGTCCACTACCTTGCAGTCAGGCGTGACAGGATCGGCGGTTTCTTTTCTTCTCAATCCTTGGCCCTCCATCCTTAGATAGTCCGGCAATTAAAAAAGCGGCTAACCACGCCGCTTTTTTTTACGTCTGCATCATAGGCAATACGATCGCATGTCC |
| T18 | Terminator[13] | CTCGGTACCAAATTCCAGAAAGAGGCCTCCCCGAAAAGGGCCTTCCGGGGCTTTTTTTATTGCGCTCTTGTTTGGTCTCTGACTGAATAGAAAAGACGAACATTAACGCATGAAAAGCCCCCCGGAAGATCACCTTCCGCTCCATCCTTAGATAG |
| T19 | Terminator[13] | CTCGGTACCAAATTCCAGAAAGAGGGGGCCTCTTTTTTCGTTTTTGGTCTCTGCCCTCCATCCTTAGTCGTTTCCGGCCAATCCTTGGCCCTTTTTTTCGTTTCGTCCATAGGCAATACGATCGCATGTCC |
| T20 | Terminator[13] | CTCGGTACCAAATTCCAGAAAGAGCGAACAATTAAGACGCTGAAAAGCCTGTCTTTTTTGGTCCTCACAATGAAAGTACATAGAAATTATTCAGCCAAAACTTAAGACCGCCGGTCTTGTCCACTACCTTGCAGTCAGGCGTGACAGGATCGGCGGTTTTCTTTTCTCAATCCTTGGCCCTCCATCCTTAGATAG |
| T21 | Terminator[13] | GGGAACTGCCAGACATGCAAATAAAACAAAAGGCTCAGTCGGAAGACTGGGCCTTTGTTTTATCTGTTGTTGTCGGTGAACACTCTCCCGACTAGTAGCCGGCCCGCTGCAGAAAGAGAGA |
| T22 | Terminator[13] | AACGCATGAGAAAGCCCCCGGAAGATCACCTTCCGCTCCCTTTTTTATTGCTCATAGGCAATACGATCGCATGTCTCCCGGCAATTAAAAAAGCGCTAACCACGCCGCTTTTTTTTACGTCTGCATCATAGGCAATGATCGCATGTCC |
| T23 | Terminator[13] | GGGAACTGCCAGACATCCAAATAAAACAAAAGGCTCAGTCGGAAGACTGGGCCTTTGTTTTATCTGTTGTTGGTCGGTGAACACTCTCCCG |
| T24 | Terminator[13] | AAAGCAAGCTGATAAACCGATACAATAAAAGGCTCTTTTTGGAGATTTTCAACATGAAAAAAATATATTGATGATCAGATAGCGGCGGGAACTGCCAGACATCAAATAAACAAAAGGCTCAGTCGGAGACTGGGCCTTTTGTTTTATCTGTTGTTGTCGGTGAACACTCTCCCG |
| T25 | Terminator[13] | AAATAAAAAAATATTATATTAAZATT CCAGAAAGAGGCCTCCCGAAAGGGGGCCTTTTTCGTTCCTCATAGGCAATACGATCGCATGTCC |
| T26 | Terminator[14] | AAATAAAAATATTATATTAAAZ1AA TTAAGACCGCCGGTCTTGTCCACTACCTTGCAGTAATGCGGTGGACAGGATCGGCGGTTTCTTTTCTTCTCAATCATAGGCAATACGATCGCATGTCC |
| P_Lux | Promoter[15] | CCTAGGACCTGTAGGATCGTACAGGTTTACGCAAGAAAATGTTTGTTACTTTCGAATAAATCTAGA |
| P_Tet | Promoter[16] | CGGTGGAATCCCTATCAGTGATAGAGATTGACATCCCTATCAGTGATAGAGATATAATGAGCACTCTAGA |

TABLE 10-continued

Genetic part sequences used in this study

| Name | Genetic part | DNA sequence (SEQ ID Nos: 122-225) |
|---|---|---|
| P$_{Cym}$ | Promoter[5] | AACAAACAGACAATCTGGTCTGTATTGTTATTATGAAATTTTCTGTATAATCAACAAACAGACAATCTGGTCTGTTGTATTAT |
| P$_{Phl}$ | Promoter[17] | AAAAAGAGTTTGACATGATACGAAACGTACCGTATCGTTAAGGTTACTAGAGTCTAGA |
| P$_{Sal}$ | Promoter[5] | GGGGCCTTCGCTTGGGTTATTGCTGGTGCCCCGGCCGGGCGCAATATTCATGTTGATGATTTATTATTATATATCGAGTGTGTATTATTATTTATATT<br>GTTTGCTCCGTTACCGTTATTAAC |
| luxR | Gene | ATGAAAAACATAAATGCCGACGACACACATACAGAATAATTAATAAAATTAAAGCTTGTAGAAGCAATAATGATATTAATCAATGCTTATCTGA<br>TATGACTAAAATGCTACATTGTCAAATATTGTCATTGTAGTATTGTCCGATCATTATTCCTGATCATTTCTATGGTTAAATCTATGGTTAAATCTAGATAATT<br>ACCCTAAAAAAATGGAGGCAATATATGATGCAGTATTAATAAAATAATAATAATAATATTCTAATCCAATCATTATCCAATT<br>AATTGGAATATATTTGAAAACATGCTGTAAATAAAAATCTCCAAATGTAATTAAAAGAGCCAAAACATCAGTCTTATCACTGGGTTTAG<br>TTTCCTATTCATACGGCTAACATGCTTCGGAATGCTAGTTTTGCCAATTCAGAAAAAAGACAACTATATAGATAGTTTATTTTACATG<br>CGTGTATGAACATACATTAATTGTTCCTTCTCTAGTTGATAATTATCGAAAAATAAATATAGCCAAATATAAATCAACAACGATTTAACC<br>AAAGAGAACATACCATTAATTGTTAGCGTGCGAAGGAAAAATCTCTGGAGATATTTCAAAAATATTTTCAGTAGCTCTGTCTCAC<br>TTTCCATTTAACCAATGCCAAATGAAACTCAATACAACAAACCGCTCCAAAGTATTTCTAAAGCAATTTTAACAGAGAGCAATTGATTGCC<br>CATACTTTAAAATTAA |
| tetR | Gene | ATGTCCAGATTAGATAAAAGTAAAGTTGATTAACAGCCGATTAGAGCTGCTCTAATGAAGCTGGAATCGAAGGTTTAACAACCGTAAACTCGC<br>CCAGAAGCTAGGTGTAGAGCAGCCTACATTGTATTGCCATTGTAAAAATAAGCGGGCTTTGCTCGACGCTTAGCCATTGAGATGTTAGATA<br>GGCACCATACTCACTTTTGCCCTTTAGAGGGGAAAGCTGGCAAGATTTTTACGTAATAACGCTAAAAGTTTTAGATGTTCTTTACTAAGT<br>CATCGCGATGGAGCAAAGTACATTAGGTACACGGCCTCGGCCGCTGGGGCATTTTACTTTTAGGTTGCGTATTGCGATTGAAGAGCATCAAGTCG<br>AGGTTTTTCACTAGACAAGATATCTATATGCACTGCACGTCCTGATTATCACCTACTGATAGTATGCCGCATTATTACGACAAGCTATCGAATTATTTGATCACCAAGGTGCAGAGCCA<br>CTAAAGAGAAAGGAAAACACCTTCAATTGATCATATGCGATTAGAAACAACTTAAATGTGAAAGTGGGTCCTAA<br>GCCTTCTTATTCGGCCTTGAATTGACATAGCACCCTGAATTGCATAGCGATTAGAAACAACTTAAATGTGAAAGTGGGTCCTAA |
| cymR | Gene | ATGAGCCCGAAACGTCGTACCCCAGGCAGAACGTGCAATGCAGAAACCCGAGGTAAACTGATTGACGCAGCAGGGTGTTCTGCGTGAAAAGG<br>TTATGCAGGTTTTCGTATTGAAGTTGTCCGGTGCAGATGTTCCGGTGCACGTGCACGCGGTTGCACGTGCACGGTAGCCGTGCACGCTCCGGCAAAACTGAACTGC<br>TGCTGGCAACCTTTGAATGGTGTATGAGCAGCAGATTTTTCTGGATGATGAATTCGTTTGCATACGATCAGCCTGGATCTGATTGTTGCAGCAGATCGTGATCCGGCACT<br>CAGATGCTGGAAGGTATTCAGCGTACCGTTGACCTCTGATTTTCAGCGCTTAATCGGCCCGTGGTGTGCAGAGATATGTGCGGGCGAATACGTCTCTGACGCGGCACGGCAGAACGTCGTGACACGGCAAACTCTCAGCAGGAGCCGTGCCGTGC<br>ATGATGCCGAAGATATTCGTGGCGCTGATTTACAGCCGCGTCATTGCACGTGAAACGTTATGCAAAATCACGCTGAAGAAAGATAAGAACGTTTTGAA<br>CGTGTGCCTAATAGCACCCCTGGAAATTGCACGGTGAACGTATGCAAAATTCAAACGTTAA |
| phlF | Gene | ATGGCACCTACCCCAGCCCGAGCCTGACCAGCATTGGTGCAGCATTGGTAGCCGTTGCGTCCGCATACCCATAAAGCAATTCTGACCAGCACATTGAAATCCTGAA<br>AGAATGTGGTTATAGCGGTCTGAGCATTCGTCTGCGAGCATTGCGAGCCGTTGCACGTCGTCGCGTTGCACGCCGTTACCACAACCGACCAAGCAACAACGACACCATTTATCGTTGTGACCAATAAAG<br>AATATTAATTAATTATATAAAAATTAATAATAATAATTAATTATTATTTAZAATTATTTT<br>CTGCGTAATCTGTGGAAAGTTTGGCGTGAAACGCATTTGGTGAAGCATTTCGTTGTGTTATTGCAGAAGCACAGCTGGACCCTGCAACCCT<br>GACCGGTGAAAGATCAGTTTATGGAACGATCCATTTATGGAACAAAAATGGTTGAAAAAATGCCATTAGCAATGCCAAATGCCATCAATGTGAACCGAAAG<br>ATACCAATCGTGAACTGCTGCTGATATGATTTTGTTTGTTTTGTGTATCGCCTGCTGCCGAACGCTGCACCGCCGTTGAACAGGATATTGAA<br>GAATTTACCTTCCTGCTGATTAATGGTGTTTGTCCGGGTACACAGCGTTAA |
| nahR | Gene | ATGGAACTGCGTGACCTGGATTTAAACCTGCTGGTGGTTTCAACCAGTTGCTGCTGTGGTCGACGACGCGTCTCTGTCACTGCGGAGAACCTGGG<br>CCTGACCCAGCCCGTGAGCAATGCGTGCGAGCATCTGCCGAGCACGTCACTTCGGCACGCATGCCGCCACGCCCTACAGCCCATGAAAGCTTCGATCCG<br>CTGACCAGCGAGCGTACCTTCACCCTGGCCATGACCACCATTGGCGAGAATCACTTCCGGGCTGATGATGCGCTGCTCACCAGGC<br>CCCAATTGCGTGATCAGTAGCGTGCCGACAGTTCAGCAGTTCGATGAGCCTGCAGAAGGAACCGTGCAGAATCAGCCTTGCCTGATATGATGAGCCTGCAGAAGGAACCGTGCAGAATCACGCCTATGTCCAGAATCACCTGCCTATGTCCAGAATCACCTGCC<br>TTCCCAATCTGCAAACTGGCTTCTTTCAGCCGCCGCACGTTCCAGCACGTCTCATGCCCTATGTCCTATGCCGCAAGGACCATCCAGTCACCCGCGAA<br>CCCCTGACTCTGGAGCGCTTCTCTGTTCCACGCCACGTCCTACGGCACCGTTCATGCCCGTCATGCCGCTGGGCACCGCACCGGCCAGTTGGACCACGTACATGACACG |

TABLE 10-continued

Genetic part sequences used in this study

| Name | Genetic part | DNA sequence (SEQ ID Nos: 122-225) |
|---|---|---|
| | | TATAATTTAATATTTTAATTAAATTTATT CGATATGTTTAGCCGACTGCTGCGTAGAGCCCTTCGGCTAGAGCGCCTTGCCGCACCCAGTCGTCTTGCCTGAAATAGCCATCAACATGTTC TATAATAAAATAAATATTTTAATATTTTATTTAATTATAA |
| $P_{Fde}$ | Promoter[18] | TCAATGTATTGATGCCGTCCATATCAATGAATCAAAACAATCATTTGATCAATATCAGCTCACTCTTAAGCTTCACTCATCCGCTCAT |
| fdeR | Gene | ATGCGTTTCAACAAGCTCGACCTCAATCTTCTGCGCCTGATGACTGCTCACGGAGATGAGCATCAGCCGCCGAAAAGATCCA TCTGAGCCAGTCGGCCATGAGCAATGCCCTGGCCGCGCCGAGCAATGCTGATCCAGGTGGGCCGGCCATGGAGC CCACGCCGCGCCGCCGAGCTGCTCAAGGATGCGGTGCATGATGTGCTGCGCGGTATCGCGGCGTCCATGCGGCGCTCGTCCG GCCGAGTCCACGCGCGAGTTTCGCATCTCGGTTTCGGACTTTACGCTCTCCGTCTCCATCCCCGGGTGTGCCGGCGCACGCCGAGGG CAAGCACATCCGCTTGCCCTGATGCCGCTGCCAAGACCCGCTGCTG3ATCGGCCGCTGCTG3GTCTTGCCGCAGG AATTCTGCACGCCGATCATCCTGCCGAAGAGAGTCTTCCGAACGCATGTCTGCCGCCTGTGGGCCAATGCGTCGTGGGGTGATGGCCAGGA CTGACGCTGGAACGCTAATGCTGCCGCCGGTGAAGTGACCAGCTTAGCTTCCGTCTGATGGTGCCGCCTGGTACAGGGAGACGGACCCATCGCCACGGTGC GCTGGGCTTTGCGCGCCCGAATGCGCTGGCTCCGCAATGCGCCCGGTGGTCATCCAAGGAGAGTCGGGCCGCAGATGACGCAG ATGCCCCGACCGTACCCGCAGCAATATTTGGCATCCCTAGTGCGTCGCTCGGGGCTGTTTCTGGAGAGTGACGCAGGAGATGGATGCGGCCGCTGCCAGG CATTGCTGA |
| $P_{BAD,10}$ | Promoter | CAGACAATTGCCGTCACTGCGTCTTTACTGGCTCTTCTGCTAACCAAACCGGTACCCGCGTTATTAAAAGCATTCTGTAACAAAGCGGGA CCAAAGCCATGACAAAAACGCGTAACAAAAGTGCTCTATAATCACGGCAGAAAAGTCCACATTGATTATTTGCACGGCGTCACACTTTGCTAT GCCATAGCCATTTTTATCCATAGATTAGGCGGATCTACCTGACGCTTTTTATCGCAACTCTCTATATTTTCCATACCGGTTTTTTTTGGGC TAGCGAATTC |
| araC | Gene | ATGCAATATGGACAATTGGTTTCTTCTCTGAATGCGGGAGTATGAAAGCGCAAATGATCCCTGCTGCCGGGATACTC GTTTAATGCCCATCTGGTGGCGGGTTTAACGCGCAATTGAGGGCCAACGGTTATCTGATTTTTTATCGACCAGCGCTGGGAATGAAAGGTT ATATCTCAATCTCACCATTCCGCGTCAGGGCGTCAGGAGCGTGTCATCCGAGGTCTGCCGGGCTGTCTGAGCGTATCCAGCTGGATCGCCAGAGGAATTTGTTTGCGACCAGCGGCGGCTGATATTTTCTGTTCCG CCAGGAGAGATTCATCACTACGGCGTCATTATTGCCAATACGGGTTCTTCGCCGATGAGCGGCCACCGACCGCATTCAGCGACCTGTTTGGCCAA ATGCTTAACTGGCCGTCAATATTTTGCCAATAGGGGGCCTATTCGGAAGGGCTCTGGCGCAAATCGCTTGAGCAATTGCTTACTGGCGCAGCACAAATTTTGATATCGC TCATTAACGCCGGCCAAGGGGAAGGGCCTATTCGGATAATCGGGTACGCGCGTCTGACCCAATCCGCAGCAGTTGACCATCAGCGATCACACCAGCTGACCATCTTTCCGGCAGTTAGGGATTAGCGTCCTTAAGCTGGCCGAGG CAGCGTCCACCACATGTTTGCTTGCCGACCATGTTTGCAGCACCAGCCGTATCGCCGTCGGTCGCAATGTGGTTTTGACGACATCCATCATC ACCAAGCTATCACCGAAGCGCTTTTGCAGCACACCCAGCGGTCCTATCGCCGTCCGCCGAATGTGGTTTTGACGATCAACTC TATTTCTCGCGGGTATTTAAAAAATGCACCCGGGCCAGTTCCCGTTGTGAAGAAAAAGTGAATGATGTAGCCCGTCAA GTTGTCATAA |
| araE | Gene | ATGGTTACTACTAATACGGAATCTGCTTCTTTGCGGATACGCGGCTATGAATGTGTTTCGGTAGTGCTGCGT CGCAGGATTGTTATTTTGCTTGATATCGCGGTTACCGGCCGGTTCATTACCGCCGATCACTTGTCTGACCAGTCGTTGCAGG AATGGGTGGTTAGTAGCATGATGCTCCGGTTCAGCAATGGTGCGCTGTTTAATGTTGGCTGTTCCGCCGTTGGCCGCTAAATACAGCCTG ATGCGGGGGCCATCCTGTTTGCCAGCAGCCGTATAGGGTCCGGTTCTATATACTGGGGCCATCCGGTCCTAGGAGATGTTAATCGCGGCCGTTGGTGCTGGG GATTGCTTCGGGATGCGTCAGCAGTCACACTCGTGCTCTGATTATCTTCCGTCTGATTTCTGGATGCAAGTGAAAACGTTCAAGGTAAGATGATCAGTATGTACC AGTTGACGCGTTATGGATGCGCAATCCGGCATCGCATCGTCGATTATTCTGGTAGTTCTTCCTGCCAATAGCCGTGGCGCAATGGTTAGGCGGA GCTTTACCAGCAGTCCTGCTGATTATTCGCGCGATACTGCGTCTGCTGAATATGCCGGAAAAGCCTCATATTGAGGCGGA AGAAGTATTGCGTATGCGTGCGCATAGCGGATACACTCGGAAAAAAGCGGAGAAGCTCAACGAAATTCGTGAAAAGCGTTAAAACAGGCGGTT GGCACTGTTTAAGATCAACCGGATCGTATCTCCTGGTGCTGCTGCCTGTCTATTGTTGCCACCAGAGCAGTTTACCCGTCATGAACATC ATCATGTACTACCGCGCCGCTATTGCCGCCCCGCTTATTTTCCGGTGTTTACCGGTAGAATAAAGCAGGGCGCTTAAACGGCTACGGCTTCCAGTGGC+32TCCTGGCCTATTTGCATTGGCTGGGCTATTGCCTGAAAATGGTTTCAGCGTGATGCGTTAGGCA CTTGGGTGCTGGGCATCCTGTTTGCCTATGCAGTTGATAACGGCTTTCCAGTGGC+32TCCTGGCCGATGGCTTCCAGTGGCATGAGCATGATGTGT ATTGCCGGTTATGCGATGAGCCGCGCTGCCGATCAGGAGTGCGCCAGTGGTGATCCAGAATTCAGCCGCCTGAAATTCAGCCGCCGATTCCGATTACCTG TTCGACCACCACGAACTGGGTGTGTCGAAATGATTATCCGCCGACCTTCCTGACACTGCTTCCATAGCATTCGCCGCGCATTGCCGCGCTACGTTCTGGC |

TABLE 10-continued

Genetic part sequences used in this study

| Name | Genetic part | DNA sequence (SEQ ID Nos: 122-225) |
|---|---|---|
| $P_{tac}$ | Promoter[10] | TCTACACTGCGTCGAACATTGCGTTTGTGGGCATTACTTTCTGGCTCATTCCGGAAACCAAAAATGTCACGCTGGAACATATCGAACGCAAA CTGATGGCAGGCGAGAAGTTGAGAAATATCGGCGTCTGA |
| $P_{noc}$ | Promoter | CTCGAGTGTTGACAATTAATCATCGGCTCGTATAATGTGTGGAATTGTGAGCGCTCACAATTTCACACATCTAGA |
| $P_{noc}$ | Promoter | AACAAATACACATGGGGCATGCCATGCCTATTACTGCCCTTGCGATATGGAAGGCAAGCTTTTAGTAACAATAGAAAACTGGGTCCTACTCTCGAA GAATGCACTGCGGCGTCACGTCAACACGTCAGTTGAAACGCCGTTGAGAATGTATGCTGGCAGATTTGCCAGCGCGTGATTTTCGGCTGTCCCGT CCTCACGGTTTTGCGCTGCATCGCAAGAGATTGGGAA |
| nocR | Gene | ATGACGTCAGCAGCGAATCTGGTGAGGATCACCGCAGCCAGCCCGACCAGCCGGTCTGATCAGGATCTCGAAGAGGAAATTGGGATCAGCTCTT CGAAAGAACGGGCAACCGGTTACGTCTCTACGCGGGAGGCCGGTATTCTGTTTCGACGAGTGTCGACACATTTCAACGGGATTCAGCACATCG ACAAAGTCGCGGCTGAACTGAAAGAAGTCTCATATGGGGTCCCTAAGGGTCGCCTTGTTATACAGCGCCAGCTCTGAGTTTTATCTCCGGCGTC ATTCAGACGCGTTCATCGCCGATCGGCCCGACGGTCGCGCGATCGGCCCGTCGGTCTGGCGACTATCCGACACAGTTCCTTCCCGACACGGTCCTCGAATTGGTCTCGCTCCAGCA CTACGATTCGGAATATCGATATTGGCTGGCGACTATCCTGGTCTCACCACCGAACCTGTCC+32CCTTTCGTGCGGTCTGCCTGCTGCCGC CGGGGCATCGTCTCGAAGACAAGGAAACGTTCTCGAGAGAGAGTCATTGATTTGCCTCTCTCCAGTGAGCCTTCTACGG ATGCAAACGGACGCCGCACTGGACAGCTCGACCCCTTCACTGCCGACTACAGTGCAAATCCGGTTATTCAGCGCTCCTTTGATCCGGTTGTCC CAGCGGAATGGGGGTTGGTATCGTCGACCCCTTCACTGCCGACTACAGTGCAAATCCGGTTATTCAGCGCTCCTTTGATCCGGTTGTCC CCTACCATTTTGCTATAGTTCTTCCGACCAGCCCACCGCCGCGTTGGTTAGCGAGTTCCGGAGTTGCTTGCGTTGAAAGCC TTGCCCTATGAAACCATTTGA |
| $P_{occ}$ | Promoter | AAACGCACCATAACATCTGCTTATTCTTGCCCGGTCATTATGAATTTGACCGAATGCATATCGAATGTAAAGCTCACCCTATAAATCACACAC TCTTATACAGACGT |
| occR | Gene | ATGAATCTTCAGGCAGGTCGAGGCGTTCCGAGGCGTCAGTCATGCTGACAGTCAGTGCAGTGCAGGCGGCGCGGCTGAACTAATGCTGTGACTCAGCCGGC CATCAGTCGCCTAATCAAGGACTTTGAACAGGCGACAAAACTGCAGCTCTTCGAGAGGCTCGGAACCATTATCCGACAGCAGGAGGCAA AGACGCTGTGAAAGAGTTCGATCGGGCGTTCGTCGGCTTAATCATATAGGCAACCTGGCTGCCGACATCGCAGGCAGGCAGCGGGACG CTCCGCATTGCTGCCTGCTCTGCAAACGGGCCGTTGCTCCGGCAGGCCGTTGCGCGTCCGCAGCAGTCGACGAACCAAATCTCCAGGTCTC CCTAATGGGACTGCCCTCAAGCATGGTCATGGAAGCCGTTCATGCCGCTGCTCCGGACATCGACTTGCTGGCCTTGACCGTGTCACGCCACAAG GTTTTCTAATCGAAACCCGGTCCTGCCTTCCCGGTTGTCGCCGTCCACTCTTTCGCCATGCGGGTAGGAGGTGGTGGTATTCAACGCGGCCGTC AATTGAAGTGAGCCTGTCGCATACTCGCCTAAGTCTCGACCAGACCTCGGCCCGGATCGCAATTATCCGGCAATGCGGATCAGTTCA CGGACAGGATCGCTACTGCACCGTTCTGACCCGGATTCCTCGAAGTCCGGTCAGCAATTGCGCTCCTCCAACCATCGTC GATCGTTTCACAACCGAATTCTCGAGGTTTCATATGATTATGAAGCAGAACGGCCTAATGGAGTAA |
| $P_{Bet}$ | Promoter[17] | AGCGCGGGTGAGAGGGATTCGTTACCAATAGACAATTGATTGGACGTTCAATATAATGCTAGC |
| $P_{Cin}$ | Promoter | CCCTTTGTCGCTCCAAACGGACCGCACGGCGCCTCTAAAGCGGGTCGCGATCTTTCAGATTCGCTCCTCCCGCTTTCAGTCTTTGTTTTGGCGC ATGTCGTTATCGCCAAAACCGCTGCACACTTTTGCGCGACATGCTCTGATCCCCCTATCTCGGGGGCCTATCTGAGGGAATTTCCGATCCG GCTCGCCTTGAACCATTCTGCTTTCCACGAACTTGAAAACGCT |
| P3858 | Promoter[5] | TTTTGTTCGATTATCGAACAAATTATTGAAATATCGAACAAAACCTCTAAACTACTGTGGCACTGAATCAAAAAATTATAAACCCTGATCAG A |
| $P_{TTg}$ | Promoter[19] | CACCCAGCAGTATTTACAAACAACCATGAATGTAAGTATATTCCTTAGCAA |
| $P_{Van}$ | Promoter[20] | ATTGGATCCAATTGACAGCTCAGCTCCTAGGTACCATTGGATCCAAT |

TABLE 11

RBS sequences used in this study

| Name | Strain | RBS sequence[a] (SEQ ID NOs: 226-291) | Strength (GFP, au) |
|---|---|---|---|
| RB5r1 | R. sp. TRBG74 | ATTTCACACATCTAGAGCTAATCATCTCGTACTAAAGAGGAGAAATTAACCATG | 8242 |
| RB5r2 | R. sp. TRBG74 | ATTTCACACATCTAGAGCTAATCATCGCGTACTCAGGAGGCAAGTAATG | 7181.5 |
| RB5r3 | R. sp. TRBG74 | ATTTCACACATCTAGAATTAAAGAGGAGAAATTAACCATG | 6238.5 |
| RB5r4 | R. sp. TRBG74 | TAACAATTTCACACATCTAGAGCTAATCATCTCGTACTAAAGAGGCAAGTAATG | 3618 |
| RB5r5 | R. sp. TRBG74 | TAACAATTTCACACATCTAGAGCTAATCATCGCGTACTAAGGAGGCAAGTAATG | 3560 |
| RB5r6 | R. sp. TRBG74 | TAACAATTTCACACATCTAGAGCTAATCATCGCGTACTCAAGAGGCAAGTAATG | 2614.5 |
| RB5r7 | R. sp. TRBG74 | TAACAATTTCACACATCTAGAGCTAATCTTCGCGTACTAAAGAGGCAAGTAATG | 2418.5 |
| RB5r8 | R. sp. TRBG74 | TAACAATTTCACACATCTAGAGCTAATCATCTCGTACTCAGGAGGCAAGTAATG | 1882.5 |
| RB5r9 | R. sp. TRBG74 | TAACAATTTCACACATCTAGAGCTAATCATCTCGTACTAATGAGGCAAGTAATG | 1593.5 |
| RBST-10 | R. sp. TRBG74 | TAACAATTTCACACATCTAGAGCTAATCATCGCGTACTAATGAGGCAAGTAATG | 1590 |
| RBST-11 | R. sp. TRBG74 | TAACAATTTCACACATCTAGAGCTAATCATCGCGTACTCACGAGGCAAGTAATG | 1554 |
| RBST-12 | R. sp. TRBG74 | TAACAATTTCACACATCTAGAGCTAATCATCGCGTACTAAAAAGGCAAGTAATG | 1138 |
| RBST-13 | R. sp. TRBG74 | TAACAATTTCACACATCTAGAGCTAATCTTCGCGTACTAAAAAGGCAAGTAATG | 895.5 |
| RBST-14 | R. sp. TRBG74 | TAACAATTTCACACATCTAGAGCTAATCTTCGCGTACTAAGAAGGCAAGTAATG | 632.5 |
| RBST-15 | R. sp. TRBG74 | TAACAATTTCACACATCTAGAGCTAATCATCTCGTACTAAATAGGCAAGTAATG | 648.5 |
| RBST-16 | R. sp. TRBG74 | TAACAATTTCACACATCTAGAGCTAATCATCTCGTACTAATAAGGCAAGTAATG | 532 |
| RBST-17 | R. sp. TRBG74 | TAACAATTTCACACATCTAGAGCTAATCTTCTCGTACTAAAGAGGCAAGTAATG | 488 |
| RBST-18 | R. sp. TRBG74 | TAACAATTTCACACATCTAGAGCTAATCATCGCGTACTCAATAGGCCAGTAATG | 305.5 |
| RBST-19 | R. sp. TRBG74 | TAACAATTTCACACATCTAGAGCTAATCATCGCGTACTAAGTAGGCAAGTAATG | 242 |
| RBST-20 | R. sp. TRBG74 | TAACAATTTCACACATCTAGAGCTAATCATCTCGTACTAACGAGGCAAGTAATG | 248 |
| RBST-21 | R. sp. TRBG74 | TAACAATTTCACACATCTAGAGCTAATCATCGCGTACTCAGCAGGCAAGTAATG | 183 |
| RBST-22 | R. sp. TRBG74 | TAACAATTTCACACATCTAGAGCTAATCTTCGCGTACTAAGTAGGCAAGTAATG | 130 |
| RBST-23 | R. sp. TRBG74 | TAACAATTTCACACATCTAGAGCTAATCTTCGCGTACTAATTAGGCAAGTAATG | 84.4 |
| RBST-24 | R. sp. TRBG74 | TAACAATTTCACACATCTAGAGCTAATCTTCTCGTACTAACAAGGCAAGTAATG | 75.15 |
| RBST-25 | R. sp. TRBG74 | TAACAATTTCACACATCTAGAGCTAATCATCTCGTACTCAATAGGCAAGTAATG | 45.45 |
| RBST-26 | R. sp. TRBG74 | TAACAATTTCACACATCTAGAGCTAATCATCTCGTACTAAGCACGCAAGTAATG | 36 |
| RBST-27 | R. sp. TRBG74 | TAACAATTTCACACATCTAGAGCTAATCATCGCGTACTAACTACGCAAGTAATG | 12.2 |
| RBST-28 | R. sp. TRBG74 | TAACAATTTCACACATCTAGAGCTAATCTTCGCGTACTAAGAACGCAAGTAATG | 13 |
| RBST-29 | R. sp. TRBG74 | TAACAATTTCACACATCTAGAGCTAATCTTCGCGTACTAAAAACGCAAGTAATG | 4.6 |
| RBST-30 | R. sp. TRBG74 | TAACAATTTCACACATCTAGAGCTAATCTTCGCGTACTAACAACGCAAGTAATG | 2.95 |
| RBST-31 | R. sp. TRBG74 | TAACAATTTCACACATCTAGAGCTAATCTTCTCGTACTCATGACGCAAGTAATG | 1.45 |
| RBST-32 | R. sp. TRBG74 | ATTTCACACATCTAGAATTAAAGAGAAGAAATTAACCATG | N/A[b] |
| RBST-33 | R. sp. TRBG74 | CTAGTGCGAACTAGCTCATACCGCAGATG | N/A[b] |
| RBSp1 | P. protegens Pf-5 | CTAGCGCAGGTCCAACGTTTTTCTAAGCAAGGAGGTCATATG | 25090 |
| R135132 | P. protegens Pf-5 | CTAGCGAAGGTCCAACGTTTTTCTAAGCAAGGAGGTCATATG | 21590 |
| R135133 | P. protegens Pf-5 | CTAGCGAAGGTCCAACGTTTTTCTAAGCCAGGAGGTCATATG | 19690 |
| RBSp4 | P. protegens Pf-5 | CTAGCGCAGGTCCAACGTTTTTCTAAGCCAGGAGGTCATATG | 19490 |
| R135135 | P. protegens Pf-5 | CTAGCGAAGCTCCAACGTTTTTCTAAGCAAGGAGGTCATATG | 17990 |

TABLE 11-continued

RBS sequences used in this study

| Name | Strain | RBS sequence[a] (SEQ ID NOs: 226-291) | Strength (GFP, au) |
|---|---|---|---|
| RBSp6 | P. protegens Pf-5 | GAATTCTACACTAACGGACAGGAGGGTCCGATG | 14490 |
| RBSp7 | P. protegens Pf-5 | GAATTCTAAACTAACGGACAGGAGGGTCCGATG | 13390 |
| RBSp8 | P. protegens Pf-5 | GAATTCTAAGCTAACGGACAGGAGGGTCCGATG | 12790 |
| RBSp9 | P. protegens Pf-5 | GAATTCTTAACTAACGGACAGGAGGGTCCGATG | 11490 |
| RBSp10 | P. protegens Pf-5 | GAATTCTACACTAACGGACAGGAGGGTCGGATG | 11090 |
| RBSp11 | P. protegens Pf-5 | GAATTCTACGCTAACGGACAGGAGGGTCCGATG | 10390 |
| RBSp12 | P. protegens Pf-5 | GAATTCTCAACTAACGGACAGGAGGGTCCGATG | 9590 |
| RBSp13 | P. protegens Pf-5 | GAATTCTAAGCTAACGGACAGGAGGGTCGGATG | 8918 |
| RBSp14 | P. protegens Pf-5 | GAATTCTCAGCTAACGGACAGGAGGGTCCGATG | 8766 |
| RBSp15 | P. protegens Pf-5 | GAATTCTCAACTAACGGACAGGAGGGTCCGATG | 7596 |
| RBSp16 | P. protegens Pf-5 | GAATTCTACGCTAACGGACAGGAGGGTCGGATG | 6055 |
| RBSp17 | P. protegens Pf-5 | GAATTCTCAACTAACGGACAGGAGATATACATATG | 5939 |
| RBSp18 | P. protegens Pf-5 | GAATTCTCAGCTAACGGACAGGAGGGTCGGATG | 5915 |
| RBSp19 | P. protegens Pf-5 | GAATTCTAAACTAACGGACAGGAGGGTCGGATG | 4867 |
| RBSp20 | P. protegens Pf-5 | GAATTCTCAGCTCACGGACAGGAGGGTCGGATG | 4426 |
| RBSp21 | P. protegens Pf-5 | GAATTCTCAACTAACGGACAGGAGGGTCGGGATG | 4110 |
| RBSp22 | P. protegens Pf-5 | GAATTCTACACTCACGGACAGGAGGGTCGGATG | 3977 |
| RBSp23 | P. protegens Pf-5 | GAATTCTAAGCTCACGGACAGGAGGGTCGGATG | 3829 |
| RBSp24 | P. protegens Pf-5 | GAATTCTCAACTCACGGACAGGAGGGTCGGATG | 3661 |
| RBSp25 | P. protegens Pf-5 | GAATTCTACACTAACGGACAGCAGGGTCGGATG | 3542 |
| RBSp26 | P. protegens Pf-5 | CTAGCGCAGGTCCAACCTT+32CTAAGCAAGTAGGTCATATG | 2139 |
| RBSp27 | P. protegens Pf-5 | GAATTCTCAGCTAACGGACAGCAGGGTCGGATG | 1265 |
| RBSp28 | P. protegens Pf-5 | CTAGCGCAGGTCCAACCTTTTTCTAAGCAACTAGGTCATATG | 389 |
| RBSp29 | P. protegens Pf-5 | CTAGCGAAGGTCCAACCTTTTTCTAAGCCAGTAGGTCATATG | 377 |
| RBSp30 | P. protegens Pf-5 | GAATTCTACGCTCACGGACAGCAGGGTCGGATG | 221 |
| RBSp31 | P. protegens Pf-5 | GAATTCTCCGCTCACGGACAGGAGGGTCCGATG | 23.3 |
| RBSp32 | P. protegens Pf-5 | CTTCTCGGCCAGCTGACAGGGGAAGCTCGCATG | N/A[b] |
| RBSp33 | P. protegens Pf-5 | CTTCTCGGCCAGCTGACAGGAGGAAGCTCGCATG | N/A[b] |

[a] The start codon is underlined.
[b] RBSs are rationally designed for the controllers by the RBS Calculator[2]

TABLE 12

Chemicals used in this study

| Chemicals | Source | Identifier |
|---|---|---|
| Tryptone | Fisher Scientific | Cat# BP1421 |
| Yeast extract | BD Bacto | Cat# DF0127 |
| NaCl | Fisher Scientific | Cat# S271 |
| $CaCl_2 \cdot 2H_2O$ | Sigma-Aldrich | Cat# C3306 |
| $MgSO_4 \cdot 7H_2O$ | Fisher Scientific | Cat# M80 |
| $FeCl_3$ | Alfa Aesar | Cat# AA1235709 |
| $Na_2MoO_4 \cdot 2H_2O$ | Sigma-Aldrich | Cat# 331058 |

TABLE 12-continued

Chemicals used in this study

| Chemicals | Source | Identifier |
|---|---|---|
| $NH_4CH_3CO_2$ | Sigma-Aldrich | Cat# A1542 |
| $Na_2HPO_4$ | Fisher Scientific | Cat# S375 |
| $KH_2PO_4$ | Sigma-Aldrich | Cat# P9791 |
| EDTA-Na2 | Sigma-Aldrich | Cat# E5134 |
| $ZnSO_4 \cdot 7H_2O$ | ACROS Organics | Cat# AC424605000 |
| $H_3BO_3$ | Fisher Scientific | Cat# A73 |
| $MnSO_4 \cdot H_2O$ | MP Biomedicals | Cat# ICN225099 |
| $CuSO_4 \cdot 5H_2O$ | Aldon Corp | Cat# CC0535 |
| $CoCl_2 \cdot 6H_2O$ | Sigma-Aldrich | Cat# C8661 |
| $FeSO_4 \cdot 7H_2O$ | Sigma-Aldrich | Cat# 215422 |
| Thiamine hydrochloride | ACROS Organics | Cat#148990100 |
| D-pantothenic acid hemicalcium salt | Sigma-Aldrich | Cat# P5155 |
| Biotin | Sigma-Aldrich | Cat# B4501 |
| Nicotinic acid | Sigma-Aldrich | Cat# 72309 |
| MOPS | Fisher Scientific | Cat# BP308 |
| Isopropyl-beta-D-thiogalactoside (IPTG) | GoldBio | Cat# 12481 |
| L-arabinose | Sigma | Cat# A3256 |
| Anhydrotetracycline hydrochloride (aTc) | Sigma | Cat# 37919 |
| N-(3-Oxohexanoyl)-L-homoserine lactone (3OC6HSL) | Sigma | Cat# K3007 |
| N-(3-Hydroxytetradecanoyl)-DL-homoserine lactone (3OC14HSL) | Sigma | Cat# 51481 |
| Naringenin | Sigma | Cat# N5893 |
| 2,4-Diacetylphloroglucinol (DAPG) | Santa Cruz | Cat# sc-206518 |
| Salicylic acid sodium salt | Sigma | Cat# S3007 |
| 3,4-Dihydroxybenzoic acid (DHBA) | Sigma | Cat# 37580 |
| Vanillic acid | Sigma | Cat# 94770 |
| Cuminic acid | Sigma | Cat# 268402 |
| Nopaline | Toronto Research Chemicals | Cat# N650600 |
| Octopine | Toronto Research Chemicals | Cat# 0239850 |
| Choline chloride | Sigma | Cat# C7017 |
| Tris (1M), pH 8.0 | Invitrogen | Cat# AM9855 |
| Triton X-100 | Sigma-Aldrich | Cat# T8787 |
| Tergitol solution | Sigma-Aldrich | Cat# NP40S |
| DNase I | Sigma-Aldrich | Cat# 4716728001 |
| RNA Fragmentation Reagents | Invitrogen | Cat# AM8740 |
| T4 Polynucleotide kinase | New England Biolabs | Cat# M0201 |
| SUPERase•In | Invitrogen | Cat# AM2694 |
| PEG 8000 | Sigma-Aldrich | Cat# 1546605 |
| T4 RNA ligase 2, truncated K277Q | New England Biolabs | Cat# M0351 |
| Superscript III reverse transcriptase | Invitrogen | Cat# 18080044 |
| CircLigase ssDNA ligase | Epicentre | Cat# CL4115K |
| Phusion High-Fidelity DNA polymerase | New England Biolabs | Cat# M0530 |
| Micrococcal nuclease | Roche | 10107921001 |

What is claimed is:

1. A rhizobia species that can fix nitrogen under aerobic free-living conditions, comprising a symbiotic *Rhizobium Sp.* IRBG74 species having an exogenous nif cluster, wherein the exogenous nif cluster confers nitrogen fixation capability on the symbiotic *Rhizobium Sp.* IRBG74 species under aerobic free-living conditions, wherein the exogenous nif cluster is:
   (i) is photosynthetic alphaproteobacteria nif cluster; or
   (ii) an inducible refactored nif cluster comprising two or more nif genes which are each preceded by a heterologous promoter, and comprise a heterologous terminator, wherein the nif genes located in the inducible refactored nif cluster encode nitrogenase subunits, proteins involved in the biosynthesis of metalloclusters, proteins involved in electron transport, and regulator proteins,
   wherein the nitrogenase subunits are encoded by a nifH sequence, a nifD sequence, and/or a nifK sequence, wherein the proteins involved in electron transport are encoded by a nifF sequence and/or a nifJ sequence, wherein the proteins involved in the biosynthesis of metalloclusters and the regulator proteins are encoded by a nifT sequence, a nifY sequence, a nifE sequence, a nifN sequence, a nifX sequence, a nifB sequence, a nifQ sequence, a nifU sequence, a nifS sequence, a nifV sequence, a nifW sequence, and/or a nifZ sequence,
   wherein the inducible refactored nif cluster is an inducible refactored free-living diazotroph nif cluster, an inducible refactored symbiotic diazotroph nif cluster, an inducible refactored photosynthetic alphaproteobacteria nif cluster, an inducible refactored gammaproteobacteria nif cluster, an inducible refactored cyanobacteria nif cluster, or an inducible refactored firmicutes nif cluster.

2. The rhizobia species of claim 1, wherein the photosynthetic alphaproteobacteria nif cluster of (i) is a *Rhodobacter sphaeroides* nif cluster or a *Rhodopseudomonas palustris* nif cluster and wherein the inducible refactored photosynthetic alphaproteobacteria nif cluster of (ii) is from *Rhodobacter sphaeroides* or *Rhodopseudomonas palustris*.

3. The rhizobia species of claim 1, wherein the inducible refactored free-living diazotroph nif cluster is an inducible refactored *Klebsiella* nif cluster.

4. The rhizobia species of claim 1, wherein the inducible refactored nif cluster of (ii) comprises:
   (a) an operon comprising the nifH sequence, the nifD sequence, the nifK sequence, and the nifY sequence,
   (b) an operon comprising the nifE sequence and the nifN sequence,
   (c) an operon comprising the nifJ sequence,
   (d) an operon comprising the nifB sequence and the nifQ sequence,
   (e) an operon comprising the nifF sequence, and
   (f) an operon comprising the nifU sequence, the nifS sequence, the nifV sequence, the nifW sequence, and the nifZ sequence.

5. The rhizobia species of claim 1, wherein each nif gene of the exogenous nif cluster is preceded by a T7 promoter.

6. The rhizobia species of claim 1, further comprising an endogenous nif cluster.

7. A plant growth promoting rhizobia species that can fix nitrogen under aerobic free-living conditions, comprising a *Rhizobium Sp.* IRBG74 species having an exogenous nif cluster having at least one inducible promoter, wherein the exogenous nif cluster confers nitrogen fixation capability on the *Rhizobium Sp.* IRBG74 under aerobic free-living conditions, wherein the exogenous nif cluster is:
   (i) a photosynthetic alphaproteobacteria nif cluster, or
   (ii) an inducible refactored nif cluster comprising two or more nif genes which are each preceded by a heterologous promoter, and comprise a heterologous terminator, wherein the nif genes located in the inducible refactored nif cluster encode nitrogenase subunits, proteins involved in the biosynthesis of metalloclusters, proteins involved in electron transport, and regulator proteins,
   wherein the nitrogenase subunits are encoded by a nifH sequence, a nifD sequence, and/or a nifK sequence, wherein the proteins involved in electron transport are encoded by a nifF sequence and/or a nifJ sequence, wherein the proteins involved in the biosynthesis of metalloclusters and the regulator proteins are encoded by a nifT sequence, a nifY sequence, a nifE sequence, a nifN sequence, a nifX sequence, a nifB sequence, a nifQ sequence, a nifU sequence, a nifS sequence, a nifV sequence, a nifW sequence, and/or a nifZ sequence,
   wherein the inducible refactored nif cluster is selected from the group consisting of: a free-living diazotroph nif cluster; a symbiotic diazotroph nif cluster; a photosynthetic alphaproteobacteria nif cluster; a gammaproteobacteria nif cluster; a cyanobacteria nif cluster; and a firmicutes nif cluster.

8. The plant growth promoting rhizobia species of claim 7, wherein the rhizobia species is a symbiotic *Rhizobium Sp.* IRBG74 species.

9. The plant growth promoting rhizobia or species of claim 7, wherein the plant growth promoting rhizobia or Sinorhizobium species is associated with a genetically modified cereal plant.

10. The plant growth promoting rhizobia species of claim 9, wherein the genetically modified cereal plant includes an exogenous gene encoding a chemical signal.

11. The plant growth promoting rhizobia species of claim 10, wherein the nitrogen fixation is under the control of the chemical signal.

12. The plant growth promoting rhizobia species of claim 10, wherein the chemical signal is opine, phlorogluconol or rhizopene.

13. The rhizobia species of claim 7, wherein the inducible promoter is a T7 promoter, and optionally wherein the inducible promoter is $P_{A1lacO1}$ promoter.

14. The rhizobia species of claim 7, wherein the inducible promoter is activated by an agent selected from a group that includes IPTG, sodium salicylate, octapine, nopaline, the quorum signal 3OC6HSL, aTc, cuminic acid, DAPG, and salicylic acid.

15. A method of engineering a rhizobia species that can fix nitrogen under aerobic free-living conditions, comprising transferring an exogenous nif cluster to a symbiotic *Rhizobium Sp.* IRBG74 species, wherein the exogenous nif cluster confers nitrogen fixation capability on the symbiotic *Rhizobium Sp.* IRBG74 under aerobic free-living conditions, wherein the exogenous nif cluster is:
  (i) a photosynthetic alphaproteobacteria nif cluster; or
  (ii) an inducible refactored nif cluster an inducible refactored nif cluster comprising two or more nif genes which are each preceded by a heterologous promoter, and comprise a heterologous terminator, wherein the nif genes located in the inducible refactored nif cluster encode nitrogenase subunits, proteins involved in the biosynthesis of metalloclusters, proteins involved in electron transport, and regulator proteins,
  wherein the nitrogenase subunits are encoded by a nifH sequence, a nifD sequence, and/or a nifK sequence, wherein the proteins involved in electron transport are encoded by a nifF sequence and/or a nifJ sequence, wherein the proteins involved in the biosynthesis of metalloclusters and the regulator proteins are encoded by a nifT sequence, a nifY sequence, a nifE sequence, a nifN sequence, a nifX sequence, a nifB sequence, a nifQ sequence, a nifU sequence, a nifS sequence, a nifV sequence, a nifW sequence, and/or a nifZ sequence,
  wherein the inducible refactored nif cluster is an inducible refactored free-living diazotroph nif cluster, an inducible refactored symbiotic diazotroph nif cluster, an inducible refactored photosynthetic alphaproteobacteria nif cluster, an inducible refactored gammaproteobacteria nif cluster, an inducible refactored cyanobacteria nif cluster, or an inducible refactored firmicutes nif cluster.

16. The method of claim 15, wherein the exogenous nif cluster is transferred to the symbiotic rhizobia species in a plasmid.

17. The method of claim 15, wherein the endogenous nifL gene is deleted.

18. A method of producing nitrogen for consumption by a cereal plant, comprising providing a plant growth promoting rhizobia species that can fix nitrogen under aerobic free-living conditions in proximity of the cereal plant, wherein the plant growth promoting rhizobia or is a symbiotic *Rhizobium Sp.* IRBG74 species having an exogenous nif cluster, wherein the exogenous nif cluster confers nitrogen fixation capability on the symbiotic *Rhizobium Sp.* IRBG74 species, enabling nitrogen fixation under aerobic free-living conditions, wherein the exogenous nif cluster is:
  (i) a photosynthetic alphaproteobacteria nif cluster; or
  (ii) an inducible refactored nif cluster an inducible refactored nif cluster comprising two or more nif genes which are each preceded by a heterologous promoter, and comprise a heterologous terminator, wherein the nif genes located in the inducible refactored nif cluster encode nitrogenase subunits, proteins involved in the biosynthesis of metalloclusters, proteins involved in electron transport, and regulator proteins,
  wherein the nitrogenase subunits are encoded by a nifH sequence, a nifD sequence, and/or a nifK sequence, wherein the proteins involved in electron transport are encoded by a nifF sequence and/or a nifJ sequence, wherein the proteins involved in the biosynthesis of metalloclusters and the regulator proteins are encoded by a nifT sequence, a nifY sequence, a nifE sequence, a nifN sequence, a nifX sequence, a nifB sequence, a nifQ sequence, a nifU sequence, a nifS sequence, a nifV sequence, a nifW sequence, and/or a nifZ sequence,
  wherein the inducible refactored nif cluster is an inducible refactored free-living diazotroph nif cluster, an inducible refactored symbiotic diazotroph nif cluster, an inducible refactored photosynthetic alphaproteobacteria nif cluster, an inducible refactored gammaproteobacteria nif cluster, an inducible refactored cyanobacteria nif cluster, or an inducible refactored firmicutes nif cluster.

19. The method of claim 18, wherein the cereal plant is a genetically modified cereal plant.

* * * * *

UNITED STATES PATENT AND TRADEMARK OFFICE
CERTIFICATE OF CORRECTION

PATENT NO. : 12,281,299 B2
APPLICATION NO. : 16/746215
DATED : April 22, 2025
INVENTOR(S) : Christopher A. Voigt et al.

Page 1 of 1

It is certified that error appears in the above-identified patent and that said Letters Patent is hereby corrected as shown below:

In the Claims

At Column 203, Line 26:
"(i) is photosynthetic alphaproteobacteria nif cluster; or"
Should read:
-- (i) a photosynthetic alphaproteobacterial nif cluster; or --

At Column 205, Line 1:
"The plant growth promoting rhizobia or species of"
Should read:
-- The plant growth promoting rhizobia species of --

At Column 205, Line 28:
"wherein the exogenous nif cluster is:"
Should read:
-- wherein the exogenous nif cluster is --

At Column 206, Line 15:
"wherein the plant growth promoting rhizobia or is a sym-"
Should read:
-- wherein the plant growth promoting rhizobia is a sym- --

Signed and Sealed this
Twenty-second Day of July, 2025

Coke Morgan Stewart
*Acting Director of the United States Patent and Trademark Office*